US006461824B1

(12) United States Patent
Better et al.

(10) Patent No.: US 6,461,824 B1
(45) Date of Patent: *Oct. 8, 2002

(54) PRODUCTION OF CHIMERIC ANTIBODIES WITH SPECIFICITY TO HUMAN TUMOR ANTIGENS

(75) Inventors: Marc D. Better; Arnold H. Horwitz; Randy R. Robinson; Shau-Ping Lei, all of Los Angeles; Changtung Paul Chang, Chatsworth, all of CA (US)

(73) Assignee: Xoma Technology Ltd., Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 08/467,142

(22) Filed: Jun. 6, 1995

Related U.S. Application Data

(63) Continuation of application No. 08/364,001, filed on Dec. 27, 1994, now Pat. No. 5,576,184, which is a continuation of application No. 07/659,401, filed as application No. PCT/US89/03852 on Sep. 6, 1989, now abandoned, and a continuation-in-part of application No. 07/382,768, filed on Jul. 21, 1989, now abandoned, and a continuation-in-part of application No. 07/367,641, filed on Jun. 19, 1989, now abandoned, and a continuation-in-part of application No. 07/253,002, filed on Oct. 4, 1988, now abandoned, and a continuation-in-part of application No. 07/243,739, filed on Sep. 13, 1988, now abandoned, and a continuation-in-part of application No. 07/241,744, filed on Sep. 8, 1988, now abandoned, which is a continuation-in-part of application No. 07/240,624, filed on Sep. 6, 1988, now abandoned.

(51) Int. Cl.[7] .................. A61K 39/395; C07K 16/30; G01N 33/574

(52) U.S. Cl. .............. 435/7.23; 424/1.49; 424/9.34; 424/133.1; 424/178.1; 435/69.6; 530/387.3; 530/391.1; 530/391.3; 530/391.7

(58) Field of Search .................. 435/7.23, 69.6, 435/172.3; 424/1.49, 9.34, 133.1, 178.1; 530/387.3, 391.1, 391.3, 391.7; 536/23.53

(56) References Cited

U.S. PATENT DOCUMENTS

| | | | |
|---|---|---|---|
| 4,612,282 | * 9/1986 | Schlom et al. | 435/68 |
| 4,816,567 | * 3/1989 | Cabilly et al. | 530/387.3 |
| 4,818,709 | 4/1989 | Primus et al. | 436/518 |
| 4,975,369 | 12/1990 | Beavers et al. | 435/69.1 |
| 5,130,116 | 7/1992 | Woo et al. | 424/1.1 |
| 5,348,887 | 9/1994 | Bumol et al. | 435/320.1 |
| 5,354,847 | * 10/1994 | Liu et al. | 530/387.3 |
| 5,500,362 | * 3/1996 | Robinson et al. | 435/7.23 |
| 5,576,184 | 11/1996 | Better et al. | 435/7.23 |
| 5,843,685 | 12/1998 | Better et al. | 435/7.23 |

FOREIGN PATENT DOCUMENTS

| | | |
|---|---|---|
| EP | 0 120 694 A2 | 10/1984 |
| EP | 0 125 023 A1 | 11/1984 |
| EP | 0 162 319 | 11/1985 |
| EP | 0173494 | * 3/1986 |
| EP | 0 252 741 B1 | 1/1988 |
| EP | 0 260 148 | 3/1988 |
| EP | 0 326 423 B1 | 8/1989 |
| EP | 0 364 096 | 4/1990 |
| EP | 0 755 683 A1 | 1/1997 |
| JP | 61-167699 | * 7/1986 |
| WO | WO 87/02671 | 5/1987 |
| WO | WO 88/03145 | 5/1988 |
| WO | WO 88/04936 | 7/1988 |
| WO | WO 93/08298 A1 | 4/1993 |

OTHER PUBLICATIONS

S.-K. Liao et al, Proc. Amer. Assoc. Cancer Res., 28, 362, Abstr. No. 1433, 1987.*

Y. Nishimura et al, Cancer Res., 47, 999–1005, 1987.*

Balzar, M. et al., "The biology of the 17–1A antigen (Ep–CAM)," *J. Mol. Med.* 77699–712, Springer–Verlag (Oct. 1999).

Smith, G.K. et al., "Toward Antibody–directed Enzyme Prodrug Therapy with the T268G Mutant of Human Carboxypeptidase A1 and Novel in Vivo Stable Prodrugs of Methotrexate," *J. Biol. Chem.* 272:15804–15816, American Society for Biochemistry and Molecular Biology, Inc. (Jun., 1997).

LoBuglio, A.F. et al., "Mouse/human chimeric monoclonal antibody in man: Kinetics and immune response," *Proc. Natl. Acad. Sci. USA* 86:4220–4224, National Academy of Sciences of the USA (Jun., 1989).

Masucci, G. et al., "Effect of Blood Mononuclear Cell Populations in Antibody Dependent Cellular cytotoxicity (ADCC) Using Two Murine (CO17–1A and Br55–2) and One Chimeric (17–1A) Monoclonal Antibodies Against a Human Colorectal Carcinoma Cell Line (SW948)," *Hybridoma* 7:429–440, Mary Ann Liebert, Inc., Publishers (1988).

Sun, L.K. et al., "Chimeric antibody with human constant regions and mouse variable regions directed against carcinoma–associated antigen 17–1A," *Proc. Natl. Acad. Sci. USA* 84:214–218, National Academy of Sciences of the USA (Jan., 1987).

Buchsbaum, D. et al., "Localization and Imaging of Radiolabeled Monoclonal Antibodies against Colorectal Carcinoma in Tumor–bearing Nude Mice," *Cancer Res.* 48:4324–4333, American Association For Cancer Research (Aug., 1988).

(List continued on next page.)

Primary Examiner—David Saunders
(74) Attorney, Agent, or Firm—Sterne, Kessler, Goldstein and Fox P.L.L.C.

(57) ABSTRACT

The invention is directed to chimeric immunoglobulins that recognize a human tumor antigen bound by antibody, ING-2, ING-3, ING-4 or KM10, the production of such chimeric immunoglobulins, and their use.

198 Claims, 61 Drawing Sheets

OTHER PUBLICATIONS

Herlyn, M. et al., "Colorectal carcinoma–specific antigen: Detection by means of monoclonal antibodies," *Proc. Natl. Acad. Sci. USA* 76:1438–1442, National Academy of Sciences of the USA (Mar. 1979).

Khazaeli, M.B. et al., "Phase I Trial of Multiple Large Doses of Murine Monoclonal Antibody CO17–1A. II. Pharmacokinetics and Immune Response," *J. Natl. Cancer Inst.* 80:937–942, U. S. Dept. of Health, Education, and Welfare, Public Health Service, National Institutes of Health (Aug., 1988).

Mattes, M.J. et al., "Binding parameters of monoclonal antibodies reacting with ovarian carcinoma ascites cells," *Cancer Immunol. Immunother.* 28:199–207, Springer–Verlag (Mar., 1989).

Mellstedt, H. et al., "The Clinical Use of Monoclonal Antibodies, Mab 17–1A, in the Treatment of Patients with Metastatic Colorectal Carcinoma," *Med. Oncol & Tumor Pharmacother.* 6:99–107, Pergamon Press PLC (1989).

Sears, H.F. et al., "Phase–I Clinical Trial of Monoclonal Antibody in Treatment of Gastrointestinal Tumours," *Lancet* 1(8275):762–765, The Lancet, Ltd. (1982).

Sears, H.F. et al., "Phase II Clinical Trial of a Murine Monoclonal Antibody Cytotoxic for Gastrointestinal Adenocarcinomas," *Cancer Res.* 45:5910–5913, American Association For Cancer Research (1985).

Weiner, L.M. et al., "Effector Characteristics of the $IgG_3$ Murine Monoclonal Antibody (113F1," *J. Biol. Resp. Modifiers* 8:227–237, Raven Press, Ltd. (1989).

Edwards, D.P. et al., "Monoclonal Antibody Identification and Characterization of a $M_r$ 43,000 Membrane Glycoprotein Associated with Human Breast Cancer," *Cancer Res.* 46:1306–1317, American Association For Cancer Research (Mar., 1986).

Shaw, D.R. et al., "Characterization of a Mouse/Human Chimeric Monoclonal Antibody (17–1A) To a Colon Cancer Tumor–Associated Antigen," *J. Immunol.* 138:4534–4538, American Association of Immunologists (1987).

Velders, M.P. et al., "New Chimeric anti–pancarcinoma monoclonal antibody with superior cytotoxicity–mediating potency," *Cancer Res.* 54:1753–1759, American Association For Cancer Research (Apr., 1994).

Velders, M.P. et al., "The impact of antigen density and antibody affinity on antibody–dependent cellular cytotoxicity: relevance for immunotherapy of carcinomas," *Br. J. Cancer* 78:478=483, Edinburgh Churchill Livingstone On Behalf Of The Cancer Research Campaign (1998).

Better, M. et al., "*Escherichia coli* Secretion of an Active Chimeric Antibody Fragment," *Science* 240:1041–1043 (May, 1988).

Boulianne, G.L. et al., "Production of functional chimaeric mouse/human antibody," *Nature* 312:643–646 (Dec., 1984).

Brown, B.A. et al., "Tumor–specific Genetically Engineered Murine/Human Chimeric Monoclonal Antibody," *Cancer Res.* 47:3577–3583 (Jul., 1987).

Goding, J.W., "Fragmentation of Monoclonal Antibodies," in *Monoclonal Antibodies: Principles and Practice*, J.W. Goding, ed., Academic Press, Inc., New York, NY, pp. 118–125 (1983).

Herlyn, D. et al., "Monoclonal Anti–Human Tumor Antibodies of Six Isotypes in Cytotoxic Reactions with Human and Murine Effector Cells," *Cell Immunol.* 92:105–114 (Apr., 1985).

Horwitz, A.H. et al., "Secretion of functional antibody and Fab fragment from yeast cells," *Proc. Natl. Acad. Sci. USA* 85:8678–8682 (Nov., 1988).

Ishida, H. et al., "A Monoclonal Antibody, KM10 Reactive with Human Gastrointestinal Cancer," *Nippon Geka Gakkai Zasshi* 89:508–515 (Apr., 1988).

Jones, P.T. et al., "Replacing the complementary–determining regions in a human antibody with those from a mouse," *Nature* 321:522–525 (May., 1986).

Morrison, S.L. et al., "Chimeric human antibody molecules: Mouse antigen–binding domains with human constant region domains," *Proc. Natl. Acad. Sci. USA* 81:6851–6855 (Nov., 1984).

Morrison, S.L. et al., "Transfectomas Provide Novel Chimeric Antibodies," *Science* 229:1202–1207 (Sep., 1985).

Neuberger, M.S. et al., "Recombinant antibodies possessing novel effector functions," *Nature* 312:604–608 (Dec., 1984).

Neuberger, M.S. et al., "A hapten–specific chimaeric IgE antibody with human physiological effector function," *Nature* 314:269–271 (1985).

Ohyanagi, H. et al., "A Monoclonal Antibody, KM10 Reactive with Human Gastrointestinal Cancer and Its Application for Immunotherapy," *Jpn. J. Cancer Res. (Gann)* 79:1349–4358 (Dec., 1988).

Oi, V.T. and S.L. Morrison, "Chimeric Antibodies," *Biotech.* 4:214–221 (1986).

Sahagan, B.G. et al., "A Genetically Engineered Murine/Human Chimeric Antibody Retains Specificity for Human Tumor–Associated Antigen," *J. Immunol.* 137:1066–1074 (Aug., 1986).

Shaw, D.R. et al., "Human Lymphocyte and Monocyte Lysis of Tumor Cells Mediated by a Mouse/Human IgG1 Chimeric Monoclonal Antibody," *J. Biol. Resp. Mod.* 7:204–211 (Apr., 1988).

Sun, L.K. et al., "Chimeric Antibodies with 17–1A–Derived Variable and Human Constant Regions," *Hybridoma* 5:S17–S19 (1986).

Sun, L.K. et al., "Chimeric antibody with human constant regions and mouse variable regions directed against carcinoma–associated antigen 17–1A," *Proc. Natl. Acad. Sci. USA* 84:214–218 (Jan., 1987).

Tan, L.K. et al., "A Human–Mouse Chimeric Immunoglobulin Gene with a Human Variable Region is Expressed in Mouse Myeloma Cells," *J. Immunol.* 135:8564–8567 (Nov., 1985).

Thorpe, P.E., "Antibody Carriers of Cytotoxic Agents in Cancer Therapy: A Review," in *Monoclonal Antibodies '84: Biological and Clinical Applications*, A. Pinchera et al., eds., Editrice Kurtis SRL, publ., Milano, Italy, pp. 475–506 (1985).

Verhoeyen, M. et al., "Reshaping Human Antibodies: Grafting on Antilysozyme Activity," *Science* 239:1534–1536 (Mar., 1988).

Waldmann, T.A., "Monoclonal Antibodies in Diagnosis and Therapy," *Science* 252:1657–1662 (Jun., 1991).

Choo, K.H. et al., "Vectors for Expression and Amplification of cDNA in Mammalian Cells: Expression of Rat Phenylalanine and Hydroxylase," *DNA* 5(6):529–537 (1986).

Dillman, R.O., "Monoclonal Antibodies for Treating Cancer," *Annals Internal Medicine* 111(7):592–603 (Oct. 1989).

Harris, W.J. et al., "Therapeutic antibodies—the coming of age," *Trends in Biotech.* 11:42–44 (Feb. 1993).

Hay, R. et al., eds., in: *American Type Culture Collection Catalogue of Cell Lines and Hybridomas Seventh Edition,* 1992, p. 381: ATTC Hybridoma 8110 (Jan. 1992).

Hird, V. et al., "Immunotherapy with Monoclonal Antibodies," in: *Genes and Cancer,* Carney, D and Sikora, K., eds., John Wiley & Sons Ltd. pp. 183–189 (Oct. 1990).

Liao, S.-K. et al., "Monoclonal Antibody Recognizing Human Melanoma–Carcinoma Cross–Reacting Oncofetal Antigen Epitopically Associated With Carcinoembryonic Antigen," *J. Natl. Can. Inst.* 74(5):1047–1057 (May 1985).

Liu, A.Y. et al., "Chimeric mouse–human IgG1 antibody that can mediate lysis of cancer cells," *Proc. Natl. Acad. Sci. USA* 84:3439–3443 (May 1987).

Liu, A.Y. et al., "Production Of A Mouse–Human Chimeric Monoclonal Antibody To CD20 With Potent Fc–Dependent Biologic Activity," *The Journal of Immunology* 139(10):3521–3526 (Nov. 1987).

Nose, M. and H. Wigzell, "Biological significance of carbohydrate chains on monoclonal antibodies," *Proc. Natl. Acad. Sci. USA* 80:6632–6636 (1983).

Okayama, H. et al., "A cDNA Cloning Vector That Permits Expression of cDNA Inserts in Mammalian Cells," *Molecular and Cellular Biology* 3(2):280–289 (1983).

Oldham, R.K. et al., "Adriamycin custom–tailored immunoconjugates in the treatment of human malignancies," *Mol. Biother.* 1(2):103–113 (Jun. 1988).

Robinson, R.R. et al., "Chimeric mouse–human anti–carcinoma antibodies that mediate different anti–tumor cell biological activities," *Hum. Antibod. Hybridomas* 2:84–93 (Apr. 1991).

Sasada, R. et al., "The Establishment of IL–2 Producing Cells by Genetic Engineering," *Cell Structure and Function* 12:205–217 (Apr. 1987).

Shaw, D.R. et al., "Mouse/Human Chimeric Antibodies to a Tumor–Associated Antigen: Biologic Activity of the Four Human IgG Subclasses," *Journal of the National Cancer Institute* 80(19):1553–1559 (Dec. 1988).

Steplewski, Z. et al., "Biological activity of human–mouse IgG1, IgG2, IgG3, and IgG4 chimeric monoclonal antibodies with antitumor specificity," *Proc. Natl. Acad. Sci. USA* 85:4852–4856 (Jul. 1988).

Wawrzynczak, E.J. et al., "Strategies in antibody therapy of cancer," *Clin. exp. Immunol.* 82:189–193 (Oct. 1990).

Whittle, N. et al., "Expression in COS cells of a mouse–human chimaeric 872.3 antibody," *Protein Engineering* 1(6):499–505 (Dec. 1987).

Barr, Ian G. Ph.D. et al., "Retargeting of Cytolytic T Lymphocytes by Heteroaggregated (Bispecific) Antibodies," *Cancer Detection and Prevention. Prev.* 12:439–450 (1988).

Gillies, Stephen D. et al., "Expression of Genetically Engineered Immunoconjugates of Lymphotoxin and a Chimeric Anti–Ganglioside GD2 Antibody," *Hybridoma* 10(3):347–356 (1991).

Mujoo, Kalpana et al., "A potent and specific immunotoxin for tumor cells expressing disialoganglioside $GD_2$," *Cancer Immunology Immunotherapy* 34:198–204 (1991).

Walker, Christopher et al., "Activation of T cells by cross–linking an anti–CD3 antibody with a second anti–T cell antibody: mechanism and subset–specific activation," *Eur. J. Immunol.* 17(6):873–880 (1987).

\* cited by examiner

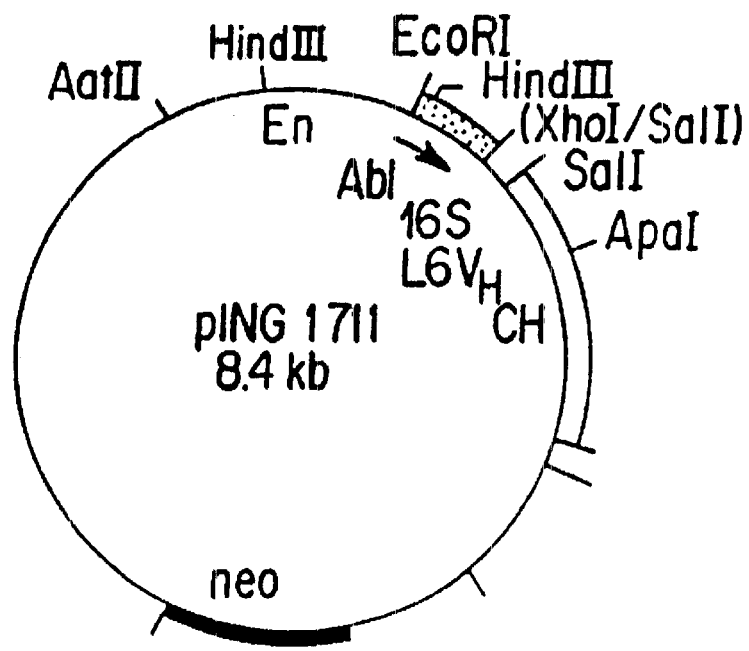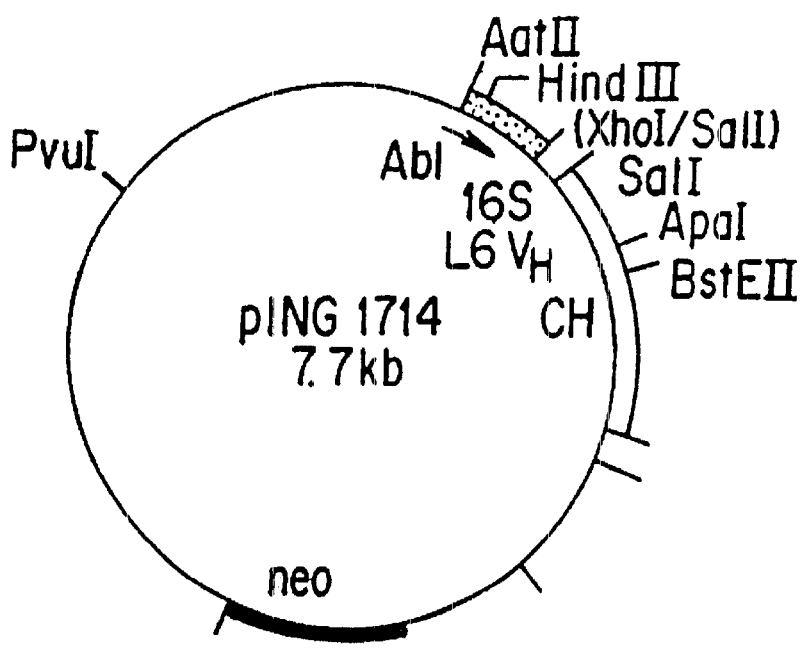
FIG. 6B

Sequence of B38.1 Light Chain V Region

```
                    SalI
       3'-CCCCAGTGACAGCTGAGTGGTA-5'                    METArgPheSerAlaGlnLeu
       GGGGGGGTCACTTTTGACTCACCATATCAAGTTCGCAGAATGAGGTTCTCTGCTCAGCTT
                15            30            45            60
                                  ApaI
                    3'-GGACCTAGGTCCCGGGTTTAACACTACTG-5'
       LeuGlyLeuLeuValLeuTrpIleProGlySerThrAlaAspIleValMETThrGlnAla
       CTGGGGCTGCTTGTGCTCTGGATCCCTGGATCCACTGCAGATATTGTGATGACGCAGGCT
                75            90           105           120

AlaPheSerAsnProValThrLeuGlyThrSerGlySerIleSerCysArgSerSerLys
       GCATTCTCCAATCCAGTCACTCTTGGAACATCAGGTTCCATCTCCTGCAGGTCTAGTAAG
                135           150           165           180

SerLeuLeuHisSerAsnGlyIleThrTyrLeuTyrTrpTyrLeuGlnLysProGlyGln
       AGTCTCCTACATAGTAATGGCATCACTTATTTGTATTGGTATCTGCAGAAGCCAGGCCAG
                195           210           225           240

SerProGlnLeuLeuIleTyrGlnMETSerAsnLeuAlaSerGlyValProAspArgPhe
       TCTCCTCAGCTCCTGATTTATCAGATGTCCAACCTTGCCTCAGGAGTCCCAGACAGGTTC
                255           270           285           300

SerSerSerGlySerGlyThrAspPheThrLeuArgIleSerArgValGluAlaGluAsp
       AGTAGCAGTGGGTCAGGAACTGATTTCACACTGAGAATCAGCAGAGTGGAGGCTGAGGAT
                315           330           345           360

3'-CGTGG
       ValGlyValTyrTyrCysAlaGlnAsnLeuGluLeuProArgThrPheGlyGlyGlyThr
       GTGGGTGTTTATTACTGTGCTCAAAATCTAGAACTTCCTCGGACGTTCGGTGGAGGCACC
                375           390           405           420
       HindIII
       TTCGAACTTTAGTTTG-5'
       LysLeuGluIleLysArgAla
       AAGCTGGAAATCAAACGGGCT
                435
```

FIG. 7

Sequence of B38.1 Heavy Chain V Region

```
                          SalI
             3'-CTGGTCAATCAGCTGTCCGTGGTGAAG-5'         METAla
CCCCGCCCCCCGCCGAGTGACCAGTTAGTCTTAAGGCACCACTTCTTAGACATCATGGCT
        15           30           45           60
                                                   SstI
                           3'-GTTTCACGGGCTCGAGTCTAGGTC
TrpValSerThrLeuLeuPheLeuMETAlaAlaAlaGlnSerAlaGlnAlaGlnIleGln
TGGGTGTCCACCTTGCTATTCCTGATGGCAGCTGCCCAAAGTGCCCAAGCACAGATCCAG
        75           90          105          120

-5'
LeuValGlnSerGlyProGluLeuLysLysProGlyGluThrValLysIleSerCysLys
TTGGTGCAGTCTGGACCTGAGCTGAAGAAGCCTGGAGAGACAGTCAAGATCTCCTGCAAG
       135          150          165          180

AlaSerGlyTyrThrPheThrLysTyrGlyMETAsnTrpValLysGlnAlaProGlyLys
GCTTCTGGATATACCTTCACAAAATATGGAATGAACTGGGTGAAGCAGGCTCCAGGAAAG
       195          210          225          240

GlyLeuLysTrpMETGlyTrpIleAsnThrTyrThrGluGluProThrTyrGlyAspAsp
GGTTTAAAGTGGATGGGCTGGATAAACACCTACACTGAAGAGCCAACATATGGTGATGAC
       255          270          285          300

PheLysGlyArgPheAlaPheSerLeuGluThrSerAlaSerThrAlaAsnLeuGlnIle
TTCAAGGGACGGTTTGCCTTCTCTTTGGAAACCTCTGCCAGCACTGCCAATTTGCAGATC
       315          330          345          360

AsnAsnLeuLysSerGluAspThrAlaThrTyrPheCysAlaArgPheGlySerAlaVal
AACAACCTCAAAAGTGAGGACACGGCTACATATTTCTGTGCAAGATTTGGCTCTGCTGTG
       375          390          405          420
                          BstEII
             3'-CCTTGGAGCCAGTGGCAGAG-5'
AspTyrTrpGlyGlnGlyThrSerValThrValSerSer
GACTACTGGGGTCAAGGAACCTCAGTCACCGTCTCCTCAG
       435          450
```

FIG. 8

Sequence of Br-3 Light Chain V Region

```
                                  METAlaTrpIleSerLeuIleLeuSerLeuLeu
GAAAAGAATAGACCTGGTTTGTGAATTATGGCCTGGATTTCACTTATACTCTCTCTCCTG
         15        30        45        60
        ApaI
3'-GAGTCCCCGGTCCCGGGTCCGAC-5'
AlaLeuSerSerGlyAlaIleSerGlnAlaValValThrGlnGluSerAlaLeuThrThr
GCTCTCAGCTCAGGGGCCATTTCCCAGGCTGTTGTGACTCAGGAATCTGCACTCACCACA
         75        90       105       120

SerProGlyGluThrValThrLeuThrCysArgSerSerThrGlyAlaValThrThrSer
TCACCTGGTGAAACAGTCACACTCACTTGTCGCTCAAGTACTGGGGCTGTTACAACTAGT
        135       150       165       180

AsnTyrAlaAsnTrpValGlnGluLysProAspHisLeuPheThrGlyLeuIleGlyGly
AACTATGCCAACTGGGTCCAAGAAAAACCAGATCATTTATTCACTGGTCTAATAGGTGGT
        195       210       225       240

ThrAsnAsnArgAlaProGlyValProAlaArgPheSerGlySerLeuIleGlyAspLys
ACCAACAACCGAGCTCCAGGTGTTCCTGCCAGATTCTCAGGCTCCCTGATTGGAGACAAG
        255       270       285       300

AlaAlaLeuThrIleThrGlyThrGlnThrGluAspGluAlaIleTyrPheCysAlaLeu
GCTGCCCTCACCATCACAGGGACACAGACTGAGGATGAGGCAATATATTTCTGTGCTCTA
        315       330       345       360
                                                        AvrII
TrpTyrSerAsnHisTrpValPheGlyGlyGlyThrLysLeuThrValLeuGlyGlnPro
TGGTACAGCAACCATTGGGTGTTCGGTGGAGGAACCAAACTGACTGTCCTAGGCCAGCCC
        375       390       405       420
```

FIG. 14

Sequence of Br-3 Heavy Chain V Region

```
                                                      SalI
                            3'-GAAAGAGAAGCAGCTGTTTGTGT-5'
    GACAGACGCACAACCCTGGACTCACAAGTCTTTCTCTTCAGTGACAAACACAGAAATAGA
             15            30            45            60

3'-ATTTTCCACAG
            METTyrLeuGlyLeuAsnCysValPheIleValPheLeuLeuLysGlyVal
    ACATTCACCATGTACTTGGGACTGAACTGTGTATTCATAGTTTTTCTCTTAAAAGGTGTC
             75            90           105           120
    AatII
GCTGCAGTTCACTTCGAA-5'
    GlnSerGluValLysLeuGluGluSerGlyGlyGlyLeuValGlnProGlyGlySerMET
    CAGAGTGAAGTGAAGCTTGAGGAGTCTGGAGGAGGCTTGGTGCAACCTGGAGGATCCATG
            135           150           165           180

LysLeuSerCysValAlaSerGlyPheThrPheSerAsnTyrTrpMETAsnTrpValArg
    AAACTCTCCTGTGTTGCCTCTGGATTCACTTTCAGTAACTATTGGATGAACTGGGTCCGC
            195           210           225           240

GlnSerProGluLysGlyLeuGluTrpValAlaGluIleArgLeuLysSerAsnAsnTyr
    CAGTCTCCAGAGAAGGGGCTTGAGTGGGTTGCTGAAATTAGATTGAAATCTAATAATTAT
            255           270           285           300

AlaThrHisTyrAlaGluSerValLysGlyArgPheThrIleSerArgAspAspSerLys
    GCAACACATTATGCGGAGTCTGTGAAAGGGAGGTTCACCATCTCAAGAGATGATTCCAAA
            315           330           345           360

SerSerValTyrLeuGlnMETAsnAsnLeuArgAlaGluAspThrGlyIleTyrTyrCys
    AGTAGTGTCTACCTGCAAATGAACAACTTAAGAGCTGAAGACACTGGCATTTATTACTGT
            375           390           405           420

PstI
    ThrPheGlyAsnGlnPheAlaTyrTrpGlyGlnGlyThrLeuValThrValSerAlaAla
    ACATTTGGTAACCAGTTTGCTTACTGGGGCCAAGGGACTCTGGTCACTGTCTCTGCAGCC
            435           450           465           480

LysThrThrProPro
    AAAACGACACCCCATC
            495
```

FIG. 15

Sequence of Co-1 Light Chain V Region

```
        MstII            MstII
                                                   METLysLeuProValArgLeu
CAGTCTCCTCAGGCTGTCTCCTCAGGTTGCCTCCTCAAAATGAAGTTGCCTGTTAGGCTG
           15           30           45           60
                                    AatII
                    3'-AGGACAAAGGTCTGCAGTTCAAAACTAC-5'
LeuValLeuMETPheTrpIleProValSerAsnSerGluValLeuMETThrGlnThrPro
TTGGTGCTGATGTTCTGGATTCCTGTTTCCAACAGTGAAGTTTTGATGACCCAAACTCCA
          75           90          105          120

LeuSerLeuProValSerLeuGlyAspGlnAlaSerIleSerCysArgSerSerGlnSer
CTCTCCCTGCCTGTCAGTCTTGGAGATCAAGCCTCCATCTCTTGCAGATCTAGTCAGAGC
         135          150          165          180

IleValHisSerAsnGlyAsnThrTyrLeuGluTrpTyrLeuGlnLysLeuGlyGlnSer
ATTGTACATAGTAATGGAAACACCTATTTAGAATGGTACCTGCAGAAACTAGGCCAGTCT
         195          210          225          240

ProLysLeuLeuIleTyrLysValSerLysArgPheSerGlyValProAspArgIleSer
CCAAAGCTCCTGATCTACAAAGTTTCCAAACGATTTTCTGGGGTCCCAGACAGGATCAGT
         255          270          285          300

GlySerGlySerGlyThrAspPheThrLeuLysIleSerArgValGluAlaGluAspLeu
GGTAGTGGATCAGGGACAGATTTCACACTCAAGATCAGCAGAGTGGAGGCTGAGGATCTG
         315          330          345          360
                                                         HindIII
                                                 3'-CCCTGGTTC
GlyValTyrHisCysPheGlnGlySerHisAlaProLeuThrPheGlyAlaGlyThrLys
GGAGTTTATCACTGCTTTCAAGGTTCACATGCTCCGCTCACGTTCGGTGCTGGGACCAAG
         375          390          405          420

GAACTCGAC-5'
ValGluLeuLys
GTGGAGCTGAAA
        435
```

FIG. 21

Sequence of Co-1 Heavy Chain V Region

```
                                                          NcoI
                                                       METGluTrp
CACCGACGATCAGTGTCCTCTCCAAAGTCCCTGAACACACTGACTCTAACCATGGAATGG
        15           30           45            60

PstI
SerTrpIlePheLeuPheLeuLeuSerGlyThrAlaGlyValHisSerGluValGlnLeu
AGTTGGATATTTCTCTTTCTCCTGTCAGGAACTGCAGGTGTCCACTCTGAGGTCCAGCTG
        75           90          105           120

GlnGlnSerGlyProGluLeuValLysProGlyAlaSerValLysMETSerCysLysAla
CAGCAGTCTGGACCTGAGCTGGTAAAGCCTGGGGCTTCAGTGAAGATGTCCTGCAAGGCT
       135          150          165            180

SerGlyTyrThrPheThrSerTyrValMETHisTrpValLysGlnLysProGlyGlnGly
TCTGGATACACATTTACTAGCTATGTTATGCACTGGGTGAAGCAGAAGCCTGGGCAGGGC
       195          210          225            240

LeuGluTrpIleGlyTyrIleAsnProTyrAsnAspGlyThrSerTyrAsnGluLysPhe
CTTGAGTGGATTGGATATATTAATCCTTACAATGATGGTACTAGTTACAATGAGAAATTC
       255          270          285            300

LysGlyLysAlaThrLeuThrSerAspLysSerSerSerThrAlaTyrMETGluLeuSer
AAAGGCAAGGCCACACTGACTTCAGACAAATCCTCCAGCACAGCCTACATGGAGCTCAGC
       315          330          345            360

SerLeuThrSerGluAspSerAlaValTyrTyrCysAlaArgArgIleTyrPheAspTyr
AGCCTGACCTCTGAGGACTCTGCGGTCTATTACTGTGCAAGGAGGATCTACTTTGATTAC
       375          390          405            420

BstEII
SerTyrValMETAspTyrTrpGlyGlnGlyThrSerValThrValSerSer
TCCTATGTTATGGACTACTGGGGTCAAGGAACCTCGGTCACCGTCTCCTCA
       435          450          465
```

FIG. 22

Sequence of ME4 Light Chain V Region

```
                                                                    SalI
                                             3'-CGAGCATAGGCAGCTG
CCCGTACCGCTCGCTTATCTATCTCGCGTGCTGCCCCCTTTAGTGCTCGTATCCCGCCGC
          15           30           45           60
                                                        PstI
TACTACAGG-5'                                 3'-AAGTTCCATGGTGACGT
METMETSerSerAlaGlnPheLeuGlyLeuLeuLeuLeuCysPheGlnGlyThrArgCys
ATGATGTCCTCTGCTCAGTTCCTTGGTCTCCTGTTGCTCTGTTTTCAAGGTACCAGATGT
          75           90          105          120

CTATAGGTCTAC-5'
AspIleGlnMETThrGlnThrThrSerSerLeuSerAlaSerLeuGlyAspArgValThr
GATATCCAGATGACACAGACTACATCCTCCCTGTCTGCCTCTCTGGGAGACAGAGTCACC
         135          150          165          180

IleSerCysArgAlaSerGlnAspIleThrThrTyrLeuAsnTrpTyrGlnGlnLysPro
ATCAGTTGCAGGGCAAGTCAGGACATTACCACTTATTTAAACTGGTATCAGCAGAAACCA
         195          210          225          240

AspGlyThrValLysLeuLeuIleTyrTyrThrSerArgLeuHisSerGlyValProSer
GATGGAACTGTTAAACTCCTGATCTACTACACATCAAGATTACACTCAGGAGTCCCATCA
         255          270          285          300

ArgPheSerGlySerGlySerGlyThrAspTyrSerLeuThrIleSerAsnLeuGluGln
AGGTTCAGTGGCAGTGGGTCTGGAACAGATTATTCTCTCACCATTAGCAACCTGGAGCAA
         315          330          345          360

3'
GluAspPheAlaThrTyrPheCysGlnGlnGlyAsnIleLeuProArgThrPheGlyGly
GAAGATTTTGCCACTTACTTTTGCCAACAGGGTAATATACTTCCTCGGACGTTCGGTGGA
         375          390          405          420
     HindIII
-CGTGGTTCGAACTTTAGTTTG-5'
GlyThrLysLeuGluIleLysArg
GGCACCAAACTGGAAATCAAACGG
         435
```

FIG. 29

Sequence of ME4 Heavy Chain V Region

```
TACTTCCCGCAATGTCTGTACCCTATGATCAGTGTCCTCTCAACAGTCCCTGAACACACT
        15          30          45          60

SalI                                      3'-GACGTCCACAA
        METAspTrpSerArgValPheIlePheLeuLeuSerValThrAlaGlyVal
ACTCTCACCATGGATTGGAGCAGAGTCTTTATCTTTCTCCTATCAGTAACTGCAGGTGTT
        75          90         105         120
   SstI
GCTCGAGTCCAGGTCAAC-5'
HisSerGlnValGlnLeuGlnGlnSerGlyAlaGluLeuValArgProGlyThrSerVal
CACTCCCAGGTCCAGTTGCAGCAGTCTGGAGCTGAGCTGGTAAGGCCTGGGACTTCAGTG
       135         150         165         180

LysValSerCysThrThrSerGlyTyrAlaPheThrAsnTyrLeuMETGluTrpMETLys
AAGGTGTCCTGCACGACTTCTGGATACGCCTTCACTAATTACTTGATGGAGTGGATGAAA
       195         210         225         240

GlnArgProGlyGlnGlyLeuGluTrpIleGlyValIleAsnProGlySerGlyAspAla
CAGAGGCCTGGACAGGGCCTTGAGTGGATTGGGGTGATTAATCCTGGAAGTGGTGATGCT
       255         270         285         300

LysTyrAsnGluAsnPheLysGlyLysAlaThrLeuThrAlaAspLysSerSerSerThr
AAGTACAATGAGAACTTCAAGGGCAAGGCAACACTGACTGCAGACAAATCCTCCAGCACT
       315         330         345         360

SerTyrMETGlnLeuSerSerLeuThrSerAspAspSerAlaValTyrPheCysAlaArg
TCCTACATGCAACTCAGCAGCCTGACATCTGATGACTCTGCGGTCTATTTCTGTGCAAGA
       375         390         405         420
                                                    BstEII
                                        3'-CCTTGGAGCCAGTGGCAG
GlyHisTyrGlyGlyTyrPheValMETAspTyrTrpGlyGlnGlyThrSerValThrVal
GGGCATTACGGGGGTTACTTTGTTATGGACTACTGGGGTCAAGGAACCTCAGTCACCGTC
       435         450         465         480
AG-5'
SerAlaAlaLys
TCCGCGGCCAAA
```

FIG. 30

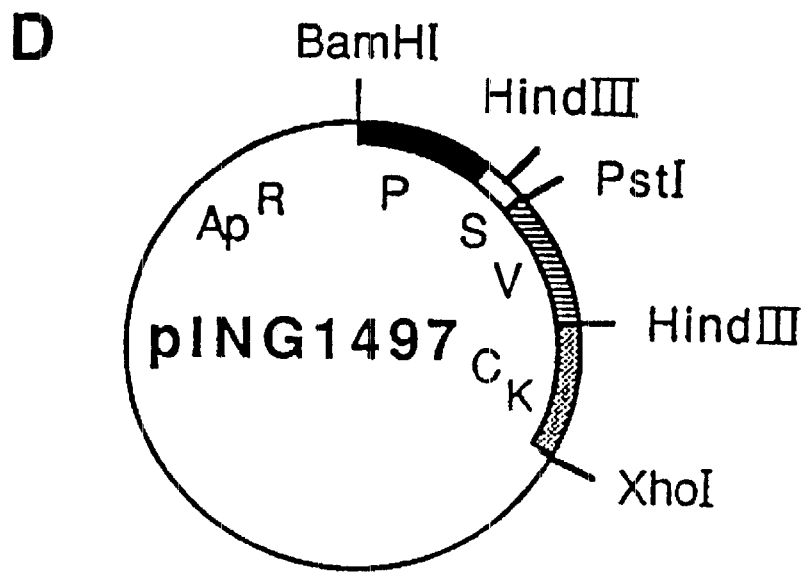
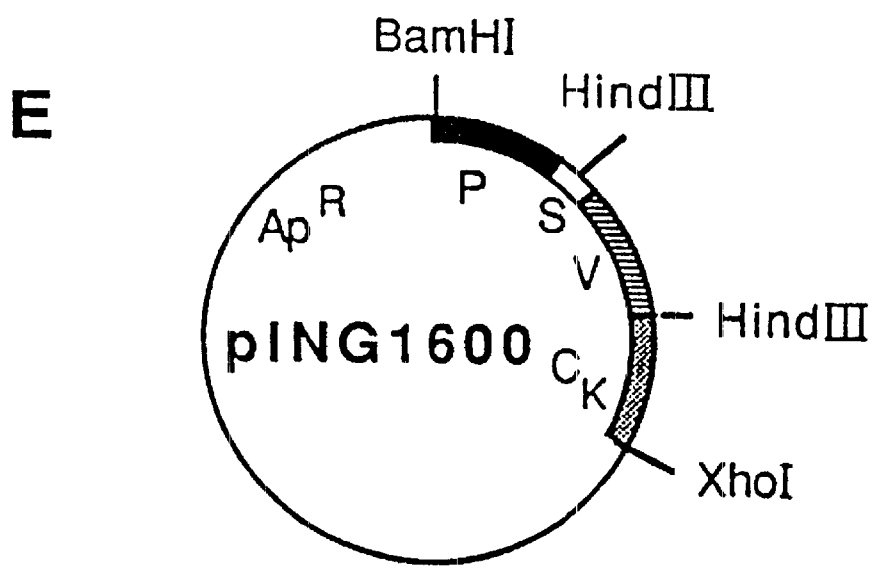
FIG. 33B

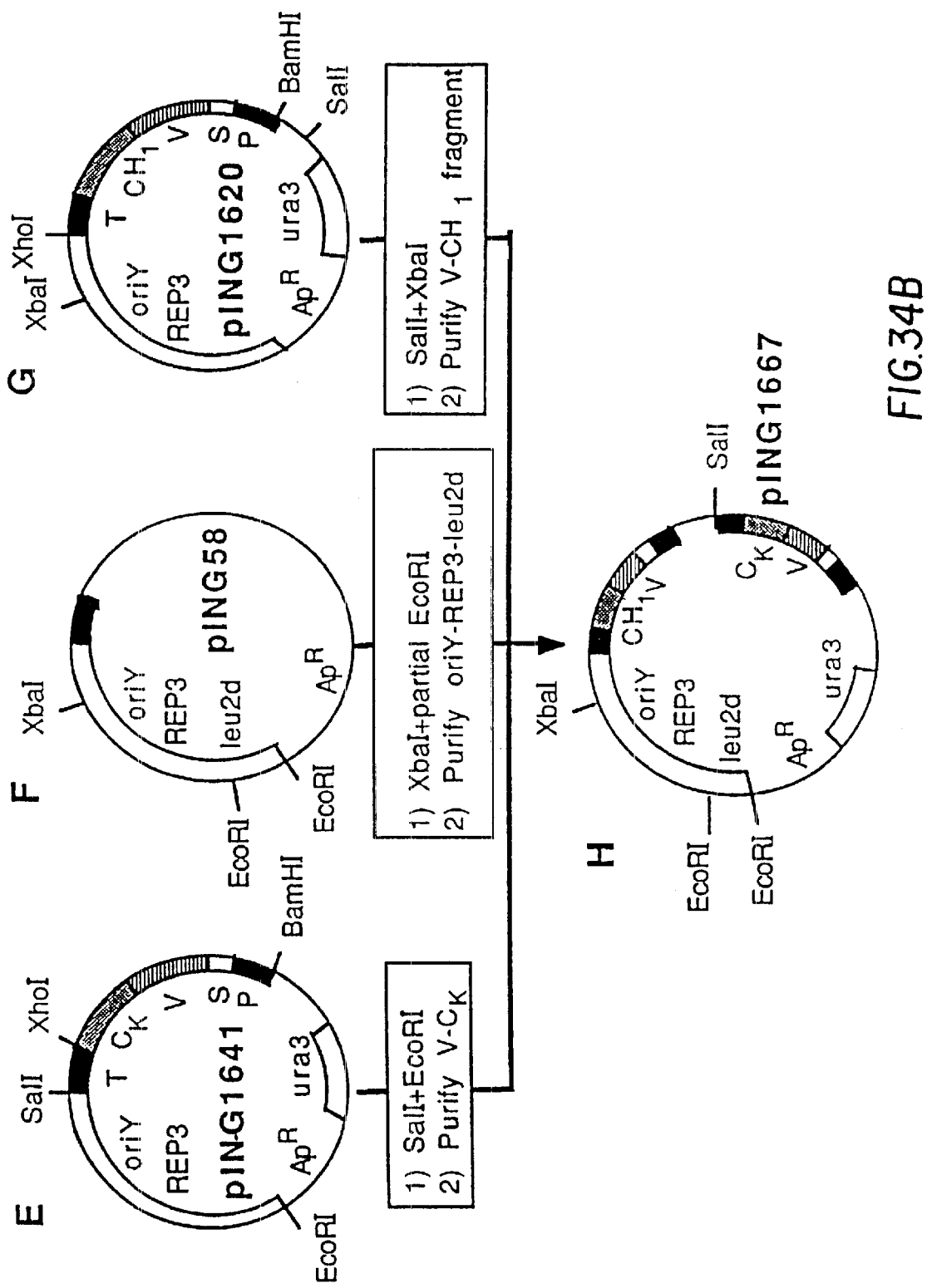

KM10 Heavy Chain DNA Sequence

```
                                                                    SalI
                                              3'-CGGGTTCCAGCAGCTG
ATACCAGCAAAGGGAGTGACCAGTTTGTCTTAAGGCACCACTGAGCCCAAGGTCTTAGAC
        15            30            45            60

TAGTACCTA-5'                                  3'-GTTTCACGGGCTCGA
  METAspTrpLeuTrpLysLeuLeuPheLeuMETAlaAlaAlaGlnSerAlaGlnAla
ATCATGGATTGGCTGTGGAAGTTGCTATTCCTGATGGCAGCTGCCCAAAGTGCCCAAGCA
        75            90           105            ↓
                                                                    SstI
GTCTAGGTCAAC-5'
GlnIleGlnLeuValGlnSerGlyProGluLeuMETLysProGlyGluThrValLysIle
CAGATCCAGTTGGTGCAGTCTGGACCTGAACTCATGAAGCCTGGAGAGACAGTCAAGATC
       135           150           165           180

SerCysLysAlaSerGlyTyrThrPheThrAsnTyrGlyMETAsnTrpValLysGlnAla
TCCTGCAAGGCTTCTGGTTATACCTTCACAAACTATGGAATGAACTGGGTGAAGCAGGCT
       195           210           225           240

ProGlyLysGlyLeuLysTrpMETGlyTrpIleAsnThrTyrThrGlyGluProThrTyr
CCAGGAAAGGGTTTAAAGTGGATGGGCTGGATAAACACCTACACTGGAGAGCCAACATAT
       255           270           285           300

AlaAspAspPheLysGlyArgPheAlaPheSerLeuGluThrSerValSerThrGlyHis
GCTGATGACTTCAAGGGACGGTTTGCCTTCTCTCTGGAGACCTCTGTCAGCACTGGCCAT
       315           330           345           360

LeuGlnIleAsnAsnLeuLysAsnGluAspThrAlaThrTyrPheCysAlaArgTrpGly
TTGCAGATCAACAACCTCAAAAATGAGGACACGGCTACATATTTCTGTGCAAGATGGGGG
       375           390           405           420
                                      BstEII
                                      3'-CCTTGGAGCCAGTGGCAGAG-5'
GlySerTyrGlyMETAspTyrTrpGlyGlnGlyThrSerValThrValSerSerAlaLys
GGTTCCTATGGTATGGACTACTGGGGTCAAGGAACCTCAGTCACCGTCTCCTCAGCCAAA
       435           450           465           480
```

FIG.36

KM10 Light Chain DNA Sequence

```
                           SalI
            3'-GTGATTAATCGGCAGCTGGTTTTAGG-5'         METAspPhe
CGGGGGATAAGACTAGCACTAATTAGCCAGAGACCAAAATCCAAATACACAATGGACTTT
            15            30            45            60

3'-CAGTGTCACAGCTTACGTCTTTAACAC
ArgValGlnIlePheSerPheLeuLeuIleSerValThrValSerArgGlyGluIleVal
CGGGTGCAGATTTTCAGCTTCCTGCTAATCAGTGTCACAGTGTCCAGAGGAGAAATTGTG
            75            90            ↓            120
                                         BsmI
GAG-5'
LeuThrGlnSerProValIleAlaAlaAlaSerLeuGlyGlnLysValThrIleThrCys
CTCACTCAGTCTCCAGTCATCGCAGCTGCATCTCTGGGGCAAAAGGTCACCATCACCTGC
            135           150           165           180

SerAlaSerSerSerValSerTyrMETTyrTrpTyrGlnGlnLysSerGlyThrSerPro
AGTGCCAGCTCAAGTGTAAGTTACATGTACTGGTACCAACAGAAGTCAGGCACCTCCCCC
            195           210           225           240

LysProTrpIleTyrGlyIleSerLysLeuAlaSerGlyValProThrArgPheSerGly
AAACCATGGATTTATGGAATATCCAAACTGGCTTCTGGAGTCCCAACTCGCTTCAGTGGC
            255           270           285           300

SerGlySerGlyThrSerTyrSerLeuThrIleSerSerValGluAlaGluAspAlaAla
AGTGGGTCTGGGACCTCTTACTCTCTCACAATCAGCAGCGTGGAGGCTGAAGATGCTGCC
            315           330           345           360
                                                      HindIII
                                            3'-CCCTGGTTCGAA
IleTyrTyrCysGlnGlnTrpAsnTyrProLeuIleThrPheGlyAlaGlyThrLysLeu
ATTTATTACTGCCAGCAGTGGAATTATCCTCTTATCACGTTCGGTGCTGGGACCAAGCTG
            375           390           405           420

CTCGAC-5'
GluLeuLys
GAGCTGAAA
            435
```

FIG. 37

PRODUCTION OF CHIMERIC ANTIBODIES WITH SPECIFICITY TO HUMAN TUMOR ANTIGENS

CROSS REFERENCE TO RELATED APPLICATIONS

This application is a continuation of U.S. application Ser. No. 08/364,001, filed Dec. 27, 1994 (now U.S. Pat. No. 5,576,184), which is a continuation of U.S. application Ser. No. 07/659,401, May 6, 1991 (abandoned) which is the U.S. National Phase of PCT/US89/03852, internationally filed on Sep. 6, 1989 (abandoned), which is a continuation-in-part of U.S. application Ser. No. 07/240,624, filed Sep. 6, 1988 (abandoned), and a continuation-in-part of U.S. application Ser. No. 07/241,744, filed Sep. 8, 1988 (abandoned), and a continuation-in-part of U.S. application Ser. No. 07/243,739, filed Sep. 13, 1988 (abandoned), and a continuation-in-part of U.S. application Ser. No. 07/367,641, filed Jun. 19, 1989 (abandoned), and a continuation-in-part of U.S. application Ser. No. 07/382,768, filed Jul. 21, 1989 (abandoned), and a continuation-in-part of U.S. application Ser. No. 07/253,002, filed Oct. 4, 1988 (abandoned).

BACKGROUND OF THE INVENTION

1. Field of the Invention

This invention relates to DNA regions and their combinations which are particularly useful for inclusion in recombinant DNA vectors for the expression of inserted genes, especially genes encoding the light (L) and heavy (H) chains of an antibody molecule.

The invention further relates to chimeric antibodies with human tumor cell specificity and their derivatives, nucleotide and protein sequences coding therefor, as well as methods of obtaining and manipulating such sequences.

2. Background

The expression of genetically engineered proteins from mammalian cells provides materials useful for the diagnosis and treatment of human and veterinary diseases and disorders. Examples of such proteins include tissue plasminogen activator, erythropoietin, hepatitis B surface antigen, and genetically engineered antibodies. Mammalian cells, such as chinese hamster ovary or hybridoma cells, provide convenient hosts for the production of many such proteins because of their ability to properly glycosylate, assemble, fold, and secrete the engineered protein. These qualities make mammalian cells particularly useful for the production of antibody molecules, which are glycosylated multimeric proteins consisting of two identical H chains combined with two identical L chains in a specific three-dimensional molecular arrangement.

Several gene expression systems for the production of genetically engineered proteins from mammalian cells have been developed. These systems include vectors designed for either the transient or permanent expression of the desired gene when introduced into the host cell. Many of these vehicles include DNA regions or elements which provide various gene expression functions, such as promotion of transcription initiation, transcription promoter enhancement, mRNA splicing, mRNA polyadenylation, and transcription termination. This invention describes specific gene expression elements and recombinant DNA expression vectors that are particularly useful for the production of genetically engineered antibodies from mammalian cells.

The majority of reported applications of genetically engineered antibodies have utilized gene expression elements which accompany the immunoglobulin coding regions upon recombinant DNA molecular cloning (reviewed by Oi, V. T., and Morrison, S. L., *Biotechniques* 4:214 (1986)). A chimeric mouse-human antibody will typically be synthe-sized from genes driven by the chromosomal gene promoters native to the mouse H and L chain variable (V) regions used in the constructs; splicing usually occurs between the splice donor site in the mouse J region and the splice acceptor site preceding the human constant (C) region and also at the splice regions that occur within the human H chain C region; polyadenylation and transcription termination occur at native chromosomal sites downstream of the human coding regions. Some of these gene expression elements, particularly the transcription promoters, are unpredictable because of their differing origins from one antibody V region gene sequence to the next. This unpredictability may be an impediment to the efficient expression of a chosen recombinant immunoglobulin gene, as noted for some chimeric L chains by Morrison, S. et al., *Proc. Natl. Acad. Sci., USA* 81:6851 (1984) (p.6854). A convenient alternative to the use of chromosomal gene fragments is the use of cDNA for the construction of chimeric immunoglobulin genes, as reported by Liu et al. (*Proc. Natl. Acad. Sci., USA* 84:3439 (1987) and *J. Immunology* 139:3521 (1987)). The use of cDNA requires that gene expression elements appropriate for the host cell be combined with the gene in order to achieve synthesis of the desired protein. This property could help overcome the unpredictability of recombinant antibody synthesis through the use of specific gene expression elements, such as viral transcriptional promoter sequences, to uniformly achieve efficient antibody synthesis. Although many gene expression elements have been tested in various systems, there are few studies on gene expression elements for recombinant immunoglobulin cDNA genes. There is therefore a substantial need for identification of improved gene expression elements and their combinations which are particularly suited for the efficient synthesis of genetically engineered antibody proteins by desired host cells. Gene expression elements that have been used for the expression of cDNA genes include:

(i) Viral transcription promoters and their enhancer elements, such as the SV40 early promoter (Okayama, H. and Berg, P., *Mol. Cell. Biol.* 3:280 (1983)), Rous sarcoma virus LTR (Gorman, C. et al., *Proc. Natl. Acad. Sci., USA* 79:6777 (1982)), and Moloney murine leukemia virus LTR (Grosschedl, R., and Baltimore, D., *Cell* 41:885 (1985))

(ii) Splice regions and polyadenylation sites such as those derived from the SV40 late region (Okayama and Berg, supra), and (iii) Polyadenylation sites such as in SV40 (Okayama and Berg, supra).

Immunoglobulin cDNA genes have been expressed as described by Liu et al., supra, and Weidle et al., *Gene* 51:21 (1987). The expression elements used for immunoglobulin cDNA gene expression were the SV40 early promoter and its enhancer, the mouse immunoglobulin H chain promoter enhancers, SV40 late region mRNA splicing, rabbit β-globin intervening sequence, immunoglobulin and rabbit β-globin polyadenylation sites, SV40 polyadenylation elements. For immunoglobulin genes comprised of part cDNA, part chromosomal gene (Whittle et al., *Protein Engineering* 1:499 (1987)), the transcriptional promoter is human cytomegalovirus, the promoter enhancers are cytomegalovirus and mouse/human immunoglobulin, and mRNA splicing and polyadenylation regions are from the native chromosomal immunoglobulin sequences. Host cells used for immunoglobulin cDNA expression include mouse hybridoma (Sp2/0), monkey COS cells, and Chinese Hamster Ovary (CHO) cells. Although immunoglobulins have been successfully synthesized using these various gene expression elements and host cells, there is substantial need for improvement in the efficiency of immunoglobulin cDNA expression.

Monoclonal antibody (mAb) technology has greatly impacted current thinking about cancer therapy and diagnosis. The elegant application of cell to cell fusion for the production of mAbs by Kohler and Milstein (*Nature* (*London*) 256:495 (1975)) spawned a revolution in biology equal in impact to that of recombinant DNA cloning. MAbs produced from hybridomas are already widely used in clinical studies and basic research, testing their efficacy in the treatment of human diseases including cancer, viral and microbial infections, and other diseases and disorders of the immune system.

Although they display exquisite specificity and can influence the progression of human disease, mouse mAbs, by their very nature, have limitations in their applicability to human medicine. Most obviously, since they are derived from mouse cells, they are recognized as foreign protein when introduced into humans and elicit immune responses. Similarly, since they are distinguished from human proteins, they are cleared rapidly from circulation.

Technology to develop mAbs that could circumvent these particular problems has met with a number of obstacles. This is especially true for mAbs directed to human tumor antigens, developed for the diagnosis and treatment of cancer. Since many tumor antigens are not recognized as foreign by the human immune system, they probably lack immunogenicity in man. In contrast, those human tumor antigens that are immunogenic in mice can be used to induce mouse mAbs which, in addition to specificity, may also have therapeutic utility in humans. In addition, most human mAbs obtained in vitro are of the IgM class or isotype. To obtain human mAbs of the IgG isotype, it has been necessary to use complex techniques (e.g. cell sorting) to first identify and isolate those few cells producing IgG antibodies. A need therefore exists for an efficient way to switch antibody classes at will for any given antibody of a predetermined or desired antigenic specificity.

Chimeric antibody technology, such as that used for the antibodies described in this invention, bridges both the hybridoma and genetic engineering technologies to provide reagents, as well as products derived therefrom, for the treatment and diagnosis of human cancer.

The chimeric antibodies of the present invention embody a combination of the advantageous characteristics of mAbs. Like mouse mAbs, they can recognize and bind to a tumor antigen present in cancer tissue; however, unlike mouse mAbs, the "human-specific" properties of the chimeric antibodies lower the likelihood of an immune response to the antibodies, and result in prolonged survival in the circulation through reduced clearance. Moreover, using the methods disclosed in the present invention, any desired antibody isotype can be combined with any particular antigen combining site.

The following mAbs were used to produce the chimeric antibody embodiments of this invention:

(a) the B38.1 mouse mAb (described in U.S. Pat. No. 4,612,282) was obtained from a mouse which had been immunized with cells from a human breast carcinoma, after which spleen cells were hybridized with NS-1 mouse myeloma cells. The antibody binds to an antigen which is expressed on the surface of cells from many human carcinomas, including lung carcinomas (adeno, squamous), breast carcinomas, colon carcinomas and ovarian carcinomas, but is not detectable in the majority of normal adult tissues tested. B38.1 is of the IgG1 isotype and does not mediate detectable antibody-dependent cellular cytotoxicity (ADCC) of antigen-positive tumor cells by human peripheral blood leukocyte effector cells.

(b) the Br-3 mouse mAb (Liao, S. K., et al., *Proc. Am. Assoc. Cancer Res.* 28:362 (1987) (where it was designated as BTMA8); *Cancer Immunol.Immunother.* 28:77–86 (1989)) was obtained from mice which had been immunized with cells from a human breast carcinoma, after which spleen cells were hybridized with NS-1 mouse myeloma cells. The antibody binds to an antigen which is expressed on the surface of cells from many human carcinomas, including lung carcinomas (adeno, squamous), breast carcinomas, colon carcinomas and ovarian carcinomas, but is not detectable in the majority of normal adult tissues tested. Br-3 is of the IgG1 isotype and mediates low level ADCC of antigen-positive tumor cells.

(c) the Co-1 mouse mAb (Oldham et al., *Mol. Biother.* 1:103–113 (1988); Avner et al., *J. Biol. Resp. Modif.* 8:25–36 (1989); Liao et al. (*Cancer Immunol. Immunother.* 28:77–86 (1989)) was obtained from a mouse which had been immunized with cells from a human colon carcinoma, after which spleen cells were hybridized with NS-1 mouse myeloma cells. The antibody binds to an antigen which is expressed on the surface of cells from many human carcinomas, including lung carcinomas (adeno, squamous), breast carcinomas, colon carcinomas and ovarian carcinomas, but is not detectable in the majority of normal adult tissues tested. Co-1 is of the IgG3 isotype and mediates ADCC of antigen-positive tumor cells.

(d) the ME4 mouse mAb (Liao, S. K., et al., *J. Natl. Cancer Inst.* 74:1047–1058 (1985)) was obtained from a mouse which had been immunized with cells from a human melanoma. The antibody binds to an antigen which is expressed at the surface of cells from many human melanomas and carcinomas (including lung carcinomas breast carcinomas, colon carcinomas, and ovarian carcinomas), but is not detectable in the majority of normal adult tissues tested. ME4 is of the IgG1 isotype and does not mediate ADCC of antigen-positive tumor cells.

(e) the KM10 mouse mAb (Japanese first patent publication No. 61-167699; Japanese Patent application No. 60-8129)) was obtained from a mouse immunized with an immunogen prepared from a human gastric adenoma-derived cell line, MKN-45, after which spleen cells were hybridized with P3U1 mouse myeloma cells. KM10 is of-the IgG1 isotype and binds to an antigen which is expressed on the surface of cells from many human carcinomas, including colon, stomach, pancreas and esophagus, but is not detectable in the majority of normal adult tissues tested. The hybridoma producing mAb KM10 was deposited at the Institute for Fermentation, Osaka (IFO) in Osaka, Japan on Mar. 24, 1989 under accession number IFO 50187.

SUMMARY OF THE INVENTION

The invention is directed to a combination of gene expression elements, and recombinant DNA vectors containing these elements, useful for the expression of immunoglobulin light chain and heavy chain cDNA genes in a desired host mammalian cell.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized.

In other embodiments, cDNA sequences encoding other proteins are combined with the above-recited expression elements to achieve expression of the proteins mammalian cells.

The invention can be used to construct recombinant DNA expression vehicles to achieve efficient synthesis of antibodies in transfected host cells. Preferably, such a vehicle is constructed by the ligation of a gene expression module, containing the elements recited above, to antibody coding cDNA sequences to form a recombinant DNA molecule. Hosts, such as Sp2/0 hybridoma or Chinese Hamster Ovary cells, are then transfected with this recombinant DNA.

The invention provides engineered chimeric antibodies of desired V region specificity and C region properties, produced after gene cloning and expression of L and H chains. The chimeric antibody and its derivatives have applicability in the treatment and diagnosis of human cancer. The cloned immunoglobulin gene products and their derivatives can be produced in mammalian or microbial cells.

The invention provides cDNA sequences coding for immunoglobulin chains comprising a human C region and a non-human, V region. The immunoglobulin chains are both H and L.

The invention provides sequences as above, present in recombinant DNA molecules in vehicles such as plasmid vectors, capable of expression in desired prokaryotic or eukaryotic hosts.

The invention provides host cells capable of producing the chimeric antibodies in culture and methods of using these host cells.

The invention also provides individual chimeric immunoglobulin chains, as well as complete assembled molecules having human C regions and mouse V regions with specificity for human tumor cell antigens, wherein both V regions have the same binding specificity.

Among other immunoglobulin chains and/or molecules provided by the invention are:

1. An antibody with monovalent specificity for a tumor cell antigen, i.e., a complete, functional immunoglobulin molecule comprising:
   (a) two different chimeric H chains, one of which comprises a V region with anti-tumor cell specificity, and
   (b) two different L chains, with the corresponding specificities as the V regions of the H chains. The resulting hetero-bifunctional antibody would exhibit monovalent binding specificity toward human tumor cells.

2. Antibody fragments such as Fab, Fab', and F(ab')$_2$.

Genetic sequences, especially cDNA sequences, coding for the 3aforementioned combinations of chimeric immunoglobulin chains are also provided herein.

The invention also provides for a genetic sequence, especially a cDNA-sequence, coding for the V region of desired specificity of an antibody molecule H and/or L chain, linked to a sequence coding for a polypeptide different than an immunoglobulin chain (e.g., an enzyme). These sequences can be assembled by the methods of the invention, and expressed to yield mixed-function molecules.

The use of cDNA sequences is particularly advantageous over genomic sequences (which contain introns), in that cDNA sequences can be expressed in bacteria or other hosts which lack appropriate RNA splicing systems.

BRIEF DESCRIPTION OF THE FIGURES

FIG. 7. Nucleotide sequence of the coding strand for the B38.1 mouse $V_\kappa$ region. Shown is the nucleotide sequence from the end of the oligo-dC tail to the $J_\kappa 1$-$C_\kappa$ junction. Also shown is the amino acid sequence deduced from the nucleotide sequence. Shown in bold are the oligonucleotides used for site-directed mutagenesis and the sites at which restriction site modifications were made.

FIG. 8. Nucleotide sequence of the coding strand for the B38.1 H chain mouse V region. Shown is the nucleotide sequence from the end of the oligo-dC tail to the $J_H 4$-$C_H 1$ junction. Also shown is the amino acid sequence deduced from the nucleotide sequence. Shown in bold are the oligonucleotides used for site-directed mutagenesis and the sites at which restriction site modifications were made.

FIG. 14. Nucleotide sequence of the coding strand for the Br-3 mouse $V_\kappa$ region. Shown is the nucleotide sequence from the end of the oligo-dC tail to the $J_\lambda$-$C_\lambda$ junction. Also shown is the amino acid sequence deduced from the nucleotide sequence. Shown in bold is the oligonucleotide used for site-directed mutagenesis to introduce an ApaI site and the position of the AvrII site at the J-$C_\lambda$ junction.

FIG. 15. Nucleotide sequence of the coding strand for the Br-3 H chain mouse V region. Shown is the nucleotide sequence from the end of the oligo-dC tail to the $J_H3$-$C_H1$ junction. Also shown is the amino acid sequence deduced from the nucleotide sequence. Shown in bold are the oligonucleotides used for site-directed mutagenesis and the sites at which restriction site modifications were made. Also shown is the position of the PstI site near the J-$C_H1$ junction.

FIG. 21. Nucleotide sequence. of the coding strand for the Co-1 κ mouse V region. Shown is the nucleotide sequence from the end of the oligo-dC tail to the $J_\kappa5$-$C_\kappa$ junction. Also shown is the amino acid sequence deduced from the nucleotide sequence. Shown in bold are the oligonucleotides used for site directed mutagenesis and the sites at which restriction site modifications were made. Also in bold is the site of the MstII site useful for introduction of a SalI restriction site.

FIG. 22. Nucleotide sequence of the coding strand for the Co-1 H chain mouse V region. Shown is the nucleotide sequence from the end of the oligo-dC tail to the $J_H^4$-$C_H1$ junction. Also shown is the amino acid sequence deduced from the nucleotide sequence. In bold are the sites of the NcoI, BstEII and PstI sites useful for gene manipulation.

FIG. 29. Nucleotide sequence of the coding strand for the ME4 mouse $V_\kappa$ region. Shown is the nucleotide sequence from the end of the oligo-dC tail to the $J_\kappa1$-$C_\kappa$ junction. Also shown is the amino acid sequence deduced from the nucleotide sequence. Shown in bold are the oligonucleotides used for site-directed mutagenesis and the sites at which restriction site modifications were made.

FIG. 30. Nucleotide sequence of the coding strand for the ME4 H chain mouse V region. Shown is the nucleotide sequence from the end of the oligo-dC tail to the $J_H^4$-$C_H1$ junction. Also shown is the amino acid sequence deduced from the nucleotide sequence. Shown in bold are the oligonucleotides used for site-directed mutagenesis and the sites at which restriction site modifications were made.

FIG. 36. Nucleotide sequence of the coding strand for the KM10 H chain mouse V region. Shown is the nucleotide sequence from the end of the oligo-dC tail to the $J_H4$-$C_H1$ junction. Also shown is the amino acid sequence deduced from the nucleotide sequence. Shown in bold are the oligonucleotides used for site directed mutagenesis and the sites at which restriction site modifications were made.

FIG. 37. Nucleotide sequence of the coding strand for the KM10 mouse $V_\kappa$ region. Shown is the nucleotide sequence from the end of the oligo-dC tail to the $J_\kappa 5$-$C_\kappa$ junction. Also shown is the amino acid sequence deduced from the nucleotide sequence. Shown in bold are the oligonucleotides used for site directed mutagenesis and the sites at which restriction site modifications were made.

DESCRIPTION OF THE PREFERRED EMBODIMENTS

Genetic Processes and Products

Figure 1:
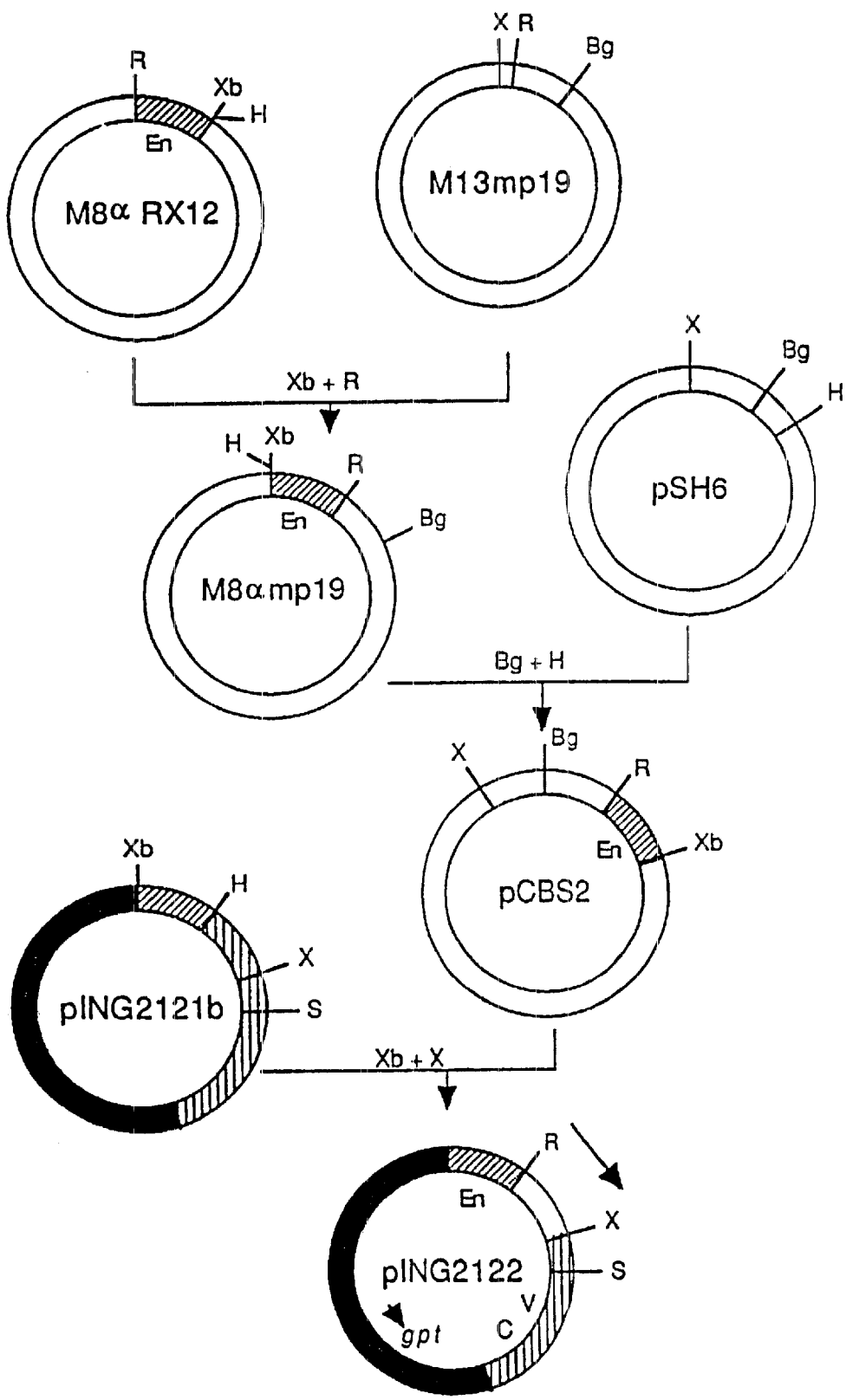
FIG. 1. Construction scheme for the promoter cassette expression vector pING2122. Promoter DNA cassettes can be placed in the region located between EcoRI and SalI sites to express chimeric L6 κ chains. Not drawn to scale. Restriction enzyme code: R, EcoRI; Xb, XbaI; Bg, BglII; H, HindIII; B, BamHI; S, SalI; X, XhoI; Ss, SStI; K, KpnI.

The invention provides antibodies that are useful for the treatment and diagnosis of human cancer, either alone or in combina- tion with other reagents. The tumor antigens to which such antibodies may be directed include those defined by the mAbs B38.1, Br-3, Co-1, ME4, and KM10.

The method of production of such antibodies combines five steps:

1. Isolation of messenger RNA (mRNA) from a rodent hybridoma cell line producing the mAb, cloning, and cDNA production therefrom;
2. Preparation of a full-length cDNA library from purified mRNA from which the appropriate V region gene segments of the L and H chain genes can be (a) identified with appropriate probes, (b) sequenced, and (c) made compatible with a C gene segment.
3. Preparation of C region gene segment modules by cDNA preparation and cloning.
4. Construction of complete H or L chain-coding sequences by linkage of the cloned specific immunoglobulin V region gene segments described in step 2 above to cloned human C region gene segment modules described in step 3.
5. Expression and production of chimeric L and H chains in selected prokaryotic and eukaryotic host cells, through production of both chains in the same cell.

One common feature of all immunoglobulin L and H chain genes and the encoded mRNAs is the so-called J region. H and L chain J regions have different, but highly homologous (>80%) sequences, among each group, especially near the C region. This homology is exploited in this invention by using consensus sequences of L and H chain J regions to design oligonucleotides for use as primers or probes for introducing useful restriction sites into the J region for subsequent linkage of V region segments to human C region segments.

C region cDNA module vectors prepared from human cells and modified by site-directed mutagenesis to place a restriction site at the analogous position in the human sequence were used. For example, the complete human $C_\lambda$ region and the complete human $C_\gamma 1$ region can be cloned. An alternative method utilizing genomic $C_H$ region clones as the source for $C_H$ region module vectors would not allow these genes to be expressed in systems such as bacteria where enzymes needed to remove intervening sequences are absent.

Cloned V region segments are excised and ligated to L or H chain C region module vectors. In addition, the human gamma$_1$ region can be modified by introducing a termination codon thereby generating a gene sequence which encodes the H chain portion of an Fab molecule.

The coding sequences with operably linked V and C regions are then transferred into appropriate expression vehicles for expression in appropriate prokaryotic or eukaryotic hosts.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Preferred among these are vehicles carrying a functionally complete human C heavy ($C_H$) or C light ($C_L$) chain sequence having appropriate restriction sites engineered so that any variable H ($V_H$) or variable L ($V_L$) chain sequence with appropriate cohesive ends can be easily inserted thereinto. Human $C_H$ or $C_L$ chain sequence-containing vehicles are thus an important embodiment of the invention. These vehicles can be used as intermediates for the expression of any desired complete H or L chain in any appropriate host.

One preferred host is yeast. Yeast provides substantial advantages for the production of immunoglobulin L and H chains. Yeast cells carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., prepeptides) (Hitzman et al., 11th International Conference on Yeast, Genetics and Molecular Biology, Montpellier, France, Sep. 13–17, 1982).

Yeast gene expression systems can be routinely evaluated for the levels of production, secretion, and the stability of chimeric H and L chain proteins and assembled chimeric antibodies. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the iso-1-cytochrome C (CYC-1) gene can be utilized. A number of approaches may be taken for evaluating optimal expression plasmids for the expression of cloned immunoglobulin cDNAs in yeast.

Bacterial strains may also be utilized as transformation hosts for the production of antibody molecules or antibody fragments described by this invention. *E. coli* K12 strains such as *E. coli* W3110 (ATCC 27325) and other enterobacteria such as *Salmonella typhimurium* or *Serratia marcescens,* and various Pseudomonas species may be used.

Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches may be taken for evaluating the expression plasmids for the production of chimeric antibodies or antibody chains encoded by the cloned immunoglobulin cDNAs in bacteria.

Other preferred hosts are mammalian cells, grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which may be useful as hosts for the production of antibody proteins include cells of lymphoid origin, such as the hybridoma Sp2/0-Ag14 (ATCC CRL 1581) or the myeloma P3C63Ag8 (ATCC TIB 9), and its derivatives. Others include cells of fibroblast origin, such as Vero (ATCC CRL 81) or CH0-K1 (ATCC CRL 61).

Many vector systems are available for the expression of cloned H and L chain genes in mammalian cells. Different approaches can be followed to obtain complete $H_2L_2$ antibodies. It is possible to co-express L and H chains in the same cells to achieve intracellular association and linkage of H and L chains into complete tetrameric $H_2L_2$ antibodies. The co-expression can occur by using either the same or different plasmids in the same host. Genes for both H and L chains can be placed into the same plasmid, which is then transfected into cells, thereby selecting directly for cells that express both chains. Alternatively, cells may be transfected first with a plasmid encoding one chain, for example L chain, followed by transfection of the resulting cell line with a H chain plasmid containing a second selectable marker. Cell lines producing $H_2L_2$ molecules via either route could be transfected with plasmids encoding additional copies of L, H, or L plus H chains in conjunction with additional selectable markers to generate cell lines with enhanced properties, such as higher production of assembled ($H_2L_2$) antibody molecules or enhanced stability of the transfected cell lines.

The invention is also directed to combinations of gene expression elements, and recombinant DNA vectors containing these elements, useful for the expression of immunoglobulin L chain and H chain cDNA genes in a desired host mammalian cell. For the expression of cDNA genes in rodent cells, the transcriptional promoter is a viral LTR sequence, the transcriptional promoter enhancer(s) are either or both the mouse immunoglobulin H chain enhancer and the viral LTR enhancer, the splice region contains an intron of greater than 31 bp, and the polyadenylation and transcription termination regions are derived from a native chromosomal sequence corresponding to the immunoglobulin chain being synthesized. The invention can be used to construct recombinant DNA expression vehicles to achieve efficient synthesis of antibodies from transfected host cells. Preferably, such a vehicle would be constructed by the ligation of gene expression modules to antibody coding sequences to form a recombinant DNA molecule. This recombinant DNA can then be used to transfect mammalian hosts such as Sp2/0 hybridoma or chinese hamster ovary cells.

For example, a recombinant DNA gene expression unit for L chain synthesis can be constructed by the ligation of the following gene expression elements:

(i) A H chain immunoglobulin transcription enhancer sequence such as the 0.7-kb XbaI to EcoRI DNA fragment from the mouse genomic H chain immunoglobulin DNA sequence;

(ii) A retroviral LTR transcription promoter sequence such as Abelson murine leukemia virus LTR;

(iii) A DNA sequence containing splice donor and splice acceptor sites such as SV40 19S/16S splice donor and the 16S splice acceptor sites, separated by greater than 31 bp of intervening sequence;

(iv) An immunoglobulin L chain cDNA or genomic DNA coding sequence;

(v) A 3' untranslated sequence, including a polyadenylation signal sequence (AATAAA), such as that from human immunoglobulin κ cDNA, and (vi) A DNA sequence derived from the polyadenylation and transcription termination region of a non-viral DNA such as the 1.1-kb BglII to BamHI DNA sequence from mouse κ genomic DNA distal to the polyadenylation site.

There are certain restrictions on the order of these gene expression elements: the order of the promoter (ii), coding sequence (iv), polyadenylation signal sequence (v), and polyadenylation and transcription termination (vi) elements is fixed. The splice region (iii) may be located at any position after the promoter (ii), but before the polyadenylation signal sequence (v). The splice region may be located within other elements such as the cDNA coding sequence. The enhancer (i) may be located anywhere in or near the unit, and may be located within some elements, such as the intervening sequence between splice donor and splice acceptor. The L chain gene expression unit can be ligated to other useful DNA sequences, such as selectable marker genes from pSV-2neo or pSV-2gpt, prior to transfection of host cells.

A recombinant DNA gene expression unit for H chain synthesis can be constructed by the ligation of the following gene expression elements:

(i) An H chain immunoglobulin transcription enhancer sequence such as the 0.7-kb XbaI to EcoRI DNA fragment from mouse genomic DNA sequences;

(ii) A retroviral LTR transcription promoter sequence such as Abelson murine leukemia virus LTR;

(iii) A DNA sequence containing splice donor and splice acceptor sites, such as the SV40 19S/16S splice donor and the 16S splice acceptor, separated by greater than 31 bp of intervening sequence;

(iv) An immunoglobulin H chain cDNA or genomic DNA coding sequence;

(v) A 3' untranslated sequence including a polyadenylation signal sequence (AATAAA), such as that from a human IgG1 genomic DNA sequence; and (vi) A DNA sequence derived from the polyadenylation and transcription termination region of a non-viral DNA, such as that from a human IgG1 genomic DNA sequence.

The order of the H chain gene expression elements has the same limitations as the L chain gene expression modules. The assembled H chain gene expression unit can be ligated to other useful DNA sequences, such as selectable marker genes, prior to the transfection of host cells. The assembled H chain expression vehicle may contain a different selectable marker than that chosen for the L chain gene expression vehicle. H and L chain gene expression vehicles can be transfected together (co-transfection) or in separate steps (sequential transfection). Both L and H chain gene expression units may be assembled in the same expression vehicle, in which only a single selectable marker may be used.

Polypeptide Products

The invention provides "chimeric" immunoglobulin chains, either H or L with specificity to human tumor antigens. A chimeric chain contains a C region substantially similar to that present in a natural human immunoglobulin, and a V region having the desired anti-tumor specificity of the invention.

The invention also provides immunoglobulin molecules having H and L chains associated so that the overall molecule exhibits the desired binding and recognition properties. Various types of immunoglobulin molecules are provided: monovalent, divalent, or molecules with the specificity-determining V binding domains attached to moieties carrying desired functions. This invention also provides for fragments of chimeric immunoglobulin molecules such as Fab, Fab', or F(ab')$_2$ molecules or those proteins coded by truncated genes to yield molecular species functionally resembling these fragments.

Antibodies having chimeric H chains and L chains of the same or different V region binding specificity can be prepared by appropriate association of the desired polypeptide chains. These chains are individually prepared by the modular assembly methods of the invention.

Uses

The antibodies of this invention can be used for therapeutic purposes by themselves, for example, acting via complement-mediated lysis and antibody-dependent cellular cytotoxicity, or coupled to toxins or therapeutic moieties, such as ricin, radionuclides, drugs, etc., in the treatment of human cancer. The antibodies may be advantageously utilized in combination with factors, such as lymphokines, colony-stimulating factors, and the like, which increase the number or activity of antibody-dependent effector cells.

Thus, the invention is also directed to a method of killing cells carrying an antigen thereon, such method comprising contacting the cells with a chimeric antibody molecule that contains two light chains and two heavy chains, each of said chains containing a constant human region and a variable region having specificity to an antigen bound by a murine monoclonal antibody selected from the group consisting of B38.1, Br-3, Co-1, ME4 and KM10. The antibody may be in detectably labeled form.

The antibodies of the invention having human C region can be utilized for passive immunization, especially in humans, with reduced negative immune reactions such as serum sickness or anaphylactic shock, as compared to whole mouse antibodies. The antibodies can also be utilized in prior art immunodiagnostic assays and kits in detectably labeled form (e.g., enzymes, $^{125}$I, $^{14}$C, fluorescent labels, etc.), or in immobilized form (on polymeric tubes, beads, etc.). They may also be utilized in labeled form for in vivo imaging, wherein the label can be a radioactive emitter, or a nuclear magnetic resonance contrasting agent such as a heavy metal nucleus, or an X-ray contrasting agent, such as a heavy metal. The antibodies can also be used for in vitro localization of the recognized tumor cell antigen by appropriate labeling.

Mixed antibody-enzyme molecules can be used for immunodiagnostic methods, such as ELISA. Mixed antibody-peptide effector conjugates can be used for targeted delivery of the effector moiety with a high degree of efficacy and specificity.

Specifically, the chimeric antibodies of this invention can be used for any and all uses in which the original murine mAbs can be used, with the obvious advantage that the chimeric ones are more compatible with the human body.

Having now generally described the invention, the same will be further understood by reference to certain specific examples which are included herein for purposes of illustration only and are not intended to be limiting unless otherwise specified.

EXAMPLE 1

Optimization of Gene Expression Elements for Chimeric Light Chain Synthesis

A series of recombinant DNA vectors were constructed to test different gene expression elements in order to optimize the expression of chimeric mouse-human immunoglobulin L chain. A vector to test different promoters and splice regions was first made (pING2122, FIG. 1). This vector is derived from a chimeric L chain cDNA expression plasmid, pING2121b. First, the mouse immunoglobulin H chain enhancer 0.7-kb XbaI to EcoRI fragment from M13 M8αRX12 (Robinson, R. R. et al., PCT US86/02269) was inserted into XbaI plus EcoRI cut M13mp19. The enhancer-containing HindIII to BglII fragment was inserted into the BglII to HindIII region of pSH6, an *E. coli* recombinant plasmid DNA that contains unique XhoI, BglII, and HindIII sites, with the BglII between the XhoI and HindIII sites. The enhancer-containing XbaI to XhoI fragment was then inserted into the enhancer XbaI to XhoI region of pING2121b, an expression plasmid identical to pING2108b (Liu, A. Y. et al., *J. Immunology* 139:3521 (1987)) except that the L6 $V_L$ region (Liu, A. Y. et al., *Proc. Natl. Acad. Sci., USA* 84:3439 (1987)) was used in its construction instead of the 2H7 $V_L$ region. The resulting plasmid was pING2122 (FIG. 1) and contained a region of DNA between unique EcoRI and XhoI sites for the insertion of various promoters to be tested. pING2122 has an SV40 19S splice region between the XhoI and unique SalI sites, allowing the insertion (or deletion) of alternate splice regions. Several promoters were obtained and introduced as EcoRI to SalI regions into the pING2122 vector to compare their transcriptional strength to the SV40 viral promoter in the reference expression plasmid pING2121b. The promoters chosen were the H chain immunoglobulin V1 (V1(Igh)), mouse metallothionein (MMT), Abelson virus LTR (Abl), and Rous sarcoma virus LTR (RSV) promoters. The mouse H chain V1(Igh) promoter was obtained as a 600-bp BamHI DNA fragment derived from the V1 gene promoter (Clarke, C. et al., *Nucleic Acids Research* 10:7731–7749 (1982)). The DNA fragment was inserted into the BamHI site of pUC19. The V1 promoter was excised as an EcoRI to SalI fragment and first ligated to the large fragment of pING2122 cut with EcoRI and XhoI to form pING2123 (V1 promoter plus SV40 19S splice). The V1 promoter DNA fragment was next ligated to pING2122 cut with EcoRI and SalI to form pING2124 (V1 promoter with no splice).

The Abelson LTR promoter was obtained from pelin2 (provided by Dr. Owen Witte, UCLA); pelin2 contains the p120 viral 3' LTR (Reddy, E. P. et al., *Proc. Natl. Acad. Sci., USA* 80:3623 (1983)), except that the BglII site at viral position 4623 has been modified by insertion of the EcoRI oligonucleotide linker GGAATTCC. The 0.8-kb EcoRI to KpnI fragment of pelin2 containing the p120 3' LTR promoter was inserted into KpnI plus EcoRI cut pUC18. The LTR was excised as an EcoRI to SalI fragment and ligated to EcoRI plus XhoI cut pING2122, placing the LTR promoter adjacent to the L6 L chain gene to form pING2125 (Abl promoter with SV40 19S splice). The Abl LTR fragment was similarly ligated to EcoRI plus SalI cut pING2122 to form plasmid pING2126 (Abl promoter with no splice). An XhoI to SalI fragment containing the SV40 19S/16S splice donor and 16S acceptor sites was excised from plasmid pUC12/pL1 (Robinson et al., PCT US86/02269) and inserted into the SalI site of pING2126, screening for the correct orientation of the splice region to form pING2133 (Abl promoter plus SV40 19S/16S splice).

The metallothionein MMT promoter was obtained from the plasmid pBPV-MMT neo (American Type Culture Collection #37224) and was excised as an EcoRI to BglII fragment and ligated to EcoRI plus BamHI cut pUC19. The EcoRI to SalI DNA fragment of the resulting plasmid was excised and ligated to EcoRI plus XhoI cut pING2122 to form pING2131 (MMT promoter plus SV40 19S splice).

The RSV promoter was obtained from pRSVcat (American Type Culture Collection #37152) and was excised as a 560-bp HindIII to SfaNI DNA fragment. After T4 DNA ploymerase treatment, the fragment was ligated to SmaI cut M13mp19 and the resultant recombinant phage were selected for the orientation where the insert EcoRI site was closest to the vector SalI site. The RSV promoter DNA was then excised by partial digestion with EcoRI followed by complete SalI digestion and ligated to the large DNA fragment from EcoRI plus XhoI cut pING2122 to form pING2132 (RSV promoter plus SV40 19S splice).

The reference expression plasmid pING2121b (SV40 promoter plus SV40 19S splice) was modified to incorporate different splice regions. First, pING2121b was digested with XhoI and SalI and self-ligated to delete the splice region, forming pING2128 (SV40 promoter, no splice). Second, the SV40 19S/16S splice region (SV40 19S/16S splice donor and splice acceptor) was excised as a 174 bp XhoI to SalI DNA fragment from pUC12/pL1 (Robinson, R. R. et al., supra), and ligated to XhoI plus SalI cut pING2121b. The resultant plasmid DNAs were screened for the proper orientation of the inserted splice region, forming pING2127 (SV40 promoter 19S/16S splice region).

Figure 2A:
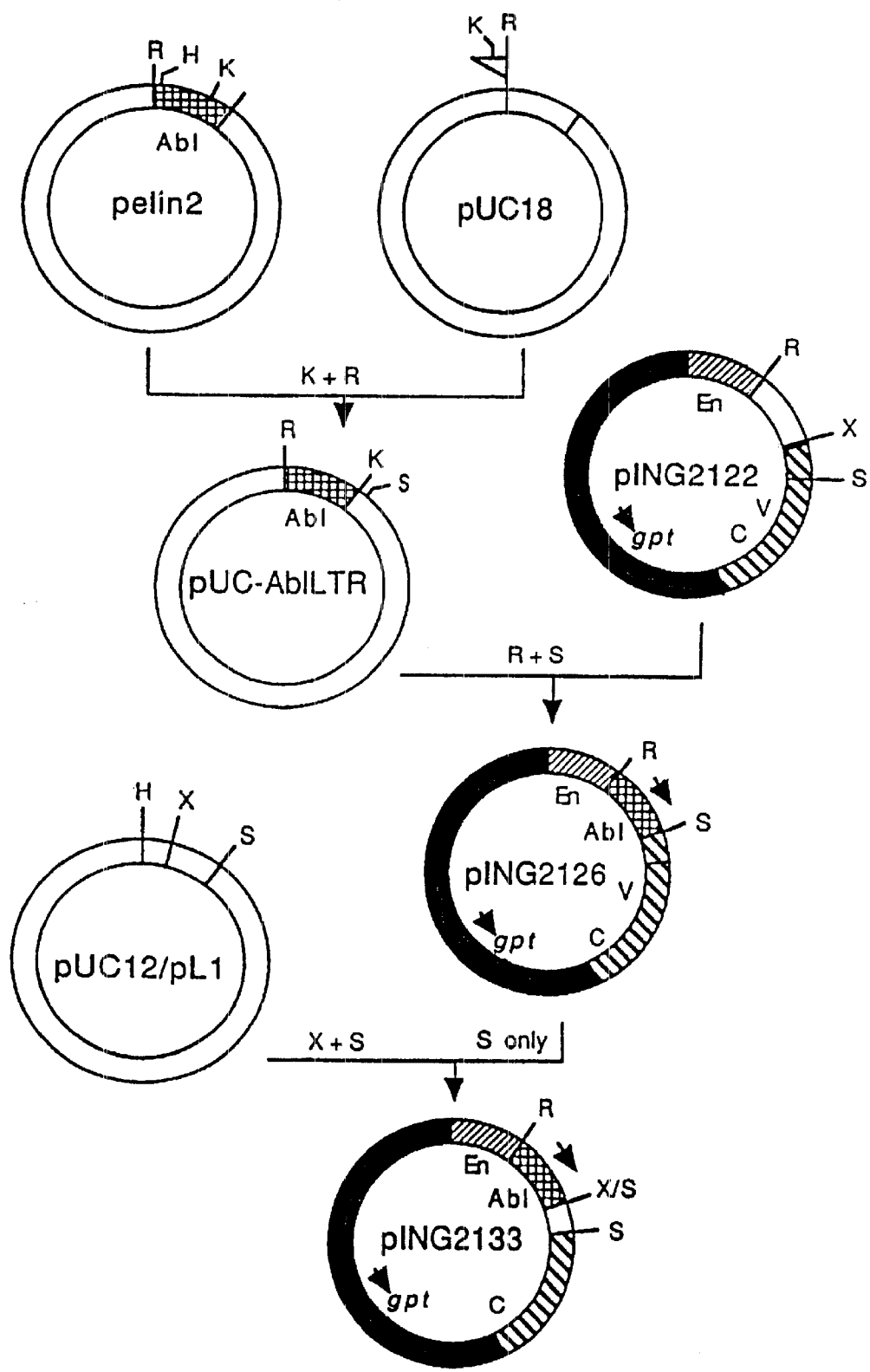
FIGS. 2(A and B). Construction scheme for κ expression vectors pING2126 (FIG. 2A), pING2133 (FIG. 2A), and pING1712 (FIG. 2B). Not drawn to scale. Restriction enzyme code is the same as for FIG. 1.
Figure 2B:
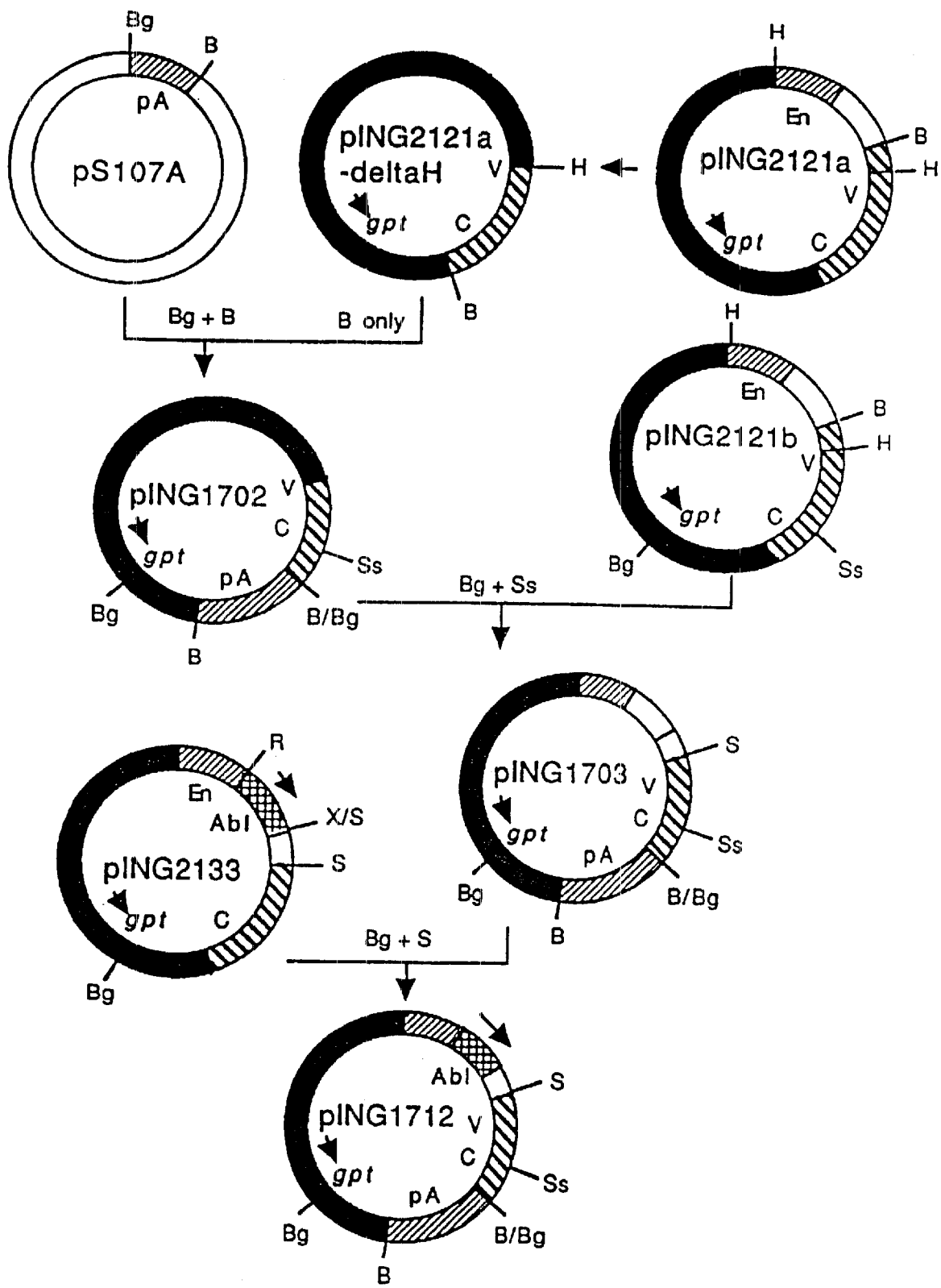

The expression vectors were modified to include L chain genomic polyadenylation and transcription termination regions. The first step was the HindIII digestion and religation of plasmid pING2121a, which is identical to pING2108a described by Liu, A. Y. et al., *J. Immunology* 139:3521 (1987), with one exception. It differed in that the $V_L$ region used in its construction was from the L6 mAb (Liu, A. Y. et al., *Proc. Natl. Acad. Sci., USA* 84:3439 (1987)) rather than the 2H7 mAb. This modified pING2121a was termed pING2121a-deltaH. The 1.1-kb BglII to BamHI fragment of mouse genomic DNA distal to the polyadenylation site (Xu, M. et al., *J. Biol. Chem.* 261:3838 (1986)) was isolated from pS107A (provided by Dr. Randolph Wall, UCLA) and inserted into the BamHI site of pING2121a-deltaH, screening for the orientation homologous to the native gene. The 3.3 kb BglII to SstI fragment containing this modified 3' region was ligated to the 5.2 kb BglII to SstI fragment of pING2121b to form pING1703 (SV40 promoter, mouse & genomic 3' region). Similarly, a 3 kb SstI to BamHI DNA fragment from the human genomic κ 3' region (Hieter et al., *Cell* 22:197 (1980) was ligated to the 5.2-kb BglII to SatI fragment of pING2121b to form pING1704 (SV40 promoter, human κ 3' genomic region). The BglII to SalI fragment of pING1703 containing the modified 3' region and chimeric κ coding sequence was ligated to the large BglII to SalI fragment of pING2133, resulting in the 9.1-kb κ expression vector pING1712 (Abl promoter, 16S/19S splice, mouse 3' region). FIG. 2 shows the construction of pING1712.

The various vectors containing different promoters, splice regions, and 3' regions described above are summarized in Table 1.

The plasmid expression vector DNAs described above were used to transfect mouse hybridoma Sp2/0 cells to test the efficacy of the various promoters and splice regions. Each plasmid DNA was linearized by PvuI digestion and transfected into Sp2/0 cells by electroporation (Potter, H. et al., *Proc. Natl. Acad. Sci., USA* 81:7161 (1984)). The electroporation conditions were: 10 to 20 µg of linearized DNA mixed with 10×10$^6$ Sp2/0 cells in 0.5 ml of phosphate buffered saline (IRVINE Scientific #9236), using a 5-msec pulse of 300V from a BTX-T100 transfector and 471 cuvette electrode (Biotechnologies and Experimental Research, San Diego, Calif.). After transfection, cells were allowed to recover in DMEM growth medium (Dulbecco's modified Eagle medium plus 10% fetal bovine serum, GIBCO) for 24 hours, and then transferred to 96-well culture plates in mycophenolic acid growth medium (DMEM growth medium supplemented with 0.006 mg/ml mycophenolic acid (Calbiochem) and 0.25 mg/ml xanthine (SIGMA)). Individual wells positive for cell growth were expanded in mycophenolic acid growth medium prior to assay of secreted or intracellular L chain by enzyme-linked immunosorbent assay (ELISA).

The results of several transfection experiments are summarized in Table 1. Experiments 1, 2, 4, and 5 show initial comparisons of the various promoters tested. The strongest promoters in this assay were the Abl and RSV LTR promoters, and the ranking from strongest to weakest is: Abl, RSV >SV40 >MMT, V1. This indicates that the use of viral LTR promoters such as Abl and RSV for the expression of immunoglobulin cDNA genes is advantageous over genomic promoters such as MMT and V1. These results are surprising because mouse H chain immunoglobulin promoters such as V1 are known to be strong promoters in the presence of the H chain immunoglobulin enhancer, which is present in all of the above vectors.

Experiments 3 and 6 in Table 1 compare the use of different splice regions in the expression of L chains. The results demonstrate that the presence of the 16S/19S splice is more efficient than either the 19S splice or no splice. Since the 19S splice is has a relatiavely small intervening sequence (31 nucleotides), the presence of an intervening sequence larger than 31 nucleotides is advantageous.

Experiment 7 compares the different polyadenylation and transcription termination regions. The use of either mouse or human genomic polyadenylation and transcription termination regions appears to result in more efficient κ synthesis than does the use of the SV40 viral polyadenylation region. The combination of the most efficient promoter, splice region, and polyadenylation and transcription termination region (pING1712) is tested in experiments.8 and 9. These experiments show that the combination of gene expression elements in pING1712 are far more efficient than the starting plasmid pING2121b, giving a 6 to 17-fold increase in κ expression level.

TABLE 1

Chimeric Light Chain Plasmid Transfection Results

| Experiment | pING# | Gene Expression Elements:[a] Promoter/Splice/3' | No. of Wells Tested | Intracellular Kappa[b] (ng/105 cells) | Secreted Kappa[c] (ng/ml) | Relative Kappa Expression[d] |
|---|---|---|---|---|---|---|
| 1 | 2121b | SV/19S/SV | 24 | .18 ± .10 | ND[e] | 1.0 |
|   | 2123 | V1/19S/SV | 24 | .12 ± .08 | ND | 0.7 |
|   | 2124 | V1/∅/SV | 24 | .09 ± .11 | ND | 0.5 |
|   | 2126 | Ab1/∅/SV | 24 | .44 ± .21 | ND | 2.4 |
| 2 | 2121b | SV/19S/SV | 7 | .22 ± .11 | ND | 1.0 |
|   | 2126 | Ab1/∅/SV | 9 | .76 ± .75 | ND | 3.5 |
|   | 2125 | Ab1/19S/SV | 12 | .28 ± .41 | ND | 1.3 |
|   | 2123 | V1/19S/SV | 24 | .10 ± .07 | ND | 0.5 |
| 3 | 2121b | SV/19S/SV | 24 | .22 ± .14 | ND | 1.0 |
|   | 2127 | SV/16S/SV | 24 | .37 ± .41 | ND | 1.7 |
|   | 2128 | SV/∅/SV | 24 | .16 ± .07 | ND | 0.7 |
| 4 | 2121b | SV/19S/SV | 24 | .49 ± .32 | ND | 1.0 |
|   | 2126 | Ab1/∅/SV | 21 | .41 ± .20 | ND | 0.8 |
|   | 2125 | Ab1/19S/SV | 13 | .64 ± .40 | ND | 1.3 |
|   | 2131 + Cd[f] | MMT/19S/SV | 18 | .48 ± .18 | ND | 1.0 |
|   | 2131 − Cd | MMT/19S/SV | 22 | .32 ± .15 | ND | 0.7 |
| 5 | 2121b | SV/19S/SV | 20 | .34 ± .11 | ND | 1.0 |
|   | 2132 | RSV/19S/SV | 8 | .50 ± .53 | ND | 1.5 |
| 6 | 2121b | SV/19S/SV | 22 | ND | 48 ± 30 | 1.0 |
|   | 2125 | Ab1/19S/SV | 14 | ND | 51 ± 30 | 1.1 |
|   | 2126 | Ab1/∅/SV | 23 | ND | 79 ± 50 | 1.6 |
|   | 2133 | Ab1/16S/SV | 22 | ND | 110 ± 80 | 2.3 |
| 7 | 2121b | SV/19S/SV | 22 | ND | 58 ± 40 | 1.0 |
|   | 1703 | SV/19S/mok | 24 | ND | 107 ± 130 | 1.8 |
|   | 1704 | SV/19S/huk | 19 | ND | 112 ± 170 | 1.9 |
| 8 | 2121b | SV/19S/SV | 23 | ND | 21 ± 14 | 1.0 |
|   | 1712 | Ab1/16S/mok | 6 | ND | 360 ± 210 | 17.2 |
| 9 | 2121b | SV/19S/SV | 24 | ND | 25 ± 21 | 1.0 |
|   | 1712 | Ab1/16S/mok | 48 | ND | 153 ± 125 | 6.1 |

LEGEND TO TABLE 1

[a] Promoter abbreviations:
SV          SV40 early promoter
V1          immunoglobulin heavy chain V1 promoter
Ab1         Abelson virus LTR promoter
MMT         mouse metallothionein promoter
RSV         Rous sarcoma virus LTR promoter
Splice region abbreviations:
∅           no splice region TABLE 1-continued

|   |   |   |
|---|---|---|
| | 16S | 19S/16S splice region |
| | 3' (polyadenylation and transcription termination) | |
| | abbreviations: | |
| | SV40 | SV40 late region |
| | mok | mouse kappa genomic region |
| | huk | human kappa genomic region |
| (b) | Intracellular kappa chain was measured by ELISA solubilized protein from healthy cells. Results are as mean (±SD) kappa chain level. | |
| (c) | Secreted kappa chain was measured by ELISA of a culture supernatant. Results are reported as mea kappa chain level. | |
| (d) | "Relative Kappa Expression" was determined by div mean expression by the mean expression of pING2121b. | |
| (e) | ND: | no data |
| (f) | +Cd: | cadmium sulfate added to culture |
| | −Cd: | no cadmium sulfate added to culture |

EXAMPLE 2

Improved Gene Expression Elements for Chimeric Heavy Chain Immunoglobulin Synthesis An approach to improve immunoglobulin H chain synthesis involves creating an L chain producing cell line; and then transfecting that cell line with H chain expression plasmids containing various gene expression elements. As an. example of this approach to make L chain producing cells, a chimeric mouse-human λ plasmid expression vector, pING2203, was constructed and then used to transfect murine Sp2/0 cells. The construction required the combination of a human $C_\lambda$ region gene module with a mouse $V_\lambda$ region.

A. Construction of a Human Lambda Constant Region Gene Module

Figure 3:
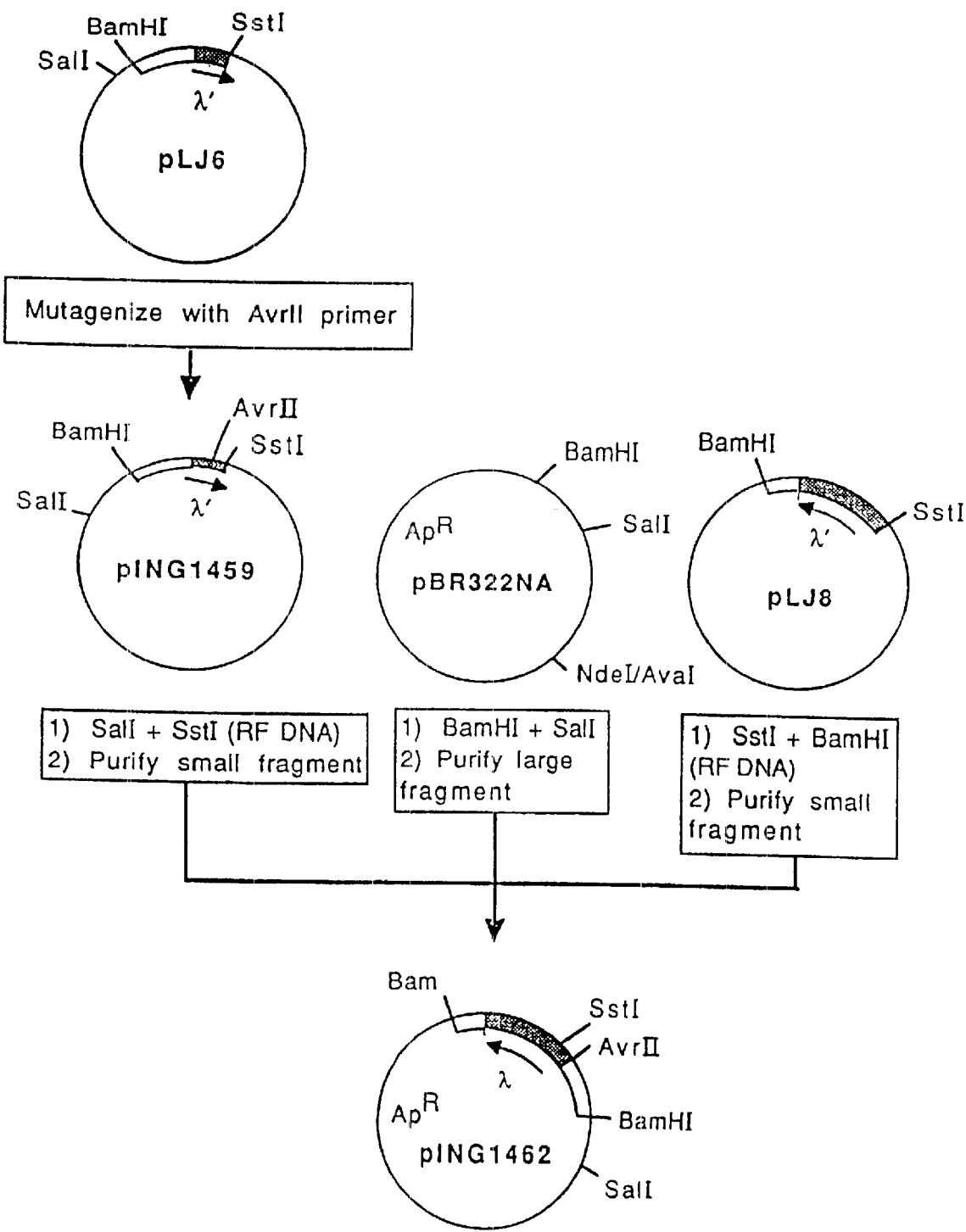
FIG. 3. Construction scheme for the λ chain C-region cassette. Plasmid pING1462 contains the entire $C_\lambda$ domain and contains an AvrII restriction site at the J-$C_\lambda$ junction. Not drawn to scale.

A human $C_\lambda$ gene cassette was constructed from the genomic human $C_\lambda$ region of plasmid pHuλI (Hieter, P. et al., Nature 294:536–540 (1981)). Initially, two BamHI to SstI fragments were subcloned into M13mp19 to generate pLJ6 and pLJ8. Plasmid pLJ6 contains the DNA sequence coding the 3' end of the human Jλ-Cλintron and the 5' end of the human $C_\lambda$ exon. The nucleotide sequence of this region was determined, and site-directed mutagenesis was used to insert an AvrII site at the intron/exon junction. The location of this restriction site was chosen so that an in-frame fusion could be made between the conserved AvrII site at the mouse J-C junction from any mouse $V_\lambda$ cDNA clone and the human $C_\lambda$ module. The oligonucleotide used for introduction of an AvrII site was: 5'-CCTTGGGCTGACCTAGGTGGA-3'. The derivative of pLJ6 containing an AvrII site was called pING1459. The entire human $C_\lambda$ region was then reconstructed by ligating DNA fragments from pING1459 and pLJ8 into pBR322NA (pBR322NA is pBR322 containing a deletion between NdeI and AvaI) to generate pING1462. This construction scheme is outlined in FIG. 3.

pING1462 was further modified to include the human λ polyadenylation region by ligation of the Cλ gene module to the contiguous 3' region (FIG. 4) of genomic DNA from pHuλ1, forming the human $C_\lambda$ region vector pING2201.

B. Construction of the Light Chain Expression Vector pING2203

RNA isolated from a hybridoma cell line secreting the Br-3 mouse mAb (IgG1, λ) (see Background) was used to generate a plasmid cDNA library by the method of Gubler and Hoffman (Gene 25:263 (1983)). From this library, a cDNA clone encoding the entire Br-3 λ chain was isolated.

This cDNA clone, pR3L-11, was modified for expression in mammalian cells as follows. The oligo-dC sequence 5' to the VA module in pR3L-11 was removed in a number of steps that resulted in the positioning of a SalI restriction site upstream of the coding sequence for Br-3 λ. First, a PstI to SstI subclone of pR3L-11 was made in M13mp19 to generate pL5. This plasmid was cut with HindIII and treated with Bal31 nuclease to remove the oligo-dC tail, followed by T4-polymerase treatment, EcoRI digestion and subcloning into SmaI and EcoRI digested pUC18. This located a SalI site upstream of the Vλ region (plasmid pWW9). A BamHI site was deleted between the SalI site and the lambda initiation codon by digestion with BamHI followed by mung bean nuclease digestion and religation to generate pWW9-2. The nucleotide sequence around the SalI site was determined to be GTCGACTCCCCGAAAAGAATAGACCTGGTMTGT GAATT<u>ATG</u>, where the SalI site and initiation codon ATG are underlined.

Figure 4A:
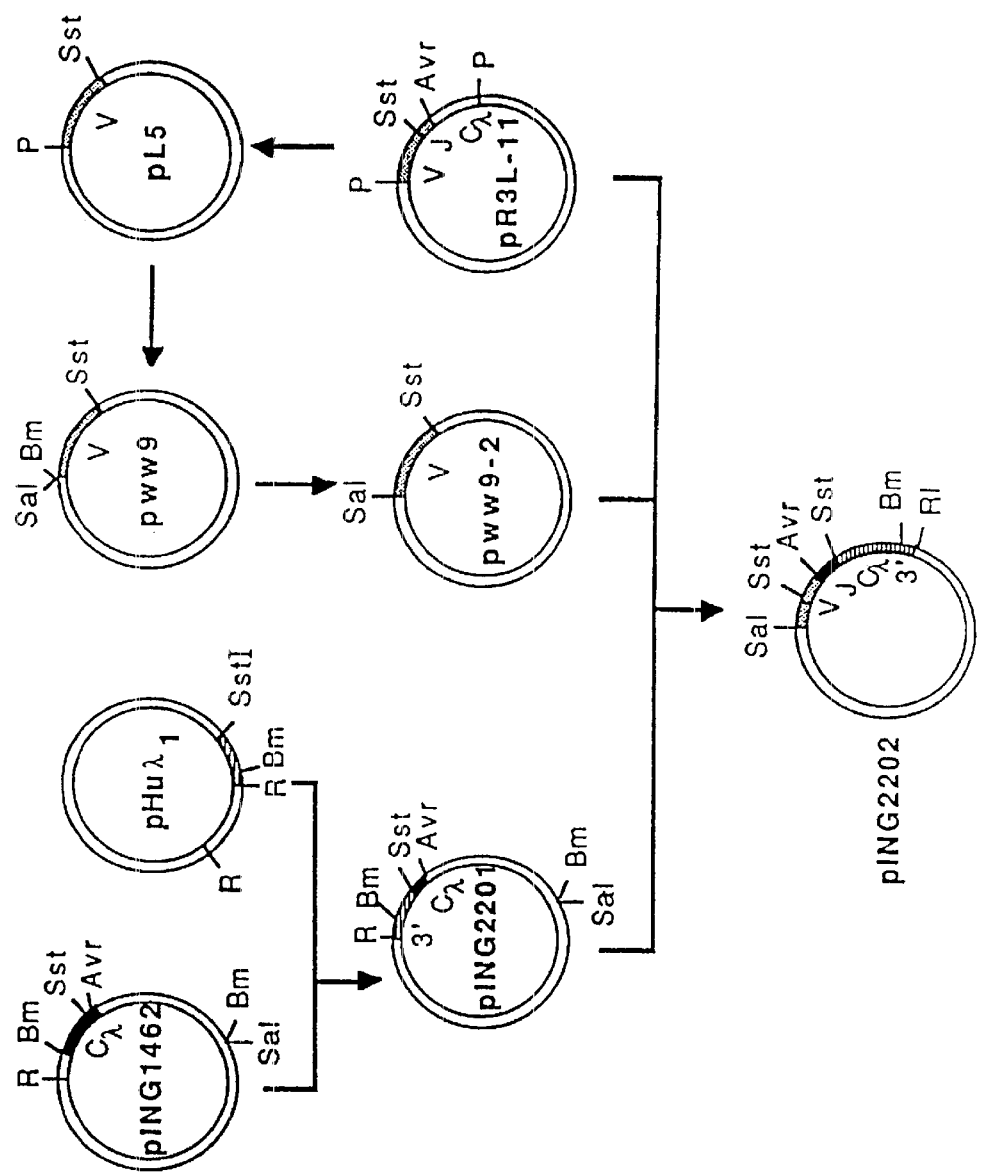
FIGS. 4(A and B). Construction scheme for the chimeric mouse-human Br-3 (ING-2) L chain mammalian expression plasmid pING2203. The V region from the cDNA clone pR3L-11 was engineered to be compatible with the mammalian expression plasmid pING1712. Plasmid pING2203 contains the following gene expression elements useful in mammalian cells: 1) the IgH enhancer element, 2) the Abelson LTR promoter, 3) the SV40 19S/16S splice module, and 4) a human λ polyadenylation region. It also contains the entire human $C_\lambda$ region, and the GPT gene which allows for mycophenolic acid resistance in transfected cells. Not drawn to scale.
Figure 4B:
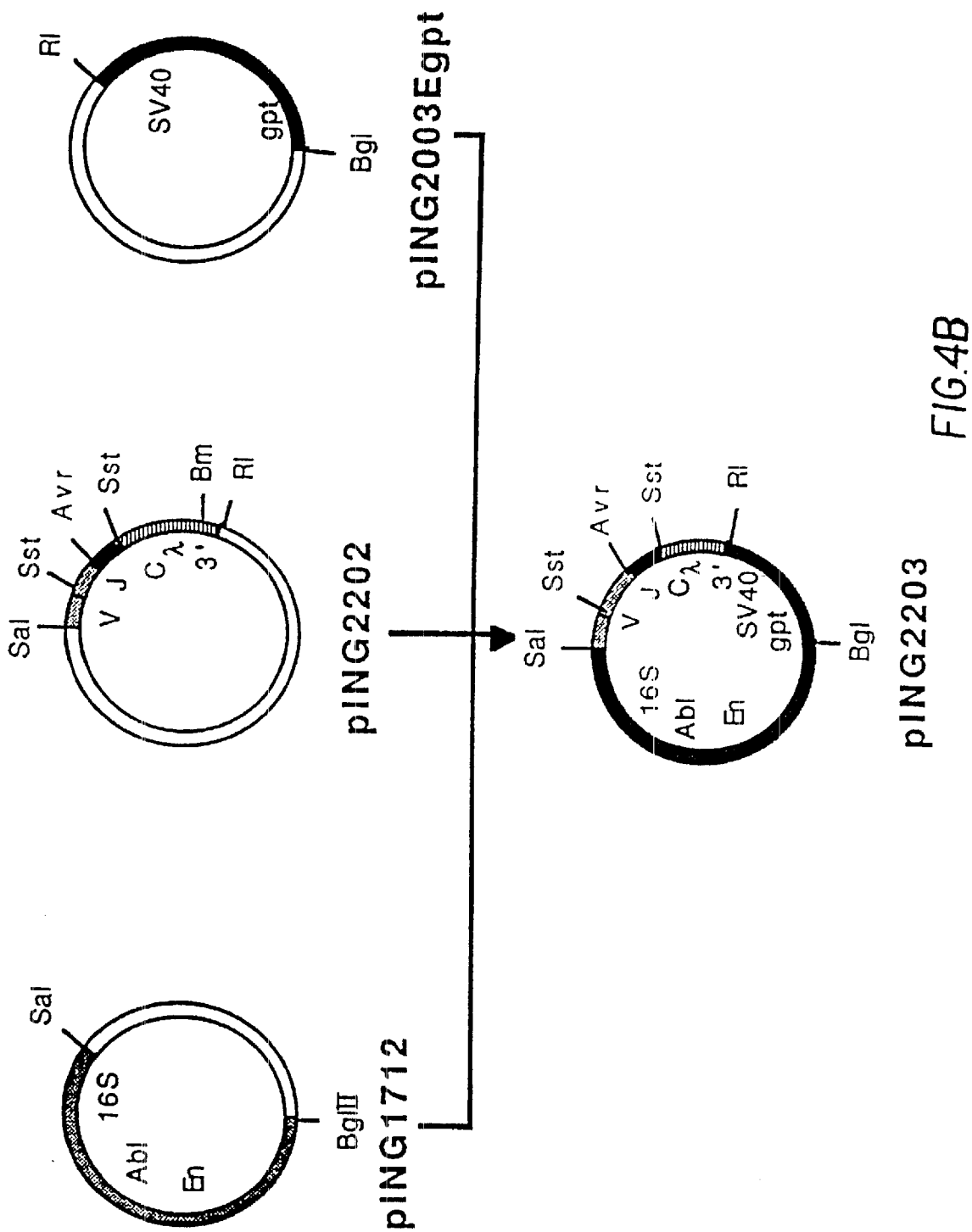

The chimeric Br-3 λ gene was constructed in a three-piece ligation from the vector AvrII to SalI fragment from pING2201, the mouse $V_\lambda$ region SalI to SstI fragment from pWW9-2, and the SstI to AvrII fragment from pR3L-1, generating -pING2202 (FIG. 4). The final chimeric L chain expression vector, pING2203, was constructed in a three-piece ligation from pING1712 (BglII to SalI fragment containing the IgH enhancer, Abelson LTR promoter, and SV40 16S splice), pING2003Egpt (Robinson, R. R. et al., PCT US86/02269, BglII to EcoRI fragment containing the GPT gene and the SV40 polyadenylation region (equivalent to pSV2gpt), and pING2202 (SalI to EcoRI containing the chimeric Br-3 λ gene and human λ polydenylation region). This construction is shown in FIG. 4. pING2203 is the chimeric Br-3 λ equivalent of the chimeric L6 κ producer, pING1712 (Example 1).

C. Construction of Heavy Chain Expression Vectors

From the Br-3 cDNA library, a H chain cDNA clone was isolated which contained the entire coding region of the Br-3 immunoglobulin H chain. This cDNA clone, pR3G-11, was adapted for expression in mammalian cells as outlined in FIG. 5. The Br-3 J region is $J_H3$ and contains a natural PstI site near the V-$C_H1$ junction that can be used to link the mouse V and human C modules. A homologous PstI site was therefore inserted into a human $C_\gamma1$ cDNA gene module. A portion of the human $C_\gamma1$ region fused to the L6 specificity (Liu, A. Y. et al., Proc. Natl. Acad. Sci., USA 84:3439 (1987)) was subcloned into M13 from a SalI site 5' of the chimeric gene to the SstI site (previously altered to a BamHI site by SstI cleavage and insertion of BamHI oligonucleotide linkers) of the $C_H2$ region to generate pING1402. This plasmid was mutagenized with the oligonucleotide 5'-TTGTGCTGGCTGCAGAGACTGTG-3' to introduce a PstI restriction site to generate pING1458. Fusion of the human pING1458 $C_H1$ region to a mouse V-$J_H3$ region at the homologous PstI sites will yield an in-frame chimeric gene with conservation of amino acid sequence. Finally, a SalI restriction site was introduced 5' to the ATG initiation codon by site-directed mutagenesis in pXX7 (FIG. 5) with the primer 5'-TGTGTTTGTCGACGAAGAGAAAG-3'.

Figure 5A:
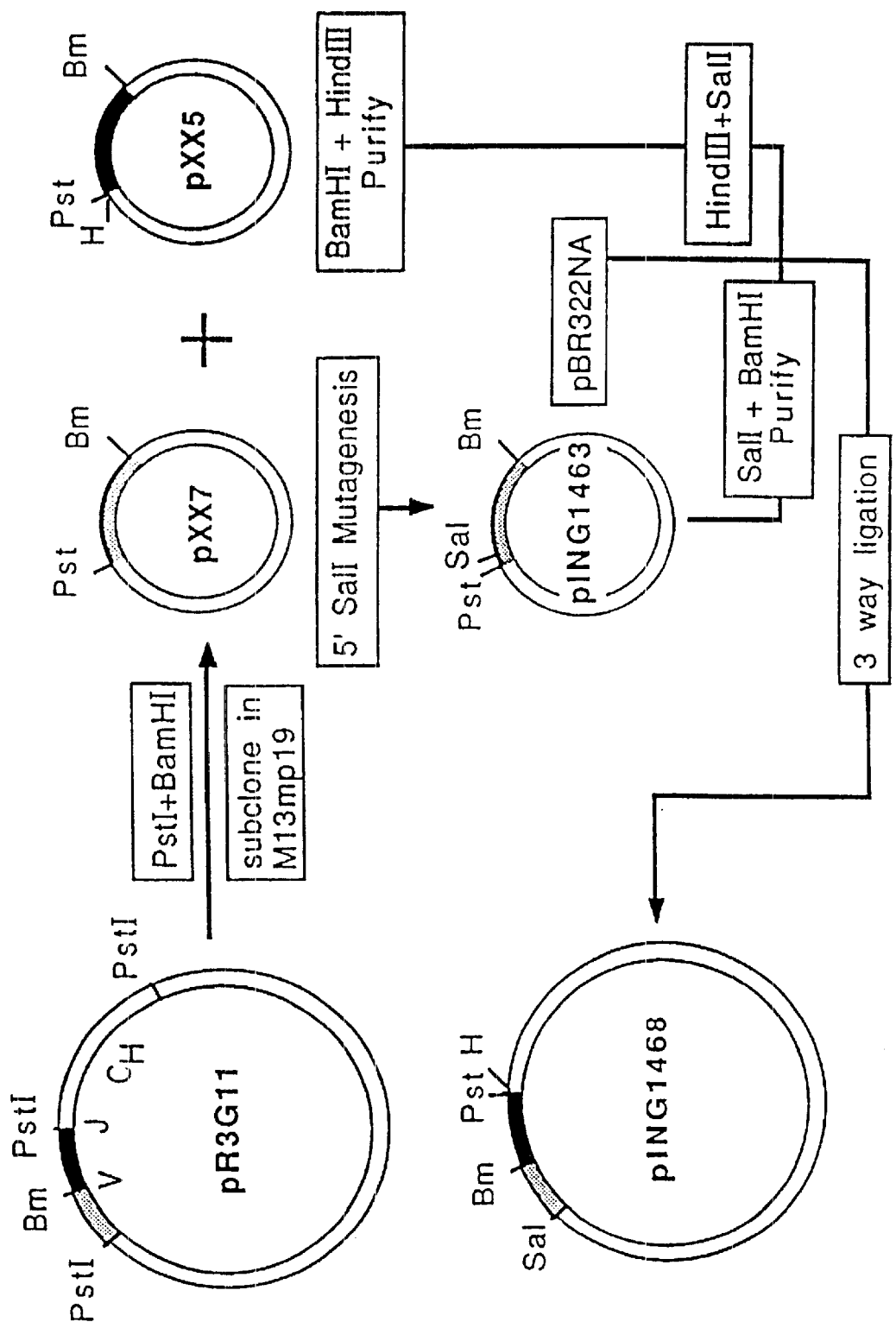
FIGS. 5(A and B). Construction scheme for the chimeric mouse-human Br-3 (ING-2) H chain mammalian expression plasmid, pING2227. The V region for the cDNA clone pR3G-11 was engineered to be compatible with the mammalian expression plasmid pING1714. Plasmid pING2227 contains the following gene expression elements useful in mammalian cells: 1) an IgH enhancer element, 2) an Abelson LTR promoter, 3) the SV40 19S/16S splice module, and 4) the genomic IgG1 polyadenylation signal sequence. It also contains the entire human IgG1 C region from pGMH-6 (Liu, A Y. et al., (1987) supra). pING1714 contains the neomycin phosphotransferase gene which allows for G418 selection in transfected cells. Not drawn to scale.
Figure 5B:
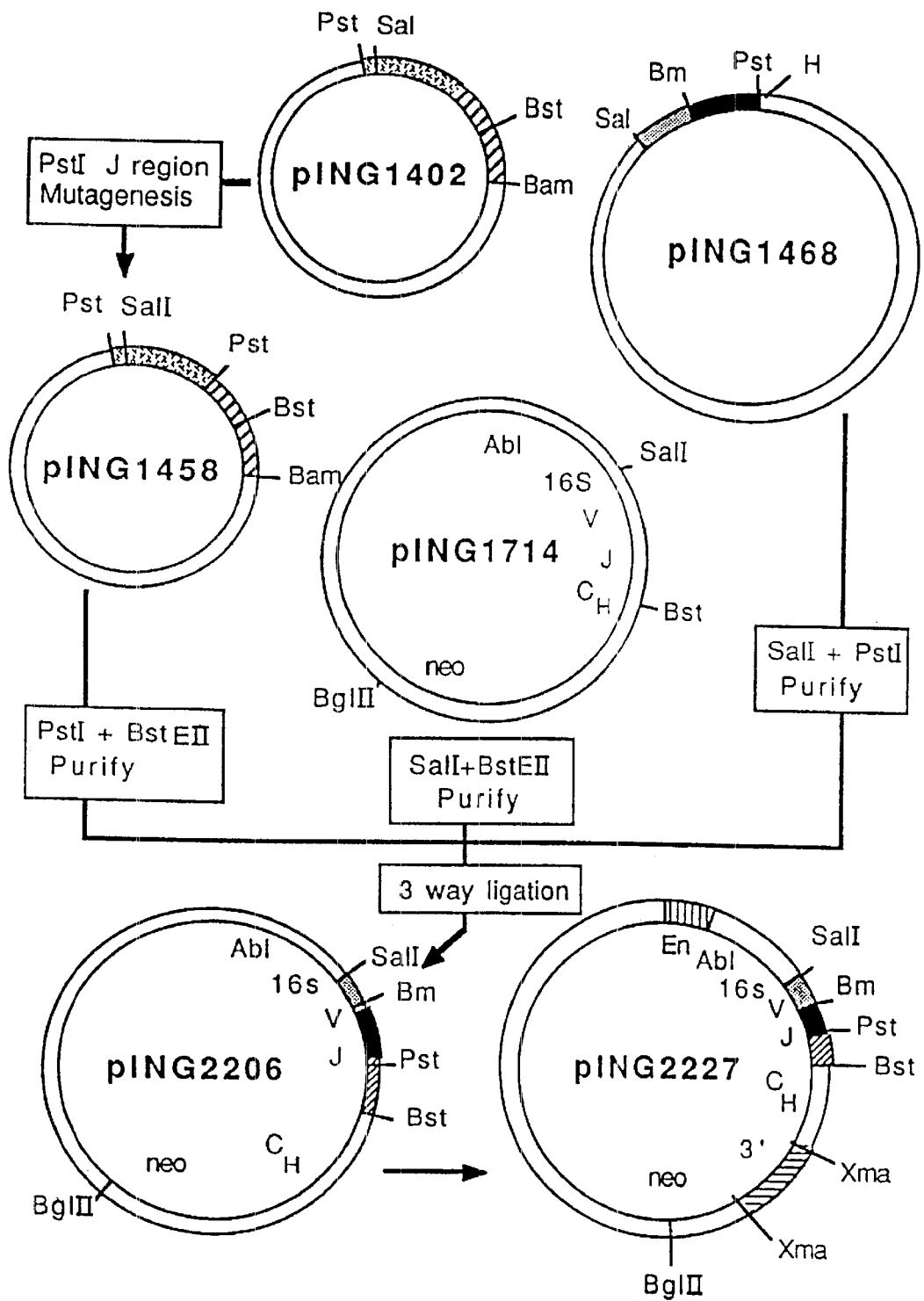
Figure 6A:
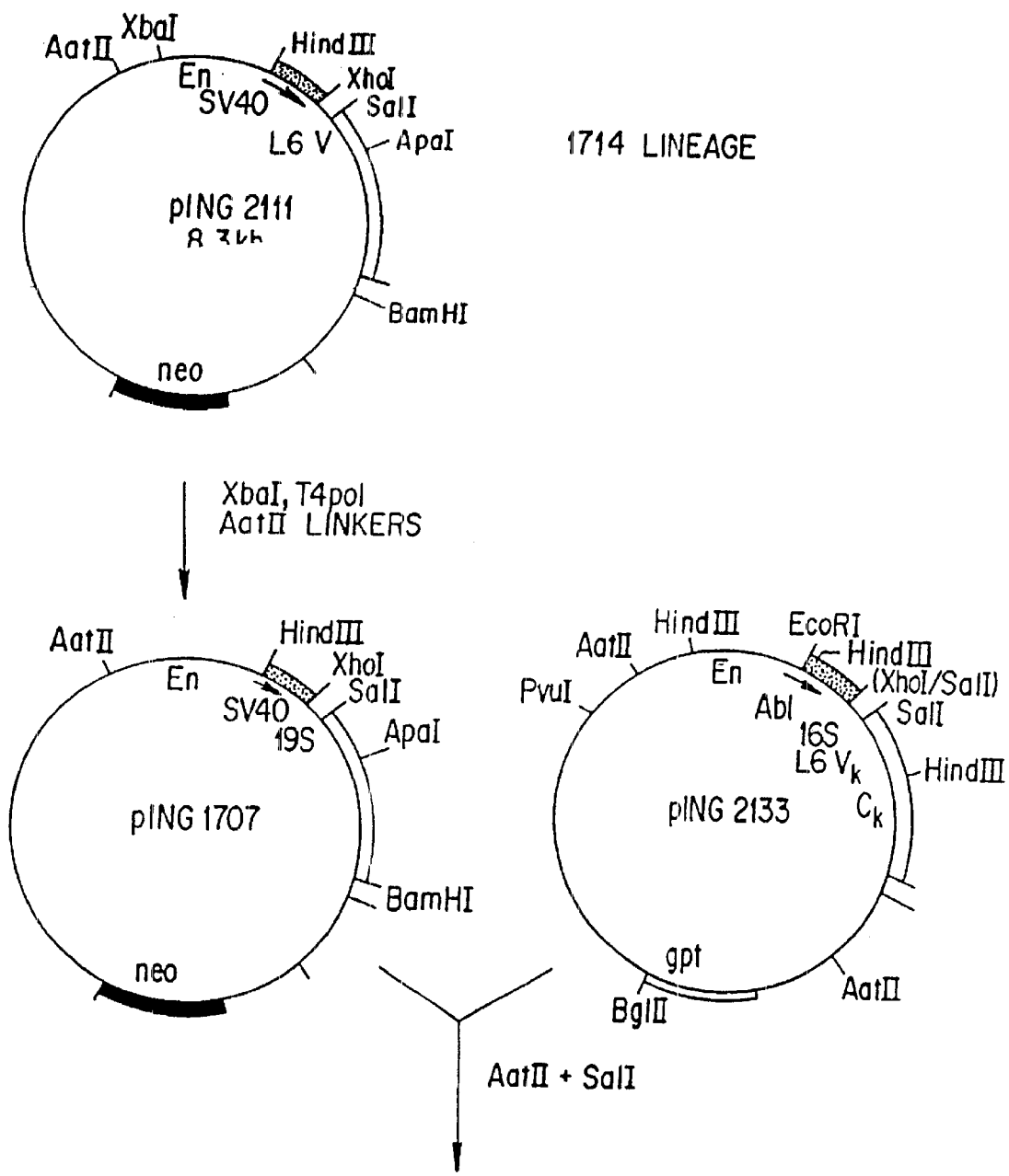
FIGS. 6(A and B). Construction scheme for the chimeric H chain expression vector pING1714. Not drawn to scale.

The modified chimeric mouse V-human $C_H1$ plasmid was used in a three-way ligation to form the expression vector, pING2206 (see FIG. 5). The vector sequences containing the Abl LTR promoter were from pING1714, which was constructed as shown in FIG. 6. First, the SV40 expression plasmid pING2111 (Robinson et al., PCT US86/02269) was modified by the insertion of an AatII oligonucleotide linker at the XbaI site, followed by AatII cleavage and religation to form pING1707. The AatII to SalI fragment containing the Abelson LTR promoter was excised from pING2133 and ligated to the large AatII to SalI fragment of pING1707 to form pING1711. The H chain enhancer was deleted from pING1711 by EcoRI digestion, T4 polymerase treatment, ligation to AatII oligonucleotide linker, and cleavage and religation with AatII to form the 7.7 kb expression vector pING1714 shown in FIGS. 5 and 6.

The reconstructed chimeric H chain expression plasmid pING2206 was modified in the promoter-enhancer region in two ways. First, a H chain IgH enhancer was placed upstream of the Abl promoter to form pING2217. Second, substitution of the AatII to SalI region of pING2217 (H chain enhancer, Abl promoter, 16S splice region) with the homologous region of pING2127 generated pING2218 (H chain enhancer, SV40 promoter, 16S splice region).

pING2206 was also modified at the 3' end in two ways. First, the poly-A stretch from the human IgG1 cDNA was deleted between the BamHI site immediately downstream of the poly-A and the XmaIII site immediately 3' to the IgG1 stop codon, bringing the SV40 polyadenylation region closer to the IgG1 gene and generating pING2220. Second, the 1300 nucleotide XmaIII fragment from human IgG1 genomic DNA (Ellison et al., Nucleic Acid Res. 10:4071 (1982)) was added at the XmaIII site 3' to the stop codon, generating pING2219. pING2219 thus contains the genomic human IgG1 polyadenylation signal and site.

D. Analysis of Heavy Chain Gene Expression Elements by Transfection

A L chain producing cell line was first made by transfection of Sp2/0 cells with pING2203 by the electroporation method in Example 1 and subcloning to generate cell line 22031B5.14.

The 22031B5.14 cell line was subsequently transfected by electroporation with the various chimeric Br-3 H chain expression plasmid DNAs. Cells expressing the associated selectable $neo^r$ gene were selected by growth in complete DMEM medium supplemented with 0.8 mg/ml G418 (GIBCO). Cultures from 96-well plates containing G418-resistant cells were expanded to 48-well plates and the secreted chimeric mouse-human H chain of terminal cultures was measured by ELISA specific for human gamma chains. The transfection results are summarized in Table 2.

In the first experiment, the effects of different promoter and enhancer combinations were examined (all of these experiments used the 19S/16S splice region). The results show that the Abl viral LTR promoter is more efficient than the SV40 promoter, and that the inclusion of an immunoglobulin H chain enhancer is advantageous for the Abl LTR promoter driving a H chain cDNA gene. The second experiment compares various 3' configurations of the chimeric Br-3 expression unit. The construct containing the IgG1 H chain genomic polyadenylation region (pING2219) results in higher H chain expression than those which contain only the SV40 polyadenylation region (pING2220), or the cDNA poly-A stretch and SV40 polyadenylation region (pING2206).

From this information, an improved vector for the expression of chimeric Br-3 H chain would combine the immunoglobulin H chain enhancer, Abl LTR promoter, and the human genomic polyadenylation region. Accordingly, the DNA fragment containing the improved gene expression elements from pING2217 (H chain enhancer, Abl LTR promoter, 16S splice) was ligated to that from pING2219 (genomic polyadenylation region) to generate the improved chimeric Br-3 H chain gene expression vector, pING2227. This vector was used for the transfection of chimeric Br-3 L chain producing cells to achieve efficient synthesis of chimeric Br-3 H chain and the resulting fully-assembled chimeric antibody.

The above-described gene expression elements are also useful for expression of immunoglobulins in cells other than mouse Sp2/0 hybridoma cells. For example, CHO cells were transfected with pING1712+pING1714 to yield efficient synthesis of fully assembled chimeric antibodies.

TABLE 2

Chimeric Heavy Chain Plasmid Transfection Results

| Experiment | pING# | Gene Expression Elements:[a] Enhancer/Promoter/3' | No. of Wells Tested | Secreted Gamma[b] (µg/ml) | Relative Gamma Expression[c] | Highest Producer (µg/ml) |
|---|---|---|---|---|---|---|
| 1 | 2206 | −/Ab1/poly A | 24 | .61 ± .38 | 1.0 | 1.3 |
|   | 2217 | +/Ab1/poly A | 23 | .83 ± .69 | 1.2 | 2.3 |
|   | 2218 | +/SV40/poly A | 22 | .52 ± .24 | .9 | 1.2 |
| 2 | 2206 | −/Ab1/poly A | 23 | .38 ± .29 | 1.0 | 1.1 |
|   | 2220 | −/Ab1/SV40 | 24 | .33 ± .23 | .9 | 0.8 |
|   | 2219 | −/Ab1/hu gamma | 23 | .67 ± .29 | 1.8 | 1.2 |

[a] Enhancer abbreviations:
    +    presence of immunoglobulin heavy chain enhancer
    −    absence of immunoglobulin enhancers
    Promoter abbreviations:
    Ab1    Abelson virus LTR
    SV40    SV40 early TABLE 2-continued 3' (polyadenylation) abbreviations:
poly A    human gammal cDNA, polyadenylation signal, and SV40 polyadenylation region
SV40      SV40 polyadenylation region only
hu gamma  human gammal immunoglobulin genomic DNA containing the chromosomal polyadenylation region (b) Secreted gamma chain was measured by ELISA of a terminal culture supernatant.
(c) "Relative Gamma Expression" is determined by dividing the mean expression by the mean expression of pING2206.

EXAMPLE 3

Chimeric House-Human Immunoglobulins with Human Tumor Specificity Produced from Mammalian Cells 1. Recombinant Plasmid and Bacteriophage DNAs The plasmids pUC18, pUC19, and dG-tailed pBR322, pSV2-neo and pSV2-gpt were purchased from BRL (Gaithersburg, Md.) as were M13mp18 and M13mp19. DNA manipulations involving purification of plasmid DNA by bouyant density centrifugation, restriction endonuclease digestion, purification of DNA fragments by agarose gel electrophoresis, ligation and transformation of *E. coli* were as described by Maniatis, T., et al., *Molecular Cloning: A Laboratory Manual* (1982), or other standard procedures. Restriction endonucleases and other DNA/RNA modifying enzymes were purchased from Boehringer-Mannheim (Indianapolis, Ind.), BRL, and New England Biolabs (Beverly, Mass.).

2. RNA Purification and cDNA Library Construction a. ING-1 (Chimeric B638.1)

One liter of B38.1 hybridoma cells at approximately $1 \times 10^6$ cells/ml were collected by centrifugation and washed in 100 ml of PBS (8 g NaCl, 0.2 g KH2PO4, 1.15 g Na$_2$HPO$_4$, and 0.2 g KCl per liter). The cells were centrifuged again and the cell pellet was suspended in a solution of guanidine thiocyanate, and total cellular RNA and poly (A)$^+$ RNA were prepared from tissue culture cells as described in Maniatis, T., et al., supra.

Oligo-dT primed cDNA libraries were prepared from poly(A)$^+$ RNA by the methods of Gubler, V., and Hoffman, B. J., *Gene* 25:263 (1983). The cDNA was dC-tailed with terminal deoxynucleotide transferase and annealed to dG-tailed pBR322. cDNA libraries were screened by hybridization (Maniatis, T. et al., supra) with $^{32}$P-labeled, nick-translated DNA fragments, i.e., for κ clones with a mouse C$_\kappa$ region probe and for H chain clones with an IgG1 C region probe.

The L and H chain V region fragments from the full length clones, pRIK-7 and pRIG-8 respectively, were inserted into M13 bacteriophage vectors for nucleotide sequence analysis. The complete nucleotide sequences of the V region of these clones were determined (FIGS. 7 and 8) by the dideoxy chain termination method. These sequences predict V region amino acid compositions that agree well with the observed compositions, and predict peptide sequences which have been verified by direct amino acid sequencing of portions of the V regions.

The nucleotide sequences of the cDNA clones show that they are immunoglobulin V region clones as they contain amino acid residues diagnostic of V domains (Kabat et al., *Sequences of Proteins of Immunological Interest: U.S. Dept. of HHS*, 1983).

The B38.1 V$_H$ belongs to subgroup II. The B38.1 V$_H$ has the J$_H$4 sequence. B38.1 V$_\kappa$ has the J$_\kappa$1 sequence.

b. ING-2 (Chimeric Br-3)

One liter of Br-3 hybridoma cells at approximately $1 \times 10^6$ cells/ml were collected by centrifugation and washed in 100 ml of PBS (8 g NaCl, 0.2 g KH$_2$PO$_4$, 1.15 g Na$_2$HPO$_4$, and 0.2 g KCl per liter). The cells were centrifuged again and the cell pellet was suspended in a solution of guanidine thiocyanate, and total cellular RNA and poly(A)$^+$ RNA were prepared from tissue culture cells by methods described in Maniatis, T., et al., supra.

Oligo-dT primed cDNA libraries were prepared from poly(A)$^+$ RNA by the methods of Gubler, V., and Hoffman, B. J., supra. The cDNA was dC-tailed with terminal deoxynucleotide transferase and annealed to dG-tailed pBR322. cDNA libraries -were screened by hybridization (Maniatis, T., et al., supra) with $^{32}$P-labeled, nick-translated DNA fragments, i.e., for λ clones with a mouse C$_\lambda$ region probe and for H chain clones with an IgG1 C region probe.

The L and H chain V region fragments from the full length clones, pR3L-11 and pR3G-11 respectively, were inserted into M13 bacteriophage vectors for nucleotide sequence analysis. The complete nucleotide sequences of the V region of these clones were determined (FIGS. 14 and 15) by the dideoxy chain termination method. These sequences predict V region amino acid compositions that agree well with the observed compositions, and predict peptide sequences which have been verified by direct amino acid sequencing of portions of the V regions.

The nucleotide sequences of the cDNA clones show that they are immunoglobulin V region clones as they contain amino acid residues diagnostic of V domains (Kabat et al., supra.)

The Br-3 V$_H$ belongs to subgroup IIIC. The Br-3 V$_H$ has the J$_H$3 sequence and the Br-3 V$_L$ has the J$_\lambda$ sequence.

c. ING-3 (Chimeric Co-1)

One liter of Co-1 hybridoma cells at approximately $1 \times 10^6$ cells/ml were collected by centrifugation and washed in 100 ml of PBS (8g NaCl, 0.2 g KH2PO$_4$, 1.15g Na2HPO4, and 0.2 g KCl per liter). The cells were centrifuged again and the cell pellet was suspended in a solution of guanidine thiocyanate, and total cellular RNA and poly(A)$^+$ RNA were prepared from tissue culture cells by methods described in Maniatis, T., et al., supra.

Oligo-dT primed cDNA libraries were prepared from poly(A)$^+$ RNA by the methods of Gubler, V. and Hoffman, B. J., supra. The cDNA was dC-tailed with terminal deoxynucleotide transferase and annealed to dG-tailed pBR322. cDNA libraries were screened by hybridization (Maniatis, T., supra) with $^{32}$P-labelled, nick translated DNA fragments, ie., for κ clones with a mouse C$_\kappa$ region probe and for H chain clones with a mouse IgG1 C region probe The L and H chain V region fragments from the full length clones, p01K-8 and p01G-11 respectively, were inserted into M13 bacteriophage vectors for nucleotide sequence analysis. The complete nucleotide sequences of the V region of these clones were determined (FIGS. 21 and 22) by the dideoxy chain termination method. These sequences predict V region amino acid compositions that -agree well with the observed compositions, and predict peptide sequences which have been verified by direct amino acid sequencing of portions of the V regions.

The nucleotide sequences of the cDNA clones show that they are immunoglobulin V region clones as they contain amino acid residues diagnostic of V domains (Kabat et al., supra).

The Co-1 $V_H$ belongs to subgroup II. The Co-1 $V_H$ has the $J_H4$ sequence and the Co-1 $V_\kappa$ has the $J_\kappa5$ sequence.

d. ING-4 (Chimeric ME4)

One liter of ME4 hybridoma cells at approximately $1 \times 10^6$ cells/ml were collected by centrifugation and washed in 100 ml of PBS (8 g NaCl, 0.2 g KH2PO$_4$, 1.15 g Na$_2$HPO$_4$, and 0.2 g KCl per liter). The cells were centrifuged again and the cell pellet was suspended in a solution of guanidine thiocyanate, and total cellular RNA and poly(A)$^+$ RNA were prepared from tissue culture cells by methods described in Maniatis, T., et al., supra.

Oligo-dT primed cDNA libraries were prepared from poly(A)$^+$ RNA by the methods of Gubler, V., and Hoffman, B. J., supra. The cDNA was dC-tailed with terminal deoxynucleotide transferase and annealed to dG-tailed pBR322. cDNA libraries were screened by hybridization (Maniatis, T., supra) with $^{32}$P-labeled, nick-translated DNA fragments, i.e., for κ clones with a mouse C$_\kappa$ region probe and for H chain clones with an IgG1 C region probe.

The L and H chain V region fragments from the full length clones, pE4K-15 and pE4G-21 respectively, were inserted into M13 bacteriophage vectors for nucleotide sequence analysis. The complete nucleotide sequences of the V region of these clones were determined (FIGS. 29 and 30) by the dideoxy chain terminations method. These sequences predict V region amino acid compositions that agree well with the observed compositions, and predict peptide sequences which have been verified by direct amino acid sequencing of portions of the V regions.

The nucleotide sequences of the cDNA clones show that they are immunoglobulin V region clones as they contain amino acid residues diagnostic of V domains (Kabat et al., supra.)

The ME4 $V_H$ belongs to subgroup II. The ME4 $V_H$ has the $J_H4$ sequence and the ME4 $V_\kappa$ has the $J_\kappa1$ sequence.

e. KM10

One liter of KM10 hybridoma cells at approximately $1 \times 10^6$ cells/ml were collected by centrifugation and washed in 100 ml of PBS (8 g NaCl, 0.2 g KH$_2$PO$_4$, 1.15 g Na$_2$HPO$_4$, and 0.2 g KCl per liter). The cells were centrifuged again and the cell pellet was suspended in a solution of guanidine thiocyanate, and total cellular RNA and poly (A)$^+$ RNA were prepared from tissue culture cells by methods described in Maniatis, T., et al., supra.

Oligo-dT primed cDNA libraries were prepared from poly(A)$^+$ RNA as above. The cDNA was dC-tailed with terminal deoxynucleotide transferase and annealed to dG-tailed pBR322. cDNA libraries were screened by hybridization (Maniatis, T., supra) with $^{32}$P-labelled, nick translated DNA fragments, i.e., for κ clones with a mouse C$_\kappa$ region probe and for H chain clones with a mouse IgG1 C region probe.

The L and H chain V region fragments from the full length cDNA clones, pM10 K-16 and pM10G-2 respectively, were inserted into M13 bacteriophage vectors for nucleotide sequence analysis. The complete nucleotide sequences of the V region of these clones were determined (FIGS. 36 and 37) by the dideoxy chain termination method. These sequences predict V region amino acid compositions that agree well with the observed compositions, and predict peptide sequences which have been verified by direct amino acid sequencing of portions of the V regions.

The nucleotide sequences of the cDNA clones show that they are immunoglobulin V region clones as they contain amino acid residues diagnostic of V domains (Kabat et al., supra).

The KM10 $V_H$ belongs to subgroup II. The KM10 $V_H$ has the $J_H4$ sequence and the KM10 $V_\kappa$ has the $J_\kappa5$ sequence.

3. In Vitro Mutagenesis to Place Restriction Enzyme Sites into the J Region for Joining to a Human C-Module, and to Remove Oligo dC Sequence 5' to the V Modules a. ING-1

M13 subcloned DNA fragments were subjected to site-directed .mutagenesis as described by Kramer, W., et al., Nucl. Acids Res. 12:9441. Oligonucleotides were purchased from Synthetic Genetics, San Diego, Calif., in their purified form.

The appropriate phage M13 subclones of pRIK-7 and pRIG-8, which contain the B38.1 L and H chain copies, were subjected to site-directed mutagenesis to insert restriction sites useful for subsequent cloning into chimeric expression vectors. For the B38.1 $V_\kappa$, the J-region mutagenesis primer $V_\kappa$1HindIII, 5'-GTTTGATTTCAAGCTTGGTGC-3', was utilized. The human C$_\kappa$ module derived from a cDNA clone was previously mutagenized to contain a HindIII site in the human J region. Liu, A. Y., et al., Proc. Natl. Acad. Sci. USA 84:3439–3443 (1987). A SalI restriction site was introduced 5' to the ATG initiation codon by site-directed mutagenesis with the primer 5'-ATGGTGAGTCGACAGTGACCCCC-3'.

Figure 9A:
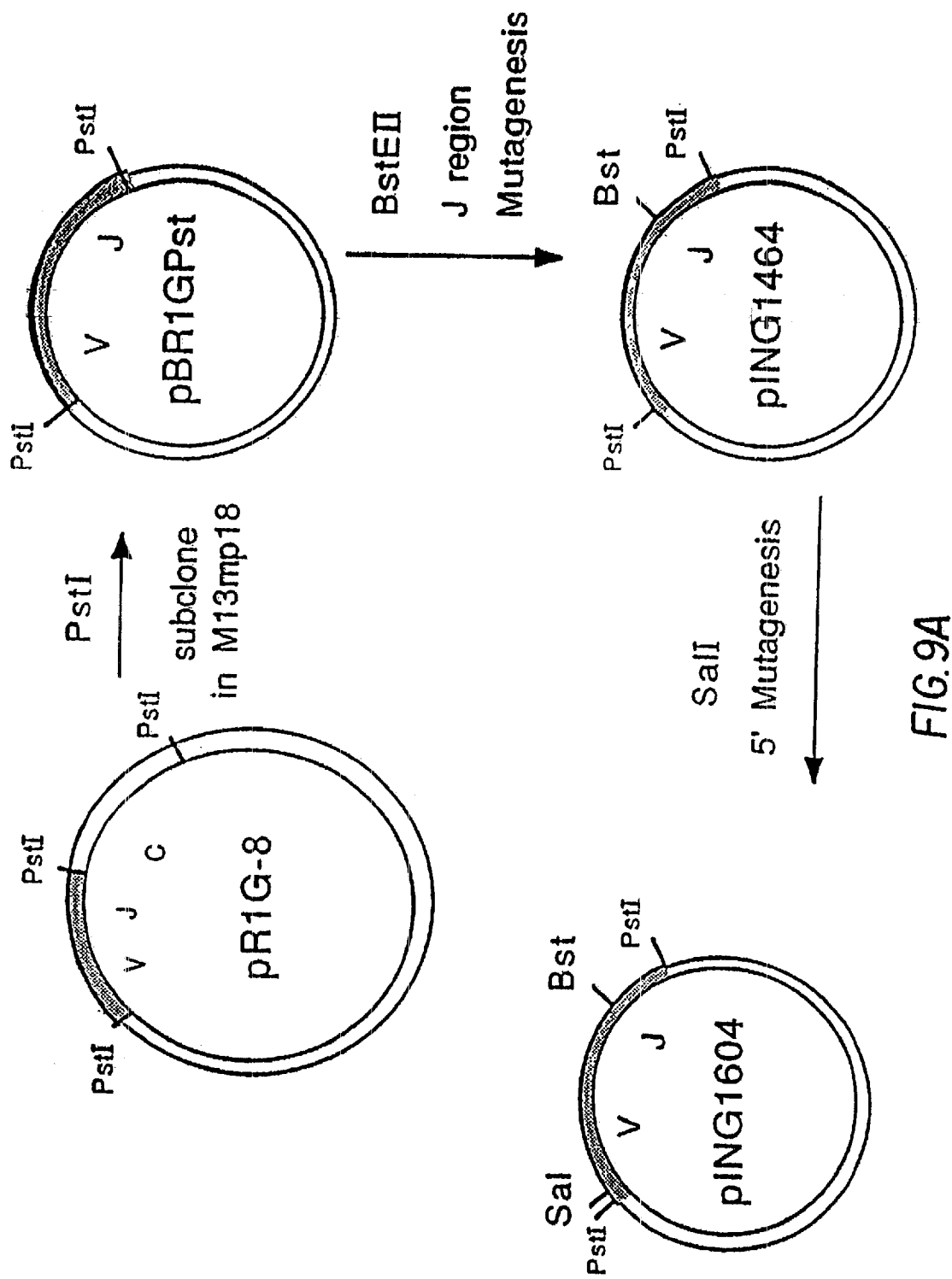
FIGS. 9(A and B). Construction scheme for the chimeric mouse-human ING-1 H chain mammalian expression plasmid, pING2225. The V region for the cDNA clone pRIG-8 was engineered to be compatible with the eukaryotic expression plasmid pING1714. Plasmid pING1714 contains the following gene regulatory elements useful for expression in mammalian cells: 1) an Abelson LTR promoter, 2) the SV40 19S/16S splice module, and 3) the SV40 polyadenylation signal sequence. It also contains the entire human IgG1 C region from pGMH-6 (Liu, A. Y., et al., (1987), supra). pING1714 contains the neomycin phosphotransferase gene which allows for G418 selection intransfected cells. Not drawn to scale.
Figure 9B:
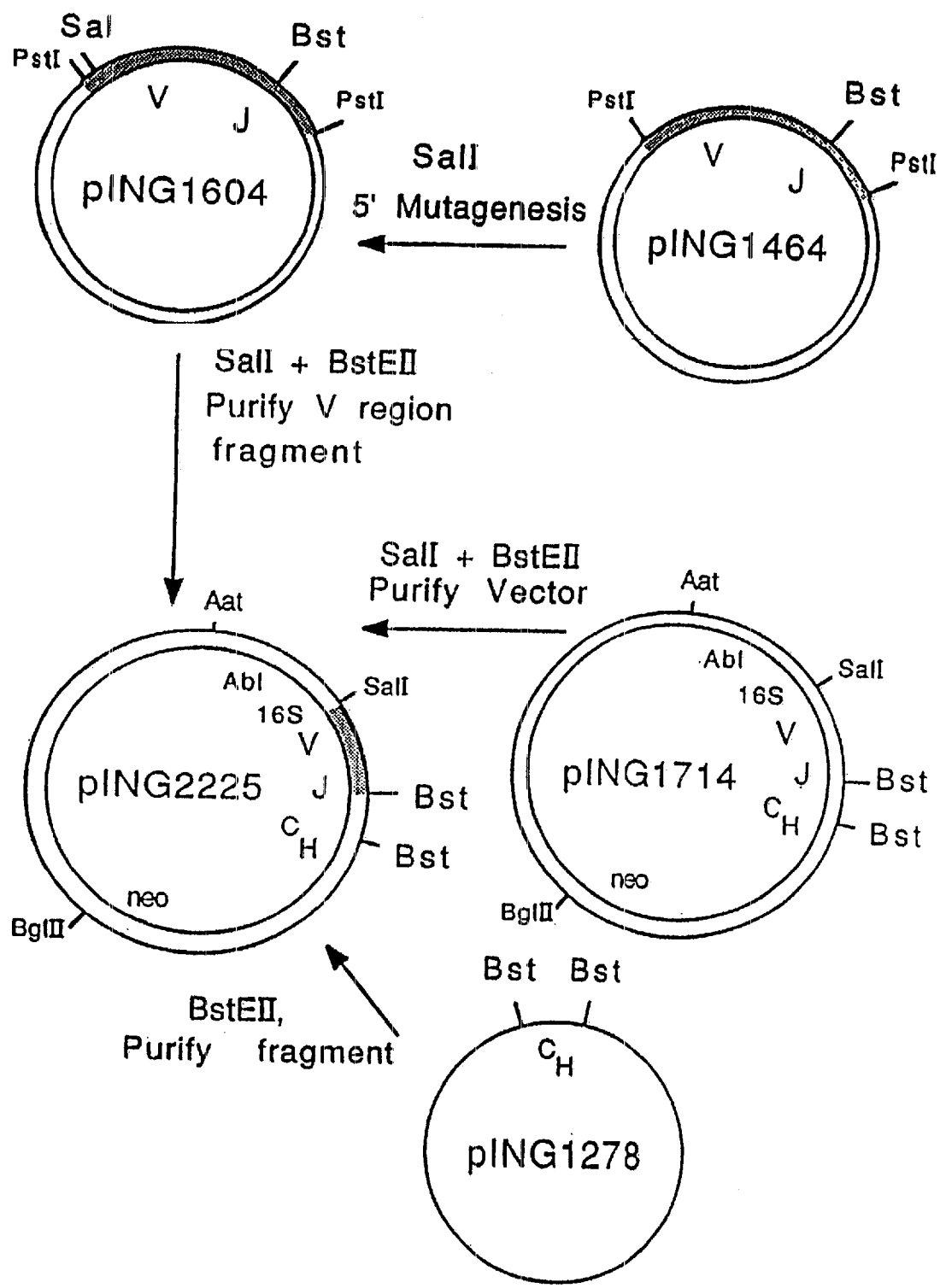

The cDNA clone containing the B38.1 H chain was likewise adapted for expression by introducing a BstEII site into the $J_H4$ for linkage to the human C domain, and a SalI site was introduced 5' of the ATG initiation codon by site-directed mutagenesis. The oligonucleotide used for mutagenesis to introduce a BstEII site was 5'-GAGACGGTGAC-CGAGGTTCC-3' and that for the SalI site was 5'-GAAGTGGTGCCTGTCGACTAACTGGTC-3'. A derivative of the human C gene cDNA clone pGMH-6, Liu, A. Y., et al., Proc. Natl. Acad. Sci. USA 84:3439–3443 (1987), contains a BstEII site to which the B38.1 H chain V region can be ligated (FIG. 9).

b. ING4

M13 subcloned DNA fragments were subjected to site-directed mutagenesis as described by Kramer, W., et al., Nucl. Acids Res. 12:9441. Oligonucleotides were purchased from Synthetic Genetics, San Diego, Calif., in their purified form.

The appropriate phage M13 subclones of pE4K-15 and pE4G-21, which contain the ME4 L and H chain copies, were subjected to site-directed mutagenesis to insert restriction sites useful for subsequent cloning into chimeric expression vectors. For the ME4 $V_\kappa$, the J-region mutagenesis primer $J_\kappa$1HindIII, 5'-GTTTGATTTCAAGCTTGGTGC-3', was utilized. The human C$_\kappa$ module derived from a cDNA clone was previously mutagenized to contain a HindIII site in the human J region. Liu, A. Y., et al. (1987) supra. A SalI restriction site was introduced 5' to the ATG initiation codon by site-directed mutagenesis with the primer 5'-GGACATCATGTCGACGGATACGAGC-3'.

Figure 31A:
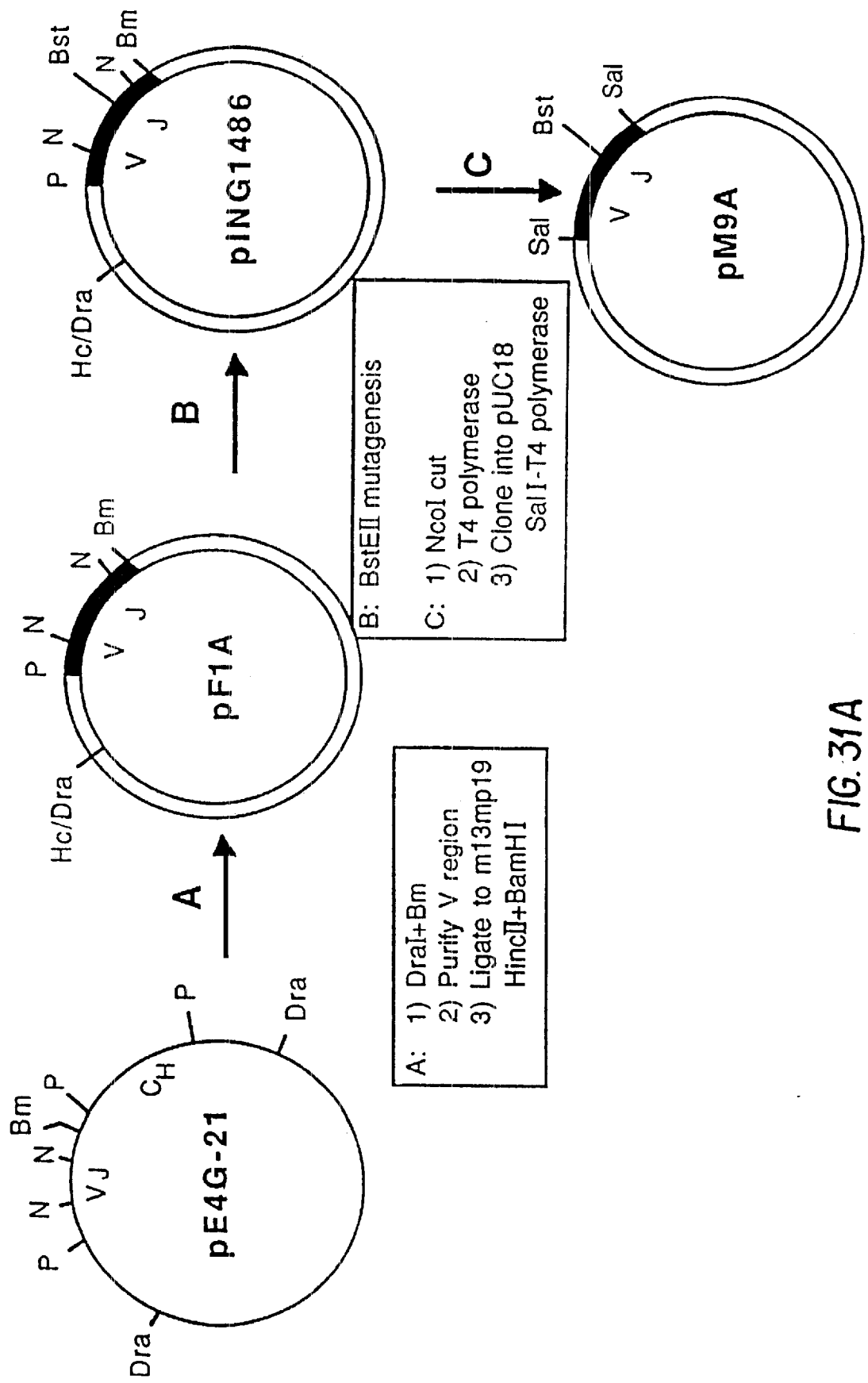
FIGS. 31(A and B). Construction scheme for the chimeric mouse-human ING-4 H chain mammalian expression plasmid, pING2232. The V region for the cDNA clone pE4G-21 was engineered to be compatible with the eukaryotic expression plasmid pING2227. Plasmid pING2232 contains the following gene regulatory elements useful for expression in mammalian cells: 1) in IgH Enhancer element, 2) an Abelson LTR promoter, 3) the SV40 19S/16S splice module, and 4) the genomic human IgG1 polyadenylation signal sequence. It also contains the entire human IgG1 C region from pGMH-6 (Liu, A. Y. et al., supra). Not drawn to scale.
Figure 31B:
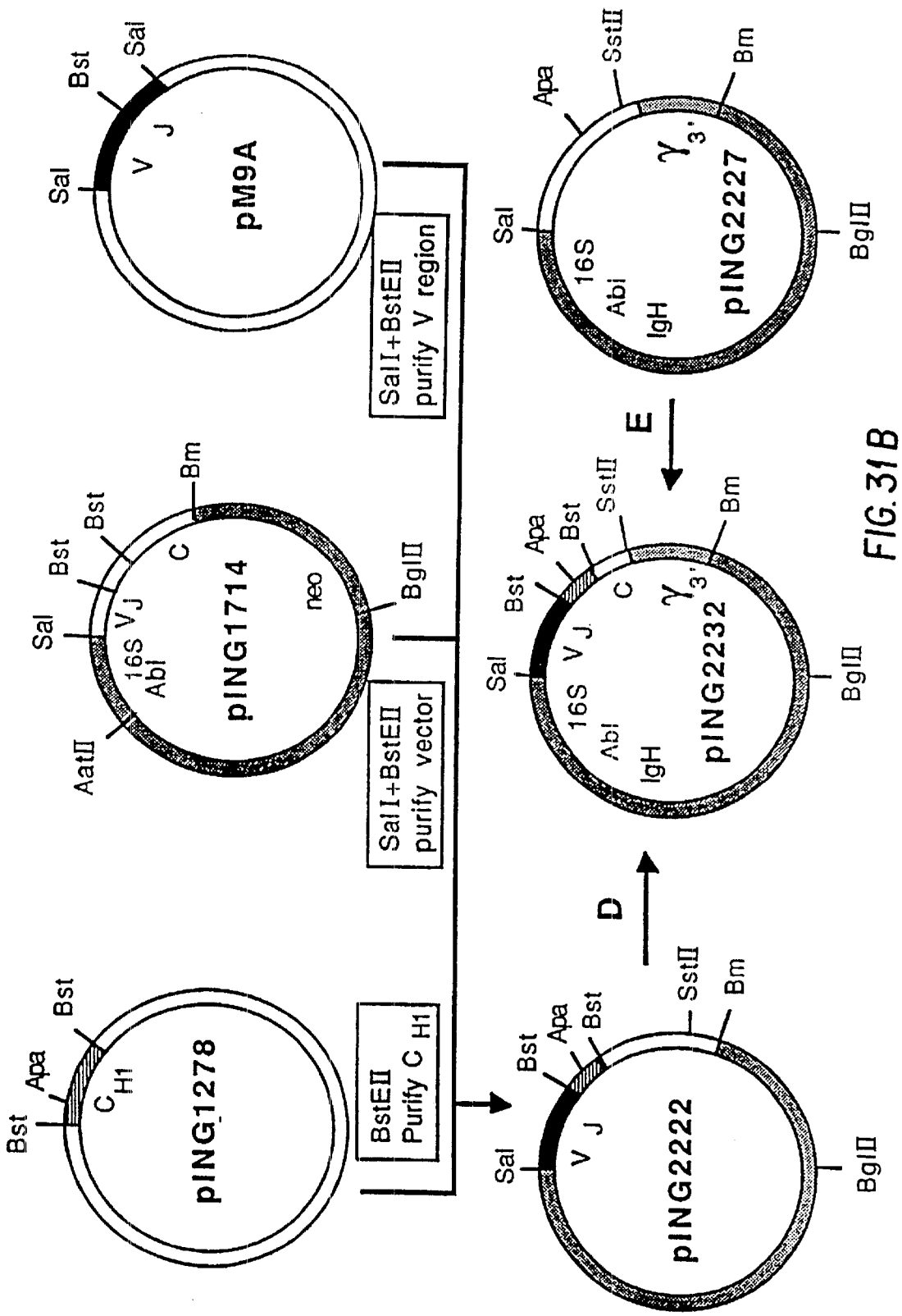

The cDNA clone containing the ME4 H chain was likewise adapted for expression by introducing a BstEII site into the $J_H4$ for linkage to the human C domain, and a SalI site was introduced 5' of the ATG initiation codon by site-directed mutagenesis. The oligonucleotide used for mutagenesis to introduce a BstEII site was 5'-GAGACGGTGAC-CGAGGTTCC-3'. A derivative of the human C gene cDNA clone pGMH-6, Liu, A. Y., et al. (1987) supra, contains a BstEII site to which the ME-4 H chain V region can be ligated (FIG. 31).

4. Expression Vectors and Chimeric Expression Plasmids
(See Example 1 and Example 2, above)
a. ING-1

The chimeric H chain expression plasmids were derived from the replacement of. the $V_H$ module in pING1714 with the $V_H$ modules of pING1604, as a SalI to BstEII fragment as outlined in FIG. 9. This plasmid, pING2225, directs the synthesis of chimeric ING-1 H chain when transfected into mammalian cells.

Figure 10A:
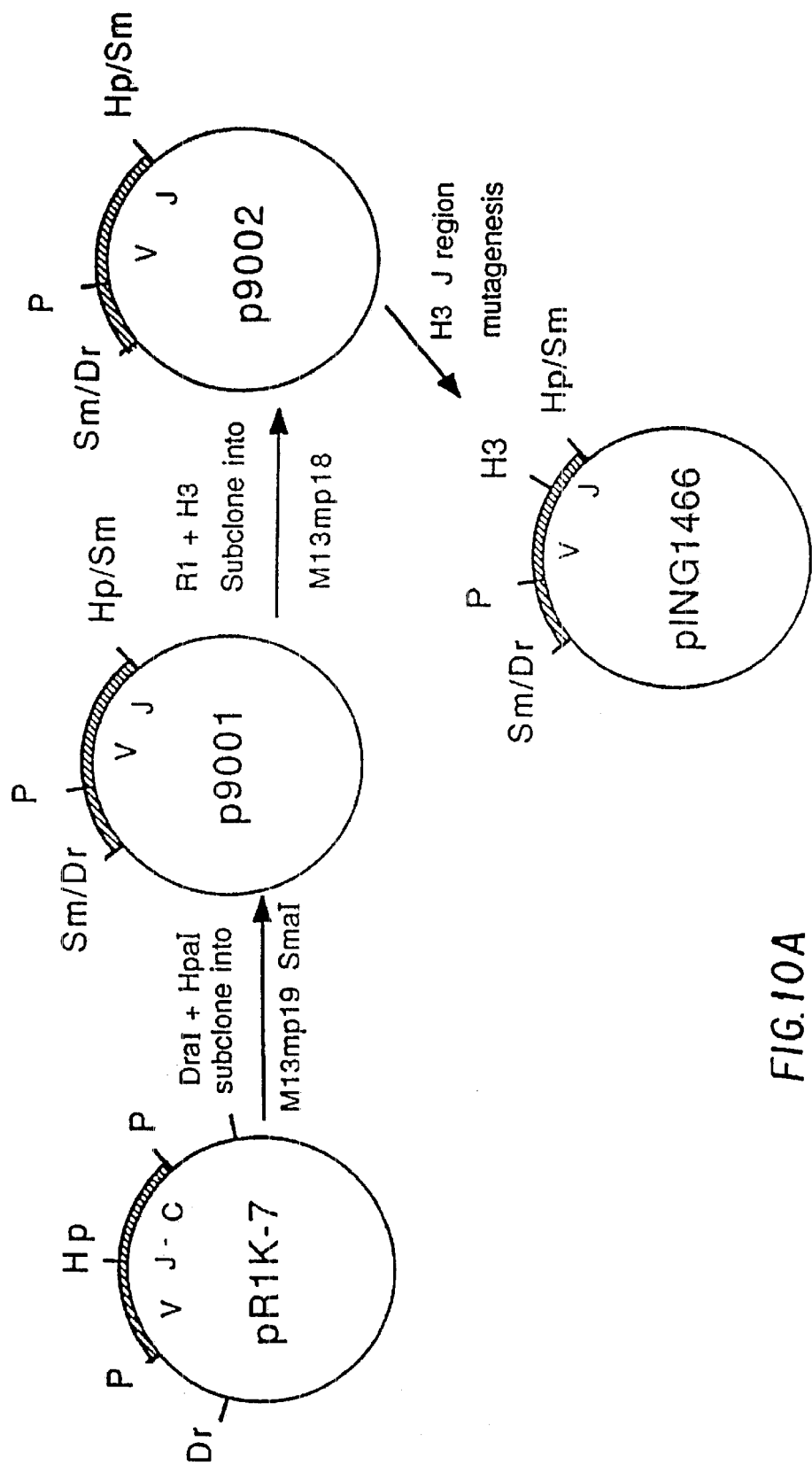
FIGS. 10(A and B). Construction scheme for the chimeric mouse-human ING-1 L chain mammalian expression plasmid pING2207. The V region from the cDNA clone pRIK-7 was engineered to be compatible with the eukaryotic expression plasmid pING1712. See FIGS. 2(A and B) for construction of plasmid pING1712. Not drawn to scale.
Figure 10B:
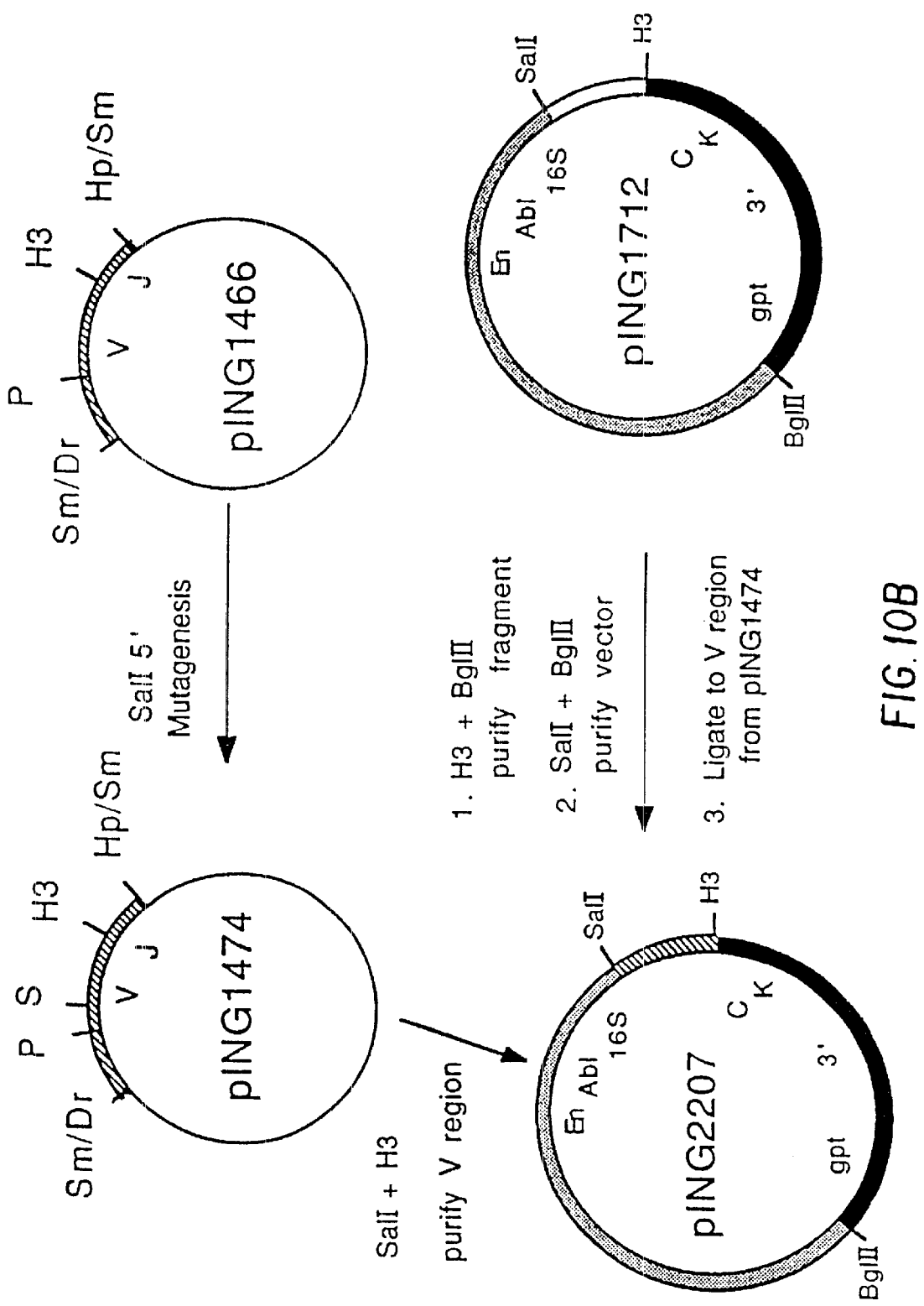

For the chimeric ING-1 L chain gene, the SalI to HindIII fragment of the mouse $V_K$ module from pING1474 was joined to the human $C_K$ module in pING1712 by the procedure outlined in FIG. 10, forming pING2207.

b. ING-2 (see Example 1 and 2, above)
c. ING3

Figure 23A:
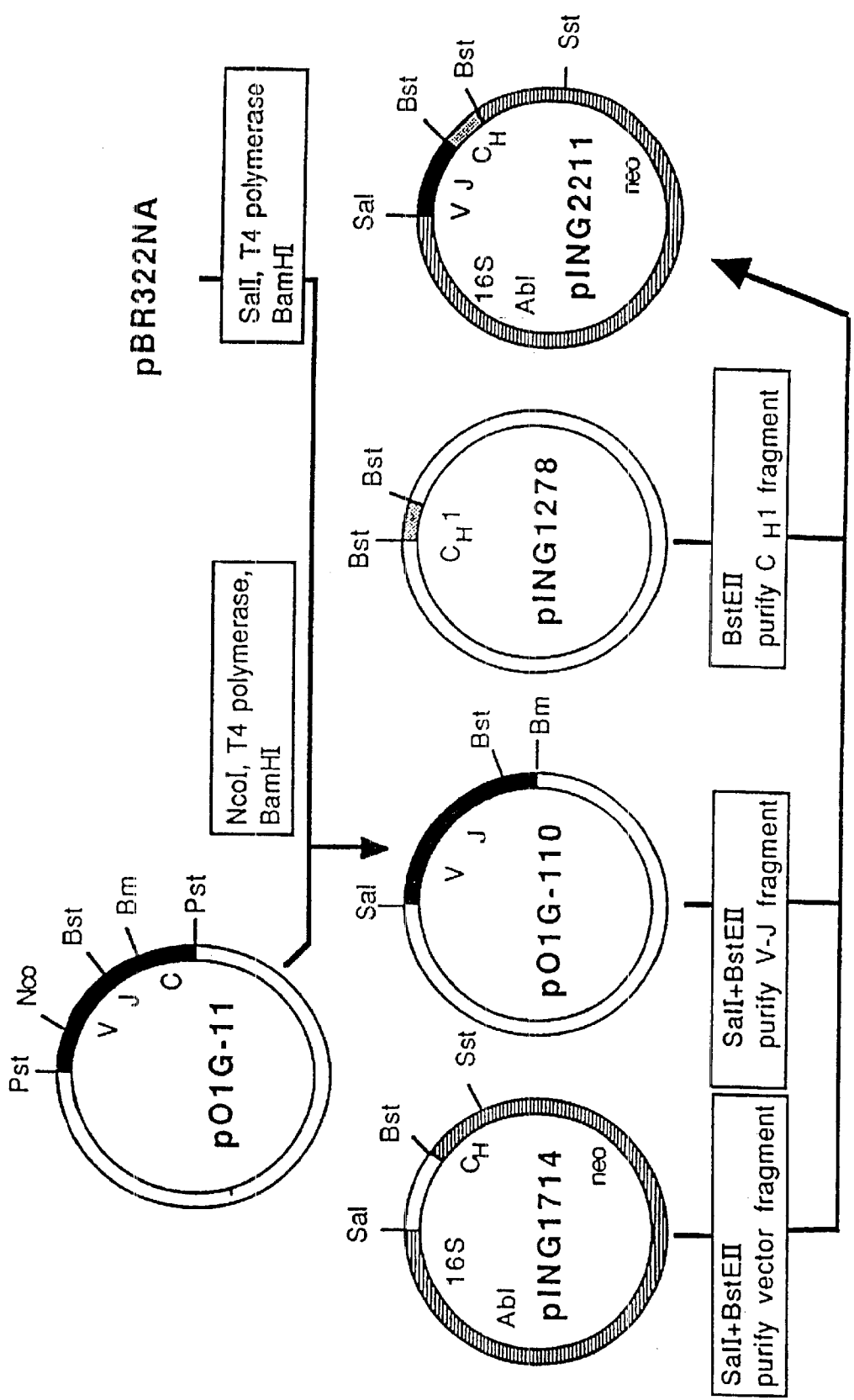
FIGS. 23(A and B). Construction scheme for the chimeric mouse-human ING-3 H chain mammalian expression plasmid, pING2234. The V region for the cDNA clone p01G-11 was engineered to be compatible with the eukaryotic expression plasmid pING2227. See FIG. 5 for construction of plasmid pING2227. Not drawn to scale.
Figure 23B:
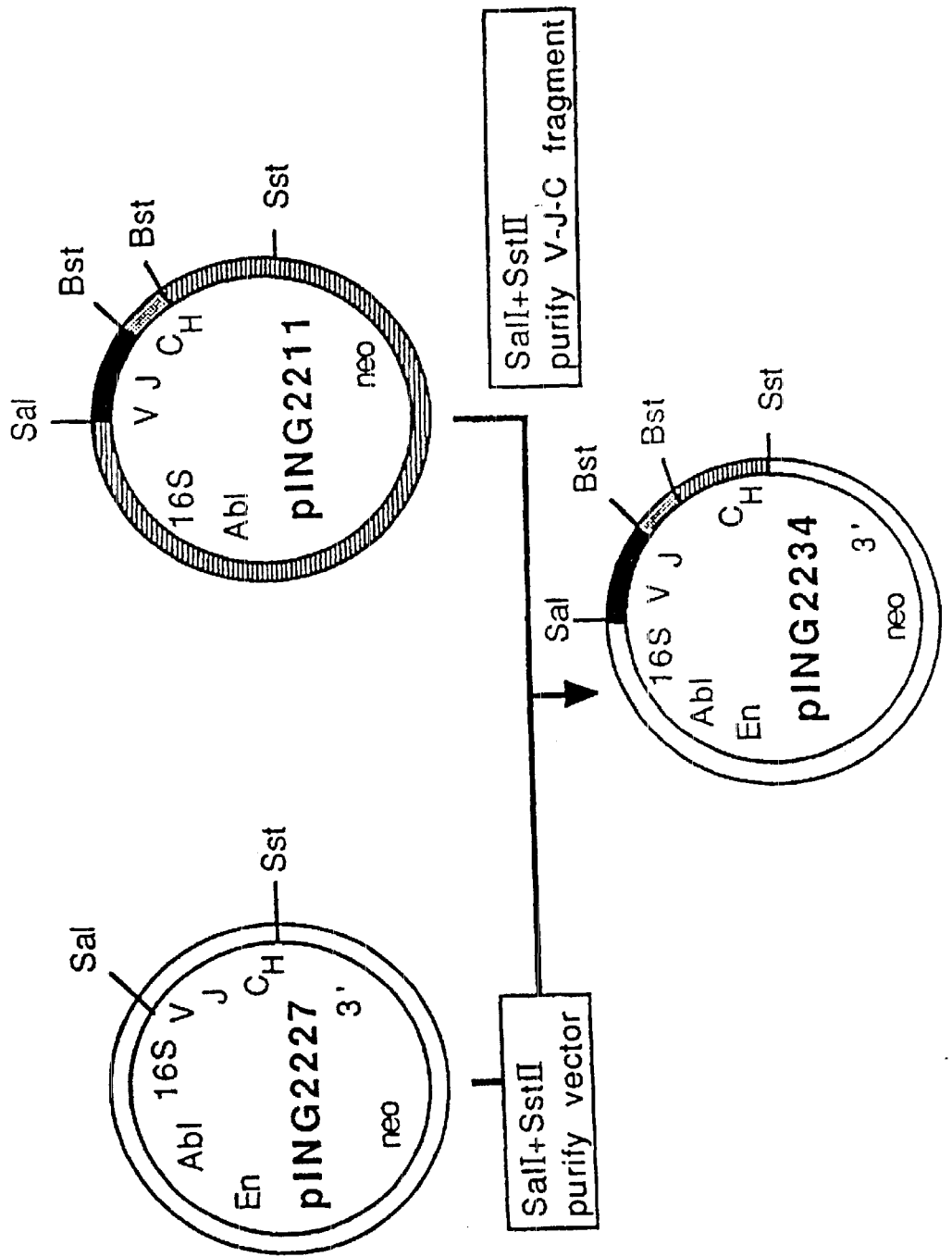

The cDNA clone containing the Co-1 H chain, p10G-11, was adapted for expression making use of restriction enzyme recognition sites occurring naturally in this plasmid, FIG. 23. An NcoI site overlaps the initiation codon ATG, and a BstEII is located in the J-region. A derivative of the human C gene cDNA clone pGMH-6, Liu, A. Y., et al., *Proc. Natl. Acad. Sci. USA* 84:3439–3443 (1987), found in pING1714 contains a BstEII site to which the Co-1 H chain V-region can be ligated. The final H chain expression plasmid is pING2234.

Figure 24A:
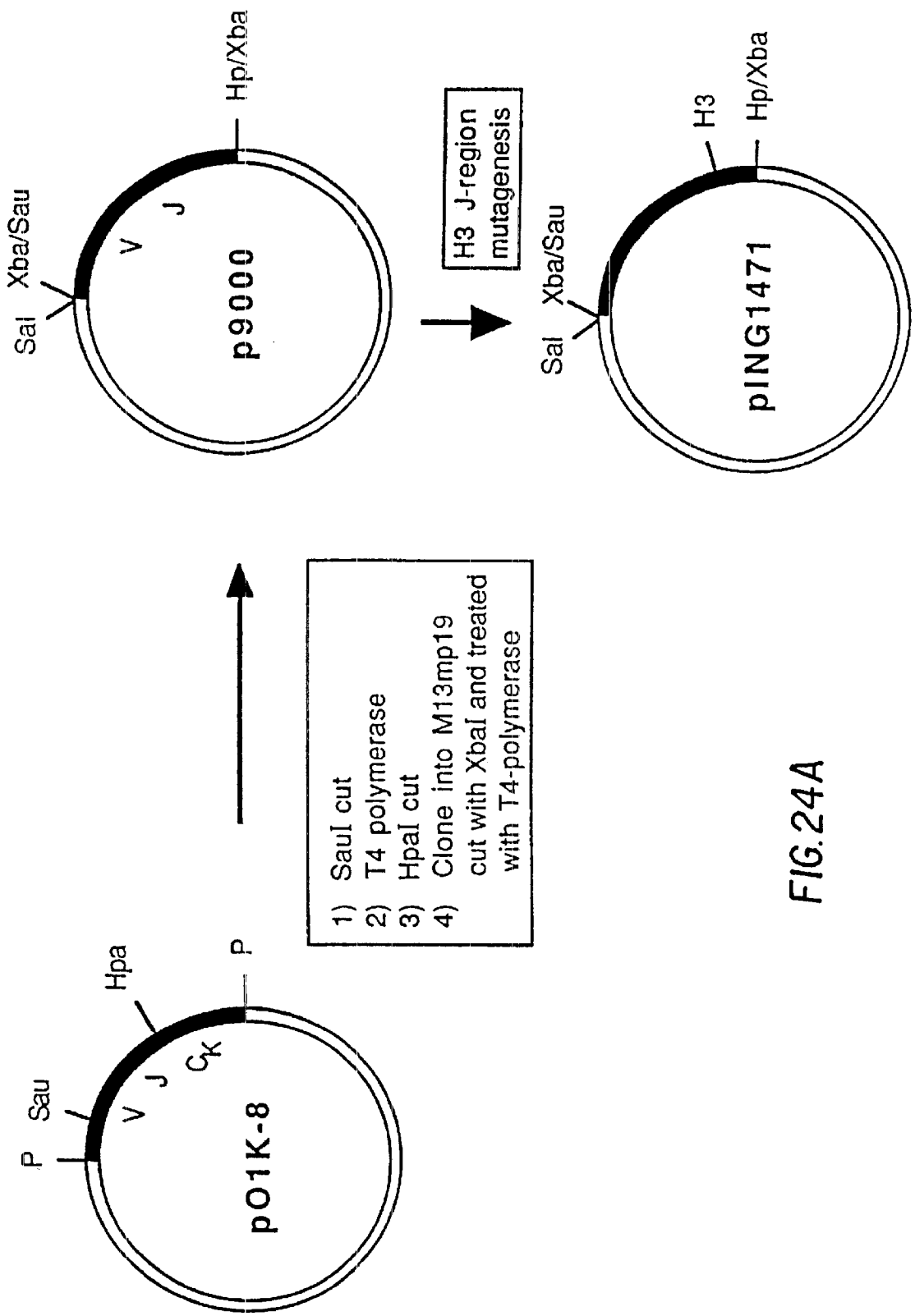
FIGS. 24(A and B). Construction scheme for the chimeric mouse-human ING-3 L chain mammalian expression plasmid pING2204. The V region from the cDNA clone p01K-8 was engineered to be compatible with the eukaryotic expression plasmid pING1712. See FIG. 2 for construction of plasmid pING1712. Not drawn to scale.
Figure 24B:
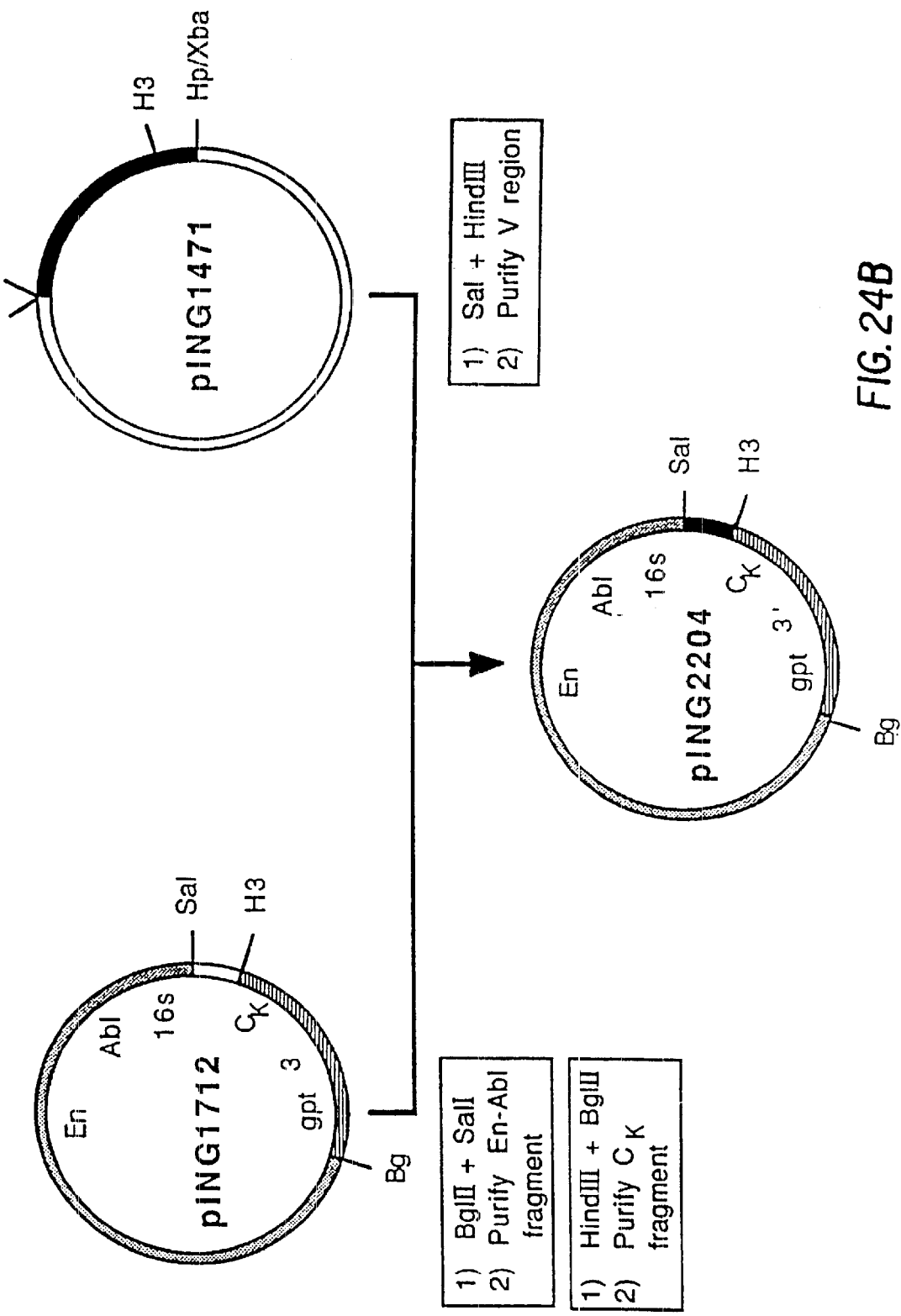

The cDNA clone containing the Co-1 L chain, p10K-8, was adapted for expression in pING1712. The naturally occurring SauI (MstII) restriction enzyme recognition site located 14 bp upstream of the initiation codon ATG (FIG. 21) was used to locate a SalI site near that position, and site directed mutagenesis as described by Kramer, W., et al., supra, was used for J-region mutagenesis with the $J_\kappa 5$ HindIII primer 5'-CAGCTCAAGCTTGGTCCC-3'. The SalI to HindIII fragment of the mouse $V_\kappa$ module from pING1471 was joined to the human $C_\kappa$ module in pING1712 by the procedure outlined in FIG. 24, forming pING2204.

d. ING-4

The chimeric H chain expression plasmid was derived from the replacement of the $V_H$ module in pING2227 with the ME4 $V_H$-J-$C_H$ module assembled in pING2222 (FIG. 31). Two restriction fragments from pING2222 containing H chain sequences (SalI to ApaI and ApaI to SstII) were ligated to pING2227 cut with SalI and SstII (FIG. 31D, E) to generate pING2232. This plasmid directs the synthesis of chimeric ING-4 H chain when transfected into mammalian cells. FIG. 31 details the cloning steps required to manipulate the cDNA $V_H$ region into pING2232.

Figure 32A:
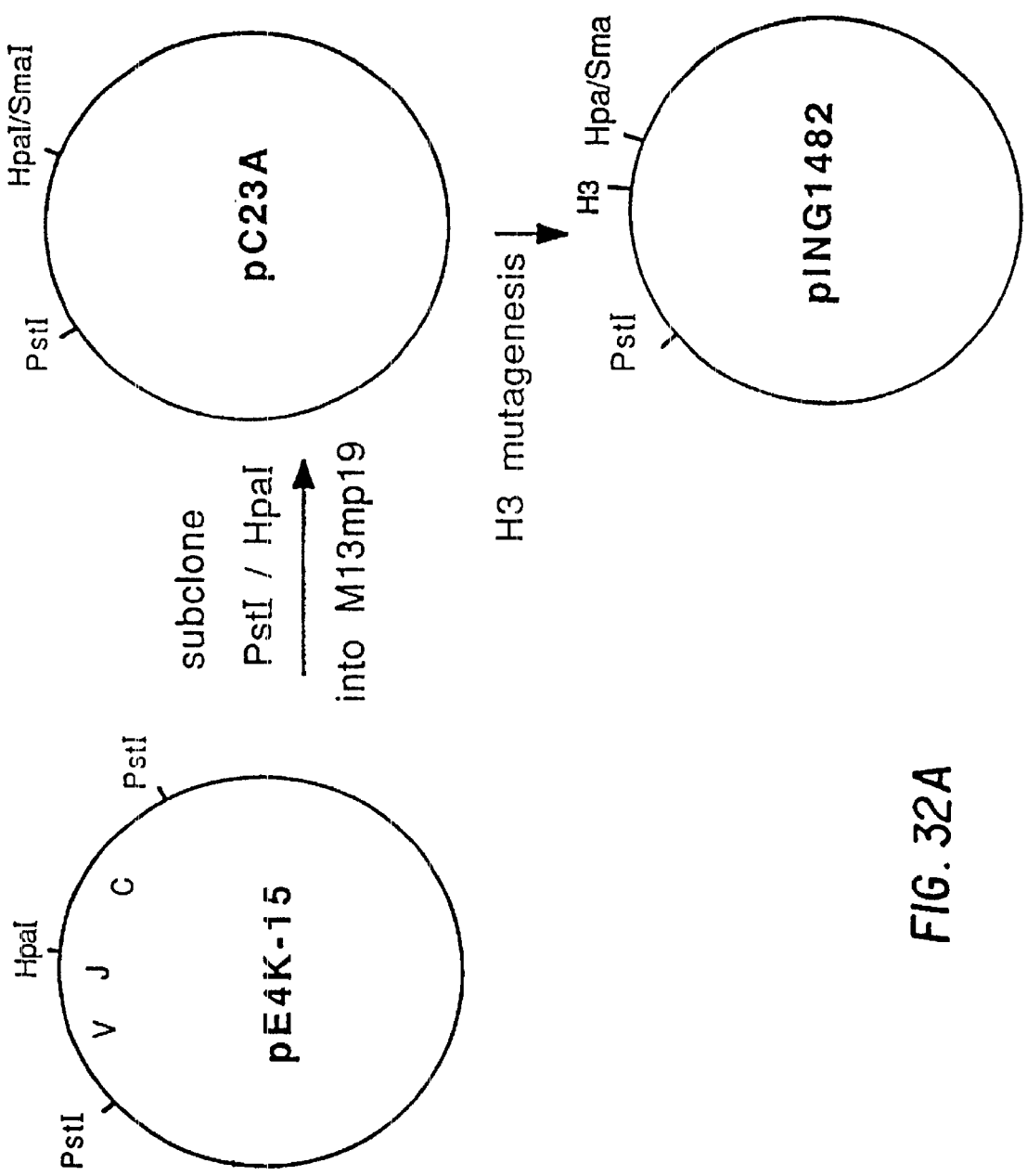
FIGS. 32(A and B). Construction scheme for the chimeric mouse-human ING-4 L chain mammalian expression plasmid pING2216. The V region from the cDNA clone pE4K-15 was engineered to be compatible with the eukaryotic expression plasmid pING1712. Plasmid pING2216 contains the following gene regulatory elements useful for expression in mammalian cells: 1) the IgH enhancer element, 2) the Abelson LTR promoter, 3) the SV40 19S/16S splice module, and 4) a human κ polyadenylation signal sequence. It also contains the entire human $C_\lambda$ region (Liu A. Y., et al. supra) and the GPT gene which allows for mycophenolic acid resistance in transfected cells. Not drawn to scale.
Figure 32B:
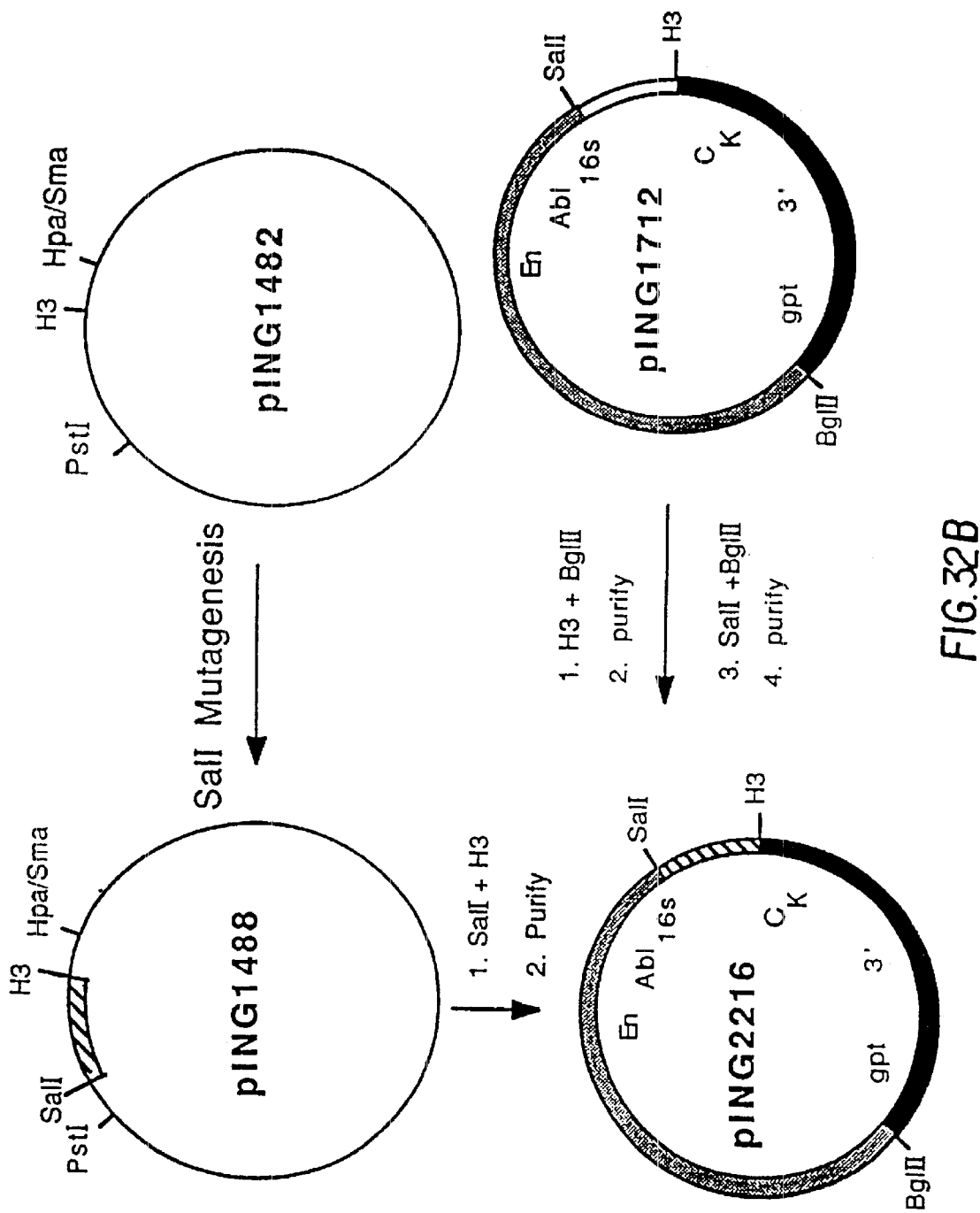

For the chimeric ING-4 L chain gene, the SalI to HindIII fragment of the mouse $V_\kappa$ module from pING1488 was joined to the human $C_K$ module in pING1712 by the procedure outlined in FIG. 32, forming pING2216.

e. KM10

Figure 39A:
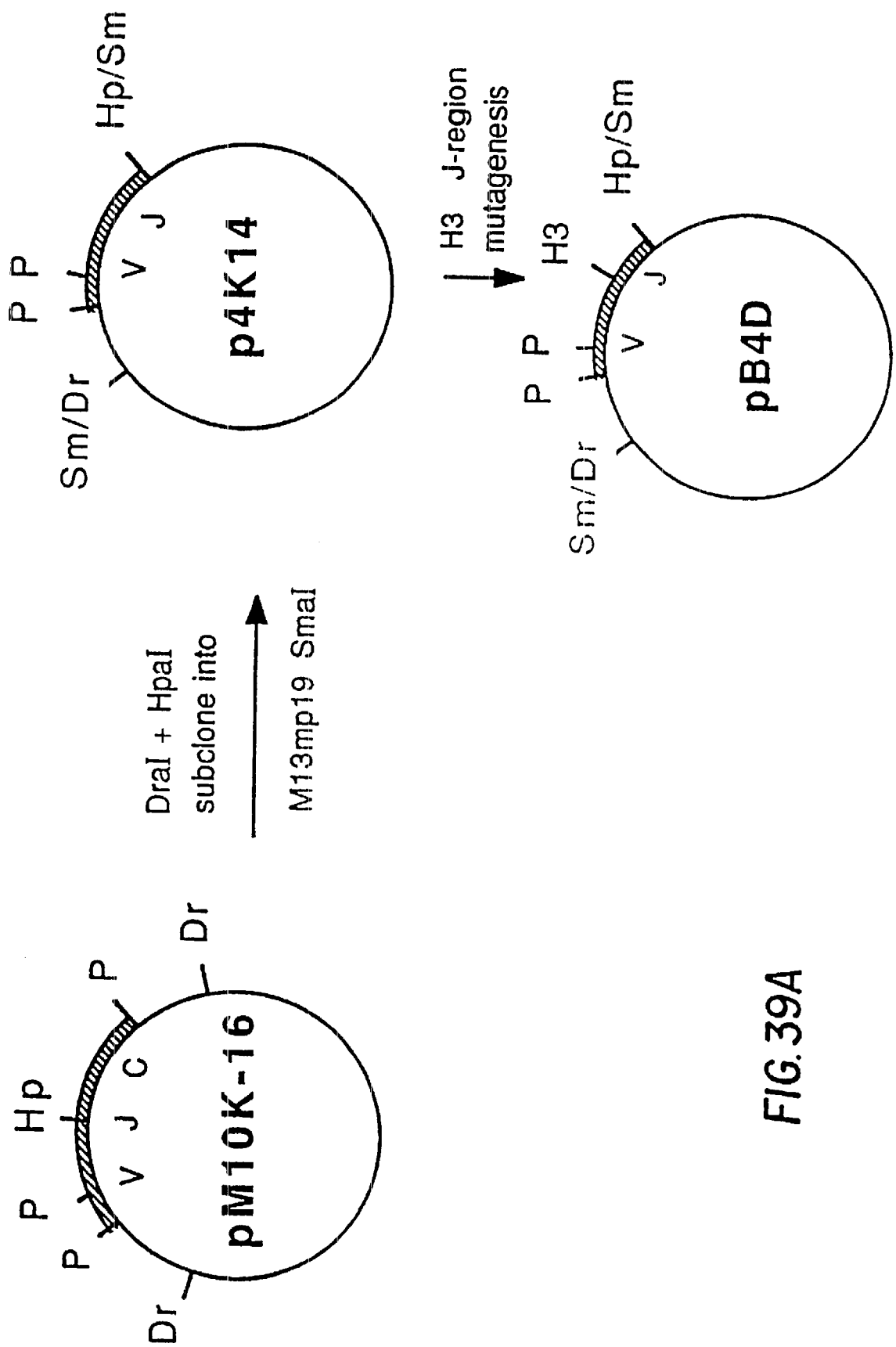
FIGS. 39(A and B). Construction scheme for the chimeric mouse-human KM10 L chain mammalian expression plasmid pING2242. The V region from the cDNA clone pM10K-16 was engineered to be compatible with the eukaryotic expression plasmid pING1712. See FIG. 2 for construction of plasmid pING1712. Not drawn to scale.
Figure 39B:
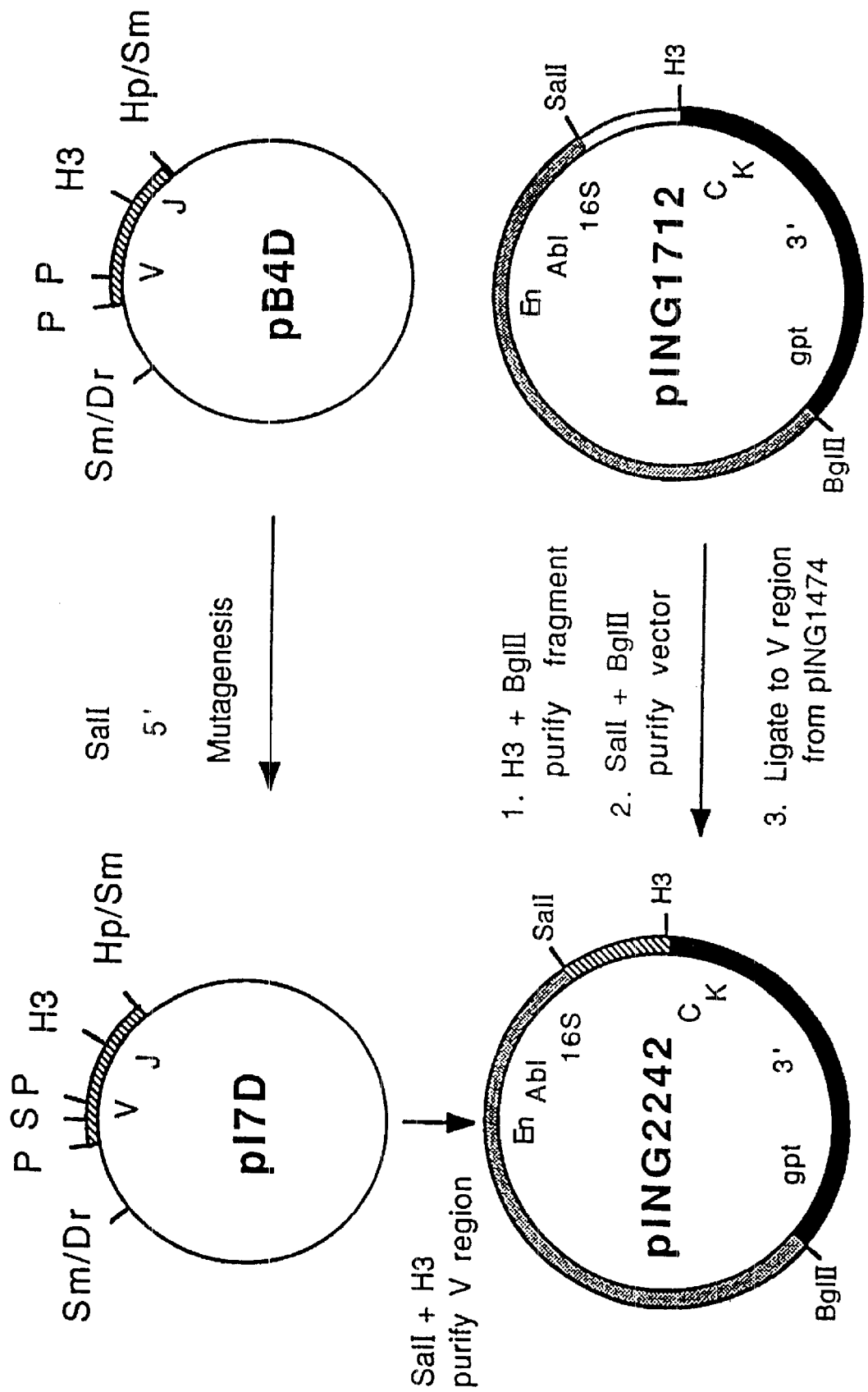

The cDNA clone containing the KM10 H chain, pK10G, was adapted for mammalian expression by introducing convenient restriction endonucleases sites by site directed mutagenesis (Kramer, W., et al., (1984), supra) into appropriate M13 subclones (FIG. 39). Oligonucleotides were synthesized on a Cyclone DNA synthesizer, New Brunswick Scientific Co.., and purified by acrylamide gel electrophoresis. The J-region mutagenesis primer 5'-GAGACGGTGACCGAGGTTCC-3' was used to insert a BstEII site into the M13 subclone p4G2, and the oligonucleotide 5'-ATCCATGATGTCGACGACCTTGGGC-3' was used to insert a SalI restriction site into pR6C upstream of the initiation codon ATG. The restriction fragment containing the KM10 H chain V-region bounded by SalI and BstEII was then cloned into the expression vector pING2227.

The cDNA clone containing the KM10 L chain, pM10K-16, was adapted for mammalian expression in a similar way (FIG. 39). The J-region mutagenesis primer 5'-CAGCTCAMGCTTGGTCCC-3' was used to insert a HindIII site into the M13 subclone p4K14, and the oligonucleotide 5'-GGATTTTGGTCGACGGCTAMTTAGTG-3' was used to insert a SalI restriction site into p4BD upstream of the initiation codon ATG. The restriction fragment containing the KM10 L chain V-region bounded by SalI and HindIII was then cloned into the expression vector pING1712.

5. Stable Transfection of Mouse Lymphoid Cells for the Production of Chimeric Antibody The cell line Sp2/0 (American Type Culture Collection # CRL1581) was grown in Dulbecco's Modified Eagle Medium plus 4.–5 g/l glucose (DMEM, Gibco) plus 10% fetal bovine serum. Media were supplemented with glutamine/penicillin/streptomycin (Irvine Scientific, Irvine, Calif.).

The electroporation method of Potter, H., et al. (*Proc. Natl. Acad. Sci. USA* 81:7161 (1984)) was used. After transfection, cells were allowed to recover in complete DMEM for 24 hours, and then seeded at 10,000 to 50,000 cells per well in 96-well culture plates in the presence of selective medium. G418 (GIBCO) selection was at 0.8 mg/ml, and mycophenolic acid (Calbiochem) was at 6 µg/ml plus 0.25 mg/ml xanthine. The electroporation technique gave a transfection frequency of $1-10\times10^{-5}$ for the Sp2/0 cells.

a. The chimeric ING-1 L chain expression plasmid pING2207 was linearized by digestion with PvuI restriction endonuclease and transfected into Sp2/0 cells, giving mycophenolic acid resistant clones which were screened for L chain synthesis. The best producer after outgrowth and subsequent subcloning, was transfected with pING2225, the expression plasmid containing the chimeric ING-1 H chain gene. After selection with G418, the clone producing the most L plus H chain was subcloned (cell line C499) and secreted antibody at approximately 10–15 µg/µl.

b. The chimeric ING-2 L chain expression plasmid pING2203 was linearized by digestion with PvuI restriction endonuclease and transfected into Sp2/0 cells, giving mycophenolic acid resistant clones which were screened for L chain synthesis. The best producer after outgrowth and subsequent subcloning, was transfected with pING2227, the expression plasmid containing the chimeric ING-2 H chain gene. After selection with G418, the clone producing the most L plus H chain was subcloned (cell line C534) and secreted antibody at approximately 10–15 µg/ml.

c. The chimeric ING-3 L chain expression plasmid pING2204 was linearized by digestion with PvuI restriction endonuclease and transfected into Sp2/0 cells, giving mycophenolic acid resistant clones which were screened for L chain synthesis. The best producer after outgrowth and subsequent subcloning was transfected with pING2234, the expression plasmid containing the chimeric ING-3 H chain gene. After selection with G418, the clone producing the most L plus H chain was subcloned (cell line C542) and secreted antibody at approximately 5 µg/ml.

d. The chimeric ING-4 L chain expression plasmid pING2216 was linearized by digestion with PvuI restriction endonuclease and transfected into Sp2/0 cells, giving mycophenolic acid resistant clones which were screened for L chain synthesis. The best producer after outgrowth and subsequent subcloning, was transfected with pING2232, the expression plasmid containing the chimeric ING-4 H chain gene. After selection with G418, the clone producing the most L plus H chain was subcloned (cell line C489) and secreted antibody at approximately 10 μg/ml.

e. The chimeric KM10 L chain expression plasmid pING2242 was linearized by digestion with PvuI restriction endonuclease and transfected into Sp2/0 cells, giving mycophenolic acid resistant clones which were screened for L chain synthesis. The best producer after outgrowth and subsequent subcloning, was transfected with PvuI-linearized pING2240, the expression plasmid containing the chimeric KM10 H chain gene. After. selection with G418, the clone producing the most L plus H chain, Sp2/0-22426G2-22401C4 (ATCC Accession #HB 10131), secreted antibody at approximately 21 μg/ml.

6. Purification of Chimeric Antibodies Secreted in Tissue Culture a. ING-1

Sp2/0.pING222071C5.B7-pING22253F2.G6 (C499) cells were grown in culture medium HB101 (Hana Biologics), supplemented with 10 mM HEPES, 1× Glutamine-Pen-Strep (Irvine Scientific #9316). The spent medium was centrifuged at about 14,000×g for 20 minutes and the supernatant was filtered through a 0.45 μg millipore nitrocellulose membrane filter and stored frozen. The antibody level was measured by ELISA. Approximately 20 L of cell culture supernatant was concentrated 10-fold using a S10 Y30 cartridge and DC-10 concentrator (Amicon Corp.). Supernatant containing about 10 mg of antibody was loaded onto a 2 ml Protein A-Sepharose column (Pharmacia) pre-equilibrated with phosphate buffered saline, pH 7.4 (PBS). After washing with 40 ml of PBS, the antibody was eluted with 20 ml each of 0.1M citric acid at pH 4.5, pH 3.5, and pH 2.3, collecting 1 ml fractions into 0.1 ml of 2M Tris (hydromethyl) amino methane (SIGMA). The loading and elution of the Protein A-Sepharose column was repeated until all the antibody was eluted. Fractions containing antibody were combined and concentrated 20-fold by ultrafiltration (YM30 membrane, stirred cell, Amicon Corp.), diluted 10-fold with PBS, reconcentrated 10-fold, diluted 10-fold with PBS, and finally reconcentrated 10-fold. The antibody was stored in 1 ml aliquots at −20°.

b. ING-2

Sp2/0.pING22031B5.14-pING22271D3.F11 (C534) cells were grown in culture medium HB101 (Hana Biologics), supplemented with 10 mM HEPES, 1×Glutamine-Pen-Strep (Irvine Scientific #9316). The spent medium was centrifuged at about 14,000×g for 20 minutes and the supernatant was filtered through a 0.45 u millipore nitrocellulose membrane filter and stored frozen. The antibody level was measured by ELISA. Approximately 20 L of cell culture supernatant was concentrated 10-fold using a S10Y30 cartridge and DC-10 concentrator (Amicon Corp.). Supernatant containing about 10 mg of antibody was loaded onto a 2 ml Protein A-Sepharose column (Pharmacia) preequilibrated with phosphate buffered saline, pH 7.4 (PBS). After washing with 40 ml of PBS, the antibody was eluted with 20 ml each of 0.1M citric acid at pH 4.5, pH 3.5, and pH 2.3, collecting 1 ml fractions into 0.1 ml of 2M Tris (hydroxymethyl) amino methane (SIGMA). The loading and elution of the Protein A-Sepharose column was repeated until all the antibody was eluted. Fractions containing antibody were combined and concentrated 20-fold by ultrafiltration (YM30 membrane, stirred cell, Amicon Corp.), diluted 10-fold with PBS, reconcentrated 10-fold,-diluted 10- fold with PBS, and finally reconcentrated 10 fold. The antibody was stored in 1 m aliquots at −20°.

c. ING-3

Sp2/0.pING2204587.F9-pING22342G11.C11 (cell line C542) cells were grown in culture medium HB101 (Hana Biologics), supplemented with 10 mM HEPES, 1×Glutamine-Pen-Strep (Irvine Scientific #9316). The spent medium was centrifuged at about 14,000×g for 20 minutes and the supernatant was filtered through a 0.45 micron millipore nitrocellulose membrane filter and stored frozen. The antibody level was measured by ELISA. approximately 20 L of cell culture supernatant was concentrated 10-fold over a S10Y30 cartridge using DC-10 concentrator (Amicon corp). Supernatant containing about 10 mg of antibody was loaded onto a 2 ml Protein A-Sepharose column (Pharmacia) preequilibrated with phosphate buffered saline, pH 7.4 (PBS). After washing with 40 ml of PBS, the antibody was eluted with 20 ml each of 0.1M citric acid at pH 4.5, pH 3.5, and pH2.3, collecting 1 ml fractions into 0.1 ml of 2M Tris (hydroxymethyl) amino methane (SIGMA). The loading and elution of the Protein A-Sepharose column was repeated until all the antibody was eluted. Fractions containing antibody were combined and concentrated 20-fold by ultrafiltration (YM30 membrane, stirred cell, Amicon Corp.), diluted 10-fold with PBS, reconcentrated 10-fold, diluted 10-fold with PBS, and finally reconcentrated 10 fold. The antibody was stored in 1 ml aliquots at −20°.

d. ING-4

Sp2/0.pING22162C2.1C7-pING22321B5.F5 (C489) cells were grown in culture medium HB101 (Hana Biologics), supplemented with 10 mM HEPES, 1× Glutamine-Pen-Strep (Irvine Scientific #9316). The spent medium was centrifuged at about 14,000×g for 20 minutes and the supernatant was filtered through a 0.45 u Millipore nitrocellulose membrane filter and stored frozen. The antibody level was measured by ELISA. approximately 20 L of cell culture supernatant was concentrated 10-fold using a S10Y30 cartridge and DC-10 of antibody was loaded onto a 2 ml Protein A-Sepharose column (Pharmacia) preequilibrated with phosphate buffered saline, pH 7.4 (PBS). After washing with 40 ml of PBS, the antibody was eluted with 20 ml each of 0.1M citric acid at pH 4.5, pH 3.5, and pH 2.3, collecting 1 ml fractions into 0.1 ml of 2M Tris (hydroxymethyl) amino methane (SIGMA). The loading and elution of the Protein A-Sepharose column was repeated until all the antibody was eluted. Fractions containing antibody were combined and concentrated 20-fold by ultrafiltration (YM30 membrane, stirred cell, Amicon Corp.), diluted 10-fold with PBS, reconcentrated 10-fold, diluted 10- fold with PBS, and finally reconcentrated 10 fold. The antibody was stored in 1 m aliquots at −20°.

e. KM10

Sp2/0–22426G2–22401C4 cells (ATCC Accession #HB 10131) were grown in culture medium HB101 (Hana Biologics) +1% Fetal Bovine Serum, supplemented with 10 mM HEPES, 1× Glutamine-Pen-Strep (Irvine Scientific #9316). The spent medium was centrifuged at about 14,000×g for 20 minutes and the supernatant was filtered through a 0.45 μM Millipore nitrocellulose membrane filter and stored frozen. The antibody content was measured by ELISA. approximately 15.5 L of cell culture supernatant were concentrated 10-fold over a S10Y30 cartridge using DC-10 concentrator (Amicon Corp.). Supernatant containing about 80 mg of antibody was loaded onto a 100 ml Protein,A-column (MabLab, Oros) in 1.5 M NaCl, pH 8.4.

The KM10 antibody was eluted with a pH gradient (pH 2–9) and was found to elute between pH 3.5–4.0. Fractions containing antibody (70% yield) were combined and concentrated 18-fold by ultrafiltration (YM30 membrane, stirred cell, Amicon Corp.), diluted 20-fold with PBS, reconcentrated 5-fold, diluted 1.5-fold with PBS, and finally reconcentrated 10 fold. The antibody was stored in 1.5 ml aliquots at −20° C.

7. Analysis of Properties of Chimeric Antibodies a. ING-1

(1) Inhibition of Binding

The mouse B38.1 and chimeric ING-1 antibodies were compared in a binding inhibition assay. Such inhibition assays are used to establish the identity of recognition of antigen. Mouse B38.1 mAb was labeled with $^{125}$I; purified unlabeled chimeric ING-1 and mouse B38.1 antibodies were examined for their ability to inhibit the binding of radiolabeled B38.1 antibody to target cells (HT29 colon tumor). The chimeric ING-1 and mouse B38.1 antibodies were identical in inhibition of the binding of labeled B38.1 antibody to HT29 tumor cells (Table 3).

As part of these studies, an estimate was made of antibody, avidity. The avidity of mouse B38.1 had been previously determined to be approximately $2.5 \times 10^8$ $M^{-1}$. The above data indicate that there are no significant differences in avidity between the chimeric ING-1 and the mouse B38.1 antibodies.

(2) Functional Assays

A comparison was made between the ability of the chimeric ING-1 and the mouse B38.1 antibodies to lyse human tumor cells in the presence of human peripheral blood leukocytes as effector cells (mediating Antibody-Dependent Cellular Cytotoxicity, ADCC), or human serum as complement (mediating Complement-Dependent Cytolysis, CDC). Table 4 shows that the chimeric ING-1 antibody is extremely efficient at mediating ADCC lysis of the human breast carcinoma cell line BT-20, but the mouse B38.1 antibody is ineffective. Table 5 shows that the chimeric ING-1 antibody mediates up to 16% lysis of human colon carcinoma HT-29 cells by CDC, but the mouse B38.1 is ineffective.

b. ING-2

(1) Inhibition of Binding

The mouse Br-3 and chimeric ING-2 antibodies were compared in a binding inhibition assay. Such inhibition assays are used to establish the identity of recognition of antigen. Mouse Br-3 mAb was labeled with $^{125}$I; purified unlabeled chimeric ING-2 and mouse Br-3 antibodies were examined for their ability to inhibit the binding of radiolabeled Br-3 antibody to target cells (BT20 breast tumor). The chimeric ING-2 and mouse Br-3 antibodies were identical in inhibition of the binding of labelled Br-3 antibody to BT20 tumor cells (Table 6).

As part of these studies, an estimate was made of antibody avidity. The avidity of mouse Br-3 had been previously determined to be approximately $7 \times 10^8$ $M^{-1}$. The above data indicate that there are no significant differences in avidity between the chimeric ING-2 and the mouse Br-3 antibodies.

(2) Functional Assays

A comparison was made between the ability of the chimeric ING-2 and the mouse Br-3 antibodies to lyse human tumor cells in the presence of human peripheral blood leukocytes as effector cells (mediating Antibody-Dependent Cellular Cytotoxicity, ADCC), or human serum as complement (mediating Complement-Dependent Cytolysis, CDC). Table 7 shows that the chimeric ING-2 antibody is more active at mediating ADCC of the human breast carcinoma cell line BT-20 than the mouse Br-3 antibody. Table 8 shows that the chimeric ING-2 and mouse Br-3 antibodies are ineffective at mediating CDC of human breast carcinoma cell line MCF-7.

c. ING-3

(1) Inhibition of Binding

The mouse Co-1 and chimeric ING-3 antibodies were compared in a binding inhibition assay. Such inhibition assays are used to establish the identity of recognition of antigen. Mouse Co-1 mAb was labeled with $^{125}$I; purified unlabeled chimeric ING-3 and mouse Co-1 antibodies were examined for their ability to inhibit the binding of radio labeled Co-1 antibody to target cells (HT29 colon tumor). The chimeric ING-3 and mouse Co-1 antibodies both inhibited the binding of labelled Co-1 antibody to HT29 tumor cells (Table 9), indicating that the ING-3 and Co-1 antibodies bind to the same target antigen.

(2) Functional Assays

A comparison was made between the ability of the chimeric ING-3 and the mouse Co-1 antibodies to lyse human tumor cells in the presence of human peripheral blood leukocytes as effector cells (mediating antibody-dependent cellular cytotoxicity, ADCC), or human serum as complement (mediating complement-dependent cytolysis, CDC). Table 10 shows that the chimeric ING-3 antibody is active at mediating ADCC of the human colon carcinoma cell line HT29, as is mouse Co-1 antibody whose H chain is of isotype IgG3. Table 11 shows that the chimeric ING-3 antibody mediates up to 7.6% lysis of human colon carcinoma HT-29 cells by CDC, as compared to 19.6% by mouse Co-1 antibody at 10 µg/ml.

d. ING-4

(1) Inhibition of Binding

The mouse ME4 and chimeric ING-4 antibodies were compared in a binding inhibition assay. Such inhibition assays are used to establish the identity of recognition of antigen. Chimeric ING-4 Fab from yeast was biotinylated; purified chimeric ING-4 and mouse ME4 antibodies were examined for their ability to inhibit the binding of biotinylated yeast chimeric ING-4 Fab to target cells (HT29 -colon tumor). The chimeric ING-4 and mouse ME4 antibodies were capable of inhibiting the binding of biotinylated yeast chimeric .ING-4 Fab to HT29 tumor cells (Table 12).

The above data indicated that the chimeric ING-4 antibody with a 50% inhibition concentration at 0.12 ug/ml, is far stronger in inhibition of the binding of biotinylated yeast chimeric ING-4 Fab than that of mouse ME4 antibody with 50% inhibition concentration at 7.5 ug/ml . The reason may be that mouse ME4 hybridoma is a poor producer, and the ME4 antibody preparation is highly contaminated with mouse IgG.

(2) Functional Assays

A comparison was made between the ability of the chimeric ING-4 and the mouse ME4 antibodies to lyse human tumor cells in the presence of human peripheral blood leukocytes as effector cells (mediating Antibody-Dependent Cellular Cytotoxicity, ADCC), or human serum as complement (mediating Complement-Dependent Cytolysis, CDC). Table 13 and Table 14 show that the chimeric ING-4 antibody is functional at mediating ADCC lysis of the human colon carcinoma cell line HT-29, and is as good as mouse ME4 antibody. However, since the mouse ME4 hybridoma is a poor producer and the antibody preparation is heavily contaminated with mouse IgG, chimeric ING-4 appears better than its counterpart, mouse ME4 antibody (Table 14). Table 15 indicates that both ING-4 and mouse ME4 antibody are slightly positive mediating lysis of human colon carcinoma HT-29 cells by CDC with ING-4 slightly better than mouse ME4.

e. KM10

(1) Inhibition of Binding

The mouse KM10 mAb and chimeric KM10 antibodies were compared in a binding inhibition assay. Such inhibition assays are used to establish the identity of recognition of antigen. Mouse KM10 mAb was labeled with $^{125}$I; purified unlabeled chimeric KM10 and mouse KM10 antibodies were examined for their ability to inhibit the binding of radio-labeled KM10 antibody to target cells (LS174T colon tumor). The chimeric KM10 and mouse KM10 antibodies were identical in inhibition of the binding of labeled KM10 antibody to LS174T tumor cells (Table 11).

(2) Functional Assays

A comparison was made between the ability of the chimeric KM10 and the mouse KM10 antibodies to lyse human tumor cells in the presence of human peripheral blood leukocytes as ADCC effector cells, or human serum as complement for CDC. Table 12 shows that the chimeric KM10 antibody was capable of mediating ADCC while the mouse antibody was not. Neither mouse nor chimeric KM10 were able to detectably lyse target LS174T cells in CDC in the presence of human serum.

TABLE 3

Inhibition of Binding of B38.1 Antibody to Tumor Cells

| Antibody | % Inhibition by Competing Antibody:[a] | | |
|---|---|---|---|
| Concentration µg/ml | Chimeric ING-1 | Mouse B38.1 | Human IgG[b] |
| 0.033 | 17 | .22 | 27 |
| 0.10 | 46 | 52 | −3 |
| 0.30 | 84 | 75 | 0 |
| 0.89 | 99 | 93 | 12 |
| 2.67 | 100 | 100 | −10 |
| 8.0 | 100 | 100 | 5 |

[a]$^{125}$I-labeled B38.1 antibody was incubated with HT-29 tumor cells in the presence of the competing antibody at 4° C. Cells were washed free of unbound antibody, and cell-bound radioactivity was used to determine the % inhibition of binding.
[b]Human IgG is used as a nonspecific antibody control.

TABLE 4

Antibody-Dependent Cellular Cytotoxicity and Complement Dependent Cytotoxicity Mediated by Chimeric ING-1 Antibody[a]

| Antibody | % Cytolysis: | | | |
|---|---|---|---|---|
| | − Serum | | + Serum | |
| Concentration µg/ml | Chimeric ING-1 | Mouse B38.1 | Chimeric ING-1 | Mouse B38.1 |
| .00001 | 58 | 37 | 23 | 20 |
| .0001 | 56 | 32 | 33 | 24 |
| .001 | 78 | 32 | 61 | 21 |
| .01 | 87 | 30 | 85 | 22 |
| 0.1 | 88 | 28 | 95 | 21 |
| 1.0 | 96 | 29 | 97 | 21 |
| 10.0 | 92 | 25 | 85 | 20 |

[a]BT-20 tumor cells were labeled with $^{51}$Cr, washed, and incubated with freshly isolated peripheral blood leukocytes at a ratio of 50 leukocytes per tumor cell for 4 hours. The amount of $^{51}$Cr released into the medium was used to calculate the % cytolysis as compared to cells lysed by the addition of 1% NP40. This assay was done with and without 17% human serum as a source of complement. The basal level of leukocyte killing was 17% for leukocytes alone, and 21% for leukocytes plus serum.

TABLE 5

Complement Dependent Cytolysis Mediated by Chimeric ING-1 Antibody[a]

| Antibody | % Cytolysis Mediated by: | |
|---|---|---|
| Concentration µg/ml | Chimeric ING-1 | Mouse B38.1 |
| .003 | 1.4 | 0.1 |
| .016 | 1.6 | 0.4 |
| .08 | 8.1 | 0.5 |
| 0.4 | 16.6 | 0.2 |
| 2.0 | 12.7 | 0.4 |
| 10.0 | 11.9 | 0.0 |
| 50.0 | 11.5 | 0.6 |

[a]HT-29 tumor cells were labeled with Cr$^{51}$, washed, and incubated with 17% human serum and antibody at the indicated concentrations for 4 hours at 37° C. The amount of $^{51}$Cr released into the medium was used to calculate the % cytolysis as compared to cells lysed by the addition of 1% NP-40.

TABLE 6

Inhibition of Binding of Br-3 Antibody to Tumor Cells[a]

| Antibody | % Inhibition by Competing Antibody: | | |
|---|---|---|---|
| Concentration µg/ml | Chimeric ING-2 | Mouse Br-3 | Human IgG[b] |
| 0.07 | −19 | −8 | 24 |
| 0.20 | −1 | 2 | 11 |
| 0.60 | 27 | 17 | −50 |
| 1.8 | 48 | 52 | −11 |
| 5.3 | 81 | 75 | −8 |
| 16.0 | 98 | 96 | −29 |

[a]$^{125}$I-labeled Br-3 antibody was incubated with BT-20 tumor cells in the presence of the competing antibody at 4° C. Cells were washed free of unbound antibody, and cell-bound radioactivity was used to determine the % inhibition of binding.
[b]Human IgG is used as a nonspecific antibody control.

TABLE 7

Antibody-Dependent Cellular Cytotoxicity Mediated by Chimeric ING-2 Antibody[a]

| Antibody | % Cytolysis Mediated by: | |
|---|---|---|
| Concentration µg/ml | Chimeric ING-2 | Mouse Br-3 |
| 0.003 | 7 | 11 |
| 0.016 | 8 | 11 |
| 0.08 | 11 | 12 |
| 0.4 | 19 | 14 |
| 2.0 | 34 | 15 |
| 10.0 | 38 | 19 |
| 50.0 | 36 | 19 |

[a]BT-20 tumor cells were labeled with $^{51}$Cr, washed, and incubated with freshly isolated peripheral blood leukocytes at a ratio of 50 leukocytes per tumor cell for 4 hours at 37° C. The amount of $^{51}$Cr released into the medium was used to calculate the % cytolysis as compared to cells lysed by the addition of 1% NP40.

TABLE 8

Complement Dependent Cytolysis Mediated by Chimeric ING-2 Antibody[a]

| Antibody | % Cytolysis Mediated by: | |
|---|---|---|
| Concentration µg/ml | Chimeric ING-2 | Mouse Br-3 |
| .016 | 0.14 | 0.09 |
| .08 | 0.21 | 0.73 |
| 0.4 | −0.40 | 0.37 |
| 2.0 | 0.77 | 0.69 |
| 10.0 | −0.25 | 0.92 |
| 50.0 | 0.84 | 0.46 |

[a]MCF-7 tumor cells were labeled with $^{51}Cr$, washed, and incubated with 17% human serum and antibody at the indicated concentrations for 4 hours at 37° C. The amount of $^{51}Cr$ released into the medium was used to calculate the % cytolysis as compared to cells lysed by the addition of 1% NP-40.

TABLE 9

Inhibition of Binding of Co-1 Antibody to HT-29 Tumor Cells

| Antibody | % Inhibition by Competing Antibody:[a] | | |
|---|---|---|---|
| Concentration µg/ml | Chimeric ING-3 | Mouse Co-1 | Human IgG[b] |
| 0.14 | 11 | 3 | −1 |
| 0.41 | 6 | −4 | 5 |
| 1.23 | 7 | 3 | −2 |
| 3.70 | 12 | 33 | 0 |
| 11.1 | 28 | 55 | 2 |
| 33.3 | 46 | 85 | 0 |
| 100 | 60 | 93 | 0 |
| 300 | 86 | 94 | −5 |

[a]-$^{125}$I-labeled Co-1 antibody was incubated with HT-29 tumor cells in the presence of the competing antibody at 4° C. Cells were washed free of unbound antibody, and cell-bound radioactivity was used to determine the % inhibition of binding.
[b]-Human IgG is used as a nonspecific antibody control.

TABLE 10

Antibody-Dependent Cellular Cytotoxicity Mediated by Chimeric ING-3 Antibody[a]

| Antibody | % Cytolysis Mediated by: | |
|---|---|---|
| Concentration µg/ml | Chimeric ING-3 | Mouse Co-1 |
| 10. | 67 | 71 |
| 2. | 58 | 64 |
| 0.4 | 53 | 57 |
| 0.08 | 43 | 50 |
| 0.016 | 37 | 45 |
| 0.0032 | 29 | 40 |
| 0.00064 | 28 | 34 |
| 0. | 19 | 19 |

[a]-HT-29 tumor cells were labeled with $^{51}Cr$, washed, and incubated with freshly isolated peripheral blood leukocytes at a ratio of 60 leukocytes per tumor cell for 4 hours at 37° C. The amount of $^{51}Cr$ released into the medium was used to calculate the % cytolysis as compared to cells lysed by the addition of 1% NP40.

TABLE 11

Complement Dependent Cytolysis Mediated by Chimeric ING-3 Antibody[a]

| Antibody | % Cytolysis Mediated by: | |
|---|---|---|
| Concentration µg/ml | Chimeric ING-3 | Mouse Co-1 |
| 10. | 7.6 | 19.6 |
| 2. | 2.5 | 7.9 |
| 0.4 | 0.4 | 1.7 |
| 0.08 | 0.8 | 1.2 |
| 0.016 | 0.7 | 0.8 |
| 0.032 | 0.3 | 1.0 |
| 0. | 0.8 | 0.9 |

[a]-HT-29 tumor cells were labeled with $Cr^{51}$ washed, and incubated with 17% human serum and antibody at the indicated concentrations for 4 hours at 37° C. The amount of $^{51}Cr$ released into the medium was used to calculate the % cytolysis as compared to cells lysed by the addition of 1% NP-40.

TABLE 12

Inhibition of Binding of ME4 Antibody to Tumor Cells[a]

| Antibody | % Inhibition by Competing Antibody: | | |
|---|---|---|---|
| Concentration[b] µg/ml | Chimeric ING-4 | Mouse ME4 | Human IgG[c] |
| .033 | 11 | 7 | 3 |
| 0.10 | 33 | 2 | 4 |
| 0.31 | 82 | 4 | 9 |
| 0.93 | 93 | 15 | −3 |
| 2.77 | 95 | 22 | −7 |
| 8.33 | 98 | 50 | 4 |
| 25.00 | 99 | 84 | −2 |

[a]Biotinylated yeast chimeric Fab is incubated with HT-29 tumor cells in the presence of the competing antibody at 4° C. Cells are washed and further incubated with avidin-peroxidase at room temperature. The cell-bound peroxidase is visualized with OPD reagent and its $OD_{490}$ is used to determine the % inhibition by the following equation:

$$\% \text{ inhibition} = 1 - \frac{OD \text{ With competing antibody}}{OD \text{ No competing antibody}} \times 100$$

[b]The content of mouse MF4 antibody is estimated to be 10% of total IgG in the preparation.
[c]Human IgG is used as a nonspecific antibody control.

TABLE 13

Antibody-Dependent Cellular Cytotoxicity Mediated by Chimeric ING-4 Antibody[a]

| Antibody | % Cytolysis Mediated by: | |
|---|---|---|
| Concentration[b] µg/ml | Chimeric ING-4 | Mouse ME4 |
| 0 | 33 | 29 |
| 0.016 | 34 | 27 |
| 0.08 | 38 | 29 |
| 0.4 | 41 | 39 |
| 2.0 | 50 | 41 |
| 10.0 | 44 | 48 |
| 50.0 | 50 | 57 |

[a]HT-29 tumor cells were labeled with $^{51}Cr$, washed, and incubated with freshly isolated peripheral blood leukocytes at a ratio of 50 leukocytes per tumor cell for 4 hours at 37° C. The amount of $^{51}Cr$ released into the medium was used to calculate the % cytolysis as compared to cells lysed by the addition of 1% NP40.
[b]Mouse ME4 concentration was corrected to its estimated level which is 10% of total IgG in the mouse ME4 antibody preparation.

TABLE 14

Antibody-Dependent Cellular Cytotoxicity Plus Complement Dependent Cytotoxicity Mediated by Chimeric ING-4 Antibody[a]

| Antibody Concentration[b] μg/ml | % Cytolysis Mediated by: | |
|---|---|---|
| | Chimeric ING-4 | Mouse ME4 |
| .00005 | 32 | 32 |
| .0005 | 32 | 30 |
| .005 | 35 | 29 |
| .05 | 42 | 32 |
| 0.5 | 42 | 33 |
| 5.0 | 44 | 37 |
| 50.0 | 51 | 34 |

[a]HT-29 tumor cells were labeled with $^{51}$Cr, washed, and incubated with freshly isolated peripheral blood leukocytes at a ratio of 50 leukocytes per tumor cell for 4 hours at 37° C. in the presence of 17% human serum. The amount of $^{51}$Cr released into the medium was used to calculate the % cytolysis as compared to cells lysed by the addition of 1% HP40. This assay was done with 17% human serum as a source of complement. The basal level of leukocyte killing was 30% for leukocytes plus serum.
[b]The content of mouse ME4 antibody was estimated to be 10% of total IgG in the preparation.

TABLE 15

Complement Dependent Cytotoxicity Mediated by Chimeric ING-4 Antibody[a]

| Antibody Concentration[b] μg/ml | % Cytolysis Mediated By: | |
|---|---|---|
| | Chimeric ING-4 | Mouse MF4 |
| 0.005 | −0.1 | −1.1 |
| 0.05 | 1.2 | 1.2 |
| 0.5 | 1.8 | 1.5 |
| 5.0 | 3.2 | 2.5 |
| 50.0 | 3.3 | 2.8 |

[a]HT-29 tumor cells were labeled with $Cr^{51}$, washed, and incubated with 17% human serum and antibody at the indicated concentrations for 4 hours at 37° C. The amount of $^{51}$Cr released into the medium was used to calculate the % cytolysis as compared to cells lysed by the addition of 1% NP-40.
[b]The content of mouse ME4 antibody was estimated to be 10% of total IgG in the preparation.

TABLE 16

Inhibition of Binding of KM10 Antibody to Tumor Cells

| Antibody Concentration μg/ml | % Inhibition by Competing Antibody:[a] | | |
|---|---|---|---|
| | Chimeric KM10 | Mouse KM10 | Human IgG[b] |
| 0.15 | 2 | 2 | −8 |
| 0.45 | 9 | 14 | 2 |
| 1.35 | 9 | 32 | 18 |
| 4.04 | 42 | 46 | 6 |
| 12.1 | 63 | 59 | 14 |
| 36.4 | 74 | 80 | −7 |
| 109 | 75 | 72 | −22 |

[a]$^{125}$I-labeled KM10 antibody was incubated with LS174T tumor cells in the presence of the competing antibody at 4° C. Cells were washed free of unbound antibody, and cell-bound radioactivity was used to determine the % inhibition of binding.
[b]Human IgG is used as a nonspecific antibody control.

TABLE 17

Antibody-Dependent Cellular Cytotoxicity Mediated by Chimeric KM10 Antibody[a]

| Antibody Concentration μg/ml | % Cytolysis Mediated by: | |
|---|---|---|
| | Chimeric KM10 | Mouse KM10 |
| 50. | 80 | 26 |
| 5. | 61 | 20 |
| .5 | 39 | 22 |
| .05 | 27 | 21 |
| .005 | 23 | 21 |
| .0005 | 23 | 21 |
| 0 | 24 | 22 |

[a]-LS174T tumor cells were labeled with $^{51}$Cr, washed, and incubated with freshly isolated peripheral blood leukocytes in the presence of 17% human serum at a ratio of 50 leukocytes per tumor cell for 4 hours at 37° C. The amount of $^{51}$Cr released into the medium was used to calculate the % cytolysis as compared to cells lysed by the addition of 1% NP40.

EXAMPLE 4

Chimeric Mouse-Human Fab with Human Tumor Cell Specificity Produced in Yeast

Yeast cells are capable of expressing and secreting foreign proteins. In this example, yeast serve as a host for the production of mouse-human chimeric Fab. This reagent may prove useful for the diagnosis of human cancer via in vivo imaging of appropriately labeled product, or therapy of cancer by its administration as a drug, radionuclide or toxin immunoconjugate.

1. Yeast Strains and Growth Conditions

*Saccharomyces cerevisiae* strain PS6 (ura3 leu2 MATa) was developed at INGENE and used as a host for yeast transformations performed as described by Ito et al., *J. Bacteriol.* 153:163–168 (1983). Yeast transformants were selected on SD agar (2% glucose, 0.67% yeast nitrogen base, 2% agar) and grown in SD broth buffered with 50 mM sodium succinate, pH5.5.

2. In Vitro Mutagenesis a. ING-1

Site directed in vitro mutagenesis was performed as described by Kramer et al., supra, to place restriction sites at the mammalian signal sequence processing sites. An ApaI restriction site was introduced into the B38.1 K L chain cDNA sequence (FIG. 7) at the junction of the leader peptide and mature coding region with the oligonucleotide primer 5'-GTCATCCAATTTGGGCCCTGGATCCAGG-3'. Likewise, as SstI restriction site was introduced into the B38.1 H chain cDNA sequence (FIG. 8) at the junction of the leader peptide and mature coding region with the oligonucleotide primer 5'CTGGATCTGAGCTCGGGCACTTTG-3'.

b. ING2

Figure 16A:
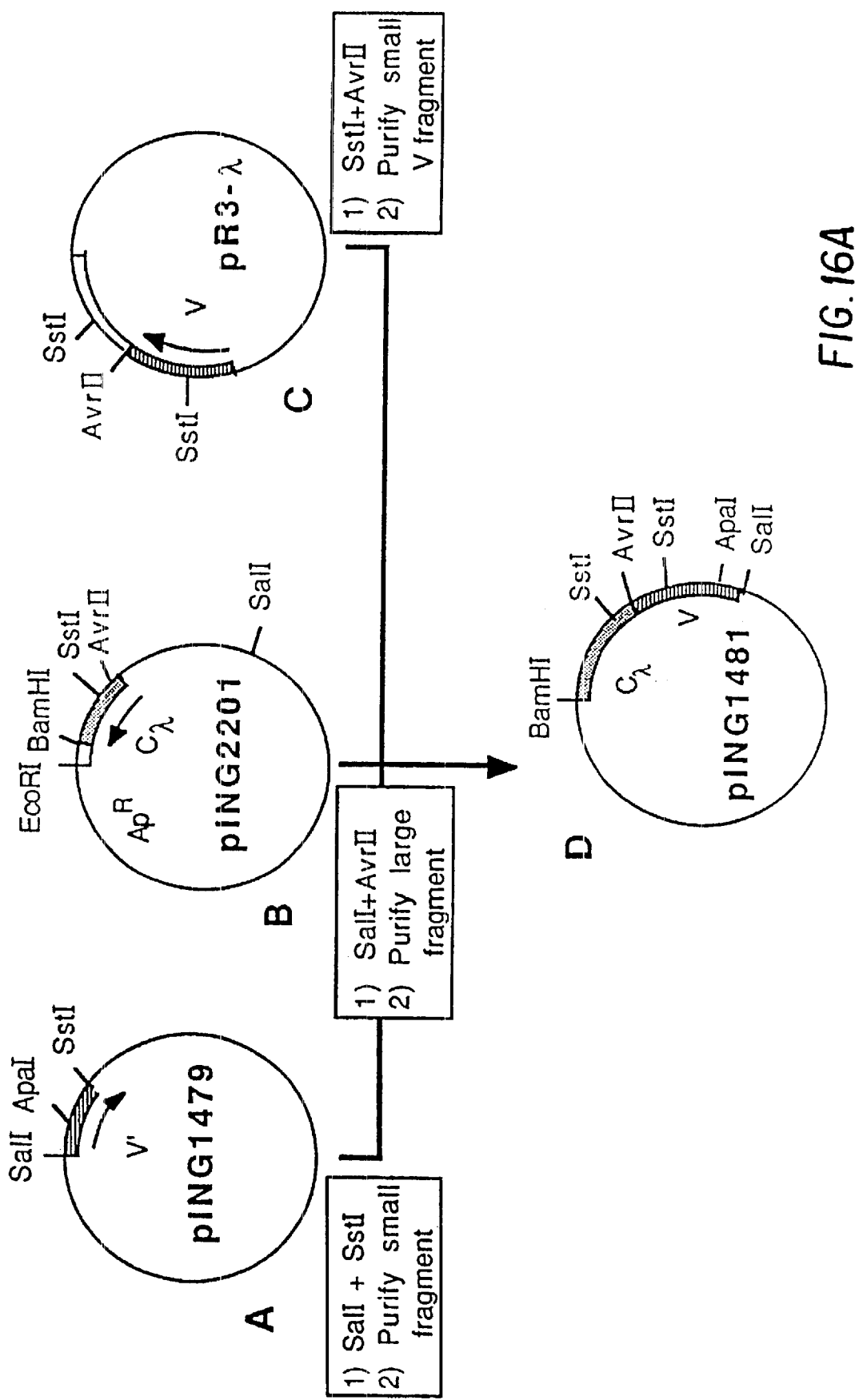
FIGS. 16(A and B). Construction scheme for the plasmid pING1602, containing the ING-2 chimeric L chain gene with an ApaI site at the gene sequences encoding the signal sequence processing site and an XhoI site 4 bp downstream from the stop codon. V', fragment of V region gene sequences. Not drawn to scale.
Figure 16B:
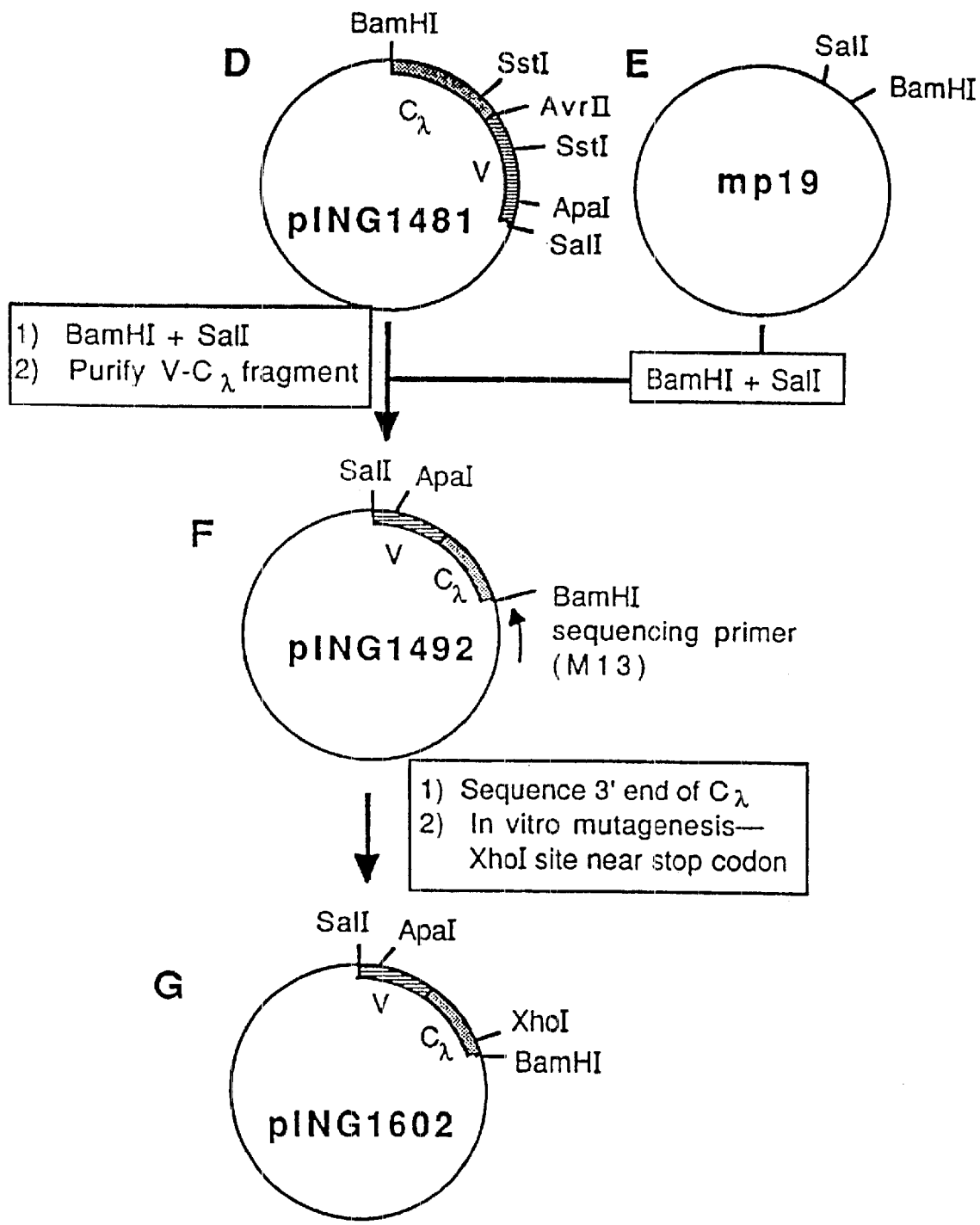

Site-directed in vitro mutagenesis was performed as described by Kramer et al., supra, to place. restriction sites at the mammalian signal sequence processing sites and at the 3' end of the human Cλ C region. An ApaI restriction site was introduced into the Br-3 λ chain cDNA sequence at the junction of the leader peptide and mature coding region with the oligonucleotide primer CAGCCTGGGCCCTGGCCCCTGAG-3' to generate the plasmid pING1479 (FIG. 16A). Following construction of a chimeric ING-2 λ chain gene containing the ApaI restriction site (FIG. 16D), the DNA sequence of 40 bp of the 3' untranslated region and approximately 150 bp of the coding sequence for the human $C_\lambda$ region was determined. Based on this information, the $C_\lambda$ region was confirmed to be of the λ-1 (Mcg) allotype. An XhoI site was next placed 4 bp downstream of the stop codon of the human Cλ C region with the oligonucleotide primer 5' GTGGGGTTAGACTC-GAGAACCTATGAAC 3' to generate the chimeric ING-2 λ chain plasmid, pING1602 (FIG. 16G). An AatII restriction site was introduced into the Br-3 H chain cDNA sequence at the junction of the leader peptide and mature coding region with the oligonucleotide primer 5' AAGCTTCACTTGACGTCGGACACCMTA-3' to generate the plasmid, pING1480 (FIG. 17A). The codon for the N-terminal amino acid of the H chain was changed by this construction from the naturally occurring GAA (glutamate) to CM (glutamine).

c. ING-3

Site directed in vitro mutagenesis was performed as described by Kramer et al., supra, to introduce an AatII restriction site into the Co-1 λ L chain cDNA sequence (FIG. 21) at the junction of the leader peptide and mature coding region with the oligonucleotide primer 5'-CATCAAAACTTGACGTCTGGAAACAGGA-3'.

d. ING-4

Site directed in vitro mutagenesis was performed as described by Kramer et al., supra, to place restriction sites at the mammalian signal sequence processing sites. A PstI restriction site was introduced into the ME4 K L chain cDNA sequence (FIG. 29) at the junction of the leader peptide and mature coding region with he oligonucleotide primer 5'-CATCTGGATATCTGCAGTGGTACCTTGAA-3'. Likewise, an SstI restriction site was introduced into the ME4 H chain cDNA sequence (FIG. 30) at the junction of the leader peptide and mature coding region with the oligonucleotide primer 5'-CMCTGGACCTGAGCTCGAACACCTGCAG-3'.

e. KM10

Site directed in vitro mutagenesis was performed as described by Kramer et al., supra, to introduce. a BsmI restriction site into the KM10 κ L chain cDNA sequence (FIG. 36) at the junction of the leader peptide and mature coding region with the oligonucleotide primer 5'-GAGCACAATTTCTGCATTCGACACTGTGAC-3'. An Sst1 site was similarly introduced at the junction of the leader peptide and mature coding region of the KM10 H chain with the oligonucleotide primer 5'-CAACTGGATCTGAGCTCGGGCACTTTG-3' (FIG. 37).

3. Construction of Yeast Expression Plasmids Containing Antibody Genes a. ING-1

The gene sequences encoding the mature form of the L chain V region of B38.1 and containing a HindIII site in the J region (as described in Example 3) and a ApaI site introduced at the signal sequence processing site was fused to the human $C_K$ region by cloning a SalI-HindII fragment containing V into a vector containing the gene sequence encoding human $C_K$ (pING1460), generating the ING-1 chimeric L chain plasmid pING1483.

Figure 11:
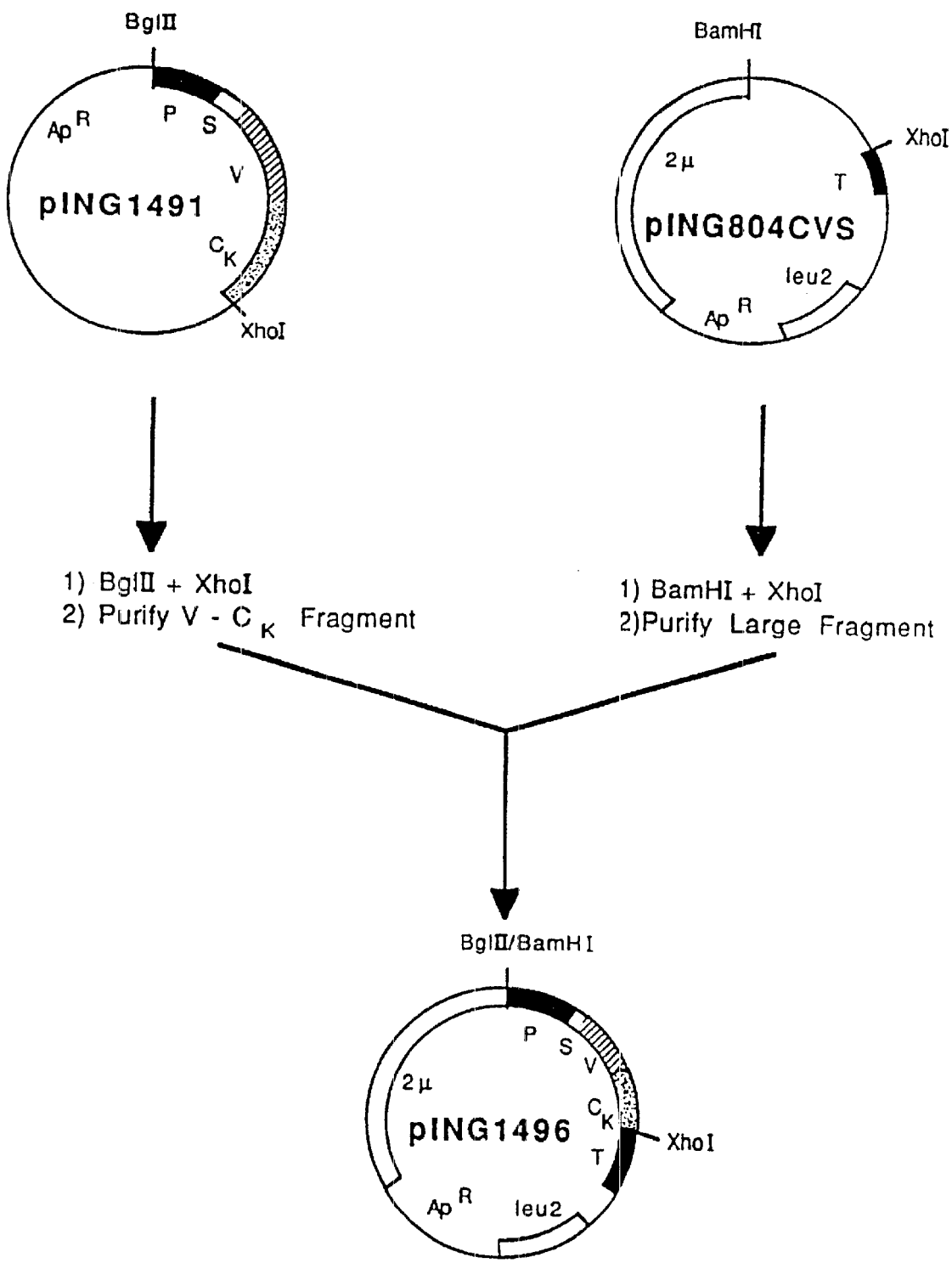
FIG. 11. Construction scheme for yeast expression plasmid containing ING-1 chimeric L chain gene fused to the yeast PGK promoter (P), invertase signal sequence (S) and PGK polyadenylation signal (T). Not drawn to scale.

The mature chimeric ING-1 L chain gene from pING1483 was next fused to the gene sequence encoding the yeast invertase signal sequence, Taussig, R. and M. Carlson, *Nucl. Acids Res.* 11:1943–1954 (1983) under control of the yeast PGK promoter, Hitzeman, R. A. et al., *Nucl. Acids Res.* 10:7791–7807 (1982) as follows: The plasmid pING1483 was digested with ApaI, treated with T-4 DNA polymerase and then digested with XhoI and a restriction fragment containing V+$A_K$ was purified. This fragment was ligated to a similarly prepared restriction fragment from the plasmid, pING1149 which contains the PGK promoter (P) fused to the invertase signal sequence (S) to generate pING1491 (FIG. 11). As the result of this fusion, gene sequence encoding the mature form of the ING-1 chimeric L chain was fused in-frame to the gene sequence encoding the yeast invertase signal sequence (S). The codon for the N-terminal amino acid of the L chain was changed by this construction from the naturally-occurring GAT (aspartate) to CAM (glutamine). The PGK promoter-invertase signal sequence-chimeric L chain ($V,C_K$) fusion was cloned into a complete 2 micron circle (2 u), Leu2 yeast expression vector containing the PGK polyadenylation signal (T) to generate pING1496 (FIG. 11).

The gene sequences encoding the mature form of the H chain V region of B38.1 and containing a BstEII site in the J region (see Example 3) and an SstI site introduced at the signal sequence processing site was fused to the gene sequence encoding the human $C_{H1}$ region (which had been previously generated by introducing a stop codon in hinge, see Robinson, R. R., et al., PCT/US86/02269) as follows. A SstI-BstEII restriction fragment containing $V_H$ was ligated with a BstEII restriction fragment containing the human J region and a portion of human $C_{H1}$ and a SstI-BstEII restriction fragment containing the remaining 3' portion of human $C_{H1}$ to generate the ING-1 chimeric Fd chain plasmid pING1606.

Figure 12:
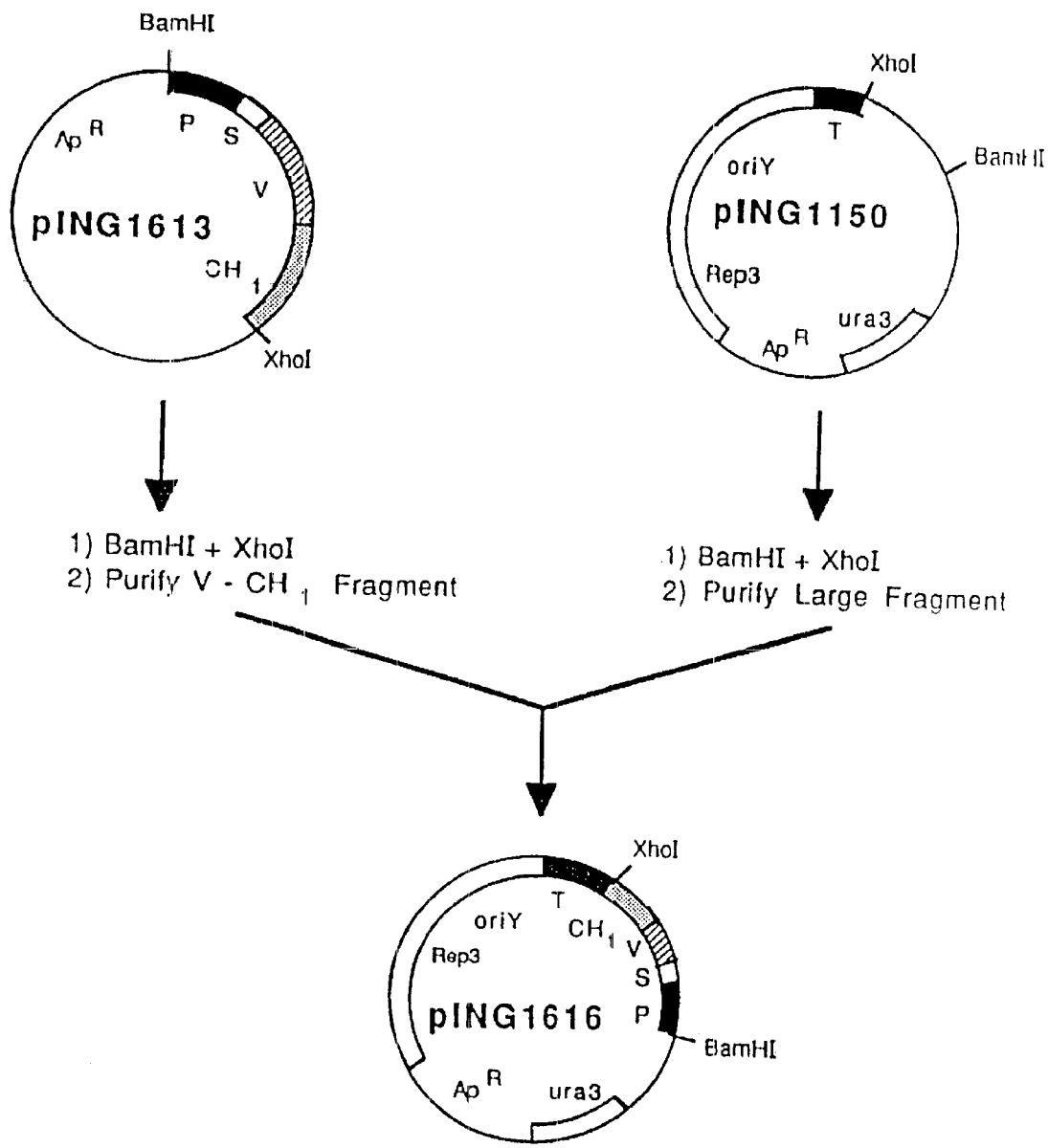
FIG. 12. Construction for yeast expression plasmid containing ING-1 chimeric Fd chain gene fused to the yeast PGK promoter (P), invertase signal sequence (S), and PGK polyadenylation signal (T). Not drawn to scale.

The chimeric ING-1 Fd chain gene in pING1606 was next fused to the yeast invertase signal sequence undercontrol of the PGK promoter using the approach taken for the L chain to generate pING1613 (FIG. 12). This fusion was then cloned as a BamHI-XhoI fragment into a partial 2 micron circle (Oriy, REP3), ura3 yeast expression vector containing the PGK polyadenylation signal (T) to generate pING1616 (FIG. 12).

b. ING-2

Figure 18:
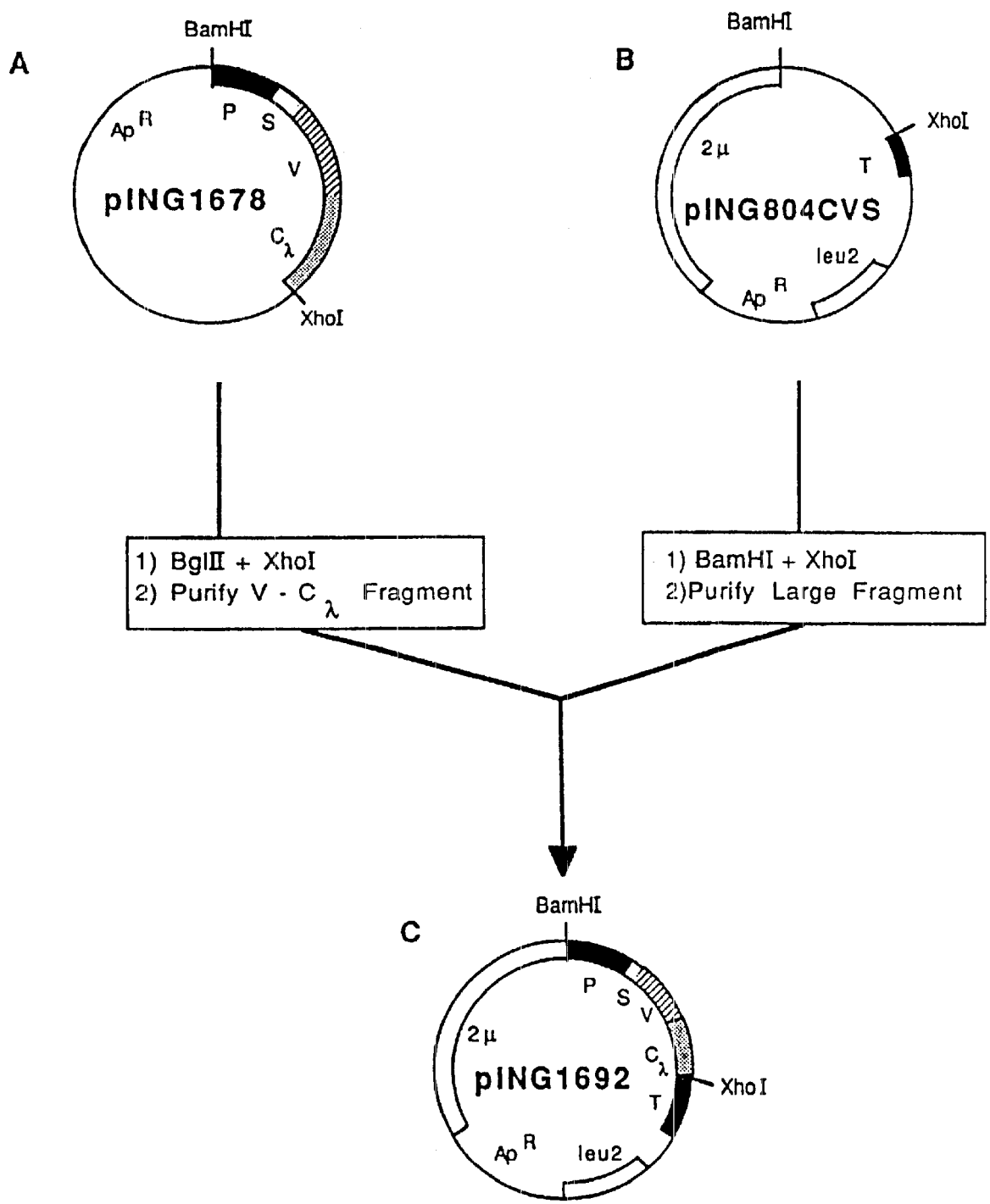
FIG. 18. Construction scheme for yeast expression plasmid containing ING-2 chimeric L chain gene fused to the yeast PGK promoter (P), invertase signal sequence and PGK polyadenylation signal (T). Not drawn to scale.

The SalI-BamHI chimeric L chain fragment from pING1602 was cloned into pBR322NA (see FIG. 3) to generate pING1609. The mature chimeric ING-2 L chain gene from pING1609 was next fused to the gene sequence encoding the yeast invertase signal sequence (Taussig et al., supra) under control of the yeast PGK promoter (Hitzeman, R. A., et al., supra) as follows: the plasmid pING1609 was digested with ApaI, treated. with T-4 DNA polymerase and then digested with XhoI and a restriction fragment containing V+$C_\lambda$ was purified. This fragment was ligated to a similarly prepared restriction fragment from the plasmid, pING1149 which contains the PGK promoter (P) fused to the invertase signal sequence (S) to generate pING1678 (FIG. 18A). As the result of this fusion, the gene sequence encoding the mature form of the ING-2 chimeric L chain was fused. sequence (S). The PGK promoter-invertase signal sequence-chimeric L chain ($V,C_\lambda$) fusion was cloned into a complete 2-micron circle (2u), leu2 yeast expression vector containing the PGK polyadenylation signal (T) to generate pING1692 (FIG. 18C).

Figure 17:
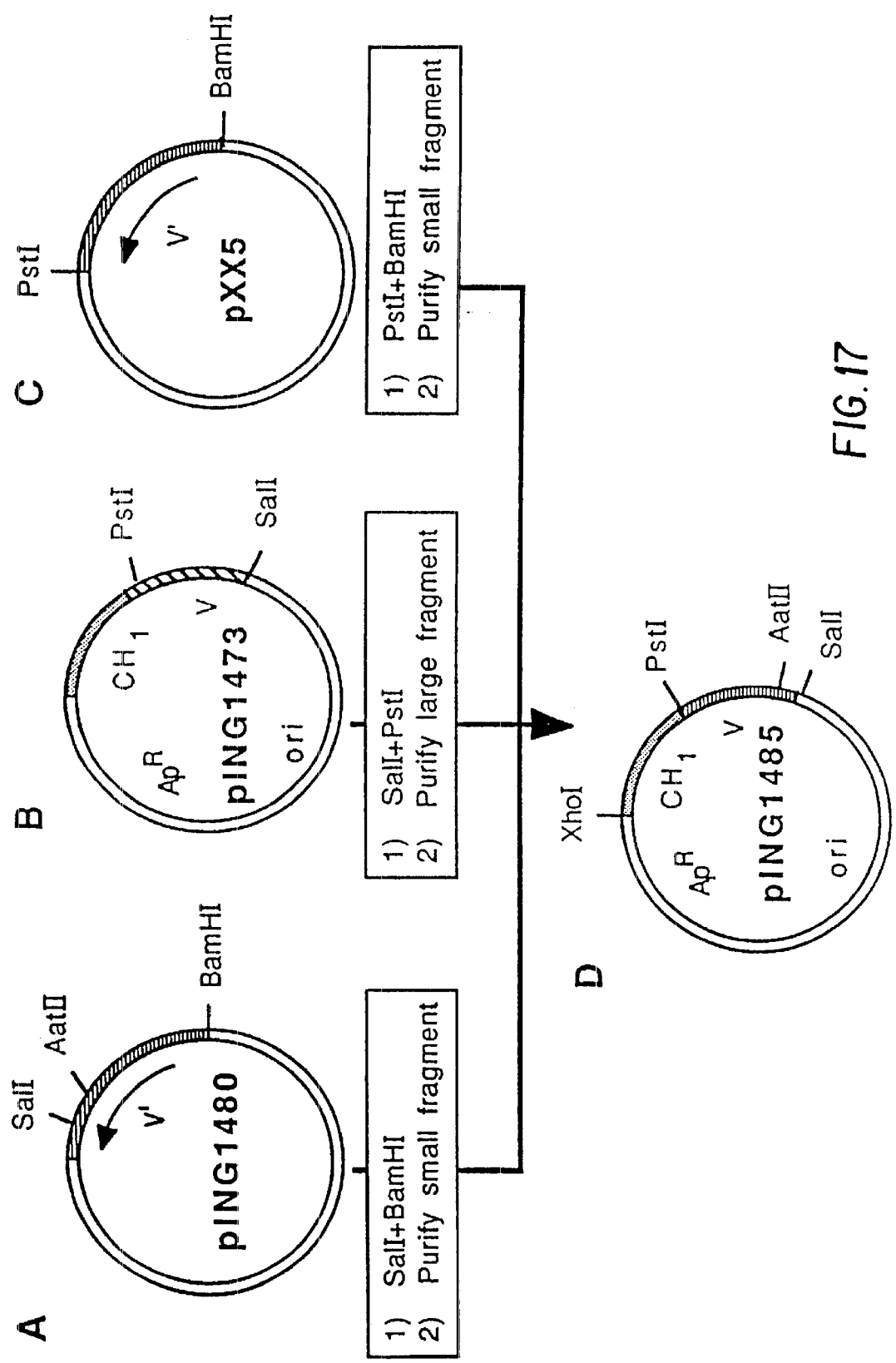
FIG. 17. Construction scheme for plasmid pING1485, containing the ING-2 chimeric Fd chain gene with an AatII site at the gene sequence encoding the signal sequence processing site. V', fragment of V region gene sequences. Not drawn to scale.
Figure 19:
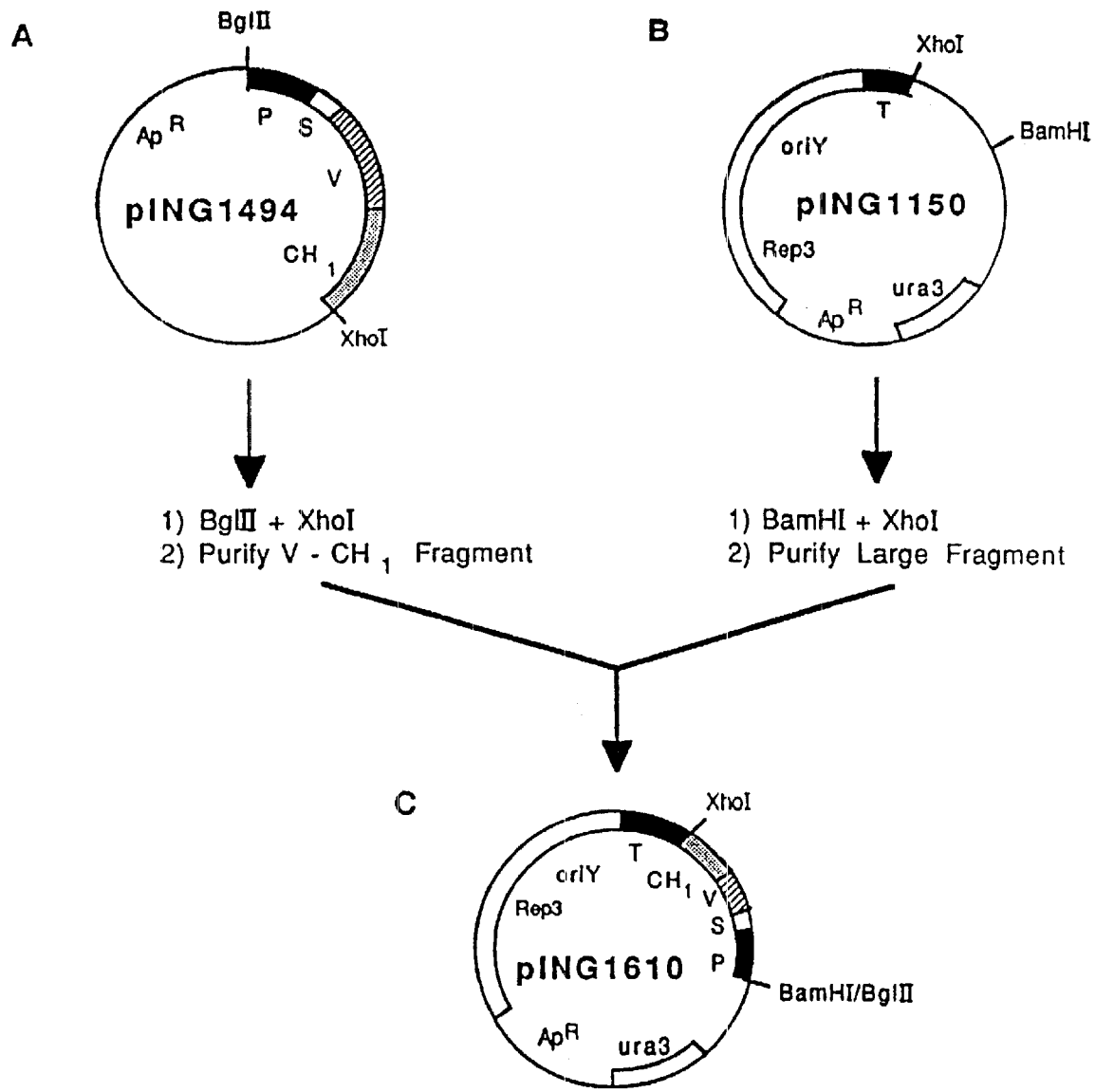
FIG. 19. Construction scheme for yeast expression plasmid containing ING-2 chimeric Fd chain gene fused to the yeast PGK promoter (P), invertase signal sequence (S), and PGK polyadenylation signal (T).

The gene sequence encoding the 5' end of the mature form of the H chain V region of Br-3 and containing an AatII site introduced at the signal sequence processing site was fused to the gene sequence encoding the 3' end of the Br-3 H chain V region containing a PstI site in the J region and the human $CH_1$ region (which had been previously generated by introducing a stop codon in hinge, Robinson, R. R., et al., PCT US86/02269) as shown in FIG. 17 to generate the ING-2 chimeric Fd chain plasmid pING1485 (FIG. 17D). The chimeric ING-2 Fd chain gene in pING1485 was next fused to the yeast invertase signal sequence (s) under control of the PGK (p) promoter using the approach taken for the L chain to generate pING1494 (FIG. 19A). This fusion was then cloned as a BglII-XhoI fragment into a partial 2-micron circle (Oriy, REP3), ura3 yeast expression vector containing the PGK polyadenylation signal (T) to generate pING1610 (FIG. 19C).

c. ING-3

The gene sequences encoding the mature form of the L chain V region of Co-1 and containing a HindIII site in the J region (as described in Example 3) and an AatII site introduced at the signal sequence processing site was fused to the human $C_K$ region by cloning a SalI-HindII fragment containing V into a vector containing the gene sequences encoding human $C_K$ (pING1460), generating the ING-3 chimeric L chain plasmid pING1682.

Figure 25:
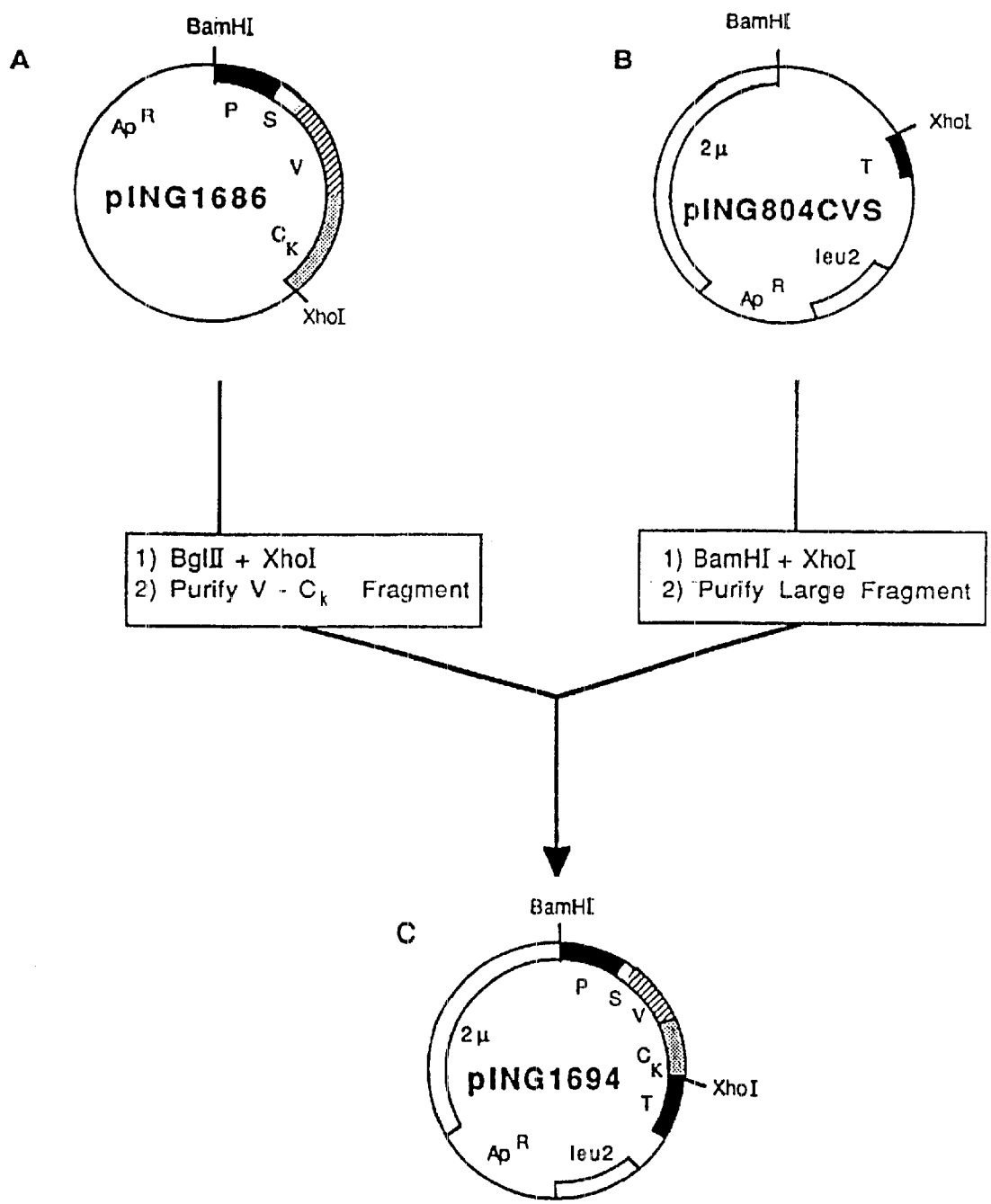
FIG. 25. Construction scheme for yeast expression plasmid containing ING-3 chimeric L chain gene fused to the yeast PGK promoter, invertase signal sequence and PGK polyadenylation signal. Not drawn to scale.

The mature chimeric ING-3 L chain gene from pING1682 was next fused to the gene sequence encoding the yeast invertase signal sequence (Taussig, R. and Carlson, M., supra) under control of the yeast PGK promoter (Hitzeman, R. A., et al., supra) as follows: The plasmid pING1682 was digested with AatII, treated with T-4 DNA polymerase and then digested with XhoI and a restriction fragment containing V+$C_K$ was purified. This fragment was ligated to a similarly prepared restriction fragment from the plasmid, pING1149 which contains the PGK promoter (P) fused to the invertase signal sequence (S) to generate pING1686 (FIG. 25A). As the result of this fusion, the gene sequence encoding the mature form of the ING-3 chimeric L chain was fused in frame to the gene sequence encoding the yeast invertase signal sequence (S). The codon for the N-terminal amino acid of the L chain was changed by this construction from the naturally-occurring GAA (glutamate) to CAM (glutamine). The PGK promoter-invertase signal sequence-chimeric L chain (V,$C_K$) fusion was cloned into a complete 2 micron circle (2u), leu2 yeast expression vector containing the PGK polyadenylation signal (T) to generate pING1694 (FIG. 25C).

Figure 26:
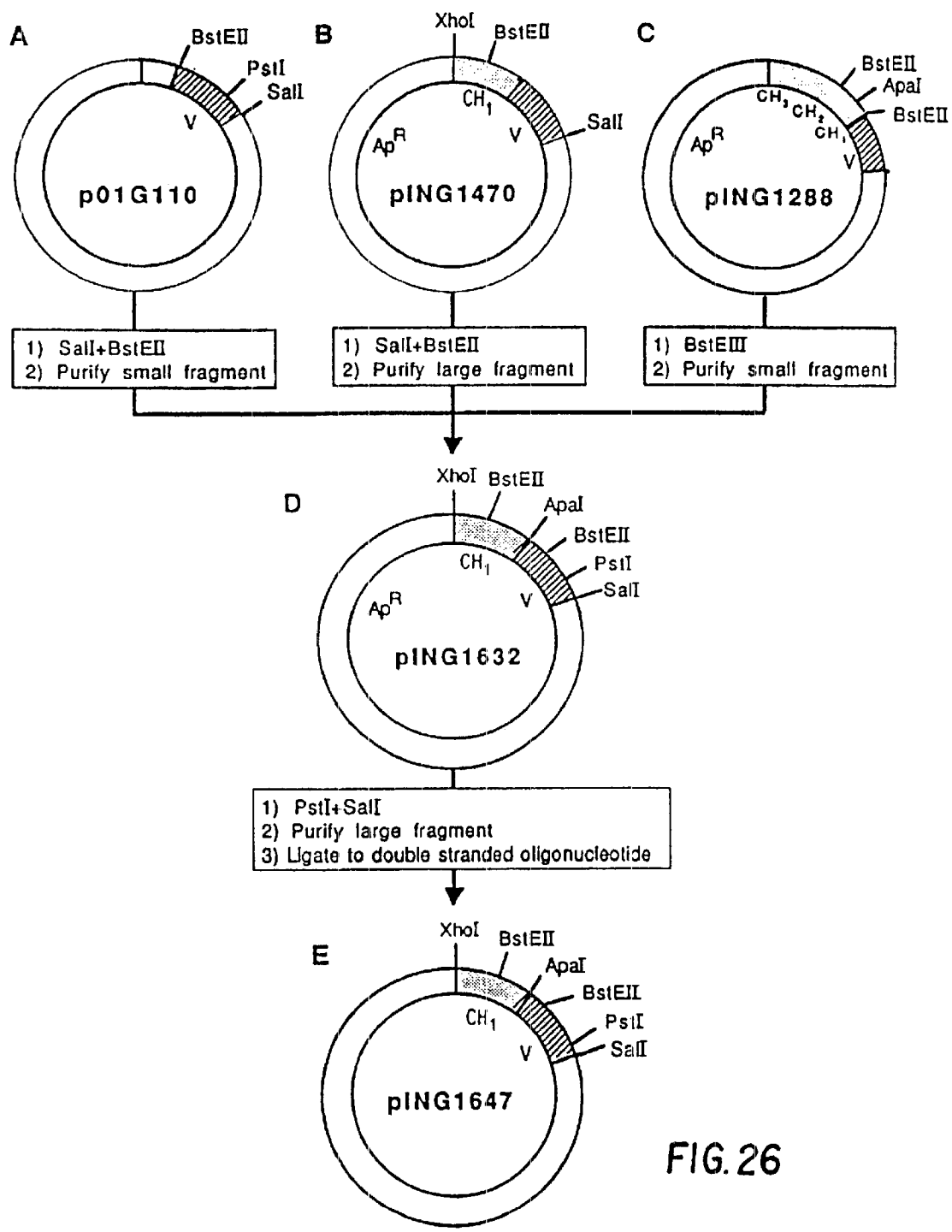
FIG. 26. Construction scheme for ING-3 chimeric Fd chain gene containing a PstI site at the gene sequence encoding the signal sequence processing site. Not drawn to scale.

The gene sequence encoding the mature form of the H chain V region of Co-1 and containing a BstEII site in the J-region (see Example 3) was fused to the gene sequence encoding the human CH1 region (which had been previously generated by introducing a stop codon in the hinge (Robinson, R. R., et al., supra) as shown in FIG. 26 to generate the ING-3 chimeric Fd chain plasmid pING1632. A PstI restriction site was introduced into the Co-1 H chain cDNA sequence at the junction of the leader peptide and mature coding region by ligating the double stranded oligonucleotide

5' TCGACCTGCAGAGGTCCAGTTGCA 3'
3' GGACGTCTCCAGGTCAA 5' into pING1632 to generate pING1647 (FIG. 26E).

Figure 27:
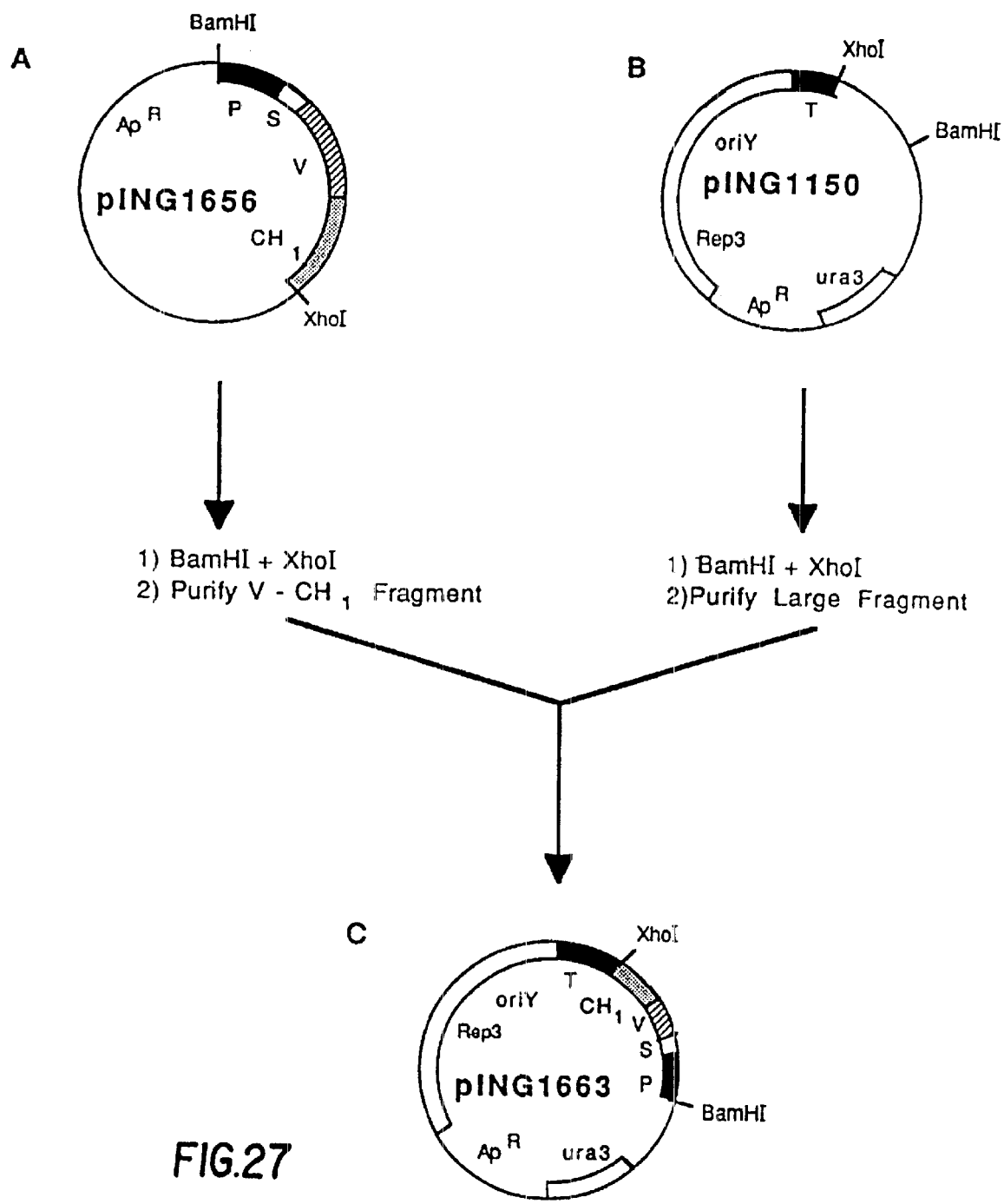
FIG. 27. Construction scheme for yeast expression plasmid containing ING-3 chimeric Fd chain gene fused to the yeast PGK promoter, invertase signal sequence and PGK polyadenylation signal. Not drawn to scale.

The chimeric ING-3 Fd chain gene in pING1647 was next fused to the yeast invertase signal sequence under control of the PGK promoter using the approach taken for the L chain to generate pING1656 (FIG. 27A). This fusion was then cloned as a BamHI-XhoI fragment into a partial 2 micron circle (Oriy, REP3), ura3 yeast expression vector containing the PGK polyadenylation signal (T) to generate pING1663 (FIG. 27C).

d. ING-4

Figure 33A:
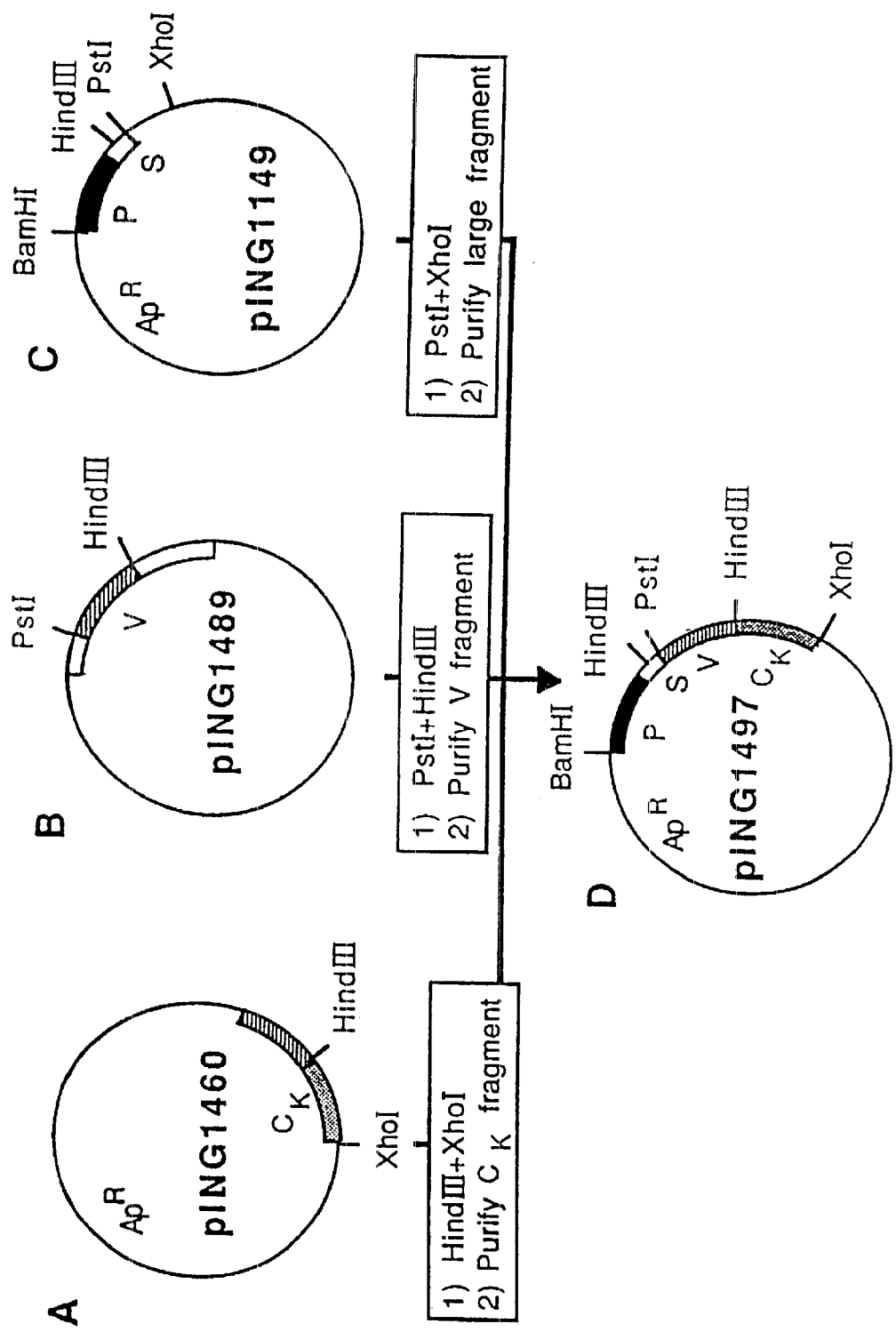
FIGS. 33(A and B). Construction scheme for the fusion of the mature form of the ING-4 chimeric L chain gene to the yeast invertase signal sequence(s) under control of the yeast PGK promoter. Not drawn to scale.

The gene sequences encoding the mature form of the L chain V region of ME4 and containing a HindIII site in the J region (as described in Example 3) and a PstI site introduced at the signal sequence processing site (pING1489, FIG. 33B) was fused to the human $C_k$ region (pING1460, FIG. 33A) and the gene sequence encoding the yeast invertase signal sequence (S) (Taussig, R. and M. Carlson, supra) under control of the yeast PGK promoter (P) (Hitzeman, R. A. et al., supra) (pING1149, FIG. 33C) to generate pING1497 (FIG. 33D). The plasmid pING1497 was next digested with PstI, treated with T-4 DNA polymerase and allowed to self-close, generating pING1600 (FIG. 33E). As the result of this step, the gene sequence encoding the mature form of the ING-4 chimeric L chain was placed in frame with the gene sequence encoding the yeast invertase signal sequence. The PGK promoter (P)-invertase signal sequence (S)-chimeric L chain (V,$C_k$) fusion in pING1600 was next cloned as a BamHI-Xho fragment into pING1152 (FIG. 34B) which is a partial 2 micron circle (oriY,REP3) ura3 yeast expression vector containing the PGK polyadenylation signal (T) to generate pING1641 (FIG. 34E).

The gene sequences encoding the mature form of the H chain V region of ME4 and containing a BstEII site in the J region (see Example 3) and an SstI site introduced at the signal sequence processing site was fused to the gene sequence encoding the human $CH_1$ region (which had been previously generated by introducing a stop codon in hinge (Robinson, R. R. et al., supra ) as follows. A SalI-BstEII restriction fragment containing $V_H$ with the SstI site at the signal sequence processing site was ligated with a BstEII restriction fragment containing the human J region and a portion of human $C_{H1}$ and a SalI-BstEII restriction fragment containing the remaining 3'portion of human $C_{H1}$ to generate the ING-4 chimeric Fd chain plasmid pING1611. The chimeric ING-4 Fd chain gene in pING1611 was next fused in frame to the yeast invertase signal sequence under control of the PGK promoter as follows: The plasmid pING1611 was digested with SstI, treated with T4 DNA polymerase and then digested with XhoI and a restriction fragment containing V+$C_{H1}$ was purified. This fragment was ligated to a similarly prepared restriction fragment from the plasmid, pING1149 (FIG. 33C), which contains the yeast PGK promoter fused to the invertase signal sequence to generate pING1614 (FIG. 340). The PGK promoter (P)-invertase signal sequence, (S)-chimeric Fd chain ($V_1CH_1$) in pING1614 was then cloned as a BamHI-XhoI fragment into a partial 2 micron circle (Oriy, REP3), ura3 yeast expression vector containing the PGK polyadenylation signal (T) to generate pING1620 (FIG. 34F).

Figure 34A:
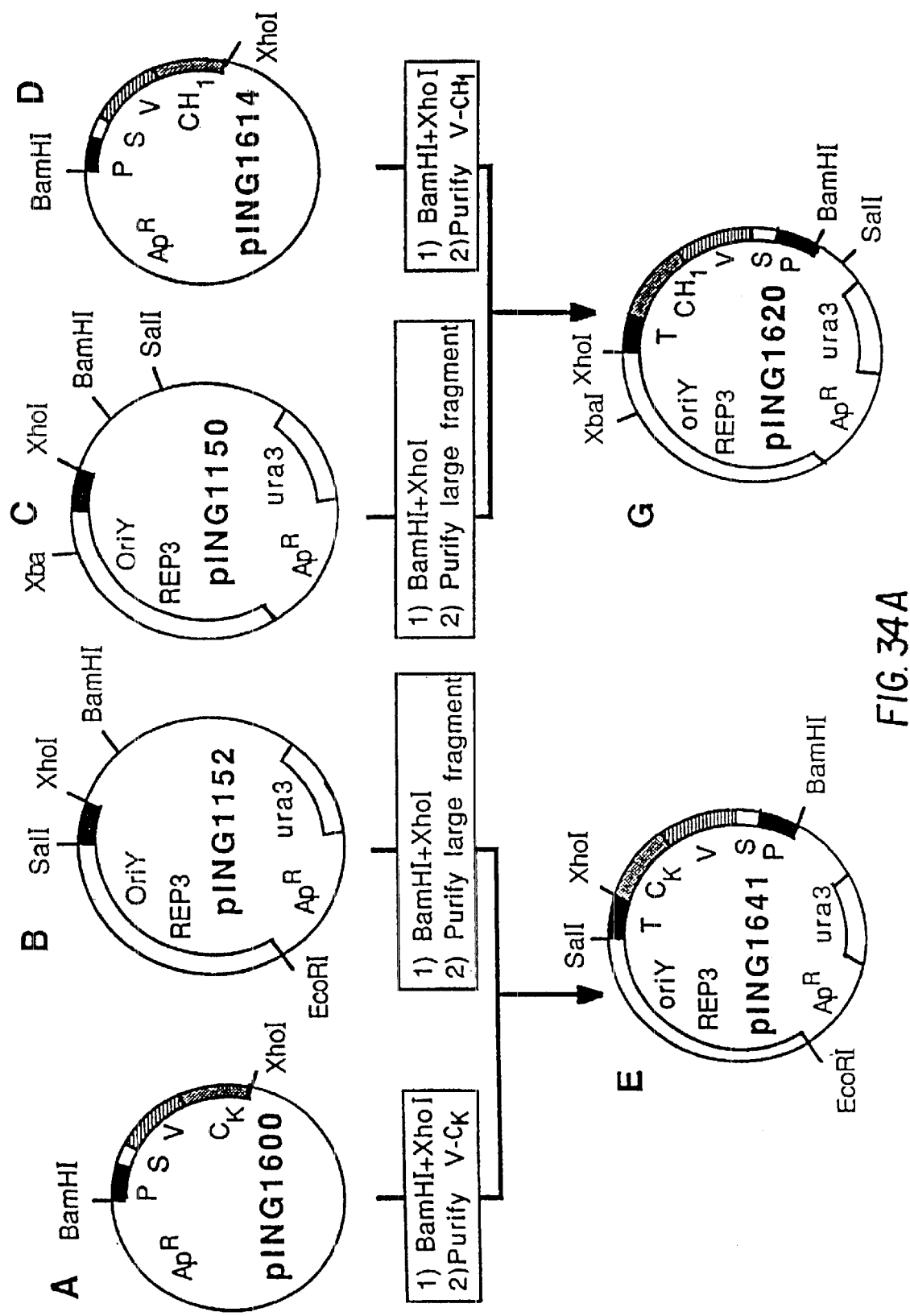
FIGS. 34(A and B). Construction scheme for a yeast expression plasmid containing the ING-4 chimeric L chain and Fd genes fused to the yeast PGK promoter (P), invertase signal sequence(s) and PGK polyadenylation signal (T). Not drawn to scale.

In order to construct a yeast expression plasmid that would optimally produce Fab, the chimeric L and Fd chain genes each fused to the yeast invertase signal sequence and PGK promoter and polyadenylation signal were placed on the same plasmid to generate pING1667 (FIG. 34H).

e. KM10

The gene sequences encoding the mature form of the L chain V region of KM10 and containing a HindIII site in the J region (as described in Example 3) and a BsmI site introduced at the signal sequence processing site was fused to the human $C_K$ region by cloning a SalI-HindII fragment containing V into a vector containing the gene sequences encoding human $C_K$ (pING1460), generating the KM10 chimeric L chain plasmid pM1D (see FIG. 41).

Figure 40:
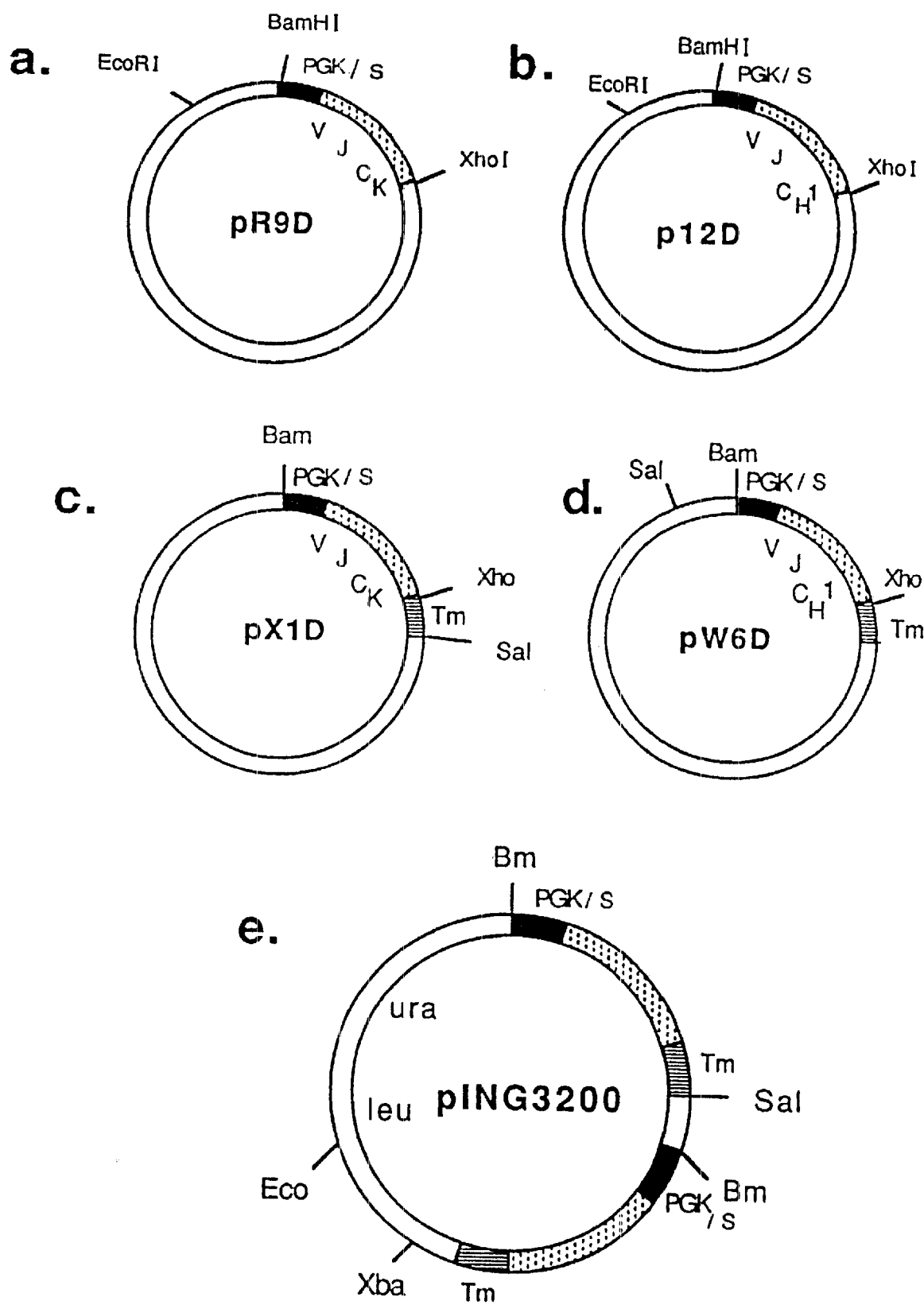
FIG. 40. Yeast expression plasmids for Fab expression. Shown are: (a) the yeast expression plasmid containing KM10 chimeric L chain gene fused to the yeast PGK promoter, invertase signal sequence and PGK polyadenylation signal; (b) the similar yeast plasmid containing the Fd gene; (c) the yeast expression plasmid containing the L chain promoter/leader fusion with PGK transcription termination signal; (d) similar yeast plasmid containing the Fd gene; and (e) the final 2 gene yeast expression plasmid pING3200. Not drawn to scale.

The mature chimeric KM10 L chain gene from pM1D was next fused to the gene sequence encoding the yeast invertase signal sequence (Taussig, R. and M. Carlson, supra) under control of the yeast PGK promoter (Hitzeman, R. A., et al., supra) as follows: The plasmid pM1D was digested with BsmI, treated with T4 DNA polymerase and then digested with XhoI and a restriction fragment containing V+$C_K$ was purified. This fragment was ligated to a similarly prepared restriction fragment from the plasmid, pING1149 which contains the PGK promoter (P) fused to the invertase signal sequence (S) to generate pR9D (FIG. 40A). As the result of this fusion, the gene sequence encoding the mature form of the KM10 chimeric L chain was fused in frame to the gene sequence encoding the yeast invertase signal sequence (S).

The PGK promoter-invertase signal sequence-chimeric L chain (V,C$_K$) fusion was cloned into a partial 2 micron circle (2μ), ura3 yeast expression vector containing the PGK polyadenylation signal (Tm) to generate pX1D (FIG. 40C).

The gene sequence encoding the mature form of the H chain V region of KM10 and containing a BstEII site in the J region (as described in Example 3) and a Sst1 site introduced at the signal sequence processing site was fused to the human C$_H$1 region (which had been previously generated by introducing a stop codon in hinge, (Robinson, R. R., et al., supra) in pING1453 to generate the KM10 Fd chain plasmid pF3D (see FIG. 41).

The mature chimeric KM10 Fd gene from pF3D was next fused to the yeast invertase signal under the control of the yeast PGK promoter in a similar manner to that described for light chain generating pP12D (FIG. 40B). The PGK promoter-invertase signal sequence-chimeric Fd chain (V,C$_H$1) fusion was cloned into a partial 2 micron circle (2μ) expression vector containing the PGK polyadenylation signal (Tm) to generate pW6D (FIG. 40D).

A single yeast expression vector containing both the chimeric light chain and Fd chain genes and their respective expression signals was constructed from pXID and pW6D. This final vector, pING3200, FIG. 5E, contains a portion of 2 micron circle (oriY, REP3) and the two selectable markers leu2d and ura3.

4. Yeast Secretion of Chimeric Fab a. ING-1

The plasmids pING1496 and pING1616 were co-transformed into S. cerevisiae PS6 and the transformants were grown in broth under selective conditions as described above. The culture supernatants were assayed by ELISA and contained Fab levels of 30 ng/ml. The yeast strain that secreted detectable Fab protein was grown in 10 liters of SD broth for 60 hours and Fab protein was purified from the culture supernatant.

b. ING-2

The plasmids pING1692 and pING1610 were co-transformed into S. cerevisiae PS6 and the transformants were grown in broth under selective conditions as described above. The culture supernatants were assayed by ELISA and contained average Fab levels of approximately 200 ng/ml. The yeast strain that secreted detectable Fab protein was grown in 10 liters of SD broth for 60 hours and Fab protein was purified from the culture supernatant.

c. ING-3

The plasmids pING1694 and pING1663 were co-transformed into S. cerevisiae PS6 and the transformants were grown in broth under selective conditions as described above. The culture supernatants were assayed by ELISA and contained Fab levels of approximately 200 ng/ml. The yeast strain that secreted 200 ng/ml Fab protein was grown in 10 liters of SD broth for 60 hours and Fab protein was purified from the culture supernatant.

d. ING-4

The plasmid pING1667 was transformed into S. cerevisiae PS6 by selection for ura$^+$leu$^+$ colonies on SD agar. The transformants were grown in SD broth lacking both uracil and leucine. The culture supernatant of one isolate (no. 714) was found by ELISA to contain Fab levels of 4 μg/ml. The yeast strain that secreted 4 μg/ml Fab protein was grown in 10 liters of SD broth for 60 hours and Fab protein was purified from the culture supernatant.

e. KM10

The plasmid pING3200 was transformed into S. cerevisiae PS6 and the transformants were grown in broth under selective conditions as described above. The culture supernatants were assayed by ELISA and contained Fab levels of approximately 100 ng/ml. The yeast strain that secreted 100 ng/ml Fab protein was grown in 50 L of SD broth for 60 hr and Fab protein was purified from the culture supernatant.

5. Isolation of Chimeric Fab from Yeast and Production of Mouse Fab from Monoclonal Antibodies a. ING-1

Fab protein was partially purified from 10 liters of culture supernatant by concentrating over an DC10 concentrator (Amicon) using a S10Y30 cartridge, washing with 20 liters of distilled water and re-concentrating to 1.5 liters. The pH of the supernatant was adjusted to 5.5, and it was loaded onto an SP disc which was previously equilibrated with 10 mM MES, pH 5.5. The disc was eluted with 6 step gradients of 30, 60, 100, 150, 200, and 300 mM NaCl in 10 mM MES, pH 5.5. Analysis of SP disc elution pools by ELISA which detected human Fab and by Western blot of reduced and non-reduced SDS PAGE, followed by goat anti-human κ detection, revealed that the ING-1 Fab was present in the 150 mM to 300 mM NaCl pools. The purity of pooled Fab was estimated at about 10% of the total protein by SDS PAGE. Western immunoblot analysis of pooled SP disc fractions containing anti-human κ cross-reactive protein revealed the presence of a 46 kd protein which co-migrated with human Fab standard on a non-reducing SDS gel. This protein migrated as a single band at approximately 24 kd on a SDS reducing gel. These results were consistent with the predicted molecular weights, based on nucleotide sequence, for fully processed B38.1 chimeric L chain and Fd chain.

b. ING-2

Fab was purified from 10 liters culture supernatant. The culture supernatant was first concentrated by a DC10 unit over S10Y30 cartridge (Amicon), washing with 20 liters of distilled water, reconcentrating, and then washing with 10 mM sodium phosphate buffer at pH 8.0, and concentrating it again. The concentrate was then loaded on a DE52 (Whatman) column pre-equilibrated with 10 mM sodium phosphate buffer at pH 8.0. Sufficient 0.2 M monosodium phosphate was added to the flow through of DE52, adjusted pH to 7.2, and the sample was concentrated over a YM10 membrane (Stirred Cell 2000, Amicon). The sample was then diluted with sufficient water and reconcentrated to 200 ml to give a conductivity of 1.4 mS/cm. The total amount of protein was estimated by a colorimetric assay, and the sample was loaded onto a CM52 (Whatman) column at a ratio of 10 mg total protein per g CM52 (pre-equilibrated with 10 mM sodium phosphate buffer, pH 7.2). The CM52 column was eluted with sequential steps of 20 column volumes each of 2, 5, 10, 15, 20, 50, 100, 200, and 500 mM NaCl in 10 mM sodium phosphate buffer, pH 7.2. The fractions containing Fab as assessed by enzyme immunoassay were combined and concentrated over a YM10 membrane to an Fab concentration of about 1 mg/ml, and stored frozen. The pooled fraction was further analyzed by SDS-PAGE and Western. They both revealed a single 46 kd band consistent with the predicted molecular weight, based on nucleotide sequence.

c. ING-3

Fab was purified from 10 liters culture supernatant. The culture supernatant was first concentrated by a DC10 unit over S10Y30 cartridge (Amicon), washing with 20 liters of distilled water, reconcentrating, and then washing with 10 mM sodium phosphate buffer at pH 8.0, and concentrating it again. The concentrate was then loaded on a DE52 (Whatman) column pre-equilibrated with 10 mM sodium phosphate buffer at pH 8.0. Sufficient 0.2M monosodium phosphate was added to the flow-through of the DE52 column to adjust pH to 7.2, and the sample was concentrated over a YM10 membrane (Stirred Cell 2000, Amicon). The sample was then diluted with sufficient water and reconcentrated to 200 ml to give a conductivity of 1.4 mS/cm. The total amount of protein was estimated by a calorimetric assay, and the sample was loaded onto a CM52 (Whatman) column at a ratio of 10 mg total protein per g CM52 (pre-equilibrated with 10 mM sodium phosphate buffer, pH 7.2). The CM52 column was eluted with sequential steps of 20 column volumes each of 2, 5, 10, 15, 20, 50, 100, 200, and 500 mM NaCl in 10 mM sodium phosphate buffer, pH 7.2. The fractions containing Fab as assessed by enzyme immunoassay were combined and concentrated over a YM10 membrane to an Fab concentration of about 1 mg/ml, and stored frozen. The pooled fractions were further analyzed by SDS-PAGE and Western. They both revealed a single 46 kd band consistent with the predicted molecular weight, based on nucleotide sequence.

d. ING-4

Fab was purified from 10 liters culture supernatant. The culture supernatant was first concentrated by a DC10 unit over S10y30 cartridge (Amicon), washing with 20 liters of distilled water, reconcentrating, and then washing with 10 mM sodium phosphate buffer at pH 8.0, and concentrating it again. The concentrate is then loaded on a DE52 (Whatman) column pre-equilibrated with 10 mM sodium phosphate buffer at pH 8.0. Sufficient 0.2M monosodium phosphate is adde4d to the flow through of DE52, adjusted pH to 7.2, and the sample was concentrated over a YM10 membrane (Stirred Cell 2000, Amicon). The sample was then diluted with sufficient water and reconcentrated to 200 ml to give a conductivity of 1.4 ms/cm. The total amount of protein was estimated by a colorimetric assay, and the sample was loaded onto a CM52 (Whatman) column at a ratio of 10 mg total protein per g CM52 (pre-equilibrated with 10 mM sodium phosphate buffer. The CM52 column was eluted with sequential steps of 20 column volmes each of 2, 5, 10, 15, 20, 50, 100, 200, and 500 mM NaCl in 10 mM sodium phosphate buffer, pH 6.8. The fractions containing Fab as assessed by enzyme immunoassay were combined and concentrated over a YM10 membrane to an Fab concentration of about 1 mg/ml, and stored frozen. The pooled fraction was further analyzed by SDS-PAGE and Western, they both reveal a single 46 kd band and consistent with an predicated molecular weight, based on nucleotide sequence.

e. KM10

Fab was purified from 43 L of culture supernatant. The culture supernatant was first concentrated by a DC10 unit over S10Y10 cartridge (Amicon), washing with 20 L of distilled water, reconcentrating, and then washing with 10 mM sodium phosphate buffer at pH 8.0, and concentrating it again. The concentrate Was then loaded onto a DE52 (Whatman) column pre-equilibrated with 10 mM sodium phosphate buffer at pH 8.0. Sufficient 0.2M monosodium phosphate was added to the flow through of DE52 to adjust pH to −7.3, and the sample was concentrated over a YM10 membrane (Stirred Cell 2000, Amicon). The sample was then diluted with sufficient water and reconcentrated to 200 ml to give a conductivity of 1.6 mS/cm. The total amount of protein was estimated by a colorimetric assay, and the sample was loaded onto a CM52 (Whatman) column at a ratio of 10 mg total protein per g CM52 (pre-equilibrated with 10 mM sodium phosphate buffer, pH 7.3). The CM52 column was eluted with sequential steps of 20 column volumes each of 2, 5, 10, 15, 20, 50, 100, 200, and 500 mM NaCl in 10 mM sodium phosphate buffer, pH 7.3. The fractions containing Fab as assessed by ELISA were combined and concentrated over a YM10 membrane to an Fab concentration of about 1 mg/ml, and stored frozen. The pooled fraction was further analyzed by SDS-PAGE and Western blotting. They both revealed a single 46 kD band consistent with the predicted molecular weight, based on nucleotide sequence.

6. Binding Characteristics of Fab Protein Secreted by Yeast a. ING-1

The purification from yeast culture supernatants of protein of the expected size of Fab suggests that yeast secrete correctly folded, functional molecules. This hypothesis was confirmed by performing direct and competition binding assays with a human carcinoma cell line. In the direct binding assay, Fab from yeast bound to the same target cancer cells as did mouse B38.1 antibody, but not to a control cell line which lacks the antigen. In the competition assay using mouse 838.1 antibody, the yeast-derived B38.1 chimeric ING-1 Fab inhibited binding of mouse B38.1 antibody to human tumor cells. Fifty percent inhibition of mouse B38.1 antibody by the yeast-derived Fab was approximately 2 $\mu$g/ml (Table 18).

b. ING-2

The purification from yeast culture supernatants of protein of the expected size of Fab suggests that yeast secrete correctly folded, functional molecules. This hypothesis was confirmed by performing direct and competition binding assays with a human carcinoma cell line. In the direct binding assay, Fab from yeast bound to the same target cancer cells as did mouse Br-3 antibody, but not to a control cell line which lacks the antigen. In the competition assay using mouse Br-3 antibody, the yeast-derived Br-3 chimeric Fab inhibited binding of mouse Br-3 antibody to human tumor cells. Fifty percent inhibition of mouse Br-3 antibody by the yeast-derived Fab was approximately 5 ug/ml (Table 19).

c. ING-3

The purification from yeast culture supernatants of protein of the expected size of Fab suggests that yeast secrete correctly folded, functional molecules. This hypothesis was confirmed by performing direct and competition binding assays with a human carcinoma cell line. In the direct binding assay, Fab from yeast bound to the same target cancer cells as did mouse Co-1 antibody, but not to a control cell line which lacks the antigen. In the competition assay using mouse Co-1 antibody, the yeast-derived chimeric ING-3 Fab inhibited binding of mouse Co-1 antibody to human tumor cells (Table 20), indicating that the ING-3 Fab binds to the same antigen as the mouse Co-1 antibody.

d. ING-4

The purification from yeast culture supernatants of protein of the expected size of Fab suggests that yeast secrete correctly folded, functional molecules. This hypothesis was confirmed by performing direct and competition binding assays with a human carcinoma cell line. In the direct binding assay, Fab from yeast bound to the same target cancer cells as did mouse ME4 antibody, but not to a control cell line which lacks the antigen. In the competition assay using biotinylated chimeric ING-4 Fab from yeast, both the yeast-derived chimeric ING-4 Fab and mouse ME4 antibody inhibited binding of biotinylated chimeric Fab to human HT-29 tumor cells. Fifty percent inhibition of the yeast-derived ING-4 Fab was approximately 0.3 $\mu$g/ml (Table 21).

e. KM10

The purification from yeast culture supernatants of protein of the expected size of Fab suggests that yeast secrete correctly folded, functional molecules. This was confirmed by performing direct and competition binding assays with the human carcinoma cell line LS174T. In the direct binding assay, Fab from yeast bound to the same target cancer cells as did mouse KM10 antibody, but not to a cell line which lacks the antigen. In the competition assay using $^{125}$I-labeled mouse KM10 antibody, the yeast-derived chimeric KM10 Fab inhibited binding of radio-labeled mouse KM10 antibody to human tumor cells (LS174T). Yeast-derived Fab caused a 50% inhibition of binding of mouse KM10 antibody at approximately 3.7 µg/ml (Table 22), similar to the inhibitory potency of KM10 mouse antibody. Yeast derived KM10 Fab inhibited binding of both intact mouse KM10 antibody and Fab fragments (prepared by papaim digestion of mouse KM10 Fab prepared by papain digestion of mouse whole antibody.

TABLE 18

Inhibition of Binding of B38.1 Antibody to Tumor Cells[a]

| Antibody Concentration | % Inhibition by Competing Antibody | | |
|---|---|---|---|
| µg/ml | Mouse B38.1 | Chimeric ING-1 Fab | Human Fab[b] |
| 80 | — | 97 | 4.7 |
| 40 | — | 93 | 4.4 |
| 20 | — | 88 | 5.3 |
| 10 | 95 | 79 | 7.6 |
| 5 | 89 | 66 | |
| 2.5 | 81 | 49 | |
| 1.25 | 63 | 36 | |
| 0.625 | 30 | 18 | |
| 0.156 | 21 | 6.3 | |

[a]$^{125}$I-labeled B38.1 antibody was incubated with MCF-7 tumor cells in the presence of the competing antibody at 4° C. Cells were washed free of unbound antibody, and cell-bound radioactivity was used to determine the % inhibition of binding.
[b]Chimeric L6 Fab was used as a nonspecific antibody control.

TABLE 19

Inhibition of Binding of Br-3 Antibody to Tumor Cells[a]

| Antibody Concentration | % Inhibition by Competing Ig | | |
|---|---|---|---|
| µg/ml | Mouse Br-3 | Chimeric ING-2 Fab | Human IgG |
| 48 | — | 92 | — |
| 16 | 94 | 72 | 7 |
| 5.33 | 81 | 47 | 23 |
| 1.78 | 73 | 27 | 10 |
| 0.59 | 29 | 09 | 13 |
| 0.20 | 19 | 15 | 6 |
| 0.07 | 9 | — | 17 |

[a]$^{125}$I-labeled Br-3 antibody was incubated with BT20 tumor cells in the presence of the competing Ig at 4° C. Cells were washed free of unbound antibody, and cell-bound radioactivity was used to determine the % inhibition of binding.
[b]Human IgG is used as a nonspecific antibody control.

TABLE 20

Inhibition of Binding of Co-1 Antibody to Tumor Cells

| Antibody Concentration | % Inhibition by Competing Antibody[a] | | |
|---|---|---|---|
| µg/ml | Mouse Co-1 | Chimeric ING-3 Fab | Human Fab[b] |
| 900 | ND[c] | 78 | 32 |
| 300 | 94 | 56 | −5 |
| 100 | 93 | 29 | 0 |
| 33.3 | 85 | 19 | 0 |

TABLE 20-continued

Inhibition of Binding of Co-1 Antibody to Tumor Cells

| Antibody Concentration | % Inhibition by Competing Antibody[a] | | |
|---|---|---|---|
| µg/ml | Mouse Co-1 | Chimeric ING-3 Fab | Human Fab[b] |
| 11.1 | 55 | 7 | 2 |
| 3.7 | 33 | 0 | 0 |
| 1.23 | 3 | 3 | −2 |
| .41 | 0 | 0 | 5 |
| .14 | 3 | 0 | −1 |

[a]$^{125}$-labeled Co-1 antibody was incubated with HT-29 tumor cells in the presence of the competing antibody at 4° C. Cells were washed free of unbound antibody, and cell-bound radioactivity was used to determine the % inhibition of binding.
[b]-Human IgG was used as a nonspecific antibody control.
[c]-ND, not determined.

TABLE 21

Inhibition of Binding of ING-4 Fab to Turnor Cells

| Antibody | % Inhibition by Competing Antibody: | | |
|---|---|---|---|
| Concentration[c] µg/ml | Chimeric ING-4 | Mouse ME4 | Human IgG[b] |
| .033 | 6 | 7 | 3 |
| 0.10 | 21 | 2 | 4 |
| 0.31 | 51 | 40 | 9 |
| 0.93 | 76 | 15 | −3 |
| 2.77 | 88 | 22 | −7 |
| 8.33 | 94 | 50 | 4 |
| 25.0 | 99 | 84 | −2 |

[a]Biotinylated yeast chimeric Fab is incubated with HT-29 tumor cells in the presence of the competing antibody at 4° C. Cells are washed and further incubated with avidin-peroxidase at room temperature. The cell-bound peroxidase is visualized with OPD reagent and its OD$_{490}$ is used to determine the % inhibition by the following equation:

$$\% \text{ inhibition} = \left(1 - \frac{\text{OD With competing antibody}}{\text{OD No competing antibody}}\right) \times 100$$

[b]Human IgG is used as a nonspecific antibody control.
[c]The content of mouse ME4 antiboody is estimated to be 10% of total IgG in the preparation.

TABLE 22

Inhibition of Binding of KM10 Antibody to Tumor Cells

| Antibody Concentration | % Inhibition by Competing Antibody[a] | | | |
|---|---|---|---|---|
| µg/ml | Mouse KM10 | Chimeric KM10 Fab | Mouse KM10 Fab by papain | Human IgG |
| 100 | 94 | 94 | 89 | 38 |
| 33.3 | 82 | 90 | 91 | 39 |
| 11.1 | 82 | 76 | 87 | 30 |
| 3.70 | 56 | 53 | 69 | 43 |
| 1.235 | 51 | 29 | 56 | 42 |
| 0.412 | 40 | 7 | 39 | 34 |
| 0.137 | 41 | 3 | | |

[a]$^{125}$I-labeled KM10 antibody was incubated with LS174T tumor cells in the presence of the competing antibody at 4° C. Cells were washed free of unbound antibody, and cell-bound radioactivity was used to determine the % inhibition of binding.
[b]-Human-IgG was used as a nonspecific antibody control.

EXAMPLE 5
Chimeric Mouse-Human Fab with Human Tumor Cell Specificity Produced in *Escherichia coli*

Bacteria are suited for production of chimeric antibodies expressed from mammalian cDNA since entire coding sequences can be expressed from well characterized promoters. *Escherichia coli* is one of many useful bacterial species for production of foreign proteins (Holland et al., *BioTechnology* 4:427 (1986)) since a wealth of genetic information is available for optimization of its gene expression. *E. coli* can be used for production of foreign proteins internally or for secretion of proteins out of the cytoplasm, where they most often accumulate in the periplasmic space (Gray et al., *Gene* 39:247 (1985); Oka et al., *Proc. Natl. Acad. Sci. USA* 82:7212 (1985)). Secretion from the *E. coli* cytoplasm has been observed for many proteins and requires a signal sequence. Proteins produced internally in bacteria are often not folded properly (Schoner et al., *BioTechnology* 3:151 (1985)). Proteins secreted from bacteria, however, are often folded properly and assume native secondary and tertiary structures (Hsiung et al., *BioTechnology* 4:991 (1986)).

An Fab molecule consists of two nonidentical protein chains linked by a single disulfide bridge. These two chains are the intact antibody L chain and the V, J, and $C_H1$ portions of the antibody H chain Fd. The proper cDNA clones for the ING-2 chimeric L and Fd genes have already been identified. In this example, these cDNA clones were organized into a single bacterial operon (a dicistronic message) as gene fusions to the pectate lyase (pelB) gene leader sequence from *Erwinia caratovora* (Lei et al., *J. Bacteriol.* 169:4379 (1987)) and expressed from a strong regulated promoter. The result is a system for the simultaneous expression of two protein chains in *E. coli*, and the secretion of immunologically active, properly assembled Fab of chimeric antibodies.

The following sections detail the secretion of chimeric ING-2 Fab from *E. coli*.

1. Assembly of the pelB Leader Sequence Cassette

*Erwinia caratovora* (EC) codes for several pectate lyases (poly-galacturonic acid trans-eliminase) (Lei et al., *Gene* 35:63 (1985)). Three pectate lyase genes have been cloned, and the DNA sequence of these genes has been determined. When cloned into *E. coli* under the control of a strong promoter, the pelB gene is expressed and large quantities of pectate lyase accumulate in the periplasmic space and culture supernatant. The pelB signal sequence functions efficiently in *E. coli* and was used as a secretion signal for antibody genes in this example. (Other signal sequences would also be useful for this application.) The nucleotide sequence surrounding the signal sequence of the pelB gene is published (Lei et al., *J. Bacteriol.* 169:4379–4383 (1987)).

The pelB signal sequence contains a HaeIII restriction site at amino acid 22, adjacent to the signal peptidase cleavage site: ala-ala. Plasmid pSS1004 (Lei et al., (1987), supra) containing the pelB gene in pUC8 (Vierra and Messing, *Gene* 19:259 (1982)) was digested with HaeIII and EcoR1. This DNA was ligated with an eight base pair SstI linker to SspI and EcoR1 cut pBR322. The resulting plasmid contained a 300 bp fragment which included the 22 amino acid leader sequence of pelB and about 230 bp of upstream *E. caratovora* DNA. This plasmid, pING173, contains an insert that upon digestion with Sst1 and treatment with T4 DNA polymerase can be ligated directly to a DNA fragment flanked by the first amino acid of a mature coding sequence for any gene to generate a protein fusion containing a functional bacterial leader sequence in frame with the incoming gene. The Sst1 to EcoR1 restriction fragment in pING173 was cloned into pUC18 (Yanich-Perron et al., *Gene* 33:103 (1985)) to generate pRR175, which contains the pelB leader and adjacent upstream non-coding sequence (including a ribosome binding site) downstream of the lac promoter. Plasmid pING1500, derived from pRR175, contains on y the region from the −48 of the pelB gene to an XhoI site downstream of the pelB leader, and includes the SstI site at the junction.

2. Preparation of Light Chain for Bacterial Expression a. ING-1

Figure 13A:
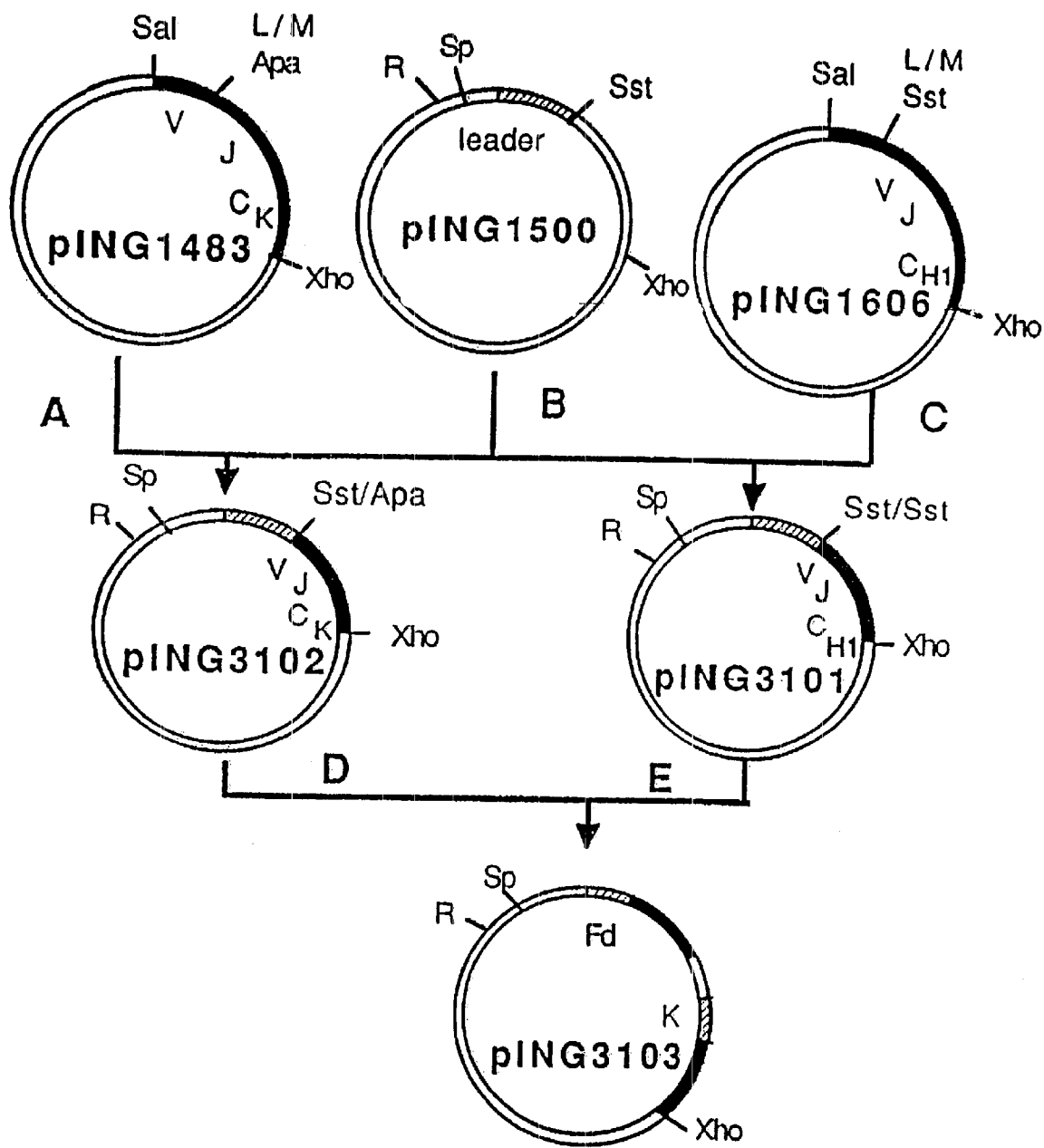
FIGS. 13(A and B). Construction scheme for the bacterial chimeric ING-1 Fab expression plasmid pING3107. Plasmid pING3107 contains the following elements useful for expression in $E.$ $coli:$ 1) the araC gene, 2) the inducible araB promoter, 3) the dicistronic chimeric Fd and chimeric κ ING-1 genes fused to the pelB leader sequence, 4) the trpA transcription termination sequence, and 5) the $tet^R$ gene, useful for selection in $E.$ $coli.$ Not drawn to scale.

The intact ING-1 chimeric L chain gene containing an ApaI restriction site at the signal sequence processing site and a unique XhoI site downstream of the gene in pING1483 served as the starting point for bacterial expression. The plasmid pING1483 was cut with ApaI, treated with T4 polymerase, and digested with XhoI. The approximately 800 bp fragment containing the L chain gene was purified and ligated to pING1500 that was cut with SstI, treated with T4 polymerase, and cut with XhoI (FIG. 13A,B). The resulting plasmid that contained a pelB::B38.1 L chain fusion was sequenced to determine that the proper in-frame fusion was formed. This plasmid was called pING3102.

b. ING-2

Figure 20A:
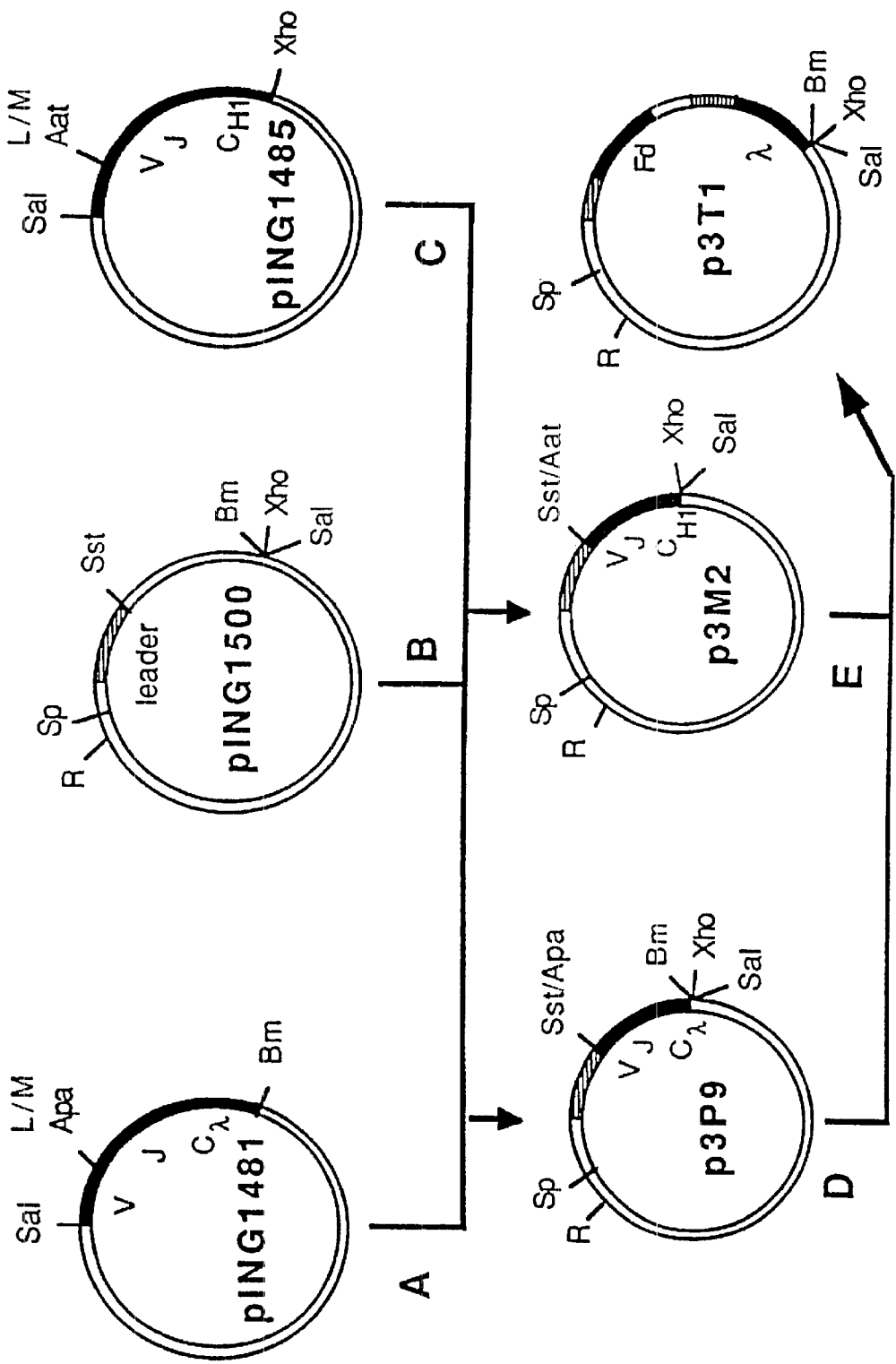
FIGS. 20(A and B). Construction scheme for the bacterial chimeric ING-2 Fab expression plasmid pBR3-3. Plasmid pBR3-3 contains the following elements useful for expression in $E.$ $coli:$ 1) the araC gene, 2) the inducible araB promoter, 3) the dicistronic Fd and λ ING-2 genes fused to the pelB leader sequence, 4) the trpA transcription termination sequence, and 5) the $tet^R$ gene, useful for selection in $E.$ $coli.$ Not drawn to scale.

The intact ING-2 chimeric L chain gene containing an ApaI restriction site at the signal sequence processing site and a BamHI site downstream of the gene in pING1481 served as the starting point for bacterial expression. The plasmid pING1481 was cut with ApaI, treated with T4 polymerase, and digested with BamHI. The approximately 800 bp fragment containing the L chain gene was purified and ligated to pING1500 that was cut with SstI, treated with T4 polymerase, and cut with BamHI (FIG. 20A, B). This plasmid was called p3P9.

c. ING-3

Figure 28A:
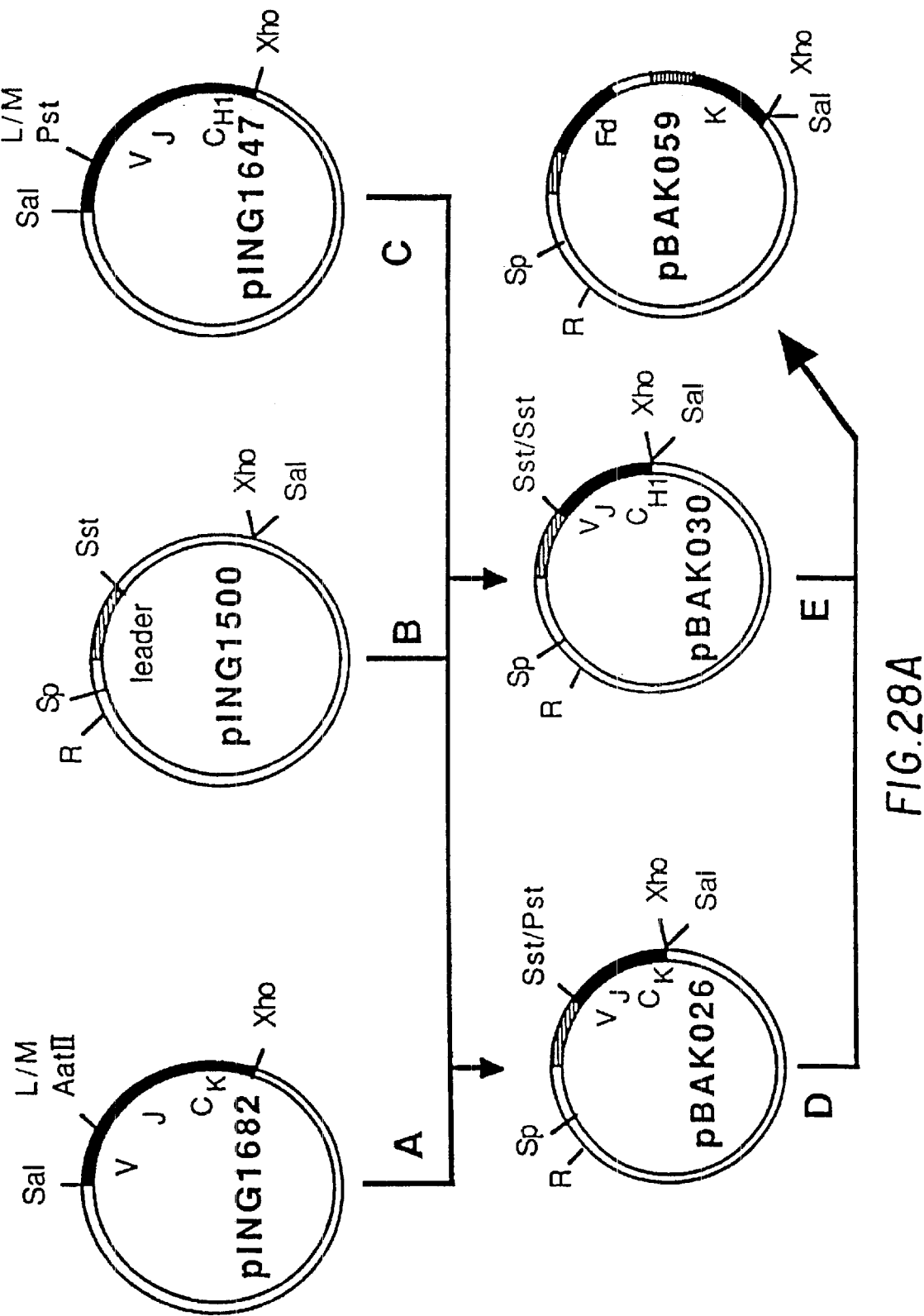
FIGS. 28(A and B). Construction scheme for the bacterial chimeric ING-3 Fab expression plasmid pING3307. Plasmid pING3307 contains the following elements useful for expression in $E.$ $coli:$ 1) the araC gene, 2) the inducible araB promoter, 3) the dicistronic Fd and κ ING-3 genes fused to the pelB leader sequence, 4) the trpA transcription termination sequence, and 5) the $tet^R$ gene, useful for selection in $E.$ $coli.$ Not drawn to scale.

The intact Co-1 chimeric L chain gene containing an AatII restriction site at the signal sequence processing site and a unique XhoI site downstream of the gene in pING1682 served as the starting point for bacterial expression. The plasmid pING1682 was cut with AatII, treated with T4 polymerase, and digested with XhoI. The approximately 800 bp fragment containing the L chain gene was purified and ligated to pING1500 that was cut with SstI, treated with T4 polymerase, and cut with XhoI (FIG. 28A, B). The resulting plasmid that contained a pelB::Co-1 L chain fusion was sequenced to determine that the proper in-frame fusion was formed. This plasmid was called pBAK026.

d. ING-4

Figure 35A:
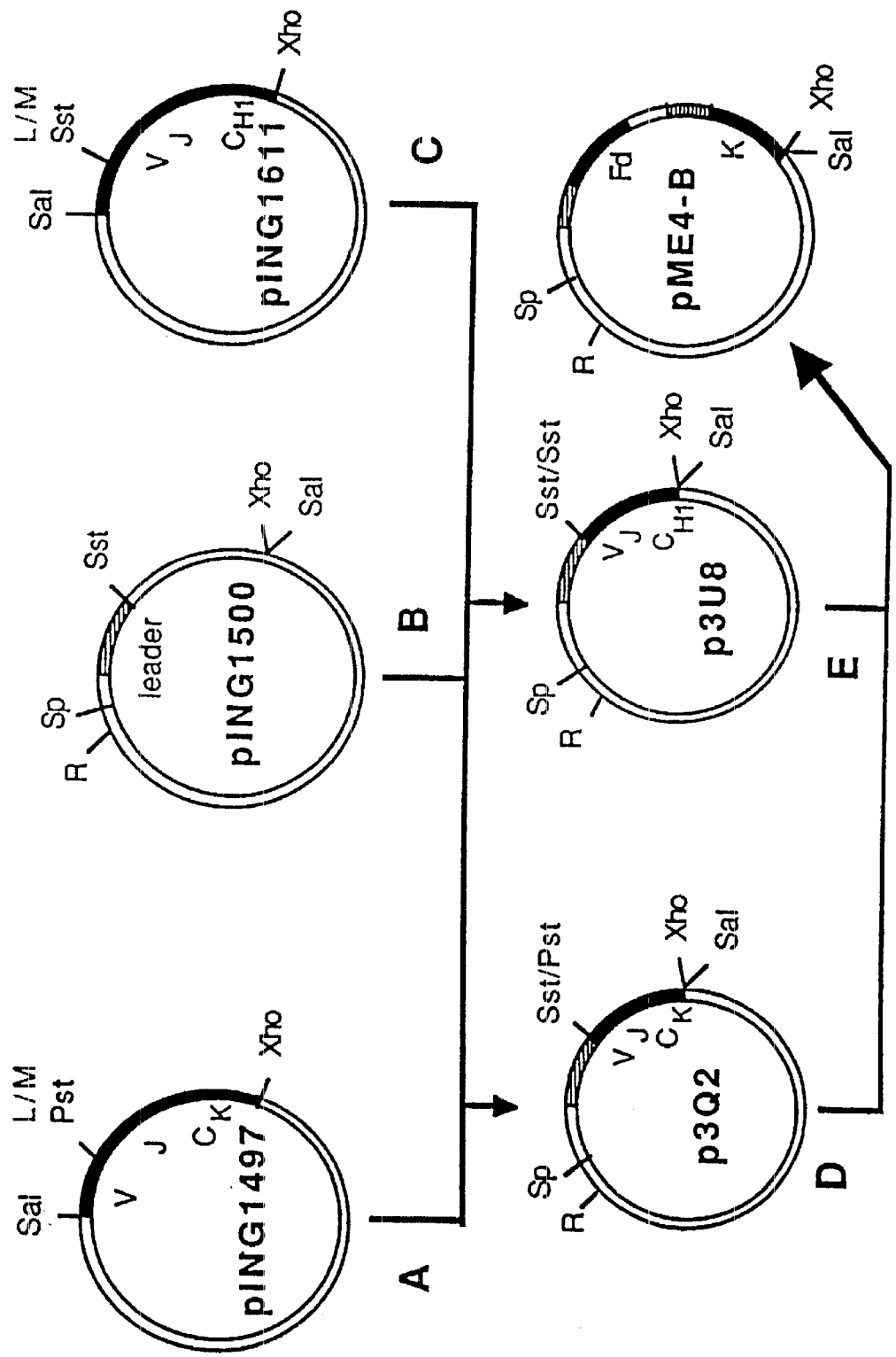
FIGS. 35(A and B). Construction scheme for the bacterial chimeric ING-4 Fab expression plasmid pME4-B3. Plasmid pME4-B3 contains the following elements useful for expression in *E. coli:* 1) the araC gene, 2) the inducible araB promoter, 3) the dicistronic Fd and K ING-4 genes fused to the pelB leader sequence, 4) the trpA transcription termination sequence, and 5) the $tet^R$ gene, useful for selection in *E. coli*. Not drawn to scale.

The intact ME4 chimeric L chain gene containing an PstI restriction site at the signal sequence processing site and a unique XhoI site downstream of the gene in pING1497 served as the starting point for bacterial expression. The plasmid pING1497 was cut with PstI, treated with T4 polymerase, and digested with XhoI. The approximately 800 bp fragment containing the L chain gene was purified and ligated to pING1500 that was cut with SstI, treated with T4 polymerase, and cut with XhoI (FIG. 35A,B). The resulting plasmid that contained a pelB::ME4 L chain fusion was sequenced to determine that the proper in-frame fusion was formed. This plasmid was called 3Q2.

e. KM10

Figure 41A:
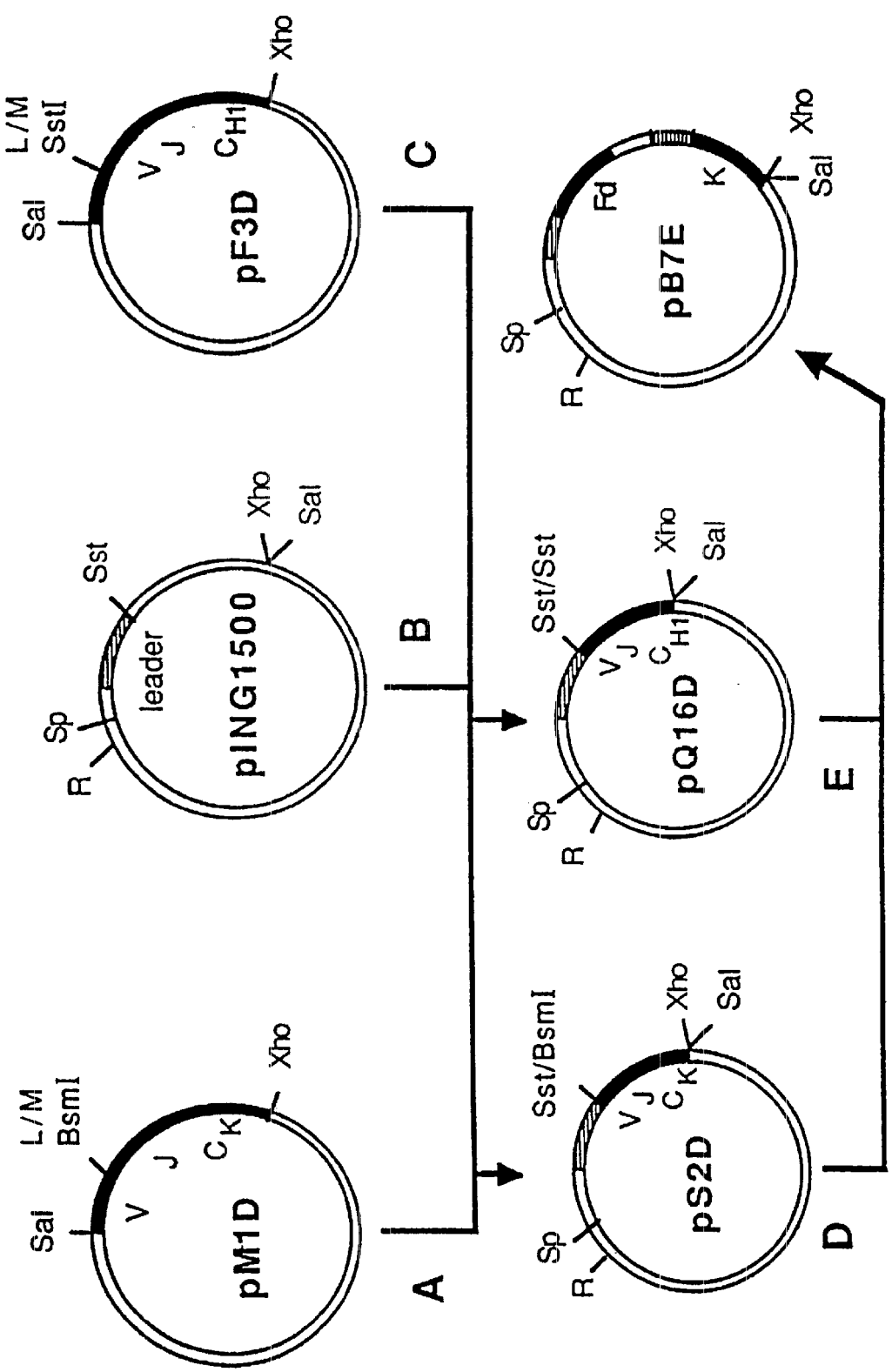
FIGS. 41(A and B). Construction scheme for the bacterial chimeric KM10 Fab expression plasmid pING3202. Plasmid pING3202 contains the following elements useful for expression in *E. coli:* 1) the araC gene, 2) the inducible araB promoter, 3) the dicistronic Fd and κ KM10 genes fused to the pelB leader sequence, 4) the trpA transcription termination sequence, and 5) the $tet^R$ gene, useful for selection in *E. coli*. Not drawn to scale.

The intact KM10 chimeric L chain gene containing a BsmI restriction site at the signal sequence processing site and a unique XhoI site downstream of the gene in pM1D served as the starting point for bacterial expression. The plasmid pM1D was cut with BsmI, treated with T4 polymerase, and digested with XhoI. The approximately 800 bp fragment containing the L chain gene was purified and ligated to pING1500 that was cut with SstI, treated with T4 polymerase, and cut with XhoI (FIG. 41A, B). The resulting plasmid that contained a pelB::KM10 L chain fusion was sequenced to determine that the proper in-frame fusion was formed. This plasmid was called pS2D.

Figure 13B:
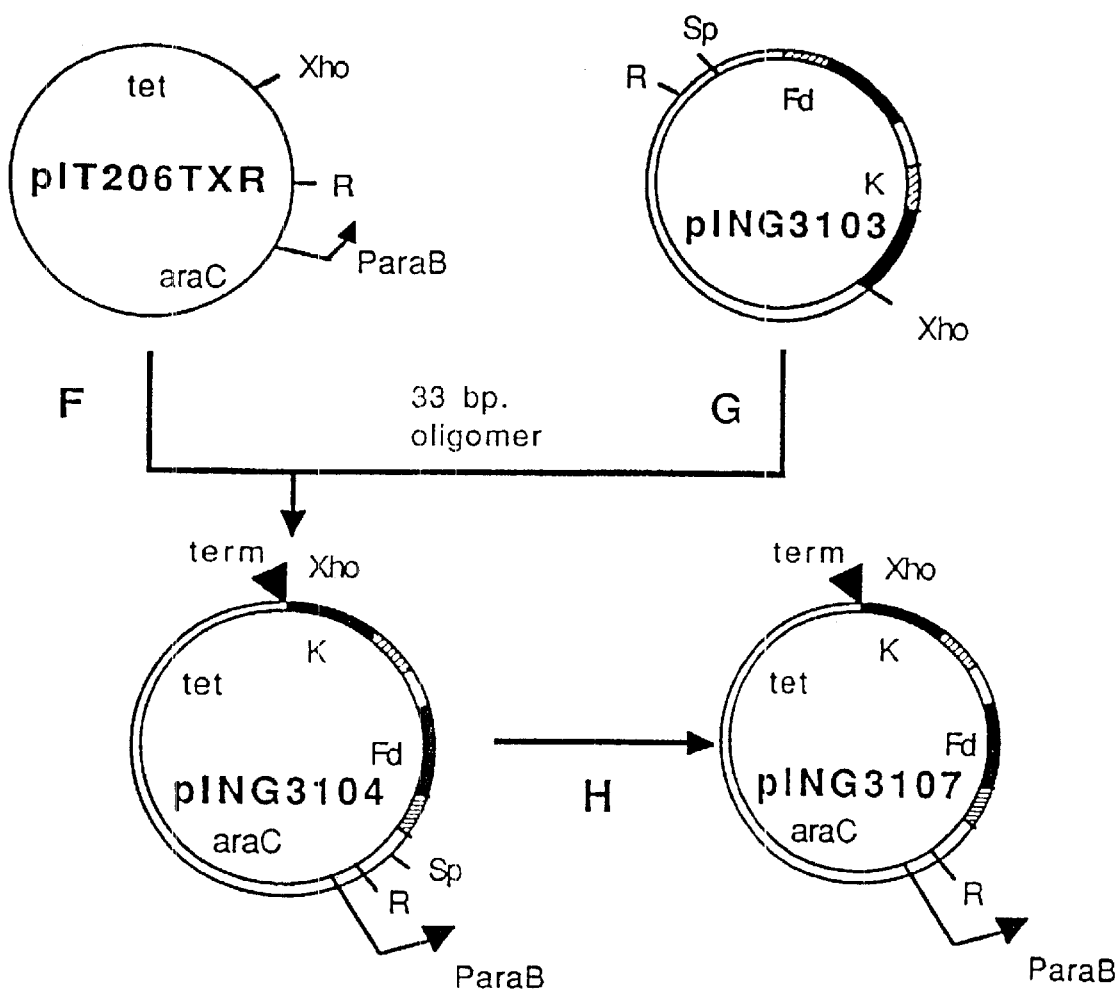
Figure 20B:
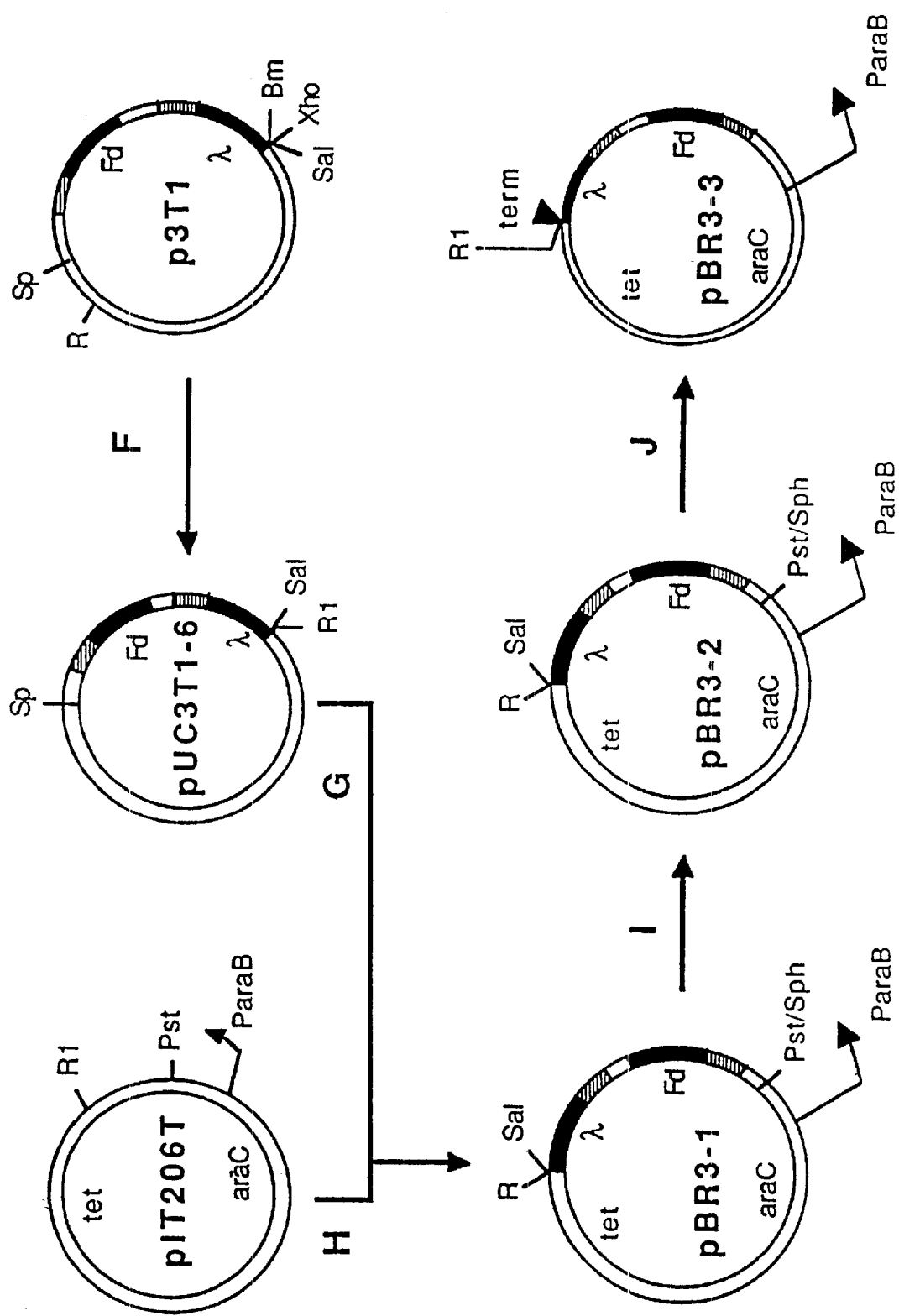
Figure 28B:
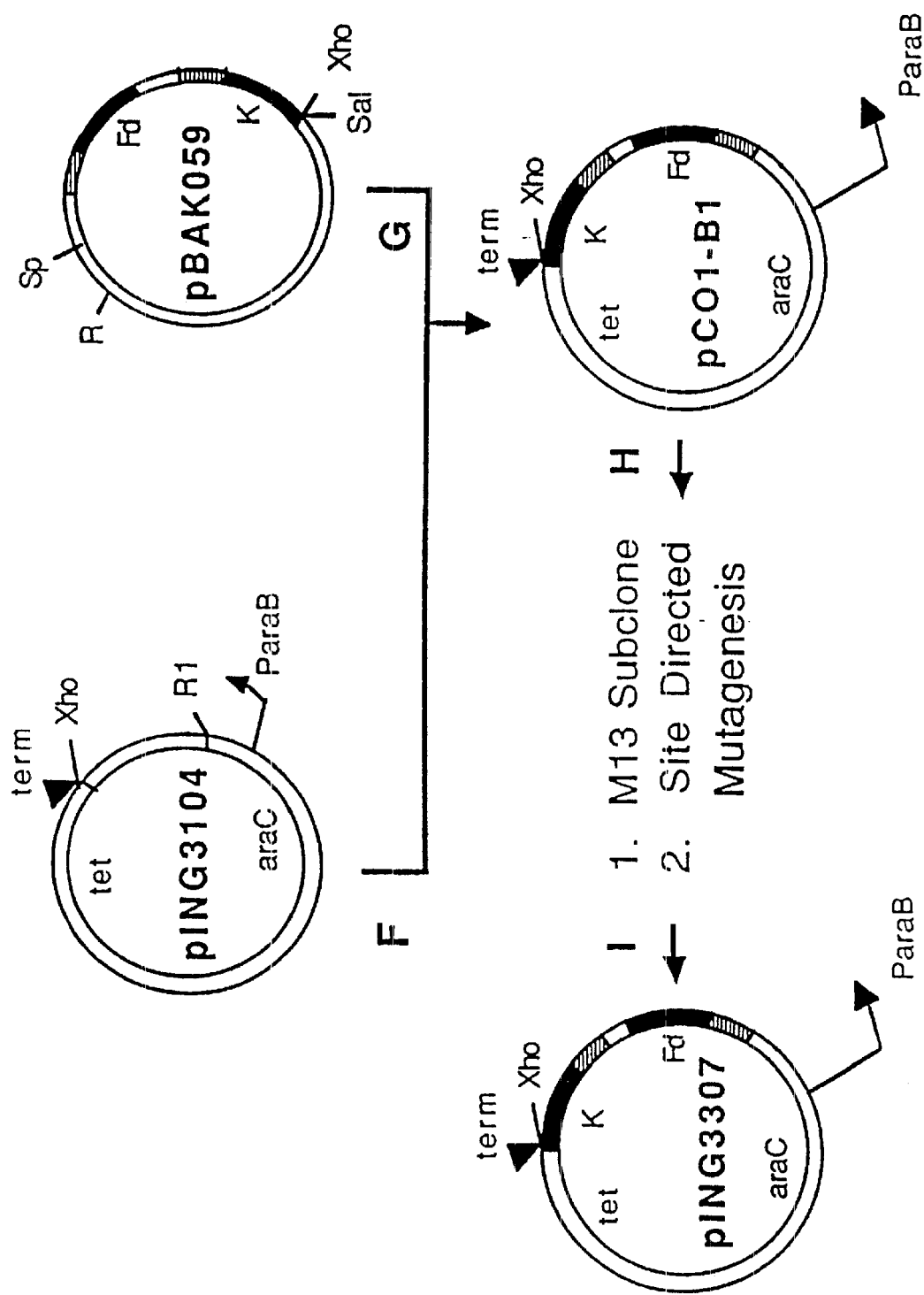
Figure 35B:
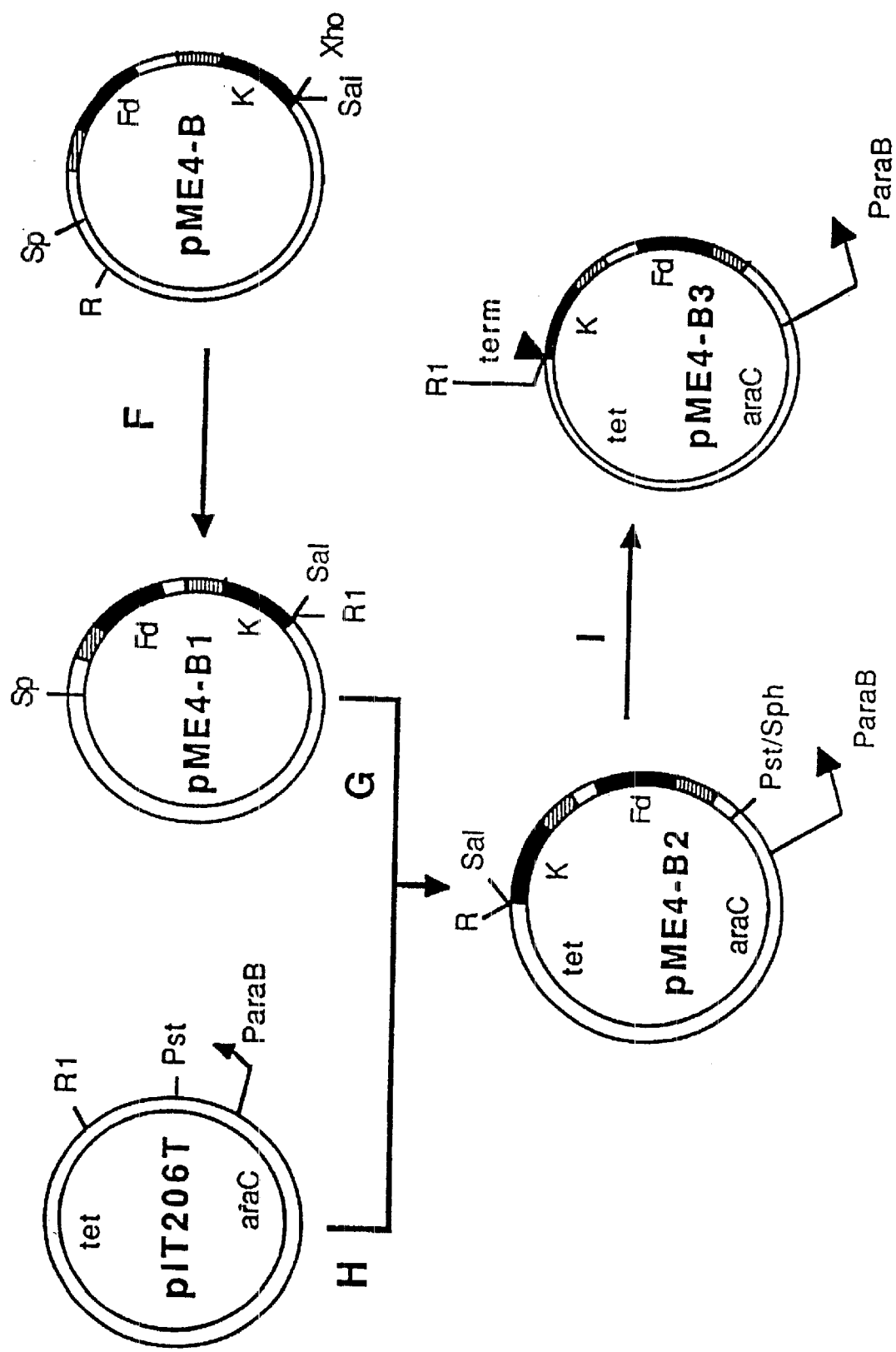
Figure 38A:
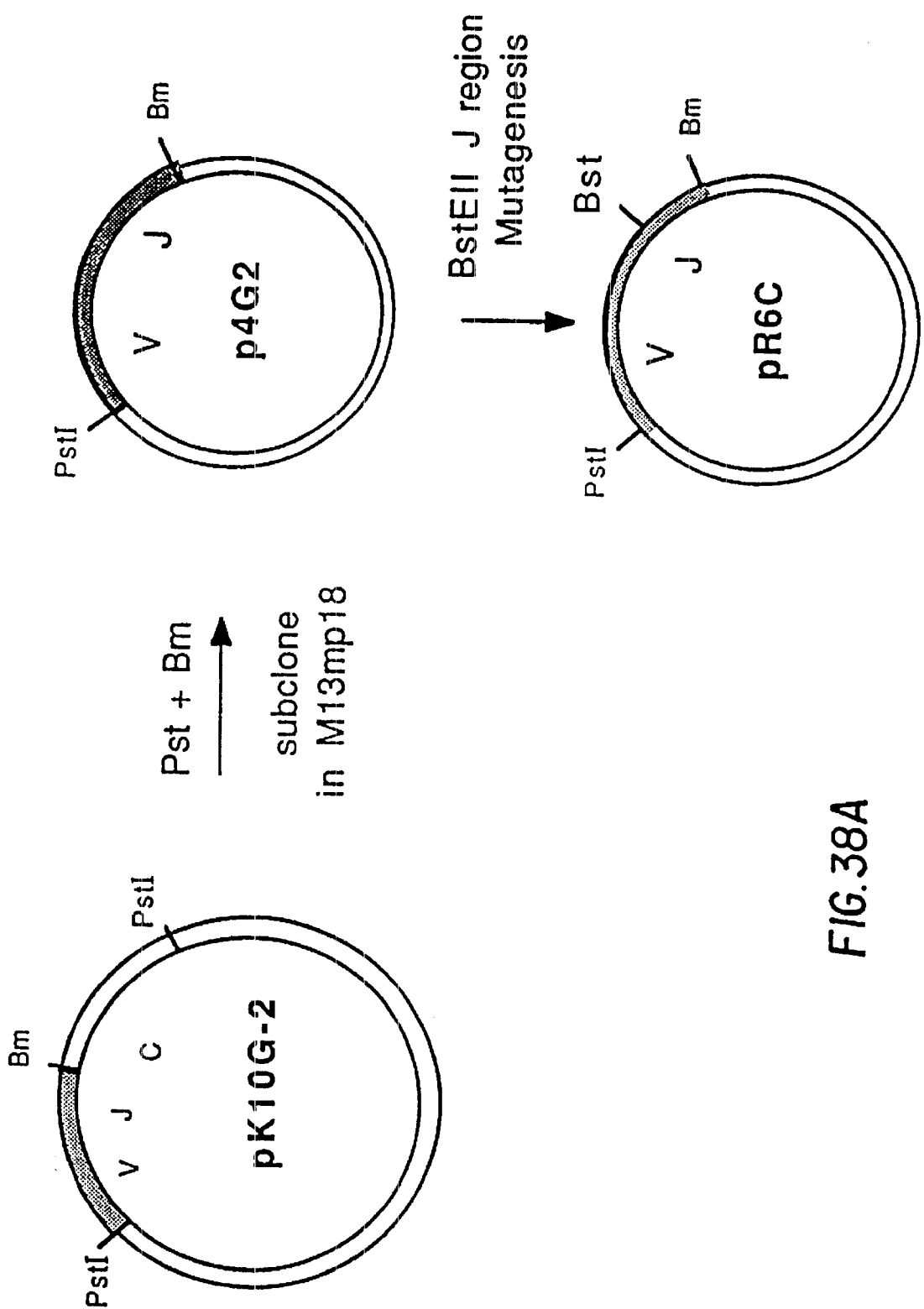
FIGS. 38(A and B). Construction scheme for the chimeric mouse-human KM10 H chain mammalian expression plasmid, pING2240. The V region for the cDNA clone pM10G-2 was engineered to be compatible with the eukaryotic expression plasmid pING2227. See FIG. 5 for construction of plasmid pING2227. Not drawn to scale.
Figure 38B:
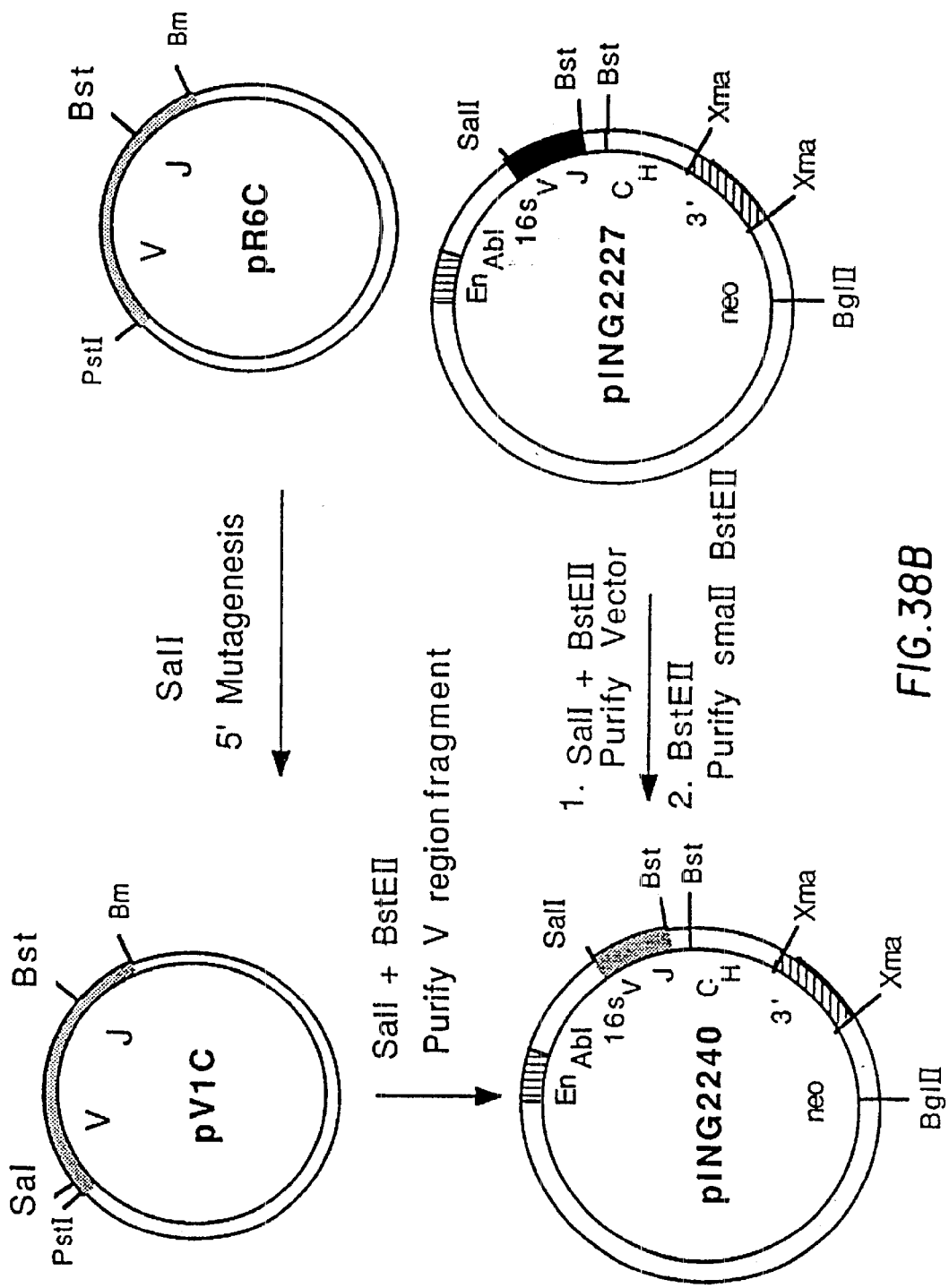
Figure 41B:
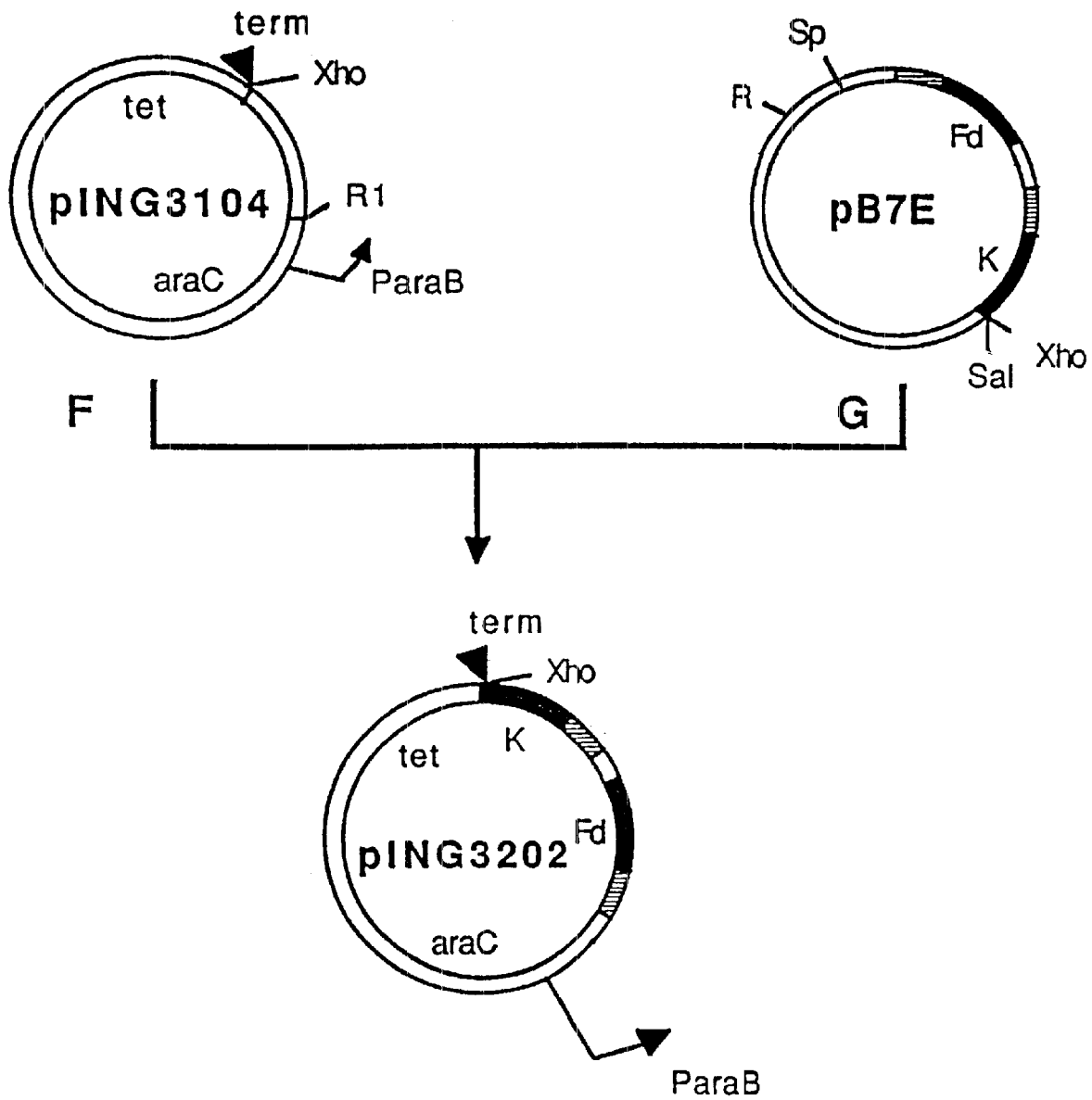

3. Preparation of Fd Chain for Bacterial Expression
   a. ING-1
   The intact ING-1 chimeric Fd gene containing an SstI restriction site at the signal sequence processing site and a XhoI restriction site downstream of the gene in pING1606 served as the starting point for bacterial expression. The plasmid pING1606 was cut with SstI, treated with T4 polymerase, and digested with XhoI. The approximately 800 bp fragment containing the L chain gene was purified and ligated to pING1500 that was cut with SstI, treated with T4 polymerase, and cut with XhoI (FIG. 13B, C). The resulting plasmid that contained a pelB::B38.1 Fd fusion was sequenced to determine that the proper in-frame fusion was formed. This plasmid was called pING3101.
   b. ING-2
   The intact ING-2 chimeric Fd gene containing an AatII restriction site at the signal sequence processing site and a XhoI restriction site downstream of the gene in pING1485 served as the starting point for bacterial expression. The plasmid pING1485 was cut with AatII, treated with T4 polymerase, and digested with XhoI. The approximately 800 bp fragment containing the H chain gene was purified and ligated to pING1500 that was cut with SstI, treated with T4 polymerase, and cut with XhoI (FIG. 20B, C). The resulting plasmid that contained a pelB::Br-3: Fd fusion was sequenced to determine that the proper in-frame fusion was formed. This plasmid was called p3M2.
   c. ING-3.
   The: intact ING-3 chimeric Fd gene containing a PstI restriction site at the signal sequence processing site and a XhoI restriction site. downstream of the gene in pING1647 served as the starting point for bacterial expression. The plasmid pING1647 was cut with PstI, treated with T4 polymerase, and digested with XhoI. The approximately 800 bp fragment containing the Fd gene was purified and ligated to pING1500 that was cut with SstI, treated with T4 polymerase, and cut with XhoI (FIG. 28B,C). The resulting plasmid was called pBAK030.
   d. ING-4
   The intact ING-4 chimeric Fd gene containing an SstI restriction site at the signal sequence processing site and a XhoI restriction site downstream of the gene in pING1611 served as the starting point for bacterial expression. The plasmid pING1611 was cut with SstI, treated with T4 polymerase, and digested with XhoI. The approximately 800 bp fragment containing the L chain gene was purified and ligated to pING1500 that was cut with SstI, treated with T4 polymerase, and cut with XhoI (FIG. 35B,C). The resulting plasmid that contained a pelB::ME4 Fd fusion was sequenced to determine that the proper in-frame fusion was formed. This plasmid was called p3U8.
   e. KM10
   The intact KM10 chimeric Fd gene containing a SstI restriction site at the signal sequence processing site and a XhoI restriction site downstream of the gene in pF3D served as the starting point for bacterial expression. The plasmid pF3D was cut with SstI, treated with T4 polymerase, and digested with XhoI. The approximately 800 bp fragment containing the Fd gene was purified and ligated to pING1500 that was cut with SstI, treated with T4 polymerase, and cut with XhoI (FIG. 41B,C). The resulting plasmid that contained a pelB::KM10 Fd fusion was sequenced to determine that the proper in-frame fusion was formed. This plasmid was called pQ16D.
4. Multicistronic Expression System for Light Chain and Fd Gene
   For production of bacterially derived Fab, both L chain and Fd need to be produced simultaneously within the cell. Using the plasmids constructed with each of these genes separately, a series of expression plasmids were constructed that contain both genes aligned so that transcription from a single promoter will specify both genes This was done in a way that minimized the noncoding DNA between the two genes. Each gene has a ribosome binding site needed for translation initiation and the identical DNA sequence from −48 to the pelB leader::antibody gene junction.
   a. ING-1
   Plasmid pING3102 was cut with SphI, treated with T4 polymerase, cut with EcoRI, and the vector fragment was purified (FIG. 13D). Similarly, pING3101 was cut with XhoI, treated with T4 polymerase, cut with EcoRI and the fragment containing the Fd gene was purified (FIG. 13E). These two purified DNA fragments were ligated to produce pING3103, which contained the two ING-1 chimeric gene fusions linked in close proximity. The two gene cistron was placed under the control of the arab promoter in pIT206TXR. First, pING3103 was cut with EcoRI and XhoI and the fragment containing the two genes was purified (FIG. 13G). Next pIT206TXR was cut with EcoRI and XhoI and ligated to the purified gene fragment in a three piece ligation along with the annealed oligonucleotides (5' TCGAGAGCCCGCCTAATGAGCGGGCTTTTTTTT-3' and 5' TCGAAAAAAAAAAGCCCGCTCATTAGGCGGGCTC-3) containing the trpA transcriptional terminator (FIG. 13F). In the plasmid constructed, pING3104, an extra 30 bp fragment of pBR322 DNA is located between the araB promoter and the Fd initiation codon. This fragment was removed to make the final 2 gene expression plasmid, pING3107 (FIG. 13H). This last vector contains all of the necessary features for expression of ING-1 chimeric Fab in E. coli.
   b. ING-2
   Plasmid p3P9 was cut with SphI, treated with T4 polymerase, cut with EcoRI, and the vector fragment was purified (FIG. 20D). Similarly, p3M2 was cut with XhoI, treated with T4 polymerase, cut with EcoRI and the fragment containing the Fd gene was purified (FIG. 20E). These two purified DNA fragments were ligated to produce p3T1, which contained the two ING-2 chimeric gene fusions linked in close proximity. The two gene cistron was placed under the control of the araB promoter in pIT206T.
   Plasmid p3T1 was cut with SalI and SphI, and the two gene module was cloned into pUC18 with SalI and SphI, generating pUC3T1-6 (FIG. 20F). Plasmid pUC3T1-6 was cut with SphI, treated with T4-polymerase, cut with EcoRI (FIG. 20G), and the two gene module was cloned into pIT206T cut with PstI, treated with T4 polymerase, and cut with EcoRI (FIG. 20H). Plasmid pBR3-1 failed to produce λ chains, and upon inspection was found to have a 1 bp deletion at the junction of pelB and the Br-3 λ chain. Site-directed mutagenesis was used to insert one bp with the primer 5'-CAACAGCCTGCGCCATCGCTG-3' using an appropriate M13 subclone from pBR3-1. Reassembly of the product from oligonucleotide mutagenesis back into pBR3-1 resulted in pBR3-2 (FIG. 20I). Insertion of the trpA transcriptional terminator as annealed oligonucleotides (5'TCGAGAGCCCGCCTAMTGAGCGGGCTTTTTTTT-3' AND 5' TCGAAAAAAAAAAGCCCGCTCATTAGGCGGGCTC-3) into a SalI restriction site downstream of chimeric Br-3 λ resulted in the final expression vector pBR3-3 (FIG. 20J).
   c. ING-3
   Plasmid pBAK026 was cut with SphI, treated with T4 polymerase, cut with EcoRI, and the vector fragment was purified (FIG. 28D). Similarly, pBAK030 was cut with XhoI, treated with T4 polymerase, cut with EcoRI and the fragment containing the Fd gene was purified (FIG. 28E). These two purified DNA fragments were ligated to produce pBAK059, which contained the two ING-3 chimeric gene fusions linked in close proximity. The two gene cistron was placed under the control of the araBAD promoter in pING3104. Plasmid pBAK059 was cut with SphI, treated with T4 polymerase, cut with XhoI, and the fragment containing the Fd and κ genes was purified (FIG. 28G). This DNA fragment was ligated to the vector fragment from pING3104 that had been cut with EcoRI, treated with T4 polymerase, and cut with XhoI (FIG. 28F), generating pC01-B1.

The pC01-B1 expression plasmid was found to have an incorrect nucleotide sequence at the joint between the pelB leader peptide and the $V_H$ peptide sequence. A single nucleotide base pair was missing at the joint, causing an incorrect translational reading frame for the Fd region protein. To correct this, a DNA fragment containing this region was excised and ligated to an M13 phage vector for site-directed mutagenesis by the method of Kramer et al., supra (FIG. 28H). The incorrect nucleotide sequence was 5'-CAGCGATGGCGAGGTCCAGTTG-3'. The oligonucleotide used for mutagenesis was 5'-CAGCGATGGCGGAGGGTCCAGTTG-3'. After the site-directed mutagenesis, the corrected DNA fragment was re-inserted into the pC01-B1 plasmid to make a new expression plasmid, pING3307, which is identical to pC01-B1 except for the inserted nucleotide (FIG. 28I). Plasmid pING3307 contains all the necessary features for expression of ING-3 Fab in E. coli.

d. ING-4

Plasmid p3Q2 was cut with SphI, treated with T4 polymerase, cut with EcoRI, and the vector fragment was purified (FIG. 35D). Similarly, p3U8 was cut with XhoI, treated with T4 polymerase, cut with EcoRI and the fragment containing the Fd gene was purified (FIG. 35E). These two purified DNA fragments were ligated to produce pME4-B, which contained the two ING-4 chimeric gene fusions linked in close proximity. The SphI to SalI fragment containing the Fd and K genes from pME4B was subcloned (FIG. 35F) into pUC19 cut with SphI and SalI, generating pME4-B1. Plasmid pME4-B1 was cut with SphI, treated with T4 polymerase, cut with EcoRI, and the fragment containing the two genes was purified (FIG. 35G). Next, pIT206T was cut with Pst1, treated with T4 polymerase, cut with EcoR1 (FIG. 35H), and ligated to the purified K and Fd gene fragment, generating pING4-B2. The final ING-4 Fab expression vector, pME4-B3, was constructed by cutting pME4-B2 with SalI and ligating it with the annealed oligonucleotides (5'TCGAGAGCCCGCCTAATGAGCGGGCTTTTTTTT-3' and 5'TCGAAAAAAAAAGCCCGCTCATTAGGCGGGCTC-3') containing the trpA transcriptional terminator (FIG. 35I). This last vector contains all of the necessary features for expression of ING-4 chimeric Fab in E. coli.

e. KM10

Plasmid pS2D was cut with SphI, treated with T4 polymerase, cut with EcoRI, and the vector fragment was purified (FIG. 41D). Similarly, pQ16D was cut with XhoI, treated with T4 polymerase, cut with EcoRI and the fragment containing the Fd gene was purified (FIG. 41E). These two purified DNA fragments were ligated to produce pB7E, which contained the two KM10 chimeric gene fusions linked in close proximity. The two gene cistron was placed under the control of the araB promoter in pING3104. Plasmid pB7E was cut with SphI, treated with T4 polymerase, cut with XhoI, and the fragment containing the Fd and κ genes was purified (FIG. 41G). This DNA fragment was ligated to the vector fragment from pING3104 that had been cut with EcoRI, treated with T4 polymerase, and cut with XhoI (FIG. 41F), generating pING3202. This vector contains all the necessary features for expression of KM10 chimeric Fab in E. coli.

5. Production of Chimeric Fab in Bacteria a. ING-1

Expression of ING-1 chimeric Fab from pING3107 in E. coli is under the inducible control of the araB promoter. Upon arabinose induction, Fab secreted into the growth medium increases more than 10 fold. Uninduced bacterial colonies harboring pING3107 are phenotypically indistinguishable from E. coli harboring pIT206TXR. The strain harboring pING3107 is cultured in 10 L of minimal medium, supplemented with 0.7% glycerol as the carbon source, and induced with 0.2% arabinose for greater than 12 hours.

Several liters of culture supernatant are concentrated using a S10Y10 cartridge (DC10 concentrator, Amicon). The concentrate is passed through a column pre-equilibrated with sodium phosphate buffer. Sufficient monosodium phosphate is added to adjust pH, and the sample is concentrated over a YM10 membrane (Stirred Cell 2000, Amicon). The sample is then diluted with sufficient water and reconcentrated. The total amount of protein is estimated by a colorimetric assay, and the sample is loaded onto a carboxymethylcellulose (CM-52) column at a ratio of 10 mg total protein per 1 g CM cellulose preequilibrated with a sodium phosphate buffer. The CM-52 column is eluted with sequential steps of increasing NaCl concentration in a phosphate buffer. The fractions containing Fab as assessed by enzyme immunoassay are combined and concentrated over a YM10 membrane to an Fab concentration of about 1 mg/ml, and stored frozen.

The ING-1 Fab purified from E. coli has identical molecular weight properties as ING-1 Fab purified from yeast (Example 4), as assessed by SDS gel electrophoresis. The bacterially-produced ING-1 Fab is correctly assembled as a κ plus Fd chain dimer because of its positive reaction in the enzyme immunoassays detecting molecules with both κ and Fd determinants, and because it competes the binding of labeled B38.1 mouse antibody to human tumor cells.

b. ING-2

Expression of ING-2 chimeric Fab from pBR3-3 in E. coli is under the inducible control of the araB promoter. Upon arabinose induction, Fab secreted into the growth medium increases more than 10 fold. Uninduced bacterial colonies harboring pBR3-3 are phenotypically indistinguishable from E. coli harboring pIT206T. The strain harboring pBR3-3 is cultured in 10 L of minimal medium, supplemented with 0.7% glycerol as the carbon source, and induced with 0.2% arabinose for greater than 12 hours.

About 7 liters of culture supernatant are concentrated to 2 liters using a S10Y10 cartridge (DC10 concentrator, Amicon). The concentrate is passed through a 500 g DEAE cellulose type DE5 (Whatman) column pre-equilibrated with 10 mM sodium phosphate at pH 8.0. Sufficient 0.2M monosodium phosphate is added to adjust pH, and the sample is concentrated over a YM10 membrane (Stirred Cell 2000, Amicon). The samples is then diluted with sufficient water and reconcentrated to 200 ml to give a conductivity of 1.1 mS. The total amount of protein is estimated by a colorimetric assay, and the sample is loaded onto a carboxymethylcellulose (CM52, Whatman) column at a ratio of 10 mg total protein per 1 g CM cellulose preequilibrated with a 10 mM sodium phosphate buffer. The CM-cellulose column is eluted with sequential steps of increasing NaCl concentration in a phosphate buffer. The fractions containing Fab as assessed by enzyme immunoassay are combined and concentrated over a YM10 membrane to an Fab concentration of about 1 mg/ml, and stored frozen.

The ING-2 Fab purified from *E. coli* has identical molecular weight properties as ING-2 Fab purified from yeast (Example 4), as assessed by SDS gel electrophoresis. The bacterially-produced ING-2 Fab is correctly folded as a λ plus Fd chain dimer because of its positive reaction in the enzyme immunoassays detecting molecules with both λ and Fd determinants, and because it competes the binding of labeled Br-3 mouse antibody to human tumor cells.

c. ING-3

Expression of ING-3 chimeric Fab from pING3307 in *E. coli* is under the inducible control of the araBAD promoter. Upon arabinose induction, Fab secreted into the growth medium increased more than 10 fold. Uninduced bacterial colonies harboring pING3307 were phenotypically indistinguishable from *E. coli* harboring pING3104. The strain harboring pING3307 was cultured in 10 L of minimal medium, supplemented with 0.7% glycerol as the carbon source, and induced with 0.2% arabinose for greater than 12 hours.

Seven liters of culture supernatant were concentrated using a S10Y10 cartridge (DC10 concentrator, Amicon). The concentrate was passed through a DE52 (Whatman) column pre-equilibrated with 10 mM sodium phosphate buffer at pH 8.0. The column flow-through was then concentrated over a YM10 membrane (Stirred Cell 2000, Amicon) and sufficient monosodium phosphate added to the flow through of the DE52 column to adjust the pH to 7.4. The sample had a conductivity of 1.45 mS/cm. The total amount of protein was estimated by a colorimetric assay, and the sample was loaded onto a CM-52 column preequilibrated with 10 mM sodium phosphate buffer at pH 7.4. The CM-52 Cellulose column was eluted with sequential steps of increasing NaCl concentration in the same phosphate buffer. The fractions containing Fab as assessed by enzyme immunoassay were combined, and the buffer was exchanged by concentration over a YM10 membrane and dilution with 10 mM sodium phosphate, pH 6.5. The Fab was bound to a Bakerbond carboxyethyl resin (J. T. Baker) column pre-equilibrated with 10 mM sodium phosphate, pH 6.5. The Fab was eluted with a linear NaCl gradient, and fractions containing Fab were pooled, the buffer was exchanged to 10 mM sodium phosphate, pH 7.2, and concentrated over a YM10 membrane to a Fab concentration of about 5 mg/ml, and stored frozen. The ING-3 Fab purified from *E. coli* had identical molecular weight properties as ING-3 Fab purified from yeast (Example 4), as assessed by SDS gel electrophoresis. The bacterially-produced ING-3 Fab was correctly folded as a κ plus Fd chain dimer because: (1) it reacted positively in the enzyme immunoassays which detect molecules with both κ and Fd determinants, and (2) it bound specifically to human tumor cells, as shown in competition assays using Co-1 mouse antibody (see Table 23).

d. ING-4

Expression of ING-4 chimeric Fab from pME4-B3 in *E. coli* is under the inducible control of the araBAD promoter. Upon arabinose induction, Fab secreted into the growth medium increases more than 10 fold. Uninduced bacterial colonies harboring pME4-B3 are phenotypically indistinguishable from *E. coli* harboring pIT206TXR. The strain harboring pME4-B3 is cultured in 10 L of minimal medium, supplemented with 0.7% glycerol as the carbon source, and induced with 0.2% arabinose for greater than 12 hours .

About 7 liters of culture supernatant is concentrated to 2 liters of using a S10Y10 cartridge (DC10 concentrator, Amicon). The concentrate is passed through a 500 g DEAE cellulose type DE52, Whatman) column pre-equilibrated with 10 mM sodium phosphate at pH 8.0. Sufficient 0.2M monosodium phosphate is added to adjust pH to 6.8, and the sample is concentrated over a YM10 membrane (Stirred Cell 2000, Amicon). The samples is then diluted with sufficient water and reconcentrated to 200 ml to give a conductivity of 1.4 mS/cm. The total amount of protein is estimated by a colorimetric assay, and the sample is loaded onto a carboxymethylcellulose type (CM52, Whatman) column at a ratio of 10 mg total protein per 1 g CM52 (preequilibrated with 10 mM sodium phosphate buffer at pH 6.8). The CM52 column is eluted with a linear gradient of increasing NaCl concentration (0–0.1N) in the same phosphate buffer. The fractions containing Fab as assessed by enzyme immunoassay are further analyzed by SDS-PAGE and the pooled. The combined Fab fractions are concentrated over a YM10 membrane to an Fab concentration of about 1 mg/ml, and stored frozen.

The ING-4 Fab purified from *E. coli* has identical molecular weight properties as ING-4 Fab purified from yeast (Example 4), as assessed by SDS gel electrophoresis. The bacterially-produced ING-4 Fab is correctly assembled as a κ plus Fd chain dimer because of its positive reaction in the enzyme immunoassays detecting molecules with both κ and Fd determinants, and because it competes the binding of labeled mouse antibody to human tumor cells.

e. KM10

Expression of KM10 chimeric Fab from pING3202 in *E. coli* is under the inducible control of the araB promoter. Upon arabinose induction, Fab secreted into the growth medium increased more than 10 fold. Uninduced bacterial colonies harboring pING3202 were phenotypically indistinguishable from *E. coli* harboring pING3104. The strain harboring pING3202 was cultured in 10 L of minimal medium, supplemented with 0.7% glycerol as the carbon source, and induced with 0.2% arabinose for over 12 hr. Fab was detected in the fermentation broth by ELISA. The Fab can be purified from this fermentation broth and has properties identical to those of the chimeric Fab described above. KM10 Fab produced in bacteria binds to LS174T cells.

TABLE 23

Inhibition of Binding ING-3 Fab to Tumor Cells

| ING-3 Fab | Binding Activity ($A_{490}$) in the Presence of Competing Co-1 Antibody:[a] | | |
|---|---|---|---|
| Concentration µg/ml | No Co-1 Competitor | Ten-fold Co-1 Excess | Thirty-fold Co-1 Excess |
| 30 | 1.30 | 0.36 | 0.51 |
| 10 | 1.36 | 0.34 | 0.39 |
| 3.3 | 1.11 | 0.39 | 0.36 |
| 1.1 | 0.74 | 0.35 | 0.33 |
| 0.37 | 0.43 | 0.34 | 0.34 |
| 0.12 | 0.22 | 0.27 | 0.30 |
| 0.04 | 0.21 | 0.28 | 0.30 |
| 0.0 | 0.21 | 0.22 | 0.31 |

[a]-LS174T cells were incubated with the indicated concentration of ING-3 Fab and with either (1) no competing Co-1 antibody, (2) a ten-fold mass excess of mouse Co-1 antibody, or (3) a thirty-fold mass excess of mouse CO-1 antibody. Cell-bound Fab was detected colorimetrically following incubation with peroxidase-conjugated goat anti-human κ chain antibody, followed by incubation with o-phenylene diamine substrate in the presence of hydrogen peroxide. Results are reported as absorbance values at 490 nm ($A_{490}$).

Conclusions

The examples presented above demonstrate a number of important qualities of the chimeric anti-tumor antibodies and the genetically engineered Fab proteins of the invention. First, both the chimeric antibodies and their Fab derivatives bind to human tumor cell lines to a similar extent as the the mouse mAbs, with approximately the same avidity.

The chimeric antibodies are significant because they bind to the surface of human tumor cells but do not bind detectably to normal cells such as fibroblasts, endothelial cells, or epithelial cells in the major organs. Thus the five chimeric mAbs described above define antigens useful for distinguishing human tumor cells from normal cells.

In addition to the ability of the chimeric antibodies of the present invention to bind specifically to malignant cells, the chimeric antibodies can initiate efficient killing of target cells by cellular components (ADCC) or enzymatic components (CDC) of the blood, which makes these chimeric antibodies prime candidates for tumor immunotherapy.

Although the prospect of tumor therapy with mAbs is attractive, to date such mAb therapy has met with only limited success. (Houghton, et al. February 1985, *Proc. Natl. Acad. Sci. USA* 82:1242–1246 (1985)). The therapeutic efficacy of unmodified mouse mAbs appears to be too low for most practical purposes. The five chimeric antibodies detailed above are improved therapeutic agents over the original mouse mAbs for treatment of human tumors in vivo. First, the high biological activity of the chimeric antibodies against human tumor cell lines combined with minimal reactivity with normal tissues imply that these antibodies may mediate selective destruction of malignant tissue. Second, the presence of human rather than murine antigenic determinants on the chimeric antibodies increases their resistance to rapid clearance from the body relative to the original murine mAbs. Third, this resistance to clearance enhances the potential utility of such chimeric antibodies, as well as their their derivatives, in tumor diagnosis and therapy, through their use as immunoconjugates with drugs, toxins, immunomodulators, radionuclides, etc. Uses of immunoconjugates and methods for their formation are known to those skilled in the art and can be employed to modify the chimeric antibodies within the scope of the present invention.

DEPOSITS

The following illustrative cell lines secreting chimeric antibodies were deposited prior to the U.S. filing date at the ATCC, Rockville, Md., under the provisions of the Budapest Treaty.
1. ING-1
   a. Transfected hybridoma Sp2/0 pING22071C5.B7-pING22253F2.G6 (C499) (ATCC accession #H89812, deposited Sep. 2, 1988)
   b. Yeast strain PS6/pING1496 and pING1616 (G263) (ATCC accession #20894, deposited Sep. 2, 1988)
2. ING-2
   a. Transfected hybridoma Sp2/0 pING22031B5.14-pING22271D3.F11 (C534) (ATCC accession #HB9818, deposited Sep. 8, 1988)
   b. Yeast strain PS6/pING1692+pING1610 (G266) (ATCC accession #20897, deposited Sep. 8, 1988)
3. ING-3
   a. Transfected hybridoma Sp2/0 pING22045B7.F9-pING22342G11.C11 (C542) (ATCC accession #H89813, deposited Sep. 2, 1988)
   b. Yeast strain PS6/pING1663+pING1694 (G264) (ATCC accession #20895, deposited Sep. 2, 1988)
4. ING-4
   a. Transfected hybridoma Sp2/0 pING22162C2.1C7-pING22321B5.F5 (C489) (ATCC accession #H89814, deposited Sep. 2, 1988)
   b. Yeast strain PS6/pING1667-714 (G265) (ATCC accession #20896, deposited Sep. 2, 1988)
5. K10
   a. Transfected hybridoma Sp2/0 (pING2240 and pING2242) (C739) (ATCC accession #HB 10131, deposited May 5, 1989)
   b. Yeast strain PS6 (pING3200) (G267) (ATCC accession #20945, deposited May 5, 1998).

What is claimed is:

1. An antibody, said antibody comprising a human constant region and a variable region having specificity for the human tumor antigen bound by the ING-1 antibody, wherein said ING-1 is produced by cell line HB9812 as deposited with the ATCC, and wherein said antibody has essentially the same affinity as said ING-1 for said human tumor antigen.

2. The antibody of claim 1, wherein said antibody mediates complement dependent cytolysis.

3. The antibody of claim 1, wherein said antibody mediates antibody dependent cellular cytotoxicity.

4. The antibody of claim 1, wherein said antibody mediates both complement dependent cytolysis and antibody dependent cellular cytotoxicity.

5. An antibody, said antibody comprising a human constant region and a variable region having specificity for the antigen bound by the ING-1 antibody, wherein said ING-1 is produced by cell line HB9812 as deposited with the ATCC, and wherein said antibody mediates complement dependent cytolysis essentially the same as said ING-1.

6. The antibody of claim 5, wherein said antibody also mediates antibody dependent cellular cytotoxicity.

7. An antibody, said antibody comprising a human constant region and a variable region having specificity for the antigen bound by the ING-1 antibody, wherein said ING-1 is produced by cell line HB9812 as deposited with the ATCC, and wherein said antibody mediates antibody-dependent cellular cytotoxicity essentially the same as said ING-1.

8. The antibody of claim 7, wherein said antibody also mediates complement dependent cytolysis.

9. A chimeric antibody or chimeric fragment thereof, wherein said chimeric antibody or chimeric fragment thereof recognizes the human tumor antigen bound by the antibody ING-1, wherein said ING-1 is produced by cell line HB9812 as deposited with the ATCC, and wherein said chimeric antibody has essentially the same affinity as said ING-1 for said human tumor antigen.

10. The chimeric antibody or chimeric fragment thereof of claim 9, wherein said chimeric antibody or chimeric fragment thereof competitively inhibits the binding of said ING-1.

11. A chimeric light chain chimeric or fragment thereof, wherein a chimeric antibody or chimeric fragment thereof that recognizes the human tumor antigen bound by antibody ING-1 is produced when said chimeric light chain or chimeric fragment thereof is combined with a chimeric heavy chain or chimeric fragment thereof, wherein said ING-1 is produced by cell line HB9812 as deposited with the ATCC and wherein said chimeric antibody has essentially the same affinity as said ING-1 for said human tumor antigen.

12. The chimeric light chain or chimeric fragment thereof of claim 11, wherein said chimeric antibody or chimeric fragment thereof competitively inhibits the binding of said ING-1 to said human tumor antigen.

13. A chimeric heavy chain or chimeric fragment thereof, wherein a chimeric antibody or chimeric fragment thereof that recognizes the human tumor antigen bound by antibody ING-1 is produced when said chimeric heavy chain or chimeric fragment thereof is combined with a chimeric light chain or chimeric fragment thereof; wherein said ING-1 is produced by cell line HB9812 as deposited with the ATCC and wherein said chimeric antibody has essentially the same affinity as said ING-1 for said human tumor antigen.

14. The chimeric heavy chain or chimeric fragment thereof of claim 13, wherein said chimeric antibody or chimeric fragment thereof competitively inhibits the binding of said ING-1 to said human tumor antigen.

15. A chimeric antibody or chimeric fragment thereof, wherein:
(A) said chimeric antibody or chimeric fragment thereof recognizes the human tumor antigen bound by antibody ING-1; and
(B) said chimeric antibody or chimeric fragment thereof mediates complement-dependent cytolysis of HT-29 tumor cells at a concentration of 0.08 $\mu$g/ml;
wherein said ING-1 is produced by cell line HB9812 as deposited with the ATCC.

16. The chimeric antibody or chimeric fragment thereof of claim 15, wherein said chimeric antibody or chimeric fragment thereof competitively inhibits the binding of said ING-1 to said human tumor antigen.

17. The chimeric antibody or chimeric fragment thereof of claim 15, wherein said chimeric antibody or chimeric fragment thereof has essentially the same affinity as said ING-1 for said human tumor antigen.

18. The chimeric antibody or chimeric fragment thereof of claim 17, wherein said chimeric antibody or chimeric fragment thereof competitively inhibits the binding of said ING-1 to said human tumor antigen.

19. A chimeric antibody or chimeric fragment thereof, wherein:
(A) said chimeric antibody or chimeric fragment thereof recognizes the human tumor antigen bound by antibody ING-1; and
(B) said chimeric antibody or chimeric fragment thereof mediates a complement-dependent cytolysis response essentially the same as that of said ING-1;
wherein said ING-1 is produced by cell line HB9812 as deposited with the ATCC.

20. The chimeric antibody or chimeric fragment thereof of claim 19, wherein said chimeric antibody or chimeric fragment thereof competitively inhibits the binding of said ING-1 to said human tumor antigen.

21. The chimeric antibody or chimeric fragment thereof of claim 19, wherein said chimeric antibody or chimeric fragment thereof has essentially the same affinity as said ING-1 for said human tumor antigen.

22. The chimeric antibody or chimeric fragment thereof of claim 21, wherein said chimeric antibody or chimeric fragment thereof competitively inhibits the binding of said ING-1 to said human tumor antigen.

23. A chimeric light chain or chimeric fragment thereof, wherein:
(A) a chimeric antibody or chimeric fragment thereof that recognizes the human tumor antigen bound by antibody ING-1 is produced when said chimeric light chain or chimeric fragment thereof is combined with a chimeric heavy chain or chimeric fragment thereof; and
(B) said chimeric antibody or chimeric fragment thereof of part (A) mediates complement-dependent cytolysis of HT-29 tumor cells at a concentration of 0.08 $\mu$g/ml;
wherein said ING-1 is produced by cell line HB9812 as deposited with the ATCC.

24. The chimeric light chain or chimeric fragment thereof of claim 23, wherein said chimeric antibody or chimeric fragment thereof competitively inhibits the binding of said ING-1 to said human tumor antigen.

25. The chimeric light chain or chimeric fragment thereof of claim 23, wherein said chimeric antibody has essentially the same affinity as said ING-1 for said human tumor antigen.

26. The chimeric light chain or chimeric fragment thereof of claim 25, wherein said chimeric antibody or chimeric fragment thereof competitively inhibits the binding of said ING-1 to said human tumor antigen.

27. A chimeric light chain or chimeric fragment thereof, wherein:
(A) a chimeric antibody or chimeric fragment thereof that recognizes the human tumor antigen bound by antibody ING-1 is produced when said chimeric light chain or chimeric fragment thereof is combined with a chimeric heavy chain or chimeric fragment thereof; and
(B) said chimeric antibody or chimeric fragment thereof of part (A) mediates a complement-dependent cytolysis response essentially the same as said ING-1;
wherein said ING-1 is produced by cell line HB9812 as deposited with the ATCC.

28. The chimeric light chain or chimeric fragment thereof of claim 27, wherein said chimeric antibody or chimeric fragment thereof competitively inhibits the binding of said ING-1 to said human tumor antigen.

29. The chimeric light chain or chimeric fragment thereof of claim 27, wherein said chimeric antibody has essentially the same affinity as said ING-1 for said human tumor antigen.

30. The chimeric light chain or chimeric fragment thereof of claim 29, wherein said chimeric antibody or chimeric fragment thereof competitively inhibits the binding of said ING-1 to said human tumor antigen.

31. A chimeric heavy chain or chimeric fragment thereof, wherein:
(A) a chimeric antibody or chimeric fragment thereof that recognizes the human tumor antigen bound by antibody ING-1 is produced when said chimeric heavy chain or chimeric fragment thereof is combined with a chimeric light chain or chimeric fragment thereof;
(B) said chimeric antibody or chimeric fragment thereof of part (A) mediates complement-dependent cytolysis of HT-29 tumor cells at a concentration of 0.08 $\mu$g/ml;
wherein said ING-1 is produced by cell line HB9812 as deposited with the ATCC.

32. The chimeric heavy chain or chimeric fragment thereof of claim 31, wherein said chimeric antibody competitively inhibits the binding of said ING-1 to said human tumor antigen.

33. The chimeric heavy chain or chimeric fragment thereof of claim 31, wherein said chimeric antibody has essentially the same affinity as said ING-1 for said human tumor antigen.

34. The chimeric heavy chain or chimeric fragment thereof of claim 33, wherein said chimeric antibody competitively inhibits the binding of said ING-1 to said human tumor antigen.

35. A chimeric heavy chain or chimeric fragment thereof, wherein:
(A) a chimeric antibody or chimeric fragment thereof that recognizes the human tumor antigen bound by antibody ING-1 is produced when said chimeric heavy chain or chimeric fragment thereof is combined with a chimeric light chain or chimeric fragment thereof;

(B) said chimeric antibody or chimeric fragment thereof of part (A) mediates a complement-dependent cytolysis response essentially the same as said ING-1;

wherein said ING-1 is produced by cell line HB9812 as deposited with the ATCC.

36. The chimeric heavy chain or chimeric fragment thereof of claim 35, wherein said chimeric antibody competitively inhibits the binding of said ING-1 to said human tumor antigen.

37. The chimeric heavy chain or chimeric fragment thereof of claim 35, wherein said chimeric antibody has essentially the same affinity as said ING-1 for said human tumor antigen.

38. The chimeric heavy chain or chimeric fragment thereof of claim 37, wherein said chimeric antibody competitively inhibits the binding of said ING-1 to said human tumor antigen.

39. A chimeric antibody or chimeric fragment thereof, wherein:

(A) said chimeric antibody or chimeric fragment thereof recognizes the human tumor antigen bound by antibody ING-1;

(B) said chimeric antibody or chimeric fragment thereof mediates an antibody-dependent cellular cytotoxicity response by human peripheral blood leukocytes against BT-20 tumor cells of 56 to 96% lysis without serum and 33 to 97% lysis with serum, with an antibody concentration of 0.0001 $\mu$g/ml to 1.0 $\mu$g/ml;

wherein said ING-1 is produced by cell line HB9812 as deposited with the ATCC.

40. The chimeric antibody or chimeric fragment thereof of claim 34, wherein said response is elicited at an effector to target ratio of 50:1.

41. The chimeric antibody or chimeric fragment thereof of claim 39, wherein said chimeric antibody or chimeric fragment thereof competitively inhibits the binding of said ING-1 to said human tumor antigen.

42. The chimeric antibody or chimeric fragment thereof of claim 39, wherein said chimeric antibody or chimeric fragment thereof has essentially the same affinity as said ING-1 for said human tumor antigen.

43. The chimeric antibody or chimeric fragment thereof of claim 42, wherein said chimeric antibody or chimeric fragment thereof competitively inhibits the binding of said ING-1 to said human tumor antigen.

44. A chimeric antibody or chimeric fragment thereof, wherein:

(A) said chimeric antibody or chimeric fragment thereof recognizes the human tumor antigen bound by antibody ING-1;

(B) said chimeric antibody or chimeric fragment thereof mediates an antibody-dependent cellular cytotoxicity response in BT-20 tumor cells essentially the same as said ING-1;

wherein said ING-1 is produced by cell line HB9812 as deposited with the ATCC.

45. The chimeric antibody or chimeric fragment thereof of claim 44, wherein said response is elicited at an effector to target ratio of 50:1.

46. The chimeric antibody or chimeric fragment thereof of claim 44, wherein said chimeric antibody or chimeric fragment thereof competitively inhibits the binding of said ING-1 to said human tumor antigen.

47. The chimeric antibody or chimeric fragment thereof of claim 44, wherein said chimeric antibody or chimeric fragment thereof has essentially the same affinity as said ING-1 for said human tumor antigen.

48. The chimeric antibody or chimeric fragment thereof of claim 47, wherein said chimeric antibody or chimeric fragment thereof competitively inhibits the binding of said ING-1 to said human tumor antigen.

49. A chimeric light chain or chimeric fragment thereof, wherein:

(A) a chimeric antibody or chimeric fragment thereof that recognizes the human tumor antigen bound by antibody ING-1 is produced when said chimeric light chain or chimeric fragment thereof is combined with a chimeric heavy chain or chimeric fragment thereof;

(B) said chimeric antibody or chimeric fragment thereof of part (A) mediates an antibody-dependent cellular cytotoxicity response by human peripheral blood leukocytes against BT-20 tumor cells of 56 to 96% lysis without serum and 33 to 97% lysis with serum, with an antibody concentration of 0.0001 $\mu$g/ml to 1.0 $\mu$g/ml;

wherein said ING-1 is produced by cell line HB9812 as deposited with the ATCC.

50. The chimeric light chain or chimeric fragment thereof of claim 49, wherein said response is elicited at an effector to target ratio of 50:1.

51. The chimeric light chain or chimeric fragment thereof of claim 49, wherein said chimeric antibody or chimeric fragment thereof competitively inhibits the binding of said ING-1 to said human tumor antigen.

52. The chimeric light chain or chimeric fragment thereof of claim 49, wherein said chimeric antibody or chimeric fragment thereof has essentially the same affinity as said ING-1 for said human tumor antigen.

53. The chimeric light chain or chimeric fragment thereof of claim 52, wherein said chimeric antibody or chimeric fragment thereof competitively inhibits the binding of said ING-1 to said human tumor antigen.

54. A chimeric light chain or chimeric fragment thereof, wherein:

(A) a chimeric antibody or chimeric fragment thereof that recognizes the human tumor antigen bound by antibody ING-1 is produced when said light chain or chimeric fragment thereof is combined with a chimeric heavy chain or chimeric fragment thereof;

(B) said chimeric antibody or chimeric fragment thereof of part (A) mediates an antibody-dependent cellular cytotoxicity response in BT-20 tumor cells essentially the same as said ING-1;

wherein said ING-1 is produced by cell line HB9812 as deposited with the ATCC.

55. The chimeric light chain or chimeric fragment thereof of claim 54, wherein said response is elicited at an effector to target ratio of 50:1.

56. The chimeric light chain or chimeric fragment thereof of claim 54, wherein said chimeric antibody or chimeric fragment thereof competitively inhibits the binding of said ING-1 to said human tumor antigen.

57. The chimeric light chain or chimeric fragment thereof of claim 54, wherein said chimeric antibody or chimeric fragment thereof has essentially the same affinity as said ING-1 for said human tumor antigen.

58. The chimeric light chain or chimeric fragment thereof of claim 57, wherein said chimeric antibody or chimeric fragment thereof competitively inhibits the binding of said ING-1 to said human tumor antigen.

59. A chimeric heavy chain or chimeric fragment thereof, wherein;

(A) a chimeric antibody or chimeric fragment thereof that recognizes the human tumor antigen bound by antibody ING-1 is produced when said heavy chain or chimeric fragment thereof is combined with a chimeric light chain or chimeric fragment thereof; and (B) said chimeric antibody or chimeric fragment thereof of part (A) mediates an antibody-dependent cellular cytotoxicity response by human peripheral blood leukocytes against BT-20 tumor cells of 56 to 96% lysis without serum and 33 to 97% lysis with serum, with an antibody concentration of 0.0001 µg/ml to 1.0 µg/ml;

wherein said ING-1 is produced by cell line HB9812 as deposited with the ATCC.

60. The chimeric heavy chain or chimeric fragment thereof of claim 59, wherein said response is elicited at an effector to target ratio of 50:1.

61. The chimeric heavy chain or chimeric fragment thereof of claim 59, wherein said chimeric antibody or chimeric fragment thereof competitively inhibits the binding of said ING-1 to said human tumor antigen.

62. The chimeric heavy chain or chimeric fragment thereof of claim 59, wherein said chimeric antibody or chimeric fragment thereof has essentially the same affinity as said ING-1 for said human tumor antigen.

63. The chimeric heavy chain or chimeric fragment thereof of claim 62, wherein said chimeric antibody or chimeric fragment thereof competitively inhibits the binding of said ING-1 to said human tumor antigen.

64. A chimeric heavy chain or chimeric fragment thereof, wherein:

(A) a chimeric antibody or chimeric fragment thereof that recognizes the human tumor antigen bound by antibody ING-1 is produced when said heavy chain or chimeric fragment thereof is combined with a chimeric light chain or chimeric fragment thereof; and (B) said chimeric antibody or chimeric fragment thereof of part (A) mediates an antibody-dependent cellular cytotoxicity response in BT-20 tumor cells essentially the same as said ING-1;

wherein said ING-1 is produced by cell line HB9812 as deposited with the ATCC.

65. The chimeric heavy chain or chimeric fragment thereof of claim 64, wherein said response is elicited at an effector to target ratio of 50:1.

66. The chimeric heavy chain or chimeric fragment thereof of claim 64, wherein said chimeric antibody or chimeric fragment thereof competitively inhibits the binding of said ING-1 to said human tumor antigen.

67. The chimeric heavy chain or chimeric fragment thereof of claim 64, wherein said chimeric antibody or chimeric fragment thereof has essentially the same affinity as said ING-1 for said human tumor antigen.

68. The chimeric heavy chain or chimeric fragment thereof of claim 67, wherein said chimeric antibody or chimeric fragment thereof competitively inhibits the binding of said ING-1 to said human tumor antigen.

69. The antibody of any one of claims 1–8, wherein said antibody is detectably labeled.

70. The antibody of claim 69, wherein said label is a radionuclide, nuclear magnetic resonance contrasting agent, X-ray contrasting agent, fluorescent label or enzyme.

71. The antibody of any one of claims 1–8, wherein said antibody is coupled to a toxin, peptide effector, therapeutic moiety or drug.

72. The antibody of claim 71 wherein said antibody is coupled to a therapeutic moiety.

73. The antibody of claim 72, wherein said therapeutic moiety is a lymphokine or colony-stimulating factor.

74. The chimeric antibody or chimeric fragment thereof of any one of claims 9, 10, 15, 19, 39 or 44, wherein said chimeric antibody or chimeric fragment thereof is detectably labeled.

75. The chimeric antibody or chimeric fragment thereof of claim 74, wherein said label is a radionuclide, nuclear magnetic resonance contrasting agent, X-ray contrasting agent, fluorescent label or enzyme.

76. The chimeric antibody or chimeric fragment thereof of any one of claims 9, 10, 15, 19, 39 or 44, wherein said chimeric antibody or chimeric fragment thereof is coupled to a toxin, peptide effector, therapeutic moiety or drug.

77. The chimeric antibody or chimeric fragment thereof of claim 76, wherein said chimeric antibody or chimeric fragment thereof is coupled to a therapeutic moiety.

78. The chimeric antibody or chimeric fragment thereof of claim 77, wherein said therapeutic moiety is a lymphokine or colony-stimulating factor.

79. The chimeric light chain or chimeric fragment thereof of any one of claims 11, 12, 23, 24, 49 or 54, wherein said chimeric antibody or chimeric fragment thereof is detectably labeled.

80. The chimeric light chain or chimeric fragment thereof of claim 79, wherein said label is a radionuclide, nuclear magnetic resonance contrasting agent, X-ray contrasting agent, fluorescent label or enzyme.

81. The chimeric light chain or chimeric fragment thereof of any one of claims 11, 12, 23, 24, 49 or 54, wherein said chimeric antibody or chimeric fragment thereof is coupled to a toxin, peptide effector, therapeutic moiety or drug.

82. The chimeric light chain or chimeric fragment thereof of claim 81, wherein said chimeric light chain or chimeric fragment thereof is coupled to a therapeutic moiety.

83. The chimeric light chain or chimeric fragment thereof of claim 82, wherein said therapeutic moiety is a lymphokine or colony-stimulating factor.

84. The chimeric heavy chain or chimeric fragment thereof of any one of claims 13, 14, 31, 35, 59 or 64, wherein said chimeric antibody or chimeric fragment thereof is detectably labeled.

85. The chimeric heavy chain or chimeric fragment thereof of claim 84, wherein said label is a radionuclide, nuclear magnetic resonance contrasting agent, X-ray contrasting agent, fluorescent label or enzyme.

86. The chimeric heavy chain or fragment thereof of any one of claims 13, 14, 31, 35, 59 or 69, wherein said chimeric antibody or chimeric fragment thereof is coupled to a toxin, peptide effector, therapeutic moiety or drug.

87. The chimeric heavy chain or chimeric fragment thereof of claim 86, wherein said chimeric heavy chain or chimeric fragment thereof is coupled to a therapeutic moiety.

88. The chimeric heavy chain or chimeric fragment thereof of claim 87, wherein said therapeutic moiety is a lymphokine or colony-stimulating factor.

89. An immunoassay method for detecting an antigen in a sample, said method comprising (A) contacting the antigen in said sample with the antibody of any one of claims 1–8, under conditions in which said antigen can be detected with a label, wherein said antibody is capable of binding antigen;

(B) detecting said label; and (C) relating said label that is detected in part (B) to the presence of said antigen.

90. The immunoassay method of claim 89, wherein said antibody is detectably labeled.

91. An immunoassay method for detecting an antigen in a sample, said method comprising (A) contacting the antigen in said sample with the chimeric antibody or chimeric fragment thereof of any one of claims 9, 10, 15, 19, 39 or 44, under conditions in which said antigen can be detected with a label, wherein said chimeric antibody or chimeric fragment thereof is capable of binding antigen;

(B) detecting said label; and (C) relating said label that is detected in part (B) to the presence of said antigen.

92. The immunoassay method of claim 91, wherein said the chimeric antibody or chimeric fragment thereof is said fragment.

93. The immunoassay method of claim 92, wherein said fragment is selected from the group consisting of Fab, Fab' and F(ab')$_2$.

94. The immunoassay method of claim 91, wherein said chimeric antibody or chimeric fragment thereof is detectably labeled.

95. The immunoassay method of claim 94, wherein said chimeric antibody or chimeric fragment thereof is said fragment.

96. The immunoassay method of claim 95, wherein said fragment is selected from the group consisting of Fab, Fab' and F(ab')$_2$.

97. An imaging method for revealing the presence of an antigen in an animal, said method comprising:

(A) contacting the antibody of any one of claims 1–8 with a part of said animal that is suspected of containing said antigen under conditions in which said antigen can be detected with a label, wherein said antibody is capable of binding antigen;

(B) detecting said label; and (C) relating said label that is detected in part (B) to said presence of said antigen.

98. The imaging method of claim 97, wherein said antibody is detectably labeled.

99. An imaging method for revealing the presence of an antigen in an animal, said method comprising:

(A) contacting the chimeric antibody or chimeric fragment thereof of any of claims 9, 10, 15, 19, 39 or 44, with a part of said animal that is suspected of containing said antigen under conditions in which said antigen can be detected with a label, wherein said chimeric antibody of chimeric fragment thereof is capable of binding antigen;

(B) detecting said label; and (C) relating said label that is detected in part (B) to said presence of said antigen.

100. The imaging method of claim 99, wherein said chimeric antibody or chimeric fragment thereof is said fragment.

101. The imaging method of claim 100, wherein said fragment is selected from the group consisting of Fab, Fab' and F(ab')$_2$.

102. The imaging method of claim 99, wherein said chimeric antibody or chimeric fragment thereof is detectably labeled.

103. The imaging method of claim 102, wherein said chimeric antibody or chimeric fragment thereof is said fragment.

104. The imaging method of claim 103, wherein said fragment is selected from the group consisting of Fab, Fab' and F(ab')$_2$.

105. A method of killing cells carrying an antigen thereon, said method comprising:

(A) contacting said cells with the antibody of any one of claims 1–8; and (B) allowing said killing to occur.

106. A method of killing cells carrying an antigen thereon, said method comprising:

(A) contacting said cells with the antibody of any one of claim 2, 4, 5, 6 or 8; and (B) allowing said killing to occur by a process comprising complement dependent cytolysis.

107. A method of killing cells carrying an antigen thereon, said method comprising:

(A) contacting said cells with the antibody of any one of claims 3, 4, 6, 7 or 8; and (B) allowing said killing to occur by a process comprising antibody dependent cellular cytotoxicity.

108. A method of killing cells carrying an antigen thereon, said method comprising:

(A) contacting said cells with the antibody of any one of claims 4, 6 or 8; and (B) allowing said killing to occur by complement dependent cytolysis and by antibody dependent cellular cytotoxicity.

109. A method of killing cells carrying an antigen thereon, said method comprising:

(A) contacting said cells with the chimeric antibody, or chimeric fragment thereof, of any one of claims 9, 10, 15, 19, 39 or 44; and (B) allowing said killing to occur.

110. A method of killing cells carrying an antigen thereon, said method comprising:

(A) contacting said cells with the chimeric antibody, or chimeric fragment thereof, of any one of claims 9 or 10; and (B) allowing said killing to occur.

111. A method of killing cells carrying an antigen thereon, said method comprising:

(A) contacting said cells with the chimeric antibody, or chimeric fragment thereof, of any one of claims 15 or 19; and (B) allowing said killing to occur.

112. A method of killing cells carrying an antigen thereon, said method comprising:

(A) contacting said cells with the chimeric antibody, or chimeric fragment thereof, of any one of claims 39 or 44; and (B) allowing said killing to occur.

113. A process for producing an antibody, wherein said process comprises:

(A) culturing a host capable of expressing said antibody, wherein:
  (i) said antibody comprises a human constant region and a variable region having specificity for the human tumor antigen bound by the antibody ING-1, wherein said ING-1 is produced by cell line HB9812 as deposited with the ATCC; and
  (ii) said antibody has essentially the same affinity as said ING-1 for said human tumor antigen; and (B) producing said antibody.

114. The process of claim 113, wherein said antibody mediates complement dependent cytolysis.

115. The process of claim 113, wherein said antibody mediates antibody dependent cellular cytotoxicity.

116. The antibody of claim 113, wherein said process mediates both complement dependent cytolysis and antibody dependent cellular cytotoxicity.

117. A process for producing an antibody, wherein said process comprises:
(A) culturing a host capable of expressing said antibody, wherein:
(i) said antibody comprises a human constant region and a variable region having specificity for the human tumor antigen bound by the antibody ING-1, wherein said ING-1 is produced by cell line HB9812 as deposited with the ATCC; and
(ii) said antibody mediates complement dependent cytolysis essentially the same as said ING-1; and
(B) producing said antibody.

118. The process of claim 117, wherein said antibody has essentially the same affinity as said ING-1 for said human tumor antigen.

119. A process for producing an antibody, wherein said process comprises:
(A) culturing a host capable of expressing said antibody, wherein:
(i) said antibody comprises a human constant region and a variable region having specificity for the human tumor antigen bound by the antibody ING-1, wherein said ING-1 is produced by cell line HB9812 as deposited with the ATCC; and
(ii) said antibody mediates antibody-dependent cellular cytotoxicity essentially the same as said ING-1; and
(B) producing said antibody.

120. The process of claim 119, wherein said antibody has essentially the same affinity as said ING-1 for said human tumor antigen.

121. A process for producing a chimeric antibody or chimeric fragment thereof, wherein said process comprises:
(A) culturing a host capable of expressing said chimeric antibody or chimeric fragment thereof, wherein:
(i) said chimeric antibody or chimeric fragment thereof recognizes the human tumor antigen bound by the antibody ING-1, wherein said ING-1 is produced by cell line HB9812 as deposited with the ATCC; and
(ii) said chimeric antibody has essentially the same affinity as said ING-1 for said human tumor antigen; and
(B) producing said chimeric antibody or chimeric fragment thereof.

122. The process of claim 121, wherein said chimeric antibody or chimeric fragment thereof competitively inhibits the binding of said antibody ING-1 to said human tumor antigen.

123. A process for producing a chimeric antibody or chimeric fragment thereof, wherein said process comprises:
(A) culturing a host capable of expressing said chimeric antibody or chimeric fragment thereof, wherein:
(i) said chimeric antibody or chimeric fragment thereof recognizes the human tumor antigen bound by the antibody ING-1, wherein said ING-1 is produced by cell line HB9812 as deposited with the ATCC; and
(ii) said chimeric antibody or chimeric fragment thereof mediates complement-dependent cytolysis of HT-29 tumor cells at a concentration of 0.08 µg/ml; and
(B) producing said chimeric antibody or chimeric fragment thereof.

124. The process of claim 123, wherein said chimeric antibody or chimeric fragment thereof competitively inhibits the binding of said antibody ING-1 to said human tumor antigen.

125. The process of claim 123, wherein said chimeric antibody or chimeric fragment thereof has essentially the same affinity as said ING-1 for said human tumor antigen.

126. The process of claim 125, wherein said chimeric antibody or chimeric fragment thereof competitively inhibits the binding of said antibody ING-1 to said human tumor antigen.

127. A process for producing a chimeric antibody or chimeric fragment thereof, wherein said process comprises:
(A) culturing a host capable of expressing said chimeric antibody or chimeric fragment thereof, wherein:
(i) said chimeric antibody or chimeric fragment thereof recognizes the human tumor antigen bound by the antibody ING-1, wherein said ING-1 is produced by cell line HB9812 as deposited with the ATCC; and
(ii) said chimeric antibody or chimeric fragment thereof mediates complement-dependent cytolysis essentially the same as that of said ING-1; and
(B) producing said chimeric antibody or chimeric fragment thereof.

128. The process of claim 127, wherein said chimeric antibody or chimeric fragment thereof competitively inhibits the binding of said antibody ING-1 to said human tumor antigen.

129. The process of any one of claims 127 or 128 wherein said chimeric antibody or chimeric fragment thereof has essentially the same affinity as said ING-1 for said human tumor antigen.

130. A process for producing a chimeric antibody or chimeric fragment thereof, wherein said process comprises:
(A) culturing a host capable of expressing said chimeric antibody or chimeric fragment thereof, wherein:
(i) said chimeric antibody or chimeric fragment thereof recognizes the human tumor antigen bound by the antibody ING-1, wherein said ING-1 is produced by cell line HB9812 as deposited with the ATCC; and
(ii) said chimeric antibody or chimeric fragment thereof mediates an antibody-dependent cellular cytotoxicity response by human peripheral blood leukocytes against BT-20 tumor cells of 56 to 96% lysis without serum and 33 to 97% lysis with serum, with an antibody concentration of 0.0001 µg/ml to 1.0 µg/ml; and
(B) producing said chimeric antibody or chimeric fragment thereof.

131. The process of claim 130, wherein said response is elicited at an effector to target ratio of 50:1.

132. The process of claim 130, wherein said chimeric antibody or chimeric fragment thereof competitively inhibits the binding of said antibody ING-1 to said human tumor antigen.

133. The process of claim 130, wherein said chimeric antibody or chimeric fragment thereof has essentially the same affinity as said ING-1 for said human tumor antigen.

134. The process of claim 133, wherein said chimeric antibody or chimeric fragment thereof competitively inhibits the binding of said antibody ING-1 to said human tumor antigen.

135. A process for producing a chimeric antibody or chimeric fragment thereof, wherein said process comprises:
(A) culturing a host capable of expressing said chimeric antibody or chimeric fragment thereof, wherein:
(i) said chimeric antibody or chimeric fragment thereof recognizes the human tumor antigen bound by the antibody ING-1, wherein said ING-1 is produced by cell line HB9812 as deposited with the ATCC; and
(ii) said chimeric antibody or chimeric fragment thereof mediates an antibody-dependent cellular cytotoxicity response against BT-20 tumor cells essentially the same as said ING-1; and (B) producing said chimeric antibody or chimeric fragment thereof.

136. The process of claim 135, wherein said response is elicited at an effector to target ratio of 50:1.

137. The process of claim 135, wherein said chimeric antibody or chimeric fragment thereof competitively inhibits the binding of said antibody ING-1 to said human tumor antigen.

138. The process of any one of claims 135, 136 or 137, wherein said chimeric antibody or chimeric fragment thereof has essentially the same affinity as said ING-1 for said human tumor antigen.

139. A process for producing a chimeric light chain or chimeric fragment thereof, said process comprising:
  (A) culturing a host that is capable of expressing said chimeric light chain or chimeric fragment thereof, wherein:
    (i) a chimeric antibody or chimeric fragment thereof that recognizes the human tumor antigen bound by antibody ING-1 is produced when said chimeric light chain or chimeric fragment thereof is combined with a chimeric heavy chain or chimeric fragment thereof, wherein said ING-1 is produced by cell line HB9812 as deposited with the ATCC; and
    (ii) said chimeric antibody has essentially the same affinity as said ING-1 for said human tumor antigen; and
  (B) producing said chimeric light chain or chimeric fragment thereof.

140. The process of claim 139, wherein said chimeric antibody or chimeric fragment thereof competitively inhibits the binding of said antibody ING-1 to said human tumor antigen.

141. A process for producing a chimeric light chain or chimeric fragment thereof, said process comprising:
  (A) culturing a host that is capable of expressing said chimeric light chain or chimeric fragment thereof, wherein:
    (i) a chimeric antibody or chimeric fragment thereof that recognizes the human tumor antigen bound by antibody ING-1 is produced when said chimeric light chain or chimeric fragment thereof is combined with a chimeric heavy chain or chimeric fragment thereof, wherein said ING-1 is produced by cell line HB9812 as deposited with the ATCC; and
    (ii) said chimeric antibody or chimeric fragment thereof of part (i) mediates complement-dependent cytolysis of HT-29 tumor cells at a concentration of 0.08 $\mu$g/ml; and
  (B) producing said chimeric light chain or chimeric fragment thereof.

142. The process of claim 141, wherein said chimeric antibody or chimeric fragment thereof competitively inhibits the binding of said antibody ING-1 to said human tumor antigen.

143. The process of claim 141, wherein said chimeric antibody or chimeric fragment thereof has essentially the same affinity as said ING-1 for said human tumor antigen.

144. The process of claim 143, wherein said chimeric antibody or chimeric fragment thereof competitively inhibits the binding of said antibody ING-1 to said human tumor antigen.

145. A process for producing a chimeric light chain or chimeric fragment thereof, said process comprising:
  (A) culturing a host that is capable of expressing said chimeric light chain or chimeric fragment thereof, wherein:
    (i) a chimeric antibody or chimeric fragment thereof that recognizes the human tumor antigen bound by antibody ING-1 is produced when said chimeric light chain or chimeric fragment thereof is combined with a chimeric heavy chain or chimeric fragment thereof, wherein said ING-1 is produced by cell line HB9812 as deposited with the ATCC; and
    (ii) said chimeric antibody or chimeric fragment thereof of part (i) mediates complement-dependent cytolysis essentially the same as said ING-1; and
  (B) producing said chimeric light chain or chimeric fragment thereof.

146. The process of claim 145, wherein said chimeric antibody or chimeric fragment thereof competitively inhibits the binding of said antibody ING-1 to said human tumor antigen.

147. The process of any one of claims 145 or 146, wherein said chimeric antibody or chimeric fragment thereof has essentially the same affinity as said ING-1 for said human tumor antigen.

148. A process for producing a chimeric light chain or chimeric fragment thereof, said process comprising:
  (A) culturing a host that is capable of expressing said chimeric light chain or chimeric fragment thereof, wherein:
    (i) a chimeric antibody or chimeric fragment thereof that recognizes the human tumor antigen bound by antibody ING-1 is produced when said chimeric light chain or chimeric fragment thereof is combined with a chimeric heavy chain or chimeric fragment thereof, wherein said ING-1 is produced by cell line HB9812 as deposited with the ATCC; and
    (ii) said chimeric antibody or chimeric fragment thereof of part (i) mediates an antibody-dependent cellular cytotoxicity response by human peripheral blood leukocytes against BT-20 tumor cells of 56 to 96% lysis without serum and 33 to 97% lysis with serum, with an antibody concentration of 0.0001 $\mu$g/ml to 1.0 $\mu$g/ml; and
  (B) producing said chimeric light chain or chimeric fragment thereof.

149. The process of claim 148, wherein said response is elicited at an effector to target ratio of 50:1.

150. The process of claim 148, wherein said chimeric antibody or chimeric fragment thereof competitively inhibits the binding of said antibody ING-1 to said human tumor antigen.

151. The process of claim 148, wherein said chimeric antibody or chimeric fragment thereof has essentially the same affinity as said ING-1 for said human tumor antigen.

152. The process of claim 151, wherein said chimeric antibody or chimeric fragment thereof competitively inhibits the binding of said antibody ING-1 to said human tumor antigen.

153. A process for producing a chimeric light chain or chimeric fragment thereof, said process comprising:
  (A) culturing a host that is capable of expressing said chimeric light chain or chimeric fragment thereof, wherein:
    (i) a chimeric antibody or chimeric fragment thereof that recognizes the human tumor antigen bound by antibody ING-1 is produced when said chimeric light chain or chimeric fragment thereof is combined with a chimeric heavy chain or chimeric fragment thereof, wherein said ING-1 is produced by cell line HB9812 as deposited with the ATCC; and
    (ii) said chimeric antibody or chimeric fragment thereof of part (i) mediates an antibody-dependent cellular cytotoxicity response essentially that of said ING-1; and (B) producing said chimeric light chain or chimeric fragment thereof.

154. The process of claim 153, wherein said response is elicited at an effector to target ratio of 50:1.

155. The process of claim 153, wherein said chimeric antibody or chimeric fragment thereof competitively inhibits the binding of said antibody ING-1 to said human tumor antigen.

156. The process of any one of claims 153, 154 or 155, wherein said chimeric antibody or chimeric fragment thereof has essentially the same affinity as said ING-1 for said human tumor antigen.

157. A process for producing a chimeric heavy chain or chimeric fragment thereof, said process comprising:
- (A) culturing a host that is capable of expressing said chimeric heavy chain or chimeric fragment thereof, wherein:
  - (i) a chimeric antibody or chimeric fragment thereof that recognizes the human tumor antigen bound by antibody ING-1 is produced when said chimeric heavy chain or chimeric fragment thereof is combined with a chimeric light chain or chimeric fragment thereof, wherein said ING-1 is produced by cell line HB9812 as deposited with the ATCC; and
  - (ii) said chimeric antibody has essentially the same affinity as said ING-1 for said human tumor antigen; and
- (B) producing said chimeric heavy chain or chimeric fragment thereof.

158. The process of claim 157, wherein said chimeric antibody or chimeric fragment thereof competitively inhibits the binding of said antibody ING-1 to said human tumor antigen.

159. A process for producing a chimeric heavy chain or chimeric fragment thereof, said process comprising:
- (A) culturing a host that is capable of expressing said chimeric heavy chain or chimeric fragment thereof, wherein:
  - (i) a chimeric antibody or chimeric fragment thereof that recognizes the human tumor antigen bound by antibody ING-1 is produced when said chimeric heavy chain or chimeric fragment thereof is combined with a chimeric light chain or chimeric fragment thereof, wherein said ING-1 is produced by cell line HB9812 as deposited with the ATCC; and
  - (ii) said chimeric antibody or chimeric fragment thereof of part (i) mediates complement-dependent cytolysis of HT-29 tumor cells at a concentration of 0.08 $\mu$g/ml; and
- (B) producing said chimeric heavy chain or chimeric fragment thereof.

160. The process of claim 159, wherein said chimeric antibody or chimeric fragment thereof competitively inhibits the binding of said antibody ING-1 to said human tumor antigen.

161. The process of claim 159, wherein said chimeric antibody or chimeric fragment thereof has essentially the same affinity as said ING-1 for said human tumor antigen.

162. The process of claim 161, wherein said chimeric antibody or chimeric fragment thereof competitively inhibits the binding of said antibody ING-1 to said human tumor antigen.

163. A process for producing a chimeric heavy chain or chimeric fragment thereof, said process comprising:
- (A) culturing a host that is capable of expressing said chimeric heavy chain or chimeric fragment thereof, wherein:
  - (i) a chimeric antibody or chimeric fragment thereof that recognizes the human tumor antigen bound by antibody ING-1 is produced when said chimeric heavy chain or chimeric fragment thereof is combined with a chimeric light chain or chimeric fragment thereof, wherein said ING-1 is produced by cell line HB9812 as deposited with the ATCC; and
  - (ii) said chimeric antibody or chimeric fragment thereof of part (i) mediates complement-dependent cytolysis essentially the same as said ING-1; and
- (B) producing said chimeric heavy chain or chimeric fragment thereof.

164. The process of claim 163, wherein said chimeric antibody or chimeric fragment thereof competitively inhibits the binding of said antibody ING-1 to said human tumor antigen.

165. The process of any one of claims 163 or 164, wherein said chimeric antibody or chimeric fragment thereof has essentially the same affinity as said ING-1 for said human tumor antigen.

166. A process for producing a chimeric heavy chain or chimeric fragment thereof, said process comprising:
- (A) culturing a host that is capable of expressing said chimeric heavy chain or chimeric fragment thereof, wherein:
  - (i) a chimeric antibody or chimeric fragment thereof that recognizes the human tumor antigen bound by antibody ING-1 is produced when said chimeric heavy chain or chimeric fragment thereof is combined with a chimeric light chain or chimeric fragment thereof, wherein said ING-1 is produced by cell line HB9812 as deposited with the ATCC; and
  - (ii) said chimeric antibody or chimeric fragment thereof of part (i) mediates an antibody-dependent cellular cytotoxicity response by human peripheral blood leukocytes against BT-20 tumor cells of 56 to 96% lysis without serum and 33 to 97% lysis with serum, with an antibody concentration of 0.0001 $\mu$g/ml to 1.0 $\mu$g/ml; and
- (B) producing said chimeric heavy chain or chimeric fragment thereof.

167. The process of claim 166, wherein said response is elicited at an effector to target ratio of 50:1.

168. The process of claim 166, wherein said chimeric antibody or chimeric fragment thereof competitively inhibits the binding of said antibody ING-1 to said human tumor antigen.

169. The process of claim 166, wherein said chimeric antibody or chimeric fragment thereof has essentially the same affinity as said ING-1 for said human tumor antigen.

170. The process of claim 169, wherein said chimeric antibody or chimeric fragment thereof competitively inhibits the binding of said antibody ING-1 to said human tumor antigen.

171. A process for producing a chimeric heavy chain or chimeric fragment thereof, said process comprising:
- (A) culturing a host that is capable of expressing said chimeric heavy chain or chimeric fragment thereof, wherein:
  - (i) a chimeric antibody or chimeric fragment thereof that recognizes the human tumor antigen bound by antibody ING-1 is produced when said chimeric heavy chain or chimeric fragment thereof is combined with a chimeric light chain or chimeric fragment thereof, wherein said ING-1 is produced by cell line HB9812 as deposited with the ATCC; and
  - (ii) said chimeric antibody or chimeric fragment thereof of part (i) mediates an antibody-dependent cellular cytotoxicity response essentially that of said ING-1; and (B) producing said chimeric heavy chain or chimeric fragment thereof.

172. The process of claim 171, wherein said response is elicited at an effector to target ratio of 50:1.

173. The process of claim 171, wherein said chimeric antibody or chimeric fragment thereof competitively inhibits the binding of said antibody ING-1 to said human tumor antigen.

174. The process of any one of claims 171, 172 or 173, wherein said chimeric antibody or chimeric fragment thereof has essentially the same affinity as said ING-1 for said human tumor antigen.

175. The antibody of any one of claims 2, 4, 5, 6 or 8, wherein said antibody mediates complement-dependent cytolysis of HT-29 tumor cells at a concentration of 0.08 µg/ml.

176. The antibody of any one of claims 3, 4, 6, 7 or 8, wherein said antibody mediates an antibody-dependent cellular cytotoxicity response by human peripheral blood leukocytes against BT-20 tumor cells of 56 to 96% lysis without serum and 33 to 97% lysis with serum with an antibody concentration of 0.0001 µg/ml to 1.0 µg/ml.

177. The antibody of claim 176, wherein said response is elicited at an effector to target ratio of 50:1.

178. Antibody ING-1 wherein said antibody ING-1 is produced by cell line HB9812 as deposited with the ATCC.

179. Antibody ING-1 of claim 178, wherein said antibody is detectably labeled.

180. Antibody ING-1 of claim 179, wherein said label is a radionuclide, nuclear magnetic resonance contrasting agent, X-ray contrasting agent, fluorescent label or enzyme.

181. Antibody ING-1 of claim 178, wherein said antibody ING-1 is coupled to a toxin, peptide effector, therapeutic moiety or drug.

182. Antibody ING-1 of claim 181, wherein said antibody ING-1 is coupled to a therapeutic moiety.

183. Antibody ING-1 of claim 182, wherein said therapeutic moiety is a lymphokine or colony-stimulating factor.

184. An immunoassay method for detecting an antigen in a sample, said method comprising (A) contacting the antigen in said sample with antibody ING-1 of claim 178, under conditions in which said antigen can be detected with a label, wherein said antibody is capable of binding antigen;

(B) detecting said label; and (C) relating said label that is detected in part (B) to the presence of said antigen.

185. The immunoassay method of claim 184, wherein said antibody ING-1 is detectably labeled.

186. An imaging method for revealing the presence of an antigen in an animal, said method comprising:

(A) contacting the antibody ING-1 of claim 178, with a part of said animal that is suspected of containing said antigen under conditions in which said antigen can be detected with a label, wherein said antibody is capable of binding antigen;

(B) detecting said label; and (C) relating said label that is detected in part (B) to said presence of said antigen.

187. The imaging method of claim 186, wherein said antibody ING-1 is detectably labeled.

188. A method of killing cells carrying an antigen thereon, said method comprising:

(A) contacting said cells with the antibody ING-1 of claim 178, and (B) allowing said killing to occur.

189. A chimeric fragment of antibody ING-1 wherein said antibody ING-1 is produced by cell line HB9812 as deposited with the ATCC.

190. The chimeric fragment of antibody ING-1 of claim 189, wherein said chimeric fragment is detectably labeled.

191. The chimeric fragment of antibody ING-1 of claim 190, wherein said label is a radionuclide, nuclear magnetic resonance contrasting agent, X-ray contrasting agent, fluorescent label or enzyme.

192. The chimeric fragment of antibody ING-1 of claim 189, wherein said chimeric fragment is coupled to a toxin, peptide effector, therapeutic moiety or drug.

193. The chimeric fragment of antibody ING-1 of claim 192, wherein said chimeric fragment is coupled to a therapeutic moiety.

194. The chimeric fragment of antibody ING-1 of claim 193, wherein said therapeutic moiety is a lymphokine or colony-stimulating factor.

195. An immunoassay method for detecting an antigen in a sample, said method comprising (A) contacting the antigen in said sample with said chimeric fragment of claim 189, under conditions in which said antigen can be detected with a label, wherein said antibody is capable of binding antigen;

(B) detecting said label; and (C) relating said label that is detected in part (B) to the presence of said antigen.

196. The immunoassay method of claim 195, wherein said chimeric fragment is detectably labeled.

197. An imaging method for revealing the presence of an antigen in an animal, said method comprising:

(A) contacting the chimeric fragment of claim 189, with a part of said animal that is suspected of containing said antigen under conditions in which said antigen can be detected with a label, wherein said antibody is capable of binding antigen;

(B) detecting said label; and (C) relating said label that is detected in part (B) to said presence of said antigen.

198. The imaging method of claim 197, wherein said chimeric fragment is detectably labeled.

* * * * *